(12) United States Patent
Sparks et al.

(10) Patent No.: US 6,709,821 B2
(45) Date of Patent: *Mar. 23, 2004

(54) POLYPEPTIDES HAVING A FUNCTIONAL DOMAIN OF INTEREST AND METHODS OF IDENTIFYING AND USING SAME

(75) Inventors: Andrew B. Sparks, Pikesville, MD (US); Noah Hoffman, Greensboro, NC (US); Brian K. Kay, Chapel Hill, NC (US); Dana M. Fowlkes, Chapel Hill, NC (US); Stephen J. McConnell, San Diego, CA (US)

(73) Assignees: University of North Carolina at Chapel Hill, Chapel Hill, NC (US); Cytogen Corp., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/879,957

(22) Filed: Jun. 13, 2001

(65) Prior Publication Data

US 2002/0034755 A1 Mar. 21, 2002

Related U.S. Application Data

(60) Division of application No. 08/630,915, filed on Apr. 3, 1996, now Pat. No. 6,309,820, which is a continuation-in-part of application No. 08/417,872, filed on Apr. 7, 1995, now abandoned.

(51) Int. Cl.$^7$ .......................... C12Q 1/68; G01N 33/53; A61K 38/00; C12N 7/00
(52) U.S. Cl. ............................. 435/6; 435/7.1; 435/7.2; 435/7.5; 435/172.1; 435/235.1; 435/240.1; 435/320.1; 435/DIG. 4; 435/DIG. 17; 435/DIG. 23; 435/DIG. 37; 436/501; 436/518; 530/300; 530/350; 530/387.9; 536/23.5
(58) Field of Search .............................. 435/7.1, 6, 7.2, 435/7.5, 172.1, 235.1, 240.1, 320.1, DIG. 4, DIG. 17, DIG. 23, DIG. 37; 530/300, 350, 387.9; 536/23.5; 436/501, 518

(56) References Cited

U.S. PATENT DOCUMENTS

| 5,096,815 A | 3/1992 | Ladner et al. |
| 5,198,346 A | 3/1993 | Ladner et al. |
| 5,223,409 A | 6/1993 | Ladner et al. |
| 5,541,109 A | 7/1996 | Searfoss, III et al. |

FOREIGN PATENT DOCUMENTS

| WO | WO 90/02809 | 3/1990 |
| WO | 91/19818 | 12/1991 |
| WO | 92/18528 | 10/1992 |
| WO | WO 93/18054 | 9/1993 |
| WO | 95/10296 | 4/1995 |
| WO | WO 95/24419 | 9/1995 |
| WO | 96/368881 | 11/1996 |
| WO | 97/37223 | 10/1997 |

OTHER PUBLICATIONS

Noah G. Hoffman, et al., 1996, *Molecular Diversity*, 2:5–12.
E. Y. Skolnik, et al., 1991, *Cell*, 65:83–90.
Barkas et al., 1987, "Mapping the main immunogenic region and toxin–binding site of the nicotinic acetylcholine receptor", *Science* 235:77–80.
Bar–Sagi et al., 1993, "SH3 domains direct cellular localization of signaling molecules", *Cell* 74:83–91.
Blond–Elguindi et al., 1993, "Affinity panning of a library of peptides displayed on bacteriophages reveals the binding specificity of BiP", *Cell* 75:717–728.
Bock et al., 1992, "Selection of single–stranded DNA molecules that bind and inhibit human thrombin", *Nature* 355:564–566.
Brunton & Workman, 1993, "Cell–signaling targets for antitumor drug development", *Cancer Chemother. Pharmacol.* 32:1–19.
Cheadle et al., 1994, "Identification of a SRC SH3 domain binding motif by screening a random phage display library", *J. Biol. Chem.* 269:24034–24039.
Chen et al., 1993, "Biased combinatorial libraries: Novel ligands for the SH3 domain of phosphatidylinositol 3–kinase", *J. Biol. Chem.* 115:12591–12592.
Chien et al., 1991, "The two–hybrid system: A method to identify and clone genes for proteins that interact with a protein of interest", *Proc. Natl. Acad. Sci. USA* 88:9578–9582.
Cicchetti et al., 1992, "Identification of a protein that binds to the SH3 region of AB1 and is similar to BCR and GAP–ρ", *Science* 257:803–806.
Clark et al., 1992, "*C. elegans* cell–signalling gene *sem–5* encodes a protein with SH2 and SH3 domains", *Nature* 356:340–344.
Cohen et al., 1995, "Modular binding domains in signal transduction proteins", *Cell* 80:237–248.
Cwirla et al., 1990, "Peptides on phage: A vast library of peptides for identifying ligands", *Proc. Natl. Acad. Sci. USA* 87:6378–6382.
Daniels & Lane, 1994, "The characterization of p53 binding phage isolated from phage peptide display libraries", *J. Mol. Biol.* 243:639–652.

(List continued on next page.)

*Primary Examiner*—Maurie Garcia Baker
(74) *Attorney, Agent, or Firm*—Morgan & Finnegan, L.L.P.; Eugene Moroz, Esq.

(57) ABSTRACT

Novel polypeptides having functional domains of interest are described, along with DNA sequences that encode the same. A method of identifying these polypeptides by means of a sequence-independent (that is, independent of the primary sequence of the polypeptide sought), recognition unit-based functional screen is also disclosed. Various applications of the method and of the polypeptides identified are described, including their use in assay kits for drug discovery, modification, and refinement.

9 Claims, 61 Drawing Sheets

OTHER PUBLICATIONS

David et al., 1994, "Autoimmunity in stiff–Man syndrome with breast cancer is targeted to the C–terminal region of human amphiphysin, a protein similar to the yeast proteins, RVS167 and RVS161", *FEBS Lett.* 351:73–79.

Dedman et al., 1993, "Selection of targeted biological modifiers from a bacteriophage library of random peptides. The identification of novel calmodulin regulatory peptides", *J. Biol. Chem.* 268:23025–23030.

Devlin et al., 1990, "Random peptide libraries: A source of specific protein binding molecules", *Science* 249:404–406.

Doorbar & Winter, 1994, "Isolation of a peptide antagonist to the thrombin receptor using phage display", *J. Mol. Biol.* 244:361–369.

Duchesne et al., 1993, "Identification of the SH3 domain of GAP as an essential sequence for RAS–GAP–Mediated signaling", *Science* 259:525–528.

Egan et al., 1993, "Association of Sos Ras exchange protein with Grb2 is implicated in tyrosine kinase signal transduction and transformation", *Nature* 363:45–51.

Ellington & Szostak, 1990, "In vitro selection of RNA molecules that bind specific ligands", *Nature* 346:818–822.

Ellington & Szostak, 1992, "Selection in vitro of single–stranded DNA molecules that fold into specific ligand–binding structures", *Nature* 355:850–852.

Evans et al., 1990, "Talin and vinculin in the oocyte, eggs, and early embryos of *Xenopus laevis*: A developmentally regulated change in distribution", *Dev. Biol.* 137:403–413.

Feng et al., 1994, "Two binding orientations for peptides to the SRC SH3 domain: Development of a general model for SH3–Ligand interactions", *Science* 266:1241–1247.

Fields & Song, 1989, "A novel genetic system to detect protein–protein interactions", *Nature* 340:245–246.

Flynn et al., 1993, "Identification and sequence analysis of cDNAs encoding a 110–kilodalton actin filament–associated $pp60^{src}$ substrate", *Mol. Cell. Biol.* 13:7892–7900.

Fowlkes et al., 1992, "Multipurpose vectors for peptide expression on the M13 viral surface", *Biotechniques* 13:422–427.

Fukamachi et al., 1994, "Identification of a protein, SPY75, with repetitive helix–turn helix motifs and an SH3 domain as a major substrate for protein tyrosine kinase(s) activated by Fc $\epsilon$ RI cross–linking", *J. Immunol.* 152:642–652.

Gao et al., 1994, "Selection of a subset of mRNAs from combinatorial 3' untranslated region libraries using neuronal RNA–binding protein Hel–N1", *Proc. Natl. Acad. Sci. USA* 91:11207–11211.

Geysen et al., 1987, "Strategies for epitope analysis using peptide synthesis", *J. Immunol. Meth.* 102:259–274.

Gilbert & Villa–Komaroff, 1980, "Useful proteins from recombinant bacteria", *Sci. Am.* 242:74–94.

Goodson et al., 1994, "High–affinity urokinase receptor antagonists identified with bacteriophage peptide display", *Proc. Natl. Acad. Sci. USA* 91:7129–7133.

Gordon et al., 1994, "Applications of combinatorial technologies to drug discovery. 2. Combinatorial organic synthesis, library screening strategies, and future directions", *J. Med. Chem.* 37:1385–1401.

Gout et al., 1993, "The GTPase dynamin binds to and is activated by a subset of SH3 domains", *Cell* 75:25–36.

Hoffman, 1995, "A novel method for identifying *src* homology 3 (SH3) domain–containing proteins", J.K. Koeppe Undergraduate Res. Symp. in Biol of UNC at Chapel Hill, Apr. 7, abstracts.

Hoffman, 1995, "A novel method for identifying *src* homology 3 (SHC) domain–containing proteins", Honors Thesis, Dept of Biology, UNC Chapel Hill.

Houghten et al., 1991, "Generation and use of synthetic peptide combinatorial libraries for basic research and drug discoveries", *Nature* 354:84–86.

Ishikawa et al., 1994, "Drebrin, a development–associated brain protein from rat embryo, causes the dissociation of tropomyosin from actin filaments", *J. Biol. Chem.* 269:29928–29933.

Iwabuchi et al., 1994, "Two cellular proteins that bind to wild–type but not mutant p53", *Proc. Natl. Acad. Sci. USA* 91:6098–6102.

Jackson et al., 1993, "Mutation of a phenylalanine conserved in SH3–containing tyrosine kinases activates the transforming ability of c–ABL", *Oncogene* 8:1943–1956.

N.K. Jerne, 1974, "Towards a network theory of the immune system", *Ann. Immunol.* (Inst. Pasteur) 125c:373–389.

Kapeller et al., 1994, "Identification of two SH3–binding motifs in the regulatory subunit of phosphatidylinositol 3–kinase", *J. Biol. Chem.* 269:1927–1933.

Kawakami et al., 1988, "Acquisition of transforming properties by FYN, a normal SRC–related human gene", *Proc. Natl. Acad. Sci. USA* 85:3870–3874.

Kay et al., 1993, "An M13 phage library displaying random 38–amino acid peptides as a source of novel sequences with affinity to selected targets", *Gene* 128:59–65.

B.K. Kay, 1994, "Biologically displayed random peptides as reagents in mapping protein–protein interactions", *Prospect. in Drug Disc. & Design* 2:251–268.

Kay et al., 1995, "Mapping protein–protein interactions with phage", *Tuscon Mtg. Discussion* abstr.

Knudsen et al., 1994, "Four proline–rich sequences of the quanine–nucleotide exchange factor C3G bind with unique specificity to the first SRC homology 3 domain of CRK", *J. Biol. Chem.* 269:32781–32787.

Krook et al., 1994, "Selection of peptides with affinity for single stranded DNA using a phage display library", *Biochem. Biophys. Res. Comm.* 204:849–854.

Lam et al., 1991, "A new type of synthetic peptide library for identifying ligand–binding activity", *Nature* 354:82–84.

R. Langer, 1990, "New methods of drug delivery", *Science* 249:1527–1533.

Lescure et al., 1992, "A factor with SP1 DNA–binding specificity stimulates Xenopus U6 snRNA in vivo transcription by RNA polymerase III", *J. Mol. Biol.* 228:387–394.

Lichte et al., 1992, "Amphiphysin, a novel protein associated with synaptic vesicles", *EMBO J.* 11:2521–2530.

Lim et al., 1994, "Stability and peptide binding affinity of an SH3 domain from the *Caenorhabditis elegans* signaling protein SEM–5", *Protein Sci.* 3:1261–1266.

Lim et al., 1994, "Structure determinants of peptide–binding orientation and of sequence specificity on SH3 domains", *Nature* 372:375–379.

Liu et al., 1993, "The v–Src SH3 domain binds phosphatidylinositol 3' kinase", *Mol. Cell. Biol.* 13:5225–5232.

Mayer et al., 1993, "A putative modular domain present in diverse signaling proteins", *Cell* 73:629–630.

McAdara & Babior, 1993, "SH3 domains appear to play a functional role in respiratory burst oxidase activity", *Blood* 82:A28.

McGlade et al., 1993, "The N–terminal region of GAP regulates cytoskelatal structure and cell adhesion", *EMBO J.* 12:3073–3081.

McLafferty et al., 1993, "M13 bacteriophage displaying disulfide–constrained microproteins", *Gene* 128:29–36.

Oldenburg et al., 1992, "Peptide ligands for a sugar–binding protein isolated from a random peptide library", *Proc. Natl. Acad. Sci. USA* 89:5393–5397.

Olivier et al., 1993, "A Drosophila SH2–SH3 adaptor protein implicated in coupling the sevenless tyrosine kinase to an activator of RAS guanine nucleotide exchange, Sos", *Cell* 73:179–191.

Parmley & Smith, 1988, "Antibody–selectable filamentous fd phage vectors: Affinity purification of target genes", *Gene* 73:305–318.

Parmley & Smith, 1989, "Filamentous fusion phage cloning vectors for the study of epitopes and design of vaccines", *Adv. Exp. Med. Biol.* 251:215–218.

Pawson & Gish, 1992, "SH2 and SH3 domains: From structure to function", *Cell* 71:359–362.

T. Pawson, 1995, "Protein modules and signalling networks", *Nature* 373:573–580.

Pleiman et al., 1994, "Activation of phosphatidylinositol–3' kinase by Src–family kinase SH3 binding to the p85 subunit", *Science* 263:1609–1612.

Rebar & Pabo, 1994, "Zinc finger phage: Affinity selection of fingers with new DNA–binding specificities", *Science* 263:671–673.

Ren et al., 1993, "Identification of a ten–amino acid proline–rich SH3 binding site", *Science* 259:1157–1161.

Reynolds et al., 1992, "Functional analysis of the SH2 and SH3 domains of the *lck* tyrosine protein kinase", *Oncogene* 7:1949–1955.

Rickles et al., 1994, "Identification of SRC, FYN, LYN, P13K and ABL SH3 domain ligands using phage display libraries", *EMBO J.* 13:5598–5604.

Rickles et al., 1995, "Phage display selection of ligand residues important for Src homology 3 domain binding specificity", *Proc. Natl. Acad. Sci. USA* 92:10909–10913.

Rozakis–Adcock et al., 1993, "The SH2 and SH3 domains of mammalian Grb2 couple the EGF receptor to the Ras activator mSos1", *Nature* 363:83–85.

Sanger et al., 1980, "Cloning in single–stranded bacteriophage as an aid to rapid DNA sequencing", *J. Mol. Biol.* 143:161–178.

Scott & Smith, 1990, "Searching for peptide ligands with an epitope library", *Science* 249:386–390.

Seidel–Dugan et al., 1992, "Effects of SH2 and SH3 deletions on the functional activities of wild–type and transforming variants of c–SRC", *Mol. Cell. Biol.* 12:1835–1845.

Sikela & Hahn, 1987, "Screening an expression library with a ligand probe: Isolation and sequence of a cDNA corresponding to a brain calmodulin–binding protein", *Proc. Natl. Acad. Sci. USA* 84:3038–3042.

Skolnik et al., 1991, "Cloning of P13 kinase–associated p85 utilizing a novel method for expression/cloning of target proteins for receptor tyrosine kinases", *Cell* 65:83–90.

Songyang et al., 1993, "SH2 domains recognize specific phosphopeptide sequences", *Cell* 72:767–778.

Wages et al., 1992, "Mutations in the SH3 domain of the *src* oncogene which decrease association of phosphatidylinositol 3'–kinase activity with pp60$^{v-src}$ and alter cellular morphology", *J. Virol.* 66:1866–1874.

Weng et al., 1993, "Detection of Src homology 3–binding proteins, including paxillin, in normal and v–Src–transformed Balb/c 3T3 cells", *J. Biol. Chem.* 268:14956–14963.

J. Winter, 1994, "Bacteriophage display: Peptide libraries and drug discovery", *Drug Dev. Res.* 33:71–89.

Wu & Parsons, 1993, "Cortactin, an 80/85–kilodalton pp60$^{src}$ substrate, is a filamentous actin–binding protein enriched in the cell cortex", *J. Cell Biol.* 120:1417–1426.

Yamanashi et al., 1987, "The YES–related cellular gene LYN encodes a possible tyrosine kinase similar to p56llck", *Mol. Cell. Biol.* 7:237–243.

Young & Davis, 1983, "Efficient isolation of genes by using antibody probes", *Proc. Natl. Acad. Sci. USA* 80:1194–1198.

Yu et al., 1992, "Solution structure of the SH3 domain of Src and identification of its ligand–binding site", *Science* 258:1665–1670.

Yu et al., 1994, "Structural basis for the binding of proline–rich peptides to SH3 domains", *Cell* 76:933–945.

Zhu et al., 1993, "Direct analysis of the binding of the *abl* Src homology 2 domain to the activated epidermal growth factor receptor", *J. Biol. Chem.* 268:1775–1779.

| Name | | | | | SEQ. ID NO. |
|---|---|---|---|---|---|
| Sc_Fus1_Sh3: | TVI QDYE PRLTDE..... | .....IRISLG EKVKIL...A | ....THTD | CLVEKCNTRK | .....68 |
| Sc_Bob1_Sh3: | RAL FDYD KTKDCGFLSQ | ..ALSFRFG DVLHVIDA..... | ....GDEE | QAR RVHSDSE | .....69 |
| Hs_Mpp1_Sh3: | RAQ FDYD PKKDNLIPCK | EAGLKFATG DIIQIINK..... | ....DDSN | QGR ..VEGSS | .....70 |
| Hs_Zo1_Sh3: | RTH PHYE KESPY...... | ..GLSFNKG EVFRAVDTLY... | .NGKLGS | AI RIGKNHKE | .....71 |
| Hs_Ncf1_Csh3: | VAI KAYT AV.EGD..E. | .....VSLLEG EAVEVIHK.... | .....LLDG | V IRKDDVTGY | .....72 |
| Hs_Rasgap_Sh3: | RAI LPYT KVPDTD..E. | .....ISFLKG DMFIVHNE.... | .....LED | .. MWVTNLRT | .....73 |
| Sc_Sla_Nsh3: | RAV YAYE ..PQTP..EE | .....LAIQED DLLYLLQKSD.. | .......IDD | TVKKR VIGSD | .....74 |
| Sc_Bem1_Nsh3: | KAK YSYQ ..AQTS..KE | .....LSFMEG EFFYV..SGD.. | ......EKD | KASNP STGKE | .....75 |
| Hs_Ncf2_Nsh3: | AHR VLFG FVPETK..EE | .....LQVMPG NIVFVL..KK | ......GND | ATVMFNG.QK | .....76 |
| Sc_Sla_Csh3: | RGI VQYD FMAESQ..DE | .....LTIKSG DKVYILDDKK.. | ......SKD | MCQLVDS.GK | .....77 |
| Hs_Grb2_Csh3: | QAL FDPD ..PQED..GE | .....LGFRRG DFIHVMD..N | S....DPN | KG.A.CH.GQ | .....78 |
| Hs_Nck_Csh3: | QAL YPFS ..SSND..EE | .....LNFEKG DWMDVIEKPE | N....DPE | KCRK.IN.GM | .....79 |
| Mm_Tec_Sh3: | VAM YDFG ..ATEA..HD | .....LRLERG QEYIILEKN... | .......DLH | RARD.KN.GQ | .....80 |
| Hs_Atk_Sh3: | VAL YDYN ..PMNA..ND | .....LQLRKG DEYFILEES... | .......NLP | RARD.KY.GW | .....81 |
| Hs_Abl_Sh3: | VAL YDFV ..ASGD..NT | .....LSITKG EKLRVLGYN... | .....HNGE | EAQT.KN.GQ | .....82 |
| Hs_Src_Sh3: | VAL YDYE ..SRTE..TD | .....LSFKKG ERLQIVNNT... | ......EGD | LAHSLST.GQ | .....83 |
| Hs_Fgr_Sh3: | IAL YDYE ..ARTE..DD | .....LTFTKG EKFHILNNT... | ......EGD | EARSLSS.GK | .....84 |
| Hs_Fyn_Sh3: | VAL YDYE ..ARTE..DD | .....LSFHGK EKFQILNSS... | ......EGD | EARSLTT.GE | .....85 |
| Hs-Yes_Sh3: | VAL YDYE ..ARTT..ED | .....LSFKKG ERFQIINNT... | ......EGD | EARSIAT.GK | .....86 |
| Mm_Fgr_Sh3: | VAL YDYE ..ARTG..DD | .....LTFTKG EKFHILNNT... | ......EYD | EARSLSS.GH | .....87 |
| Hv_Stk_Sh3: | VAL YDYE ..ARIS..ED | .....LSFKKG ERLQIINTA... | ......DGD | YARSLIT.NS | .....88 |
| Hs_Hck_Sh3: | VAL YDYE ..AIHH..ED | .....LSFQKG DQMVVLEES... | .........GE | KARSLAT.RK | .....89 |
| Hs_Lyn_Sh3: | VAL YPYD ..GIHP..DD | .....LSFKKG EMKVLEEH.... | .........GE | KAKSLLT.KK | .....90 |
| Mm_Blk_Sh3: | VAL PDYA ..AVND..RD | .....LQVLKG EKLQVLRST... | ........GD | LARSLVT.GR | .....91 |
| Hs_Lck_Sh3: | IAL HSYE ..PSHD..GD | .....LGFEKG EQLRILEQS... | .........GE | KAQSLTT.GQ | .....92 |
| Hs_Nck_Nsh3: | VAK FDYV ..AQQE..QE | .....LDIKKN ERLWLLDDSK | SW....... | VRNSM..NK | .....93 |
| Sc_Sla_Msh3: | RAI YDYE QVQNAD..EE | .....LTFHEN DVFDVFKKD... | ......DAD | LVKSTVS.NE | .....94 |

FIG. 6A

| | | | | | SEQ. ID NO. |
|---|---|---|---|---|---|
| Hs_Hs1_Sh3: | VAL YDYQ | ..GEGS..DE | .........DEG | RG...RCH.GH | .....95 |
| Sc_Abp1_Sh3: | TAE YDYD | ..AAED..NE | ....LSFDPD DVITDIEMV. | ........DDD | LGELEKD.GS | .....96 |
| Hs_Nck_Msh3: | YVK FNYN | ..AERE..DE | ....LTFVEN DKIINIEFV. | ........SDG | RG...SYN.GQ | .....97 |
| Hs_Vav_Sh3: | KAR YDFC | ..ARDR..SE | ....LSLIKG TKVIVMEKC. | ........GQQ | WRGEIY..GR | .....98 |
| Hs_Grb2_Nsh3: | IAK YDFK | ..ATAD..DE | ....LSLKEG DIIKILNKK. | ........CDQ | YKAELN..GK | .....99 |
| Hs_Plcg2_Sh3: | KAL YDYK | ..AKRS..DE | ....LSFKRG DILKVLNEE. | .........PG | WKGDYGT.RI | ....100 |
| Hs_Plcg1_Sh3: | KAL FDYK | ..AQRE..DE | ....LSFCRG ALIHNVSKE | | WRGDYGG.KK | ....101 |
| Ac_Mys1b_Sh3: | KAL YDYD | ..AQTG..DE | ....LTFIKS AIIQNVEKQ. | ..........EG | WEGELN..GK | ....102 |
| Ac_Mys1c_Sh3: | RAL YDFA | ..AENP..DE | ....LTFKEG DTIIVHQKD. | .........PA | WEGELN..GQ | ....103 |
| Dd_Mys1b_Sh3: | KAL YDYD | ..ASST..DE | ....LTFNEG AVVTVINKS. | .........NP | TQGELKS.GQ | ....104 |
| Hs_Ncf2_Csh3: | EAL FSYE | ..ATQP..ED | ....LSFKEG DIIFIVQKD. | ..........NG | LEGECK..GK | ....105 |
| Hs_Ncf1_Nsh3: | RAI ADYE | ..KTSG..SE | ....LEFQEG DIILVLSKV. | ..........NE | FCQM..K.AK | ....106 |
| Hs_Spectrin_Sh3: | MAL VDFQ | ..ARSP..RE | ....MALSTG DVVEVEKS. | ........ESG | KVEA..A.DH | ....107 |
| Sc_Bem1_Csh3: | YAI VLYD | FKAEKA..DE | ....VTMKKG DVLTLLSSI. | ........NKD | IAKPIGRLGG | ....108 |
| Sc_Cde25_Sh3: | VAA YDFN | YPIKKD..SS | ....LTTYVG ENLFICAH.. | .......HNCE | ...DGL VIDD | ....109 |
| Sp_Ste_Sh3: | .MR FQTT | AISDYENSSN | SQLLSVQQG ETIYILNKS | ..........SG | ...DGL VIDD | ....110 |
| Hs_Pf3ka_Sh3: | RAL VDYK | KEREEDIDLH | .PSFLKFSAG DTIIVEVLE | ..........D | CDG........ | ....111 |
| | | | LGDILTVNKG SLVALGFSDG QEARPEEI | | LNGYNETTGE | |

FIG. 6B

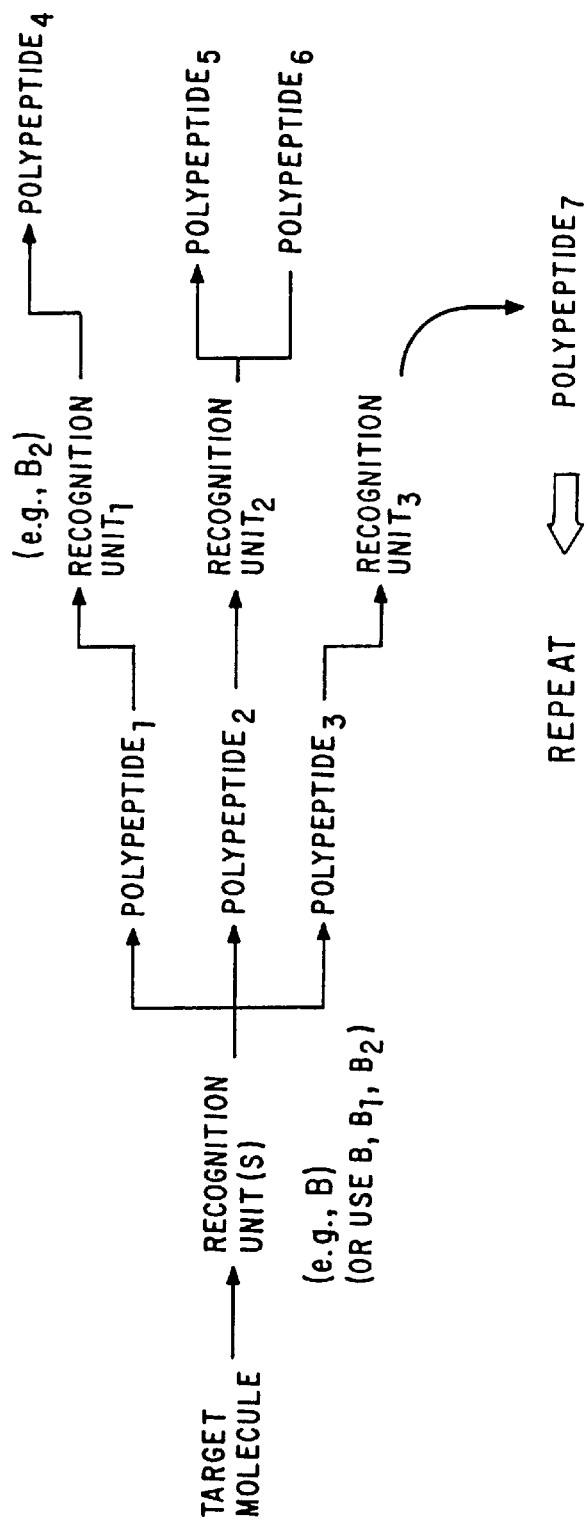
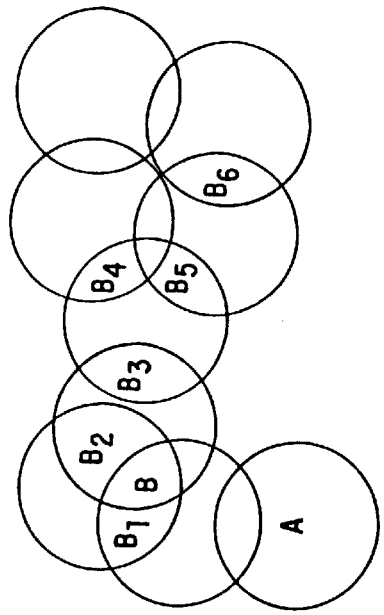
FIG. 7B
FIG. 7A

FIG. 9

| | | | | SEQ. ID NO. |
|---|---|---|---|---|
| SH3P1 | p53bp2 | NKGTVYALWDYEAQNSDELSFHEGDAITILRRKDEN..ETEWWWARLG... | ...DREGYVPKNLLGLY | ....112 |
| SH3P2 | Novel | QVKVFRALYFEPRTPDELYFEEGDIIYITDMS...DTSWWKGTCK... | ...GRTGLIPSNYVAEQ | ....113 |
| SH3P3 | Novel | HWTPYRAMYQYRPQNEDELELREGDRVDVMQQC...DDGWFVGVSRRT... | ...QKFGTFPGNYVAPV | ....114 |
| SH3P4 | Novel | DQPSCKALYDFEPENDGELGFREGDLITLTNQI...DENWYEGMLH... | ...GQSGFFPLSYVQVL | ....115 |
| SH3P5 | Cortactin | LGITAIALYDYQAAGDDEISFDPDDIITNIEMI...DDGWRGVCK... | ...GRYGLFPANYVELR | ....116 |
| SH3P6 | MLN50 | GGKRYRAVYDYSAADEDEVSFQDGDTIVNVQQI...DDGWMYGTVERT... | ...GDTGMLPANYVEAI | ....117 |
| SH3P7 | Novel | QGLCARALYDYQAADDTEISFDPENLITGIEVI...DEGWWRGYGPD... | ...GHFGMFPANYVELI | ....118 |
| SH3P8 | Novel | DQPCCRALYDLEPENEGELAFKEGDIITLTNQI...DENWYEGMLH... | ...GQSGFFPINYVEIL | ....119 |
| SH3P9 | Novel, m | FMFKVQAQHDYTATDTDELQLKAGDVVLVIPFQNPEEQDEGWLMGVKESDWNQHKELEKCRGVFPENFTERV | ....120 |
| | Novel, h | FMFKVQAQHDYTATDTDELQLKAGDVVLVIPFQNPEEQDEGWLMGVKESDWNQHKELEKCRGVFPENFTERV | ....121 |
| SH3P10 | HS1 | AGISAIALYDYQGEGSDELSFDPDDIITDIEMV...DEGWWRGQCR... | ...GHFGLFPANYVKLL | ....122 |
| SH3P11 | Crk A | EAEYVRALFDFNGNDEEDLPFKKGDILRIRDKP...EEQWWNAEDSE... | ...GKRGMIPVPYVEKY | ....123 |
| | B | RVIQKRVPNAYDKTALALEVGELVKVTKINV...SGQWEGECN... | ...GKRGHFPFTHVRLL | ....124 |
| SH3P12 | Novel A | EMRPARAKFDFKAQTLKELPLQKGDVVYIYRQI...DQNWYEGEHH... | ...GRVGIFPRTYIELL | ....125 |
| | B | EYGEAIAKFNFNGDTQVEMSFRKGERITLLRQV...DENWYEGRIPGT... | ...SRQGIFPITYVDVL | ....126 |
| | C | DLCSYQALYSYVPQNDDELELRDGDIVDVMEKC...DDGWFVGTSRRT... | ...RQFGTFPGNYVKPL | ....127 |
| SH3P13 | Novel | DQPCCRGLYDFEPENEGELGFKEGDIITLTNQI...DENWYEGMLR... | ...GESGFFPINYVEVI | ....128 |
| SH3P14 | H74, m | TEVRVRALDYEGQEHDELSFKAGDELTKMEDED...EQGWCKGRLDN... | ...GQVGLYPANYVEAI | ....129 |
| | H74, h | KGVRVRALYDYDGQEQDELSFKAGDELTKLGEED...EQGWCRGRLDS... | ...GQLGLYPANYVEAI | ....130 |
| SH3P15 | Lyn | QGDIVVALYPYDGIHPDDLSFKKGEKMKVLEE...HGEWWKAKSLLT... | ...KKEGFIPSNYVAKL | ....131 |
| SH3P16 | Fyn | GVTLFVALYDFVARTEDDLSFHKGEKFQILNSS...EGDWWEARSLTT... | ...GETGYIPSNYVAPV | ....132 |
| SH3P17 | Novel A | KVVYYRALYPFESRSHDEITIQPGDIVMVDESQTG...EPGWLGGELK... | ...GKTGWFPANYAEKI | ....133 |
| | B | EGLQAQALYPWRAKKDNHLNFNKNDVITVLEQ...QDMWWFGEVQ... | ...GQKGWFPKSYVKLI | ....134 |
| | C | GEEIAQVIASYTATGPEQLTLAPGQLLIRKKN...PGGWWEGELQARGKK... | ...RQIGWFPANYVKLL | ....135 |
| | D | AVCQVIAMYDYTAQNDDELAFNKGQIINVLNKE...DPDWWKGEVN... | ...GQVGLFPSNYVKLT | ....136 |

FIG. 10A

|  |  |  | SEQ. ID NO. |
|---|---|---|---|
| SH3P18 Novel B | VGEEYIALYPYSSVEPGDLTFTEGEEILVTQK......DGEWWTGSIG......DRSGIFPSNYVKPK | | .....137 |
| C | KPEIAQVTSAYVASGSEQLSLAPGQLILILKKN......TSGWWQGELQARGKK......RQKGWFPASYVKLL | | .....138 |
| D | PVCQVIGMYDYAANNEDELSFSKGQLINVMNKD......DPDWWQGEIN......GVTGLFPSNYVLEE | | .....139 |
| Src | GVTTFVALYDYESRTETDLSFKKGERLQIVNNT......EGDWWLAHSLTT......GQTGYIPSNYVAPS | | .....140 |

FIG. 10B

| | | | SEQ. ID NO. |
|---|---|---|---|
| CLONE 5 P3-6 | QVKVFRALYTFEPRTPDELYFEEGDIIYITDM | DTNWWKGTS | GRTGLIPSNYVAEQ ....204 |
| CLONE 34 Crk LIKE | TGEEYIAVGDFTAQQVGDLTFKKGEILLVIEKK | PDGWWIAKDAK | GNEGLVPRTYLEPY ....205 |
| CLONE 40 Abl BINDING PROTEIN | YLEKVVAIYDYTKDKEDELSFQEGAIIYVIKKN | DDGWYEGVMN | GVTGLSPGNYVESI ....206 |
| CLONE 41 Nck LIKE A | LNIPAFVKFAYVAIEREDELSLVKGSRVTVMEKC | SDGWWRGSYN | GQIGWFPSNYVLEE ....207 |
| Nck LIKE B | VLHVVQTLYPFSSVTEEELNEFEKGETMEVIEKPENDPEWWKCKNAR | | GQVGLVPKNYVVVL ....208 |
| CLONE 45 Nck A | EEVVVAKFDYVAQQEQELDIKKNERLWLDD | SKSWRVRNSM | NKTGFVPSNYVERK ....209 |
| Nck B | LNMPAYVKFNYMAEREDELSLIKGTKVIVMEKIC | SDGWWRGSYN | GQVGWFPSNYVTEE ....210 |
| Nck C | VLHVVQALYPFSSSNDEELNFEKGDVMDVIEKPEN | DPEWWKCRKIN | GMVGLVPKNYVTVM ....211 |
| CLONE 53 NAB | DLFSYQALYSYIPQNDDELERDGDIVDVMEKC | DDGWFVGTSRRT | KQFGTFPGNYVKPL ....212 |
| CLONE 55 NOVEL A | QGRKERARYDLEAAQDNELTFKAGEIMTVLDDS | DPNWWKGETH | QGIGLFPSNFVTAD ....213 |
| CLONE 56 NOVEL B | QGLCARALYDYQAADTEISFDPENLITGIEVI | DEGWRGYGPD | GHFGMFPANYVELI ....214 |
| CLONE 65 NOVEL C | VLVNRALYPFEARNHDEMSFNSGDIIQVDEKTVG | EPGWLYGSFQ | GNFGWFPCNYVEKM ....215 |
| NOVEL A | VENLKAQALCSWTAKK DNHLNFSKHDIITVLEQQ | ENFWWFGEVH | GGRGWFPKSYVKII ....216 |
| NOVEL B | VGEEYIALYPYSSVEPGDLTFTEGEEILVTQK | DGEWWTGSIG | DRSGIFPSNYVKPK ....217 |
| NOVEL C | KPEIAQVTSAYVASGS EQLSLAPGQLILILKKN | TSGWWQGELQARGKKRQKGWFPASWVKLL ....218 | |
| NOVEL D | PVCQVIAMYDYAANNEDELSFSKGQLINVMNKD | DPDWWQGEIN | GVTGLFPSNYVKMT ....219 |

FIG. 10C

| | | |
|---|---|---|
| NONSPECIFIC BINDING | PEPTIDE | IDENTIFIES NOTHING SPECIFIC |
| GENERIC SPECIFICITY | SA-AP PEPTIDE COMPLEX | IDENTIFIES FAMILY OF PROTEINS WITH SPECIFIC BINDING FUNCTION |
| | PHAGE DISPLAYED PEPTIDE | |
| SPECIFIC BINDING | POLYCLONAL ANTI-BODIES HIGH AF-FINITY MABS SOME GST-FUSION PEPTIDES | IDENTIFIES SPECIFIC PROTEIN SCREENED FOR |

| PEPTIDE | NAME | SEQUENCE | SEQ ID NO | 5 | 11 | 12 | 13 | 14 | 18 | 34 | 40 | 41 | 45 | 46 | 53 | 55 | 56 | 65 |
|---|---|---|---|---|---|---|---|---|---|---|---|---|---|---|---|---|---|---|
| SH3001 | WBP-1 | PGTPPPPYTVGPGY | 141 | – | – | – | – | – | – | – | – | – | – | – | – | – | – | – |
| TPPY | WBP-1 | HGPTPPPPYTVGP | 142 | – | – | – | – | – | – | – | – | – | – | – | – | – | – | – |
| QPPY | WBP-2 | YVQPPPPYPGPM | 143 | – | – | – | – | – | – | – | – | – | – | – | – | – | – | – |
| YPPE | WBP-2 | PGYPYPPPEFY | 144 | – | – | – | – | – | – | – | – | – | – | – | – | – | – | – |
| WW005 | WBP-1 | PGTPAPPYTVGPGY | 145 | – | – | – | – | – | – | – | – | – | – | – | – | – | – | – |
| WW006 | WBP-1 | PGTPPAPYTVGPGY | 146 | – | – | – | – | – | – | – | – | – | – | – | – | – | – | – |
| bSH3002 | K+ CHANNEL | DSGVRPLPPLPDPGV | 147 | – | – | + | + | + | – | ++ | – | – | – | – | – | – | – | – |
| bSH3003 | K+ CHANNEL | VRPLPPLPEELPRPRPPPED | 148 | – | – | – | – | + | – | ++ | – | – | – | – | – | – | – | – |
| bSH3004 | M4 AChr | PPPALPPPPRPVADK | 149 | – | – | – | – | – | – | – | – | – | – | – | – | – | – | – |
| bSH3005 | β1 ADRENERGIC | APAPPGPPPAAAA | 150 | – | – | – | – | – | – | – | – | – | – | – | – | – | – | – |
| bSH3006 | RasGap | GGGFPPLPPPPYLPPLG | 151 | – | + | + | – | ++ | – | – | – | – | – | – | – | – | – | – |
| bSH3007 | MEK | SISPRPRPPGRPVSG | 152 | – | – | – | +++ | ++++ | +++ | – | – | – | – | – | – | – | – | – |
| bSH3008 | P Tyr PHOSP. | PPPEHIPPPRPKRILE | 153 | – | – | + | + | + | – | – | + | – | – | – | – | – | – | – |
| bSH3009 | Fak | KEGERALPSIPKLAN | 154 | – | – | – | – | – | – | – | – | – | – | – | – | – | – | – |
| bSH3010 | c-Abl | SRLKPAPPPPAASAG | 155 | – | – | – | – | – | – | – | – | – | – | – | – | – | – | – |
| bSH3011 | c-Cbl | QASLPPVPPRDLLLP | 156 | – | – | – | – | – | – | – | – | – | – | – | – | – | – | – |
| bSH3012 | c-Cbl | PVPPTLRDLPPPPPDRPYS | 157 | – | – | – | – | – | – | – | – | – | – | – | – | – | – | – |
| bSH3013 | Ca2+ CHANNEL | SDQGRNLPGTPVPAS | 158 | – | – | – | – | – | – | – | – | – | – | – | – | – | – | – |
| bSH3014 | Ca2+ CHANNEL | RHSRRQLPPVPPKPRPLL | 159 | – | – | + | – | – | – | – | – | – | – | – | – | – | – | – |
| bSH3015 | Nef | EKVGFPVTPQVPLRPMTY | 160 | – | – | – | – | – | – | – | – | – | – | – | – | – | – | – |
| bSH3016 | MUS CADHERIN | PQPHRVLPTSPSDIA | 161 | – | – | – | – | – | – | – | – | – | – | – | – | – | – | – |
| bSH3017 | AP2 | ADFQPPYFPPPYQPTYPQS | 162 | – | – | + | – | ++ | ++ | – | + | – | – | ++ | – | – | – | – |
| bSH3018 | ACTIN BINDING | SSAAPPPPRRATPEK | 163 | + | +++ | +++ | – | +++ | +++ | – | +++ | – | – | – | +++ | – | – | – |

SH3 DOMAIN CLONES

|  |  | SEQ ID NO |  |  |  |  |  |  |  |  |  |  |  |  |  |  |  |  |  |
|---|---|---|---|---|---|---|---|---|---|---|---|---|---|---|---|---|---|---|---|---|
| bSH3019 | EZRIN | SKKGVMTAPPPPPPVYEPGG | 164 | - | - | - | - | - | - | - | - | - | - | - | - | - | - | - | - |
| bSH3020 | VINCULIN | EAFQQEPDFPPPPPDLE | 165 | - | - | - | - | - | - | - | - | - | - | - | - | - | - | - | - |
| bSH3021 | VINCULIN | DELAPPKPPLPEGVPPPRPPPPE | 166 | - | - | - | - | - | - | - | - | - | - | - | - | - | - | - | - |
| bSH3022 | DYNAMIN | PQRRAPAVPPARPGSR | 167 | - | - | - | - | - | - | - | - | - | - | - | - | - | - | - | 5 |
| bSH3023 | DYNAMIN | LGGAPPVPSRPGASPDG | 168 | - | +++ | - | - | - | - | - | - | - | - | - | - | - | - | - | - |

| NUMBER | DOMAINS ENCODED BY CLONE | 1 | 4 | 3 | 1 | 1 | 1 | 1 | 1 | 2 | 3 | 1 | 1 | 1 | 1 | 1 |
|---|---|---|---|---|---|---|---|---|---|---|---|---|---|---|---|---|

SH3 DOMAIN CLONES

| PEPTIDE | NAME | SEQUENCE | SEQ ID NO. | 5 | 11 | 12 | 13 | 14 | 18 | 34 | 40 | 41 | 45 | 46 | 53 | 55 | 56 | 65 |
|---|---|---|---|---|---|---|---|---|---|---|---|---|---|---|---|---|---|---|
| bSH3024 | FosAqLiq | PPPPLPPLPLPPLKKRGNH | 169 | - | - | - | - | - | - | - | - | - | - | - | - | - | - | - |
| bSH3025 | Rb | AAEPPAPPPPPPEDPGG | 170 | - | - | - | - | - | - | - | - | - | - | - | - | - | - | - |
| bSH3026 | Rb | DEEVNIPPHTPVRTV | 171 | - | - | - | - | - | - | - | - | - | - | - | - | - | - | - |
| bSH3027 | Rb | SAEGSNPPKPLKKLRFD | 172 | - | - | - | - | - | - | - | - | - | - | - | - | - | - | - |
| WW001 | DYSTROPHIN | AWMMGSPPEEGWF | 173 | - | - | - | - | - | - | - | - | - | - | - | - | - | - | - |
| WW002 | DYSTROPHIN | AEWLEGPPWYDRKEGF | 174 | - | - | - | - | - | - | - | - | - | - | - | - | - | - | - |
| WW003 | DYSTROPHIN | GLEGWYWERGWV | 175 | - | - | - | - | - | - | - | - | - | - | - | - | - | - | - |
| WW004 | DYSTROPHIN | WGLDGWLVDGWS | 176 | - | - | - | - | - | - | - | - | - | - | - | - | - | - | ++ |
| T12SRC1 | Src | GILAPPVPPRNIR | 177 | ++ | + | ++ | ++++ | ++++ | ++ | + | ++ | - | - | ++ | - | - | - | + |
| T12SRC4 | Src | VLKRPLPIPPVTR | 178 | - | + | - | ++++ | ++++ | - | - | - | - | - | - | - | - | - | +++ |
| T12SRC4M | Src | VLKRPLPPLPVTR | 179 | - | - | - | +++ | ++++ | + | - | - | - | - | - | - | - | - | - |
| NCKS1/4 | Nck | SRSLSEVSPKPPIRSVSLSR | 180 | ++++ | + | + | ++ | ++ | ++ | - | - | - | - | - | - | - | - | - |
| ABL G1/2M | c-Abl | SRPPRWSPPPVPLPISLDSR | 181 | ++++ | + | + | + | - | - | +++ | - | - | - | - | - | - | - | - |
| CORT.M4 | CORTACTIN | SRLGEFSKPPIPQKPTWMSR | 182 | - | - | - | + | + | - | - | ++++ | - | - | - | - | - | - | + |
| P53BP2.C0 | P53 Bd PROT. | SFAAPARPPVPPRKSRPGG | 183 | - | - | - | - | - | - | - | ++++ | - | - | - | - | - | - | - |
| P53BP2.P5 | P53 Bd PROT. | SYDASSAPQRPPLPVRKSRPGG | 184 | - | - | - | - | - | - | - | ++++ | - | - | - | - | - | - | - |
| PLCG.CON | PLC-γ | SPPPVPPRPPATLGG | 185 | - | - | - | +++ | - | ++ | - | - | ++ | - | ++ | - | - | - | + |
| CRK.CON | Crk | SVPAPPPLPPKSGG | 186 | - | - | - | - | - | - | - | - | - | - | - | - | - | - | - |
| NCK1.CON3 | Nck | SFSFPPLPPAPGG | 187 | - | +++ | - | ++ | + | - | - | - | - | ++ | +++ | ++ | ++ | - | +++ |
| NCK2.CON | Nck | SVPLPPLRTVSLGG | 188 | - | - | - | + | - | + | +++ | + | + | + | +++ | - | ++ | + | - |
| NUMBER OF DOMAINS ENCODED BY CLONE | | | | 1 | 4 | 3 | 3 | 1 | 1 | 1 | 1 | 2 | 3 | 1 | 1 | 1 | 1 | 5 |

```
  1 GTGAATGCTG CAGACAGTGA CGGATGGACA CCACTGCATT
 41 GTGCTGCCTC TTGCAACAGT GTCCACCTCT GCAAGCAGCT
 81 GGTGGAAAGT GGAGCCGCTA TCTTTGCCTC CACCATCAGT
121 GACATTGAGA CTGCTGCAGA CAAGTGTGAA GAGATGGAAG
161 AGGGATACAT CCAGTGTTCC CAGTTTCTGT ATGGGGTACA
201 AGAGAAGCTG GGAGTGATGA ACAAAGGCAC CGTGTATGCT
241 TTGTGGGACT ACGAGGCCCA GAACAGCGAT GAGCTGTCCT
281 TCCATGAAGG GGATGCCATC ACCATCCTGA GGCGCAAAGA
321 TGAAAACGAG ACCGAGTGGT GGTGGGCTCG TCTTGGGGAC
361 CGGGAGGGCT ACGTGCCCAA AAACTTGCTG GGGTTGTATC
401 CACGGATCAA ACCCCGGCAG CGAACACTTG CCTGAACCCC
441 CTGGAGTACC ACAGTCTCGT TTGCTCCCAG GAGCTACTGG
481 AGGAGATCCC ACTGCCCTGG GAAAACTGAA GCTAGGATGG
521 TCTCCTGGTG CTCACTTTAG CAGACAGTGT CCACAATGTG
561 AATCCCACTT CCCAGGTGAG GCCCTCTCCA GGCTGCAGGA
601 GCTGG (SEQ. ID NO:5)
```

FIG. 18

```
  1 VNAADSDGWT PLHCAASCNS VHLCKQLVES GAAIFASTIS
 41 DIETAADKCE EMEEGYIQCS QFLYGVQEKL GVMNKGTVYA
 81 LWDYEAQNSD ELSFHEGDAI TILRRKDENE TEWWWARLGD
121 REGYVPKNLL GLYPRIKPRQ RTLA (SEQ ID NO:6)
```

FIG. 19

```
  1 SGCARSGAAA ASAGLAPSCR VRVGLPRLSL VAPCSAMSKP
 41 PPKPVKPGQV KVFRALYTFE PRTPDELYFE EGDIIYITDM
 81 SDTSWWKGTC KGRTGLIPSN YVAEQAESID NPLHEAAKRG
121 NLSWLRECLD NRVGVNGLDK AGSTALYWAC HGGHKDIVEV
161 LFTQPNVELN QQNKLGDTAL HAAAWKGYAD IVQLLLAKGA
201 RTDLRNNEKK LALDMATNAA CASLLKKQQ GTDGARTLSN
241 AEDYLDDEDS D   (SEQ ID NO:8)
```

FIG 21

```
   1    GAATTCAA  GCTCGGGTTG  CGCGCGGTCC  GGAGCGGCCG
  41    CGGCCAGCGC  AGGCTTGGCG  CCCAGTTGTC  GTGTGCGTGT
  81    GGGGCTCCCG  CGGCTGAGCC  TGGTCGCTCC  GTGTAGCGCC
 121    ATGTCCAAGC  CACCTCCCAA  ACCGGTCAAA  CCAGGGCAAG
 161    TTAAAGTCTT  CAGAGCTCTA  TATACATTTG  AACCCAGAAC
 201    TCCAGATGAA  TTATACTTTG  AAGAAGGAGA  CATTATCTAC
 241    ATCACTGACA  TGAGTGATAC  CAGCTGGTGG  AAAGGGACAT
 281    GCAAGGGCAG  AACAGGACTG  ATCCCGAGCA  ACTATGTGGC
 321    TGAGCAGGCA  GAATCCATTG  ACAATCCATT  GCATGAAGCT
 361    GCAAAAAGAG  GCAACCTGAG  CTGGTTGAGG  GAGTGCTTGG
 401    ACAACCGGGT  GGGTGTGAAC  GGCCTGGACA  AAGCTGGAAG
 441    CACAGCCCTG  TACTGGGCCT  GCCACGGTGG  CCATAAAGAC
 481    ATAGTGGAGG  TTCTGTTTAC  TCAGCCGAAT  GTGGAGCTGA
 521    ACCAGCAGAA  TAAGCTGGGA  GACACAGCTC  TGCACGCGGN
 561    TGCCTGGAAG  GGTTATGCAG  ACATTGTCCA  GTTGCTACTG
 601    GCAAAAGGTG  CGAGGACAGA  CTTGAGAAAC  AATGAGAAGA
 641    AGCTGGCCTT  GGACATGGCC  ACCAACGCTG  CCTGTGCATC
 681    GCTCCTGAAG  AAGAAGCAGC  AGGGAACAGA  TGGGGCTCGA
 721    ACGTTAAGCA  ACGCCGAGGA  CTACCTCGAT  GACGAAGACT
 761    CAGACTGATT  CCCCCCGGGG  CCGCTTTGAT  TGTTGCCTAA
 801    ACTTCTTTTG  CTTTTGCCAT  TCCGGAGCCT  GGGTTGTTTG
 841    CCAGAAGAGT  ATTGATAACT  GTTGCTTTTA  AAGTCTGTAT
 881    GAGCGCGACA  CTGCTGCACT  GTGATCTGTG  AGGAGTCGTT
 921    GTGAGGGTGG  CTCATTCTCA  CCCACGCCTT  GNCAATAAGT
 961    GAAGAGATAC  TTTGTTGTAT  AAAATACATA  TATGCTCACC
1001    AGGGTAAAAT  AAACGAAAAA  AANTTATTTC  TATTTATCAA
1041    GCTAAAAAAA  AAAAGCTTGG  GCCCTNTTCT  ATAGTGTCAC
1081    CTAAATACTA  GCTTGANCCG  GNTGCTAACA  AAGCCCGAAA
1121    GGAAGCTGAG  TTGCTGCTGC  CACCGNTGAG  CAATAACTAG
1161    CATANCCCCT  TGGGGCCTCT  AAACGGGTCT  TGAGGGGTTT
1201    TTNGNTGAAA  GGAGGANCTA  TTTCCGGATA  ACCTGGNGTA
1241    ATAGGGAAGA  GGCCCGNACC  GATCGCCCTT  CCCAACAGA
```

(SEQ ID NO:7)

FIG. 20

1    ACTCACGNC GGTGGAGTGG TACCGGATCG AATTCAAGCC GCATCACTGG
51   CACTGGACGC CAGGGCATCT TCCCTGCCAG CTACGTGCAG ATAAACCGAG
101  AGCCCCGGCT CAGGCTTTGT GATGATGGTC CCCAGCTCCC TGCATCACCT
151  AACCCGACAA CCACTGCTCA CCTAAGCAGC CACTCCCACC CCTCCTCAAT
201  ACCTGTGGAC CCCACTGACT GGGGAGGTCG AACCTCCCCT CGACGCTCCG
251  CCTTTCCCTT CCCCATCACC CTCCAGGAGC CCAGATCCCA AACCCAGAGT
301  CTCAATACCC CTGGACCAAC CCTGTCCCAT CCTCGAGCCA CCAGCCGTCC
351  CATAAACCTG GGACCCTCCT CCCCAAACAC AGAGATACAC TGGACTCCGT
401  ACCGGGCCAT GTACCAGTAC AGGCCCCAGA ATGAGGACGA GCTGGAACTT
451  CGAGAGGGGG ACCGTGTGGA TGTCATGCAG CAATGTGACG ATGGCTGGTT
501  TGTGGGTGTC TCCCGGCGAA CTCAGAAATT TGGACATTC CCTGGAAATT
551  ATGTAGCCCC AGTGTGAGTG GTCTCCATGG CAGTTTGGAG CCAACGAGGA
601  TCGGGAGGGG AGCAGTAGCA CTATGGGAGG GAGAGAGGCC TTCCATAGCC
651  TCCTCCCCAG GACCTGTGCT CCCAGCTTCT GCAGAGACCC CAGCAACTTT
701  CCCTCCAAGC CTCCTTGAAG TCCGATTCCC ACCCCGCAAG TCACAGGCAT
751  TCCTTTGACA GCCCCCTTCA CCGCCCCTCA AATACAGACA TCTGCTTTCA
801  TGTGGGNAAA AAAAAAAAAT TAAAAGGTGG CCCTAT (SEQ ID NO:9)

FIG.22

1    RITGTGRQGI FPASYVQINR EPRLRLCDDG PQLPASPNPT
41   TTAHLSSHSH PSSIPVDPTD WGGRTSPRRS AFPFPITLQE
81   PRSQTQSLNT PGPTLSHPRA TSRPINLGPS SPNTEIHWTP
121  YRAMYQYRPQ NEDELELREG DRVDVMQQCD DGWFVGVSRR
161  TQKFGTFPGN YVAPV    (SEQ ID NO:10)

FIG.23

1    MSVAGLKKQF HKATQKVSEK VGGAEGTKLD DDFKEMERKV
41   DVTSRAVMEI MTKTIEYLQP NPASRAKLSM INTMSKIRGQ
81   EKGPGYPQAE ALLAEAMLKF GRELGDDCNF GPALGEVGEA
121  MRELSEVKDS LDMEVKQNFI DPLQNLHDKD LREIQHHLKK
161  LEGRRLDFGY KKKRQGKIPD EELRQALEKF DESKEIAESS
201  MFNLLEMDIE QVSQLSALVQ AQLEYHKQAV QILQQVTVRL
241  EERIRQASSQ PRREYQPKPR MSLEFATGDS TQPNGGLSHT
281  GTPKPPGVQM DQPCCRALYD LEPENEGELA FKEGDIITLT
321  NQIDENWYEG MLHGQSGFFP INYVEILVAL PH
                                    (SEQ ID NO:12)

FIG.25

```
   1 TTNNNNYYMM SKYSKKGKKK KGKWMSGRTC GATTCAAGCC GACCAGCGGC
  51 GGCCCGGCGA CCCCAGCCGC CTCTCCGCAT CTGCATCTGC ATCTGCCGGC
 101 CGCGCAGCCT CCCGCATCCC ATCATGTCGG TGGCAGGGCT GAAGAAGCAG
 151 TTCCACAAAG CCACTCAGAA AGTGAGTGAG AAGGTGGGAG GAGCGGAAGG
 201 CACCAAGCTC GATGATGACT TCAAAGAGAT GGAGAGGAAA GTGGATGTCA
 251 CCAGCAGGGC TGTGATGGAG ATAATGACAA AAACGATTGA ATACCTCCAA
 301 CCCAATCCAG CTTCCAGGGC TAAGCTCAGT ATGATCAACA CCATGTCGAA
 351 AATCCGCGGC CAAGAGAAGG GGCCAGGCTA CCCTCAGGCG GAAGCACTGC
 401 TGGCAGAGGC CATGCTCAAG TTCGGCAGGG AGCTGGGTGA TGATTGCAAC
 451 TTTGGTCCTG CTCTCGGTGA GGTGGGAGAA GCCATGAGGG AGCTCTCGGA
 501 GGTCAAGGAC TCATTGGACA TGGAAGTGAA GCAGAATTTC ATCGACCCCC
 551 TTCAGAATCT TCATGACAAG GATCTGAGGG AGATTCAGCA TCATCTGAAA
 601 AAGCTGGAAG GCCGACGCTT AGACTTTGGT TATAAGAAGA AGCGACAAGG
 651 CAAGATTCCA GATGAAGAAC TCCGCCAAGC TCTGGAGAAA TTCGATGAGT
 701 CTAAAGAAAT CGCCGAGTCG AGCATGTTCA ACCTCTTGGA GATGGATATA
 751 GAACAGGTGA GCCAGCTCTC CGCACTTGTT CAGGCTCAGC TGGAGTACCA
 801 CAAGCAGGCA GTGCAGATCC TGCAGCAGGT CACTGTCAGA CTGGAAGAAA
 851 GAATAAGACA AGCTTCATCT CAGCCAAGAA GGGAATATCA GCCCAAACCA
 901 CGGATGAGCC TAGAGTTTGC CACTGGAGAC AGTACTCAGC CCAACGGGGG
 951 TCTCTCCCAC ACAGGCACAC CCAAACCTCC AGGTGTCCAA ATGGATCAGC
1001 CCTGCTGCCG AGCTCTGTAT GACTTGGAAC CTGAAAATGA AGGGGAATTG
1051 GCTTTTAAAG AGGGCGATAT CATCACACTC ACTAATCAGA TTGACGAGAA
1101 CTGGTATGAG GGGATGCTTC ATGGCCAGTC TGGCTTTTTC CCCATCAACT
1151 ATGTAGAAAT TCTGGTTGCT CTGCCCCATT AGGATCCTGT GCTGGCTGGC
1201 TCACCTCCTT CTGACCCAGA TAGTTAAGTT TAACCACTGC TTTGGTAATG
1251 CTGCTTCCAA TACATCACGA ATGCAGGCCG CAGTGGATGA GTCACCAAGC
1301 CCACACGTGC CCTGGGTTGA CCCGTGTGCT CCTCCAGGAG ACGCGGTGAT
1351 AGATGGTATC TTCCAAGGCC AGTGGGCCTG GTACATGCTT TAAAACACCA
1401 TCTGAGACTA GCCAGGAGTC CCAGAACTGG CTTCACAGTT CTCAGGAGGC
1451 TGTGGTTCCT GGTAACATGC CTGTGAACCA CATGGCAGAA AAACTCTCCT
1501 CACTGAAGAT ATTGTCTCTC ACCCAGGGGC CATCTCAAGG TCTCCAGTTC
1551 TCCATTTACA GAGGAGAAAG TCCTTTTTGT TGCACTTTCC CTTCCTAAAT
1601 ATGTGAGTCA CAGAATTGTT GGCAAAAACA TCCCCTCACC AGCAAGATGT
1651 CTGCTGGTTT AAGCAACTTG GTCTCTTGAT GCCATTAGCA AAAGTATTAA
1701 TTGTCCAAAG CACCTTTGTT CACTAATATC TATCTATCTA TCTATCTATC
1751 TATCTATCTA TCTATCTATC TATCTATCAT CTATCTACCT ACCTATCTAC
1801 CTATCATCTA TCTATCTATC ATCTATTATC TATCTATCTA TCTATCTATC
1851 NNTCNATCTA TCTATCTATC CATCTATCTA TCCATCATCT ATCTACCTAC
1901 CTATCTACTA TCCATCTATC TATCTATCCA TCATCTATCT ACCTACCTAT
1951 CTACTATCCA TCCATTTATC TATCTATCTA TCTATCTATC TATCTATCTA
2001 TCTCCCTCAT ACTTCTGAGA CATGGCCAGT TTTCTTCCCT CCCTGCTGTT
2051 AAGCACTTGG NAGATGAGGG GGGGGGTCCC ATTTNATTTC TGAGTGAGAT
2101 GGTGAGCAGG GTGTATGTTG GCTGTNNTNN GGGGGTGGCC CTA
```
(SEQ ID NO:11)

FIG. 24

```
   1 CGGGCGCGGC GGGAGCCTGG TGGACCCTGC TTTGGCGGTA
  41 ATCATTGATC ATCGCAGATG CCCTCATATC CACTTTGGAT
  81 TCCTTGGATT CGGACAGACT CTGAACTGCT TTTCCCAGCA
 121 AAAGAGAAAG ATGTGGAAAG CCTCTGCAGG CCATGCTGTG
 161 TCCATCACGC AGGATGATGG AGGAGCTGAT GACTGGGAGA
 201 CTGATCCTGA TTTTGTGAAT GATGTGAGTG AAAAGGAGCA
 241 GAGATGGGGT GCTAAAACCG TGCAGGGATC GGGGCACCAG
 281 GAACACATCA ACATTCACAA GCTTCGAGAG AATGTCTTCC
 321 AAGAACACCA GACGCTCAAG GAGAAGGAGC TGGAAACGGG
 361 ACCCAAGGCT TCCCACGGCT ATGGCGGGAA GTTCGGTGTG
 401 GAGCAGGATA GGATGGACAG ATCAGCCGTG GGCCATGAGT
 441 ACCAGTCGAA GCTTTCCAAG CACTGCTCAC AAGTGGACTC
 481 GGTCCGGGGC TTCGGAGGCA AGTTCGGTGT CCAGATGGAC
 521 AGGGTGGATC AGTCTGCTGT AGGCTTTGAA TACCAGGGGA
 561 AGACTGAGAA GCATGCCTCC CAGAAAGACT ACTCTAGTGG
 601 CTTCGGTGGC AAATACGGTG TGCAAGCTGA CCGTGTAGAC
 641 AAGAGTGCCG TGGGCTTTGA CTACCAGGGC AAGACGGAGA
 681 AGCATGAGTC TCAGAAAGAT TACTCCAAAG GTTTTGGTGG
 721 CAAATATGGG ATTGACAAGG ACAAGGTGGA TAAAAGTGCT
 761 GTGGGCTTTG AGTATCAAGG CAAGACAGAG AAGCACGAAT
 801 CCCAGAAAGA CTATGTAAAA GGCTTTGGAG AAAGTTTGG
 841 TGTGCAGACA GACAGACAGG ACAAGTGTGC CCTTGGCTGG
 881 GACCATCAGG AGAAGCTGCA GCTGCATGAA TCCCAAAAAG
 921 ACTATAAGAC TGGTTTCGGA GGCAAATTTG GTGTTCAGTC
 961 CGAGAGGCAG GACTCCTCCG CTGTGGGGTT TGATTACAAG
1001 GAGAGATTGG CCAAGCACGA GCCCCAGCAA GACTATGCCA
1041 AAGGATTCGG CGGGAAGTAT GGGGTGCAGA AGGATCGGAT
1081 GGACAAGAAT GCATCCACCT TTGAAGAAGT GGTCCAGGTG
1121 CCATCTGCCT ATCAGAAGAC TGTCCCCATT GAGGCCGTAA
1161 CCAGCAAAAC CAGTAATATC CGTGCTAACT TTGAAAACCT
1201 GGCAAAGGAG AGAGAGCAGG AGGACAGGCG GAAGGCAGAA
1241 GCCGAGAGAG CTCAGCGGAT GGCCAAAGAA AGACAGGAGC
1281 AGCAGGAGGC GCGCAGGAAG CTGGAAGAGC AAGCCAGAGC
1321 CAAGAAGCAG ACGCCCCCTG CATCCCCTAG TCCTCAACCA
1361 ATTGAAGACA GACCACCCTC CAGCCCCATC TATGAGGATG
1401 CAGCTCCGTT CAAGGCCGAG CCGAGCTACC GAGGTAGCGA
1441 ACCTGAGCCT GAGTACAGCA TCGAGGCCGC AGGCATTCCT
1481 GAGGCTGGCA GCCAGCAAGG CCTGACCTAT ACATCAGAGC
1521 CCGTGTACGA GACTACAGAG GCTCCTGGCC ACTATCAAGC
1561 AGAGGATGAC ACCTACGATG GGTATGAGAG TGACCTGGGC
1601 ATCACAGCCA TCGCCCTGTA TGACTACCAG GCTGCTGGCG
```

FIG. 26A

```
1641 ATGATGAGAT CTCCTTTGAC CCTGATGACA TCATCACCAA
1681 CATAGAAATG ATTGACGATG GCTGGTGGCG TGGGGTGTGC
1721 AAGGGCAGAT ACGGGCTCTT CCCAGCCAAC TATGTGGAGC
1761 TGCGGCAGTA GGGCTGCCAC CCAGAGCCTA CCGGCACCAG
1801 CACAGGGTTC ACACTACAGA GCATCTGCGT GTGTTTGAGT
1841 TGGTTTCTGC TTCCGTTTCT GTTTTTG
```

(SEQ ID NO:13)

FIG. 26B

```
  1  MWKASAGHAV SITQDDGGAD DWETDPDFVN DVSEKEQRWG
 41  AKTVQGSGHQ EHINIHKLRE NVFQEHQTLK EKELETGPKA
 81  SHGYGGKFGV EQDRMDRSAV GHEYQSKLSK HCSQVDSVRG
121  FGGKFGVQMD RVDQSAVGFE YQGKTEKHAS QKDYSSGFGG
161  KYGVQADRVD KSAVGFDYQG KTEKHESQKD YSKGFGGKYG
201  IDKDKVDKSA VGFEYQGKTE KHESQKDYVK GFGGKFGVQT
241  DRQDKCALGW DHQEKLQLHE SQKDYKTGFG GKFGVQSERQ
281  DSSAVGFDYK ERLAKHEPQQ DYAKGFGGKY GVQKDRMDKN
321  ASTFEEVVQV PSAYQKTVPI EAVTSKTSNI RANFENLAKE
361  REQEDRRKAE AERAQRMAKE RQEQEEARRK LEEQARAKKQ
401  TPPASPSPQP IEDRPPSSPI YEDAAPFKAE PSYRGSEPEP
441  EYSIEAAGIP EAGSQQGLTY TSEPVYETTE APGHYQAEDD
481  TYDGYESDLG ITAIALYDYQ AAGDDEISFD PDDIITNIEM
521  IDDGWWRGVC KGRYGLFPAN YVELRQ (SEQ ID NO:14)
```

FIG. 27

```
   1  AAGCAGTCCT TCACCATGGT GGCCGACACT CCGGAAAACC TCCGCCTCAA
  51  GCAACAGAGC GAGCTGCAGA GTCAGGTGCG CTACAAGGAG GAGTTTGAGA
 101  GAATAAGGG CAAAGGTTTC AGCGTGGTGG CAGACACGCC TGAGCTGCAG
 151  AGAATCAAGA AGACCCAGGA CCAGATCAGC AATATCAAAT ACCATGAGGA
 201  GTTTGAGAAG AGCCGCATGG GGCCCAGTGG AGGAGAAGGG GTGGAACCAG
 251  AGCGCCGAGA AGCCCAGGAC AGCAGCAGCT ACCGGAGGCC ACAGAGCAG
 301  CAGCAGCCGC AGCCTCACCA TATCCCGACC AGTGCCCCCG TGTACCAGCA
 351  GCCCCAGCAG CAGCAGATGA CCTCGTCCTA TGGTGGGTAC AAGGAGCCAG
 401  CAGCCCCTGT CTCCATACAG CGCAGTGCCC AGGTGGCGG TGGGAAACGG
 451  TACCGTGCAG TGTATGACTA CAGCGCTGCC GACGAGGACG AGGTCTCCTT
 501  CCAGGATGGG GACACCATCG TCAATGTGCA GCAGATCGAT GACGGCTGGA
 551  TGTACGGGAC CGTAGAGCGC ACCGGTGACA CGGGGATGCT GCCAGCCAAC
 601  TACGTGGAGG CCATCTGAAC CCTGTGCCGC CCGCCCTGT CTTCAATGCA
 651  TTCCATGGCA TCACATCTGT CCTGGGGCCT GACCCGTCCA CCCTTCAGTG
 701  TCTCTGTCTT TTAAGATCTT CAACTGCTTC TTTATCCCCG CCCCTCCAGC
 751  TTATTTTACC ATCCCAAGCC TTGTTCTGCC CCTGTCATGG CTCCTTCCT
 801  CTGGCAGGTT TTCCCTTGGA CCAATCAACT GATTGATTTT TCTCTCTGGA
 851  TGGAACAGGC TGGGCACTCT GGGGAGGGCA GGATTGTTCT TAGCTAGGTA
 901  GACTCCCAGG GCTGGGCTGA ACTAGGAGAC CCACTAAGGA GATCAGTTTA
 951  GACTGGGTGC AGTGGCAAAC ACCTTAATT CCCAGCGAAG GGAGTCAGAG
1001  GCAGGCAGAT CTGTGACTTG GAAGCCAGCC TGGTCTACAT CGAGAGTTTC
1051  AGGACAGCCA GAGCTATGTA GTGAGGCCCT GTCTCGGAGG AAGAGTGGGG
1101  GTTGGTTAGC TCTCAGCTTC ACTTCCTGCC TTAGGCTCCT CAGAACCCCT
1151  GGCCCAGCTC CCCCAACTCC CTTCCTCCTA GAGGTGGGGT GAGCTGTGC
                                            (SEQ ID NO:15)
```

FIG. 28

```
  1  KQSFTMVADT PENLRLKQQS ELQSQVRYKE EFEKNKGKGF SVVADTPELQ
 51  RIKKTQDQIS NIKYHEEFEK SRMGPSGGEG VEPERREAQD SSSYRRPTEQ
101  QQPQPHHIPT SAPVYQQPQQ QQMTSSYGGY KEPAAPVSIQ RSAPGGGGKR
151  YRAVYDYSAA DEDEVSFQDG DTIVNVQQID DGWMYGTVER TGDTGMLPAN
201  YVEAI (SEQ ID NO:16)
```

FIG. 29

```
   1  ATGGCGGTGA ACCTGAGCCG GAACGGGCCG GCGCTGCAGG AGGCCTACGT
  51  GCGCGTAGTC ACCGAGAAAT CCCCGACCGA CTGGGCTCTT TTTACCTATG
 101  AAGGCAACAG CAATGACATC CGTGTGGCTG GCACAGGAGA GGGAGGCCTG
 151  GAGGAGCTGG TGGAAGAGCT CAACAGCGGG AAGGTGATGT ACGCCTTCTG
 201  CAGGGTGAAG GACCCCAACT CCGGCCTGCC CAAGTTTGTC CTCATCAACT
 251  GGACAGGAGA GGGTGTGAAT GATGTGCGGA AAGGAGCATG TGCCAACCAC
 301  GTCAGCACCA TGGCCAACTT CCTGAAGGGT GCCCACGTGA CCATCAATGC
 351  CCGGGCCGAG GAGGATGTGG AGCCTGAGTG CATCATGGAG AAGGTTGCCA
 401  AGGCCTCTGG GGCCAACTAC AGCTTCCATA GGAAAGCAC CTCCTTCCAG
 451  GATGTAGGGC CGCAGGCCCC AGTGGGCTCT GTGTACCAGA AGACCAATGC
 501  CATATCTGAG ATCAAGAGAG TCGGCAAGGA TAACTTCTGG GCCAAAGCTG
 551  AGAAGGAAGA AGAGAACCGC CGCCTGGAGG AGAAGCGGCG TGCCGAAGAG
 601  GAGCGGCAGC GGTTGGAGGA GGAGCGACGA GAGCGGGAGC TGCAGGAGGC
 651  TGCCCGACGT GAGCAGCGCT ACCAGGAACA GCACAGATCA GCTGGAGCCC
 701  CGAGCAGGAC AGGTGAGCCA GAGCAGGAAG CCGTTTCAAG GACCAGACAG
 751  GAGTGGGAGT CTGCTGGGCA GCAGGCCCCA CACCACGAG AGATTTTCAA
 801  GCAGAAGGAA AGGGCAATGT CCACCACCTC TGTCACCAGC TCGCAGCCGG
 851  GCAAGCTGAG GAGCCCCTTC CTGCAGAAGC AACTCACTCA ACCAGAAACC
 901  TCCTACGGCC GAGAGCCCAC AGCTCCTGTC TCCCGGCCTG CAGCAGGTGT
 951  CTGTGAGGAG CCAGCGCCTA GCACTCTGTC TTCTGCCCAG ACAGAAGAAG
1001  AACCTACATA TGAAGTACCC CCAGAGCAGG ACACCCTCTA TGAGGAACCA
1051  CCACTGGTAC AGCAGCAAGG GGCTGGCTCC GAACACATTG ACAACTACAT
1101  GCAGAGCCAG GGCTTCAGTG ACAAGGGCT GTGCGCCCGG GCCTTGTATG
1151  ACTACCAGGC AGCTGATGAC ACCGAGATCT CCTTTGACCC TGAGAACCTA
1201  ATCACAGGCA TCGAGGTGAT TGACGAAGGC TGGTGGCGAG GCTATGGGCC
1251  TGACGGCCAC TTTGGCATGT TCCCTGCCAA CTACGTGGAG CTCATAGAGT
1301  GA (SEQ ID NO:17)
```

FIG. 30

```
  1  MAVNLSRNGP ALQEAYVRVV TEKSPTDWAL FTYEGNSNDI RVAGTGEGGL
 51  EELVEELNSG KVMYAFCRVK DPNSGLPKFV LINWTGEGVN DVRKGACANH
101  VSTMANFLKG AHVTINARAE EDVEPECIME KVAKASGANY SFHKESTSFQ
151  DVGPQAPVGS VYQKTNAISE IKRVGKDNFW AKAEKEEENR RLEEKRRAEE
201  ERQRLEEERR ERELQEAARR EQRYQEQHRS AGAPSRTGEP EQEAVSRTRQ
251  EWESAGQQAP HPREIFKQKE RAMSTTSVTS SQPGKLRSPF LQKQLTQPET
301  SYGREPTAPV SRPAAGVCEE PAPSTLSSAQ TEEEPTYEVP PEQDTLYEEP
351  PLVQQQGAGS EHIDNYMQSQ GFSGQGLCAR ALYDYQAADD TEISFDPENL
401  ITGIEVIDEG WWRGYGPDGH FGMFPANYVE LIE   (SEQ ID NO:18)
```

FIG. 31

```
  1  MSVAGLKKQF YKASQLVSEK VGGAEGTKLD DDFKDMEKKV DVTSKAVAEV
 51  LVRTIEYLQP NPASRAKLTM LNTVSKIRGQ VKNPGYPQSE GLLGECMVRH
101  GKELGGESNF GDALLDAGES MKRLAEVKDS LDIEVKQNFI DPLQNLCDKD
151  LKIEQHHLKK LEGRRLDFDY KKKRQGKIPD EELRQALEKF EESKEVAETS
201  MHNLLETDIE QVSQLSALVD AQLDYHRQAV QILEELADKL KRRVREASSR
251  PKREFKPRPR EPFELGELEQ PNGGFPCAPA PKITASSSFR SSDKPIRMPS
301  KSMPPLDQPS CKALYDFEPE NDGELGFREG DLITLTNQID ENWYEGMLHG
351  QSGFFPLSYV QVLVPLPQ   (SEQ ID NO:20)
```

FIG. 33

```
  1  MAEMGSKGVT AGKIASNVQK KLTRAQEKVL QKLGKADETK DEQFEQCVQN
 51  FNKQLTEGTR LQKDLRTYLA SVKAMHEASK KLSECLQEVY EPEWPGRDEA
101  NKIAENNDLL WMDYHQKLVD QALLTMDTYL GQFPDIKSRI AKRGRKLVDY
151  DSARHHYESL QTAKKKDEAK IAKAEEELIK AQKVFEEMNV DLQEELPSLW
201  NSRVGFYVNT FQSIAGLEEN FHKEMSKLNQ NLNDVLVSLE KQHGSNTFTV
251  KAQPSDNAPE KGNKSPSPPP DGSPAATPEI RVNHEPEPAS GASPGATIPK
301  SPSQPAEASE VVGGAQEPGE TAASEATSSS LPAVVVETFS ATVNGAVEGS
351  AGTGRLDLPP GFMFKVQAQH DYTATDTDEL QLKAGDVVLV IPFQNPEEQD
401  EGWLMGVKES DWNQHKELEK CRGVFPENFT ERVQ   (SEQ ID NO:22)
```

FIG. 35

```
   1 TTNNCACTCA CCGTCCGTGG TNNNNSTMMC SGWYNKRNTK YRRKMSSKRW
  51 YKWKKCRRKS GCGGCGCCGA CCTGCGCGCG GAGGAAAGAA GTCGGTTCGG
 101 CGGCGCCGGC GGAAACCGGA GTTCGAGCGG GAGGCCTGAC GGCGGCAGGC
 151 GGCATGTCGG TGGCGGGGCT GAAGAAGCAG TTCTACAAGG CGAGCCAGCT
 201 GGTCAGCGAG AAGGTTGGTG GGGCCGAAGG GACCAAACTG GATGATGACT
 251 TTAAAGATAT GGAAAAGAAG GTGGATGTCA CCAGCAAGGC CGTGGCAGAG
 301 GTGCTGGTCA GAACCATAGA ATATCTGCAG CCTAACCCAG CCTCGAGAGC
 351 CAAGCTGACT ATGCTGAACA CCGTATCCAA GATCCGGGGC CAAGTGAAGA
 401 ACCCTGGCTA CCCACAGTCA GAGGGTCTGT TGGGAGAGTG CATGGTTCGC
 451 CATGGCAAGG AACTAGGTGG AGAGTCCAAC TTCGGTGATG CCCTGCTAGA
 501 TGCAGGTGAG TCCATGAAGC GCCTGGCTGA GGTGAAGGAC TCACTGGACA
 551 TCGAGGTCAA GCAGAACTTC ATTGACCCAC TACAGAACCT GTGTGACAAG
 601 GATCTGAAGG AGATCCAGCA CCACCTGAAG AAATTGGAGG GCCGCCGCCT
 651 TGACTTTGAC TACAAGAAGA AGCGCCAGGG CAAGATCCCC GATGAGGAGC
 701 TGCGCCAGGC CCTAGAGAAG TTCGAGGAGT CCAAGGAGGT GGCGGAGACC
 751 AGTATGCACA ACCTCCTGGA GACTGATATA GAGCAGGTGA GCCAGCTCTC
 801 GGCCCTGGTG GATGCCCAGC TGGACTACCA CCGGCAGGCA GTGCAGATCC
 851 TGGAGGAGCT GGCTGACAAG CTGAAGCGCA GGGTTCGGGA AGCCTCCTCA
 901 CGCCCCAAGC GGGAGTTCAA GCCCCGGCCC CGGGAGCCCT TTGAGCTTGG
 951 AGAGCTGGAG CAGCCCAATG GGGATTCCC CTGTGCCCCA GCACCTAAGA
1001 TCACAGCCTC CTCATCATTT AGATCGTCAG ACAAGCCCAT CAGGATGCCC
1051 AGCAAGAGCA TGCCACCCCT GGACCAGCCA AGCTGCAAGG CGCTTTATGA
1101 TTTTGAGCCA GAGAATGATG GCGAGCTGGG CTTCCGTGAG GGGGACCTCA
1151 TCACGCTTAC CAACCAGATC GACGAGAACT GGTATGAGGG GATGCTGCAC
1201 GGCCAATCAG GCTTCTTCCC ACTCAGCTAC GTGCAGGTGC TGGTGCCTCT
1251 GCCTCAGTGA CTGGGCCTTT ACACCGCTGC CAGTCACAGT GCAGCAGCAG
1301 TCTAATGCCA AGGTGCTCTA GAAACACTAA TGTTCCTCCA GGGGGGACTC
1351 CTCCCCACTC CCTCAGCCCT GGGGCCCCCC TATCCTAAGA CTCGGAAAGG
1401 CCCACCCTGA GGTTCTATTG CCTTCCTGGT GGTATCAGCT TCCAGCTGTT
1451 TCAACCCTTC CCAGCCCGTT GCTGGCGATG GSCCNNYGCC CCCTCTCTAG
1501 GCTCTCTAGA GGCAGGCAGG TCCTTGGAAT CCCCAGCCTG CAAGCAGAGG
1551 CTGGCCAGCT CCCCAGCTCA GCACACAGAC ACACCTGGCA CCTGCTGCTC
1601 ATGAAGAAGT GCACAAGGCA CAAATGTGTA CACTTCCCAT GGGACCACAG
1651 ACCCAGCTCA GCTCTGTTGA AGACCAAGCA CAAAGGCCTT GAAGAGTGGA
1701 CATTCCCAGG TCCCTGGCAC CTTCCCTTGA GCCAGCTCCA TTGCTACTTA
1751 TTCATGTGAC TGAAGCTGAC CACAGGCAGC TGGCAGGTCC TTTTTTCAAC
1801 CAGCAGGCTA GGCTGGCCAT AGACCCAGCT CTGCCTCACC CTGCCATGTT
1851 CCAGTAATGG AGGCCTCCAG CCTGGGCTCT ATTACATTCT TCTCTACAGC
1901 TGCCCCATAA CCCGTGGCTT ATCCCTGGCA CGTGGGGCCA CACCCCACGC
1951 CCCCTGGATA GGCAACACTG TCCTGCTCCA GCCTGTGCTG ANATGAACTG
2001 TACTCCTAAT TTTTTTTTAA AAAAAAAGTA TTAAATNTCT CTTTCTATAT
2051 AAAANAAAGN TGGCCCTANN NGGA (SEQ ID NO:19)
```

FIG. 32

```
   1 CCTCACTCGC TCTCCCCGCG CACGCTCCGT CTCCGTCAGT CCCCTGAGCT
  51 GTTCTAGTGC GCGGCGTGGA GCCAGGGCTC AGGCTGGTGG AGCGGCCGGG
 101 GCTGGAGGCT GGGAGTGCGG CGCGCACGGC CTCCCCGCGC CATTATCCGC
 151 GCTCGCTTCG GCGAGGCCG GCGCCAGGAT GGCAGAGATG GGGAGCAAGG
 201 GGGTGACGGC GGGGAAGATC GCCAGCAACG TACAGAAGAA GCTGACCCGA
 251 GCGCAGGAGA AGGTCCTGCA GAAACTGGGG AAGGCGGACG AGACGAAGGA
 301 CGAGCAGTTT GAGCAGTGTG TCCAGAACTT CAATAAGCAG CTGACAGAGG
 351 GTACCCGGCT GCAGAAGGAT CTTCGGACCT ATCTGGCTTC TGTTAAAGCG
 401 ATGCACGAAG CCTCCAAGAA GCTGAGTGAG TGTCTTCAGG AGGTGTACGA
 451 GCCCGAGTGG CCTGGCAGGG ATGAAGCAAA CAAGATTGCA GAGAACAATG
 501 ACCTACTCTG GATGGACTAC CACCAGAAGC TGGTGGACCA GGCTCTGCTG
 551 ACCATGGACA CCTACCTAGG CCAGTTCCCT GATATCAAGT CGCGCATTGC
 601 CAAGCGGGGG CGGAAGCTGG TGGACTATGA CAGTGCCCGG CACCACTATG
 651 AGTCTCTTCA AACCGCCAAA AAGAAGGATG AAGCCAAAAT TGCCAAGGCA
 701 GAAGAGGAGC TCATCAAAGC CCAGAAGGTG TTCGAGGAGA TGAACGTGGA
 751 TCTGCAGGAG GAGCTGCCAT CCCTGTGGAA CAGCCGTGTA GGTTTCTATG
 801 TCAACACGTT CCAGAGCATC GCGGGTCTGG AGGAAAACTT CCATAAAGAG
 851 ATGAGTAAGC TCAATCAGAA CCTCAATGAT GTCCTGGTCA GCCTAGAGAA
 901 GCAGCACGGG AGCAACACCT TCACAGTCAA GGCCCAACCC AGTGACAATG
 951 CCCCTGAGAA AGGGAACAAG AGCCCGTCAC CTCCTCCAGA TGGCTCCCCT
1001 GCTGCTACCC CTGAGATCAG AGTGAACCAT GAGCCAGAGC CGGCCAGTGG
1051 GGCCTCACCC GGGGCTACCA TCCCCAAGTC CCCATCTCAG CCAGCAGAGG
1101 CCTCCGAGGT GGTGGGTGGA GCCCAGGAGC CAGGGGAGAC AGCAGCCAGT
1151 GAAGCAACCT CCAGCTCTCT TCCGGCTGTG GTGGTGGAGA CCTTCTCCGC
1201 AACTGTGAAT GGGGCGGTGG AGGGCAGCGC TGGGACTGGA CGCTTGGACC
1251 TGCCCCCGGG ATTCATGTTC AAGGTTCAAG CCCAGCATGA TTACACGGCC
1301 ACTGACACTG ATGAGCTGCA ACTCAAAGCT GGCGATGTGG TGTTGGTGAT
1351 TCCTTTCCAG AACCCAGAGG AGCAGGATGA AGGCTGGCTC ATGGGTGTGA
1401 AGGAGAGCGA CTGGAATCAG CACAAGGAAC TGGAGAAATG CCGCGGCGTC
1451 TTCCCGGAGA ATTTTACAGA GCGGCTACAG TGACGGAGGA GCCTTCCGGA
1501 GTGTGAAGAA CCTTTCCCCC AAAGATGTGT G   (SEQ ID NO:21)
```

FIG. 34

```
   1 GAATTCGTCG ACCCACGCGT CCGGTTTGAG CAGTGCGTCC
  41 AGAATTTCAA CAAGCAGCTG ACGGAGGGCA CCCGGCTGCA
  81 GAAGGATCTC CGGACCTACC TGGCCTCCGT CAAAGCCATG
 121 CACGAGGCTT CCAAGAAGCT GAATGAGTGT CTGCAGGAGG
 161 TGTATGAGCC CGATTGGCCC GGCAGGGATG AGGCAAACAA
 201 GATCGCAGAG AACAACGACC TGCTGTGGAT GGATTACCAC
 241 CAGAAGCTGG TGGACCAGGC GCTGCTGACC ATGGACACGT
 281 ACCTGGGCCA GTTCCCCGAC ATCAAGTCAC GCATTGCCAA
 321 GCGGGGGCGC AAGCTGGTGG ACTACGACAG TGCCCGGCAC
 361 CACTACGAGT CCCTTCAAAC TGCCAAAAAG AAGGATGAAG
 401 CCAAAATTGC CAAGGCCGAG GAGGAGCTCA TCAAAGCCCA
 441 GAAGGTGTTT GAGGAGATGA ATGTGGATCT GCAGGAGGAG
 481 CTGCCGTCCC TGTGGAACAG CCGCGTAGGT TTCTACGTCA
 521 ACACGTTCCA GAGCATCGCG GGCCTGGAGG AAAACTTCCA
 561 CAAGGAGATG AGCAAGCTCA ACCAGAACCT CAATGATGTG
 601 CTGGTCGGCC TGGAGAAGCA ACACGGGAGC AACACCTCCA
 641 CGGTCAAGGC CCAGCCCAGT GACAACGCGC CTGCAAAAGG
 681 GAACAAGAGC CCTTCGCCTC CAGATGGCTC CCCTGCCGCC
 721 ACCCCGAGA TCAGAGTCAA CCACGAGCCA GAGCCGGCCG
 761 GCGGGGCCAC GCCCGGGGCC ACCCTCCCCA AGTCCCCATC
 801 TCAGCCAGCA GAGGCCTCGG AGGTGGCGGG TGGGACCCAA
 841 CCTGCGGCTG GAGCCCAGGA GCCAGGGGAG ACGGCGGCAA
 881 GTGAAGCAGC CTCCAGCTCT CTTCCTGCTG TCGTGGTGGA
 921 GACCTTCCCA GCAACTGTGA ATGGCACCGT GGAGGGCGGC
 961 AGTGGGGCCG GCGCTTGGA CCTGCCCCCA GGTTTCATGT
1001 TCAAGGTACA GGCCCAGCAC GACTACACGG CCACTGACAC
1041 AGACGAGCTG CAGCTCAAGG CTGGTGATGT GGTGCTGGTG
1081 ATCCCCTTCC AGAACCCTGA AGAGCAGGAT GAAGGCTGGC
1121 TCATGGGCGT GAAGGAGAGC GACTGGAACC AGCACAAGGA
1161 GCTGGAGAAG TGCCGTGGCG TCTTCCCCGA GAACTTCACT
1201 GAGAGGGTCC CATGACGGCG GGGCCCAGGC AGCCTCCGGG
1241 CGTGTGAAGA ACACCTCCTC CCGAAAAATG TGTGGTTCTT
1281 TTTTTTGTTT TGTTTTCGTT TTTCATCTTT TGAAGAGCAA
1321 AGGGAAATCA AGAGGAGACC CCCAGGCAGA GGGGCGTTCT
1361 CCCAAAGATT AGGTCGTTTT CCAAAGAGCC GCGTCCCGGC
1401 AAGTCCGGCG GAATTCACCA GTGTCCTGAA GCTGCTGTGT
1441 CCTCTAGTTG AGTTCTGGCG CCCCTGCCTG TGCCCGCATG
1481 TGTGCCTGGC CGCAGGGCGG GGCTGGGGGC TGCCGAGCCA
1521 CCATGCTTGC CTGAAGCTTC GGCCGCGCCA CCCGGGCAAG
1561 GGTCCTCTTT TCCTGGCAGC TGCTGTGGGT GGGGCCCAGA
1601 CACCAGCCTA ACCTGGCTCT GCCCCGCAGA CGGTCTGTGT
1641 GCTGTTTGAA AATAAATCTT AGTGTTCAAA ACAAAATGAA
1681 ACAAAAAAAA TGATAAAAAA AAAAAAAAAA AAAAAAAAAA
1721 AAAAGGGCGG CCGC  (SEQ ID NO:23)
```

FIG. 36

```
  1 EFVDPRVRFE QCVQNFNKQL TEGTRLQKDL RTYLASVKAM
 41 HEASKKLNEC LQEVYEPDWP GRDEANKIAE NNDLLWMDYH
 81 QKLVDQALLT MDTYLGQFPD IKSRIAKRGR KLVDYDSARH
121 HYESLQTAKK KDEAKIAKAE EELIKAQKVF EEMNVDLQEE
161 LPSLWNSRVG FYVNTFQSIA GLEENFHKEM SKLNQNLNDV
201 LVGLEKQHGS NTSTVKAQPS DNAPAKGNKS PSPPDGSPAA
241 TPEIRVNHEP EPAGGATPGA TLPKSPSQPA EASEVAGGTQ
281 PAAGAQEPGE TAASEAASSS LPAVVVETFP ATVNGTVEGG
321 SGAGRLDLPP GFMFKVQAQH DYTATDTDEL QLKAGDVVLV
361 IPFQNPEEQD EGWLMGVKES DWNQHKELEK CRGVFPENFT
401 ERVP    (SEQ ID NO:24)
```

FIG. 37

```
  1 MWKSVVGHDV SVSVETQGDD WDTDPDFVND ISEKEQRWGA KTIEGSGRTE
 51 HINIHQLRNK VSEEHDILKK KELESGPKAS HGYGGQFGVE RDRMDKSAVG
101 HEYVADVEKH SSQTDAARGF GGKYGVERDR ADKSAVGFDY KGEVEKHASQ
151 KDYSHGFGGR YGVEKDKRDK AALGYDYKGE TEKHESQRDY AKGFGGQYGI
201 QKDRVDKSAV GFNEMEAPTT AYKKTTPIEA ASSGARGLKA KFESLAEEKR
251 KREEEEKAQQ MARQQQERKA VVKMSREVQQ PSMPVEEPAA PAQLPKKISS
301 EVWPPAESHL PPESQPVRSR REYPVPSLPT RQSPLGNHLE DNEEPPALPP
351 RTPEGLQVVE EPVYEAAPEL EPEPEPDYEP EPETEPDYED VGELDRQDED
401 AEGDYEDVLE PEDTPSLSYQ AGPSAGAGGA GISAIALYDY QGEGSDELSF
451 DPDDIITDIE MVDEGWWRGQ CRGHFGLFPA NYVKLL (SEQ ID NO:26)
```

FIG. 39

```
  1 MAGNFDSEER SSWYWGRLSR QEAVALLQGQ RHGVFLVRDS STSPGDYVLS
 51 VSENSRVSHY IINSSGPRPP VPPSPAQPPP GVSPSRLRIG DQEFDSLPAL
101 LEFYKIHYLD TTTLIEPVAR SRQGSGVILR QEEAEYVRAL FDFNGNDEED
151 LPFKKGDILR IRDKPEEQWW NAEDSEGKRG MIPVPYVEKY RPASASVSAL
201 IGGNQEGSHP QPLGGPEPGP YAQPSVNTPL PNLQNGPIYA RVIQKRVPNA
251 YDKTALALEV GELVKVTKIN VSGQWEGECN GKRGHFPFTH VRLLDQQNPD
301 EDFS   (SEQ ID NO:28)
```

FIG. 41

```
   1 CAGCCGCTGG AGGGGGCGCC TGGTGTAGAT GTGAAAAGCC GTAACCAGGA
  51 ACCAGTAAAG ATGTGGAAGT CTGTAGTGGG GCATGATGTA TCGGTTTCCG
 101 TGGAGACCCA GGGTGATGAC TGGGATACAG ACCCTGACTT TGTGAATGAC
 151 ATCTCCGAGA AGGAGCAACG GTGGGGAGCC AAGACCATTG AGGGCTCTGG
 201 ACGCACAGAG CACATCAACA TCCACCAGCT GAGGAACAAA GTGTCAGAGG
 251 AGCACGACAT CCTCAAGAAG AAGGAGCTGG AATCGGGGCC TAAGGCATCC
 301 CATGGCTATG GCGGTCAGTT TGGAGTGGAG AGAGACCGGA TGGACAAGAG
 351 TGCCGTGGGC CACGAGTATG TTGCTGATGT GGAGAAACAC TCATCTCAGA
 401 CTGATGCSGC CAGAGGCTTT GGGGGCAAAT ATGGAGTTGA GAGGGACCGG
 451 GCAGACAAGT CAGCGGTGGG CTTTGACTAC AAAGGAGAAG TGGAAAAGCA
 501 TGCATCTCAG AAAGATTACT CTCATGGCTT TGGTGGCCGC TACGGGGTAG
 551 AGAAGGATAA ACGGGACAAA GCAGCCCTGG GATACGACTA CAAAGGAGAG
 601 ACGGAGAAGC ACGAGTCTCA GAGAGATTAT GCCAAGGGCT TTGGTGGCCA
 651 ATATGGAATC CAGAAAGACC GAGTGGATAA GAGTGCTGTT GGCTTCAATG
 701 AAATGGAGGC CCCAACCACG GCGTATAAGA AGACAACACC CATAGAAGCT
 751 GCTTCCAGTG GTGCCCGTGG GCTGAAGGCA AAATTTGAGT CCCTGGCTGA
 801 GGAGAAGAGG AAGCGAGAGG AAGAAGAGAA GGCACAGCAG ATGGCCAGGC
 851 AGCAACAGGA GCGAAAGGCT GTGGTAAAGA TGAGCCGAGA AGTCCAGCAG
 901 CCATCCATGC CTGTGGAAGA GCCAGCGGCA CCAGCCCAGT TGCCCAAGAA
 951 GATCTCCTCA GAGGTCTGGC CTCCAGCAGA GAGTCACCTA CCGCCAGAGT
1001 CTCAGCCAGT GAGAAGCAGA AGGGAATACC CTGTGCCCTC TCTGCCCACG
1051 AGGCAGTCTC CATTGCAGAA TCACTTGGAG GACAACGAGG AGCCCCCAGC
1101 TCTGCCCCCT AGGACCCCAG AAGGCCTCCA GGTGGTGGAA GAGCCAGTGT
1151 ACGAAGCAGC ACCCGAGCTG GAGCCGGAGC CAGAGCCTGA CTATGAGCCA
1201 GAGCCAGAGA CAGAGCCTGA CTATGAGGAT GTTGGGGAGT TAGATCGGCA
1251 GGATGAGGAT GCAGAGGGAG ACTATGAGGA TGTGCTGGAG CCCGANGACA
1301 CCCCTTCTCT GTCCTACCAA GCTGGACCCT CAGCTGGGGC TGGTGGTGCG
1351 GGGATCTCTG CTATAGCCCT GTATGATTAC CAAGGAGAGG GAAGCGATGA
1401 GCTTTCCTTT GATCCAGATG ACATCATCAC TGACATTGAG ATGGTGGATG
1451 AAGGCTGGTG GCGGGGCCAA TGCCGTGGCC ACTTTGGACT TTTCCCTGCA
1501 AACTATGTCA AGCTCCTCTA ATGACCAGCC CATTGTCTTC CGACTTCCCG
1551 AATTCGAAGC TGCTCTGCCT CCCTCTTCCC ACTCCATGGT ACTGCTGCAA
1601 GGACCTGGCT GAACATCATG AGATGCCTGA AGTTCTGGCA GTCTGTCTCC
1651 CGCCTCTTTA AGAGCTTTAG GTAGAATCGC TCCAGGTGGG GGTGGGGGTG
1701 GGGGTGGGAT CCCTCTGTCC CTCTGTGACC ACTCTTCCCT GAGGTAGCTC
1751 ATGAAATCAT CTTGCAGACC TGCCTCCTTC AGCCGCACCC CAGCTCTGCC
1801 AACCTTGCTC TAGAGTGCTG GGATTCCCTT GCCCCGACCC TGGGTGCCAG
1851 CCTAGAGGGG AGGCTCTCAC AGGGCTGCCT GATTCGCCCT GTTGTGCTTT
1901 TGCTCATTTT TCTTCCCTTA GCAGACAAAT TGGAACTGCC CTTCTGTTTA
1950 GTCCTAAAAC TGAAAATAAA ATGAGACTGT GGCTAAAAAA AAAAAAAAA
2003 AAA  (SEQ ID NO:25)
```

FIG. 38

```
  1  GGATCCCCGG AGCCGGTCCG CTGGGCGGGG CGCAGGGCTG GAGGGGCGCG
 51  CGTGCCGGCG GCGGCCCAGC GTGAAAGCGC GGAGGCGGCC ATGGCGGGCA
101  ACTTCGACTC GGAGGAGCGG AGTAGCTGGT ACTGGGGCCG CCTGAGCCGG
151  CAGGAGGCGG TGGCGCTATT GCAGGGCCAG CGGCACGGGG TGTTCCTGGT
201  GCGGGACTCG AGCACCAGCC CCGGGGACTA TGTGCTTAGC GTCTCCGAAA
251  ACTCGCGCGT CTCCCACTAC ATCATCAACA GCAGCGGCCC GCGCCCTCCA
301  GTGCCTCCGT CGCCCGCTCA GCCTCCGCCG GGAGTGAGTC CCTCCAGGCT
351  CCGAATAGGA GATCAAGAAT TTGATTCATT GCCTGCTTTA CTGGAATTCT
401  ACAAAATACA CTATTTGGAC ACTACAACAT TGATAGAACC AGTGGCCAGA
451  TCAAGGCAGG GTAGTGGAGT GATTCTCAGG CAGGAGGAGG CAGAGTATGT
501  GCGGGCCCTG TTTGACTTTA ATGGGAATGA TGAAGAAGAT CTTCCCTTTA
551  AGAAAGGAGA CATCCTGAGA ATCCGGGATA AGCCTGAAGA CGAGTGGTGG
601  AATGCAGAGG ACAGCGAAGG AAAGAGGGGG ATGATTCCTG TCCCTTACGT
651  GGAGAAGTAT AGACCTGCCT CCGCCTCAGT ATCGGCTCTG ATTGGAGGTA
701  ACCAGGAGGG TTCCCACCCA CAGCCACTGG GTGGGCCGGA GCCTGGGCCC
751  TATGCCCAAC CCAGCGTCAA CACTCCGCTC CCTAACCTCC AGAATGGGCC
801  CATTTATGCC AGGGTTATCC AGAAGCGAGT CCCTAATGCC TACGACAAGA
851  CAGCCTTGGC TTTGGAGGTC GGTGAGCTGG TAAAGGTTAC GAAGATTAAT
901  GTGAGTGGTC AGTGGGAAGG GGAGTGTAAT GGCAAACGAG GTCACTTCCC
951  ATTCACACAT GTCCGTCTGC TGGATCAACA GAATCCCGAT GAGGACTTCA
1001 GCTGAGTATA GCTCGACAGT TTGCTGACAG ATGGAACAAT CTGTTTTCCC
1051 CCAATTGCCA TCTATACAAT TTCTTACAG GTGTCAAAGC AGTCTAGTTT
1101 ATATAAGCAT TCTGTTACCT GGGATCTTTT TTAAGACTGA ACTACTCCAT
1151 TCTCACTTGT ATTTACCATA TTCAGGGTAC GAAACCGGAG GGCTTATGTG
1201 GTTAACTTCT GAGTTGGCAG TTTTAGGTGG TAGTGGCCGT GCCTGTATGA
1251 GAAGACGTAA ATACATTGCC TCCTTTCTTT TGGGCAAAAC AGATCA
```

(SEQ ID NO:27)     FIG. 40

```
  1  MSSECDVGSS KAVVNGLASG NHGPDKDMDP TKICTGKGTV TLRASSSYRG
 51  TPSSSPVSPQ ESPKHESKSD EWKLSSSADT NGNAQPSPLA AKGYRSVHPS
101  LSADKPQGSP LLNEVSSSHI ETDSQDFPPT SRPSSAYPST TIVNPTIVLL
151  QHNREQQKRL SSLSDPASER RAGEQDPVPT PAELTSPGRA SERRAKDASR
201  RVVRSAQDLS DVSTDEVGIP LRNTERSKDW YKTMFKQIHK LNRDDDSDVH
251  SPRYSFSDDT KSPLSVPRSK SEMNYIEGEK VVKRSATLPL PARSSSLKSS
301  PERNDWEPLD KKVDTRKYRA EPKSIYEYQP GKSSVLTNEK MSRDISPEEI
351  DLKNEPWYKF FSELEFGRPS SAVSPTPDIT SEPPGYIYSS NFHAVKRESD
401  GTPGGLASLE NERQIYKSVL EGGDIPLQGL SGLKRPSSSA STKDSESPRH
451  FIPADYLEST EEFIRRRHDD KEKLLADQRR LKREQEEADI AARRHTGVIP
501  THHQFITNER FGDLLNIDDT AKRKSGLEMR PARAKFDFKA QTLKELPLQK
551  GDVVYIYRQI DQNWYEGEHH GRVGIFPRTY IELLPPAEKA QPRKLAPVQV
601  LEYGEAIAKF NFNGDTQVEM SFRKGERITL LRQVDENWYE GRIPGTSRQG
651  IFPITYVDVL KRPLVKTPVD YIDLPYSSSP SRSATVSPQA SHHSLSAGPD
701  LTESEKNYVQ PQAQQRRVTP DRSQPSLDLC SYQALYSYVP QNDDELELRD
751  GDIVDVMEKC DDGWFVGTSR RTRQFGTFPG NYVKPLYL (SEQ ID NO:30)
```

FIG. 43

```
   1 CCTCACCGNN CCTGGTGTAG GTACCGGATC GAATTCAAGC GAAAAACAGA
  51 GCGGGGCTGA CTGTAGCGTG GAGCGCGAGC CGGGCTGGAC GCGCGCAAGC
 101 CCTTGCCGGG GACCCGCGAG GCAAGCAGTC TCCCTGTGGA GCGTCGTCCT
 151 CCATCCCTGT AAGCACCGTT ACAGAGAATG AAACAAGGGC AGAAGTTACA
 201 GAGCCCGTGA GGCATCTTCA AATAGAAGAC TGGAGACTAG AAASAGAATA
 251 TTGCCAGGAG TTGGCATCCA TTGGAAGACC TTGAGATCCT CTCAGCTCAC
 301 AACTCCAGGA CCGATGCATC TTCCCACCAC CTTGAAGCAC TGAGCCCTCC
 351 AGAGCTGCAT CTGGGAAGAC TCGCCTGCCT CCAGCATGAG TTCTGAATGT
 401 GATGTTGGAA GCTCTAAAGC TGTGGTGAAT GGCTTGGCAT CTGGCAACCA
 451 TGGACCAGAC AAAGACATGG ACCCTACCAA AATCTGCACT GGGAAAGGAA
 501 CAGTGACTCT TCGGGCCTCG TCTTCCTACA GGGGAACCCC AAGCAGCAGC
 551 CCTGTGAGCC CCCAGGAATC TCCGAAGCAT GAAAGCAAGT CAGATGAATG
 601 GAAACTTTCT TCCAGTGCAG ATACCAATGG CAACGCCCAG CCCTCCCCAC
 651 TTGCTGCCAA GGGCTATAGA AGTGTGCATC CCAGCCTTTC TGCTGACAAG
 701 CCCCAGGGCA GTCCTTTACT AAACGAAGTT TCTTCTTCCC ACATTGAAAC
 751 CGATTCCCAA GACTTCCCTC CAACAAGCAG ACCTTCGTCT GCCTACCCCT
 801 CCACCACCAT CGTCAACCCT ACCATTGTGC TCCTGCAGCA CAATCGAGAG
 851 CAGCAAAAGC GACTCAGTAG TCTTTCAGAT CCTGCCTCAG AGAGAAGAGC
 901 GGGTGAGCAG GACCCAGTAC CAACCCCAGC AGAACTCACT TCGCCCGGCA
 951 GGGCTTCTGA GAGAAGGGCA AAGGATGCTA GCAGACGGGT GGTGAGGAGC
1001 GCACAGGACC TGAGCGATGT GTCTACAGAT GAAGTGGGCA TTCCACTCCG
1051 GAATACCGAG CGATCGAAAG ACTGGTACAA AACTATGTTT AAACAGATCC
1101 ACAAACTGAA CAGAGATGAT GATTCTGATG TCCATTCCCC TCGATACTCC
1151 TTCTCTGATG ACACAAAGTC TCCCCTTTCT GTGCCTCGCT CAAAAAGTGA
1201 GATGAACTAC ATCGAAGGGG AGAAAGTGGT TAAGAGGTCC GCCACACTCC
1251 CCCTCCCAGC CCGCTCTTCC TCACTCAAGT CCAGCCCGGA AAGAAACGAC
1301 TGGGAGCCCC TAGATAAGAA AGTGGATACG AGAAAATACC GAGCAGAGCC
1351 CAAAAGCATT TACGAATATC AGCCGGGCAA GTCTTCGGTC CTGACCAATG
1401 AGAAGATGAG TCGGGATATA AGCCCAGAAG AGATAGATTT AAAGAATGAA
1451 CCTTGGTATA AATTCTTTTC GGAATTGGAG TTTGGGAGAC CGAGCTCAGC
1501 AGTCAGCCCG ACTCCAGACA TTACGTCAGA GCCTCCTGGA TATATCTATT
1551 CTTCCAACTT CCATGCAGTG AAGAGAGAAT CGGACGGGAC CCCCGGGGGT
1601 CTCGCTAGCT TGGAGAATGA GAGGCAGATC TATAAGAGTG TCTTGGAAGC
1651 TGGCGACATC CCTCTTCAGG GCCTCAGTGG GCTCAAGCGA CCTTCCAGCT
1701 CAGCTTCCAC TAAAGATTCA GAGTCACCAA GACATTTTAT ACCAGCTGAT
1751 TACTTGGAGT CCACAGAAGA ATTTATTCGG AGACGGCACG ATGATAAAGA
1801 GAAACTTTTA GCGGACCAGA GACGACTTAA GCGCGAGCAA GAAGAGGCCG
1851 ATATTGCAGC TCGCCGCCAC ACAGGTGTCA TCCCGACTCA TCATCAGTTT
1901 ATCACTAATG AGCGCTTTGG GGACCTCCTC AATATAGATG ATACGGCCAA
1951 AAGGAAATCT GGGTTAGAGA TGAGACCTGC TCGAGCCAAA TTTGACTTTA
2001 AAGCCCAGAC CCTGAAGGAG CTGCCTCTGC AGAAGGGAGA CGTTGTTTAC
2051 ATCTACAGAC AGATTGACCA GAACTGGTAT GAAGGTGAAC ACCATGGCCG
2101 GGTGGGAATC TTCCCACGCA CCTATATCGA GCTTCTTCCT CCAGCTGAGA
2151 AGGCTCAGCC CAGAAAGTTG GCACCCGTAC AAGTTTTGGA ATATGGAGAA
```

FIG. 42A

```
2201 GCCATTGCAA AGTTTAACTT TAATGGAGAT ACACAAGTAG AAATGTCTTT
2251 CCGAAAGGGG GAGAGGATCA CGCTGCTCCG ACAGGTGGAT GAGAACTGGT
2301 ATGAAGGGAG GATTCCTGGG ACATCTCGCC AAGGCATTTT CCCTATCACC
2351 TATGTAGATG TGCTTAAGAG GCCATTGGTG AAAACCCCTG TGGATTACAT
2401 CGACCTGCCT TATTCTTCTT CCCCAAGTCG CAGTGCCACT GTGAGCCCAC
2451 AGGCTTCTCA TCATTCATTG AGCGCAGGAC CTGATCTCAC AGAATCTGAA
2501 AAGAACTATG TGCAACCTCA AGCCCAGCAG CGAAGAGTCA CCCCAGACAG
2551 GAGTCAGCCC TCACTGGATT TGTGTAGCTA CCAAGCGTTA TATAGTTATG
2601 TGCCACAGAA CGATGATGAG TTGGAACTCC GAGATGGAGA TATTGTTGAT
2651 GTCATGGAAA AATGTGACGA TGGATGGTTT GTTGGCACTT CGAGAAGGAC
2701 GAGGCAGTTT GGTACTTTTC CAGGCAACTA TGTAAAACCT TTATATCTAT
2751 AAGAAGACTA AAAAGCACAG AGATTATTTT TTATCGGAGG ATGAAGCATC
2801 ATTCATGAAC TGGTCTCTTT ATTTAAGTAC TGAGTCAGTA AGAAAACTAA
2851 TGCAGTTGGT AAAGAAAGAA TTCAAAGAAG GAACAGAGAA GTGTGTTTGA
2901 AACCCATTGT GTATCAGGGA TTAACTATCT GCTGAAGACA TCTGTATTTA
2951 CATGACTGCT TCTGGGAGCT GCTCTAGCCC CCGCTGCTTG GGGAATCTGA
3001 TCTGGAGCAT GTCCATGAGC AACATTAGCC AAAAAAAAAA GCTTGGGCCC
3051 TATTCTATAG TGTCACCTAA ATACTAGCTT GATCCGGCTG CTAACAAAGC
3101 CCGAAAGGAA GCTGAGTTGC TGCTGCCACC GCTGAGCAAT AACTAGCATA
3151 ACCCCTTGGG GCCTCTAAAC GGGTCTTGAG GGGTTTTTTG CTGAAAGGA
3201 GGAACTATAT CCGGATAACC TGGCGTAATA GCGAAGAGGC CCGCACCGAT
3251 CGCCCTTCCC AACAGTTGGG CAGCCTGAAT GGCGAATGGA CGCGCCCTGT
3301 AGCGGCGCAT TAAGCGCGGC GGGTGTGGTG GTTACGCGCA GGGTG
                                                    (SEQ ID NO:29)
```

FIG. 42B

```
   1 TTNNCACTCA CCGTCCTGGT GATGGTACCG GATCGAATTC AAGCGTGGCC
  51 GTGGCCGTGG GGCGCGCGGG GACCGCCCGG GGTGCCCGCT CCGCTCAGCG
 101 TCCGGGCCGC GTGGTCCGGC GGAGCCCCGA GACCACCCCC GGGCGGGGCG
 151 CCGCCGCGAT GTCGGTGGCT GGGCTCAAGA AGCAGTTCCA CAAAGCCAGC
 201 CAGCTGTTTA GTGAAAAAAT AAGTGGTGCC GAAGGAACGA AGCTAGATGA
 251 AGAATTTCTG AACATGGAAA AGAAAATAGA TATCACCAGT AAAGCTGTTG
 301 CAGAAATCCT TTCAAAAGCC ACAGAGTATC TCCAACCCAA TCCAGCATAC
 351 AGAGCTAAGC TAGGAATGCT GAACACTGTG TCGAAGCTCC GAGGGCAGGT
 401 GAAGGCCACC GGCTACCCAC AGACGGAAGG CTTGCTGGGG GACTGCATGC
 451 TGAAGTATGG CAAGGAGCTC GGAGAAGACT CTGCTTTTGG CAACTCGTTG
 501 GTAGATGTTG GTGAGGCCCT GAAACTCATG GCTGAGGTGA AAGACTCTCT
 551 GGATATTAAT GTGAAGCAAA CTTTTATTGA CCCACTGCAG CTACTGCAAG
 601 ACAAAGATTT AAAGGAGATC GGGCACCACC TGAGAAAGCT GGAAGGCCGT
 651 CGCCTGGATT ATGATTATAA AAAGCGGCGG GTAGGTAAGA TCCCCGAGGA
 701 AGAAATCAGA CAAGCAGTAG AGAAGTTTGA AGAGTCAAAG GAGTTGGCCG
 751 AAAGGAGCAT GTTTAATTTT TTAGAAAATG ATGTAGAGCA AGTGAGCCAG
 801 CTGGCTGTGT TTGTAGAGGC GGCATTAGAC TATCACAGGC AGTCCACAGA
 851 GATCCTCCAG GAGCTGCAGA GCAAGCTGGA GTTGCGAATA TCTCTTGCAT
 901 CCAAAGTCCC CAAGCGAGAA TTCATGCCAA AGCCTGTGAA CATGAGTTCC
 951 ACCGATGCCA ATGGGGTCGG ACCCAGCTCT TCATCAAAGA CACCAGGTAC
1001 TGACACTCCC GCGGACCAGC CCTGCTGTCG TGGTCTCTAT GACTTTGAGC
1051 CAGAAAATGA AGGAGAATTA GGATTTAAAG AAGGGGACAT CATTACATTA
1101 ACCAATCAGA TAGATGAAAA CTGGTATGAA GGGATGCTTC GTGGGGAATC
1151 CGGCTTCTTC CCCATTAATT ACGTGGAAGT CATTGTGCCT TTACCTCCGT
1201 AAATGTGTCT TTTGGACCTA ACTTCAGAAC TGAAATGAAT TGGCACCAGT
1251 GCTCTCTCAG TGTGGTGTTC TGTGACANCC TCGCTCTCTG GCCCACTTAA
1301 TCACTTTTGT ATGTGTGTTT TCTTTATAAT GTATTTTGTA TCAATTTAAT
1351 TTGTATAACT GATTTCTTTG TCCTAACTCA TAAAAATAGT TTTCTTCTTG
1401 TTCTAAAAAG TCATTGGTTA AATGTATTTG CTTCCTGTTG CTAAAACGAG
1451 TAAATTGCGC CCATTCGAAT GGCCTGGGTA GTCCTTGACT GCAGTGGGAA
1501 CGCACCCTTT GCAGCCATGA AAGCTAAAGG TTTGTTTCCT GACATTATTG
1551 ATGGCCTCTG GTCTTTTCCT GTTTTAAGCT TACCTGTGAA CAGCCCAATA
1601 AACNTGACAC ACTGTANAAT AANAAGGGTG GCCCNA (SEQ ID NO:31)
```

FIG. 44

```
1   MSVAGLKKQF HKASQLFSEK ISGAEGTKLD EEFLNMEKKI DITSKAVAEI
51  LSKATEYLQP NPAYRAKLGM LNTVSKLRGQ VKATGYPQTE GLLGDCMLKY
101 GKELGEDSAF GNSLVDVGEA LKLMAEVKDS LDINVKQTFI DPLQLLQDKD
151 LKEIGHHLRK LEGRRLDYDY KKRRVGKIPE EEIRQAVEKF EESKELAERS
201 MFNFLENDVE QVSQLAVFVE AALDYHRQST EILQELQSKL ELRISLASKV
251 PKREFMPKPV NMSSTDANGV GPSSSSKTPG TDTPADQPCC RGLYDFEPEN
301 EGELGFKEGD IITLTNQIDE NWYEGMLRGE SGFFPINYVE VIVPLPP
        (SEQ ID NO:32)
```

FIG. 45

```
1   MSGSYDEASE EITDSFWEVG NYKRTVKRID DGHRLCNDLM SCVQERAKIE
51  KAYAQQLTDW AKRWRQLIEK GPQYGSLERA WGAMMTEADK VSELHQEVKN
101 SLLNEDLEKV KNWQKDAYHK QIMGGFKETK EAEDGFRKAQ KPWAKKMKEL
151 EAAKKAYHLA CKEERLAMTR EMNSKTEQSV TPEQQKKLVD KVDKCRQDVQ
201 KTQEKYEKVL EDVGKTTPQY MEGMEQVFEQ CQQFEEKRLV FLKEVLLDIK
251 RHLNLAENSS YMHVYRELEQ AIRGADAQED LRWFRSTSGP GMPMNWPQFE
301 EWNPDLPHTT AKKEKQPKKA EGATLSNATG AVESTSQAGD RGSVSSYDRG
351 QTYATEWSDD ESGNPFGGNE ANGGANPFED DAKGVRVRAL YDYDGQEQDE
401 LSFKAGDELT KLGEEDEQGW CRGRLDSGQL GLYPANYVEA I
        (SEQ ID NO:34)
```

FIG. 47

```
   1 CGGGCTTGAG GCTGGGCCGC CGCCGCCGCC CGCTTTGCCA CCCGCCCCGC
  51 TGATGGTGTC CGGTGCTCCG GCGCCCAGGG ACACAGACCG GGAGCAGGAC
 101 CACTTCTCTC ACCTCCGGAT CTCTCCTGCT TCCGCAGCCT GTGAGCAGCA
 151 GGCCTGCTAA CTGCAGATCC ACAACCGCAC AGCTCGCTAC AGGTGCACCA
 201 TGTCTGGCTC CTACGATGAG GCCTCAGAGG AGATCACAGA TAGCTTCTGG
 251 GAGGTGGGGA ACTACAAGCG GACGGTGAAG CGCATCGACG ATGGGCACCG
 301 CCTGTGCAAC GACCTCATGA GCTGCGTGCA GGAGCGCGCC AAGATCGAGA
 351 AGGCATACGC GCAGCAGCTC ACCGACTGGG CCAAGCGCTG GCGCCAGCTC
 401 ATCGAGAAAG GTCCTCAGTA TGGCAGCCTG GAGCGGGCGT GGGGCGCCAT
 451 GATGACAGAA GCAGATAAGG TCAGCGAGCT GCACCAGGAG GTGAAGAACA
 501 GCCTGCTGAA TGAGGACCTG GAGAAAGTCA AGAACTGGCA GAAGGATGCC
 551 TATCACAAGC AGATCATGGG TGGCTTCAAG GAGACGAAAG AGGCCGAGGA
 601 TGGCTTCCGA AAGGCCCAGA AGCCCTGGGC TAAAAAGATG AAGGAGCTAG
 651 AGGCGGCCAA GAAGGCCTAT CACTTGGCTT GTAAGGAGGA AAGGCTGGCC
 701 ATGACCCGGG AGATGAACAG TAAGACAGAG CAGTCGGTCA CCCCTGAACA
 751 GCAGAAGAAA CTTGTGGACA AAGTGGACAA ATGCAGACAG GATGTGCAAA
 801 AGACTCAGGA GAAGTATGAG AAGGTCCTGG AAGATGTGGG CAAGACCACA
 851 CCACAGTACA TGGAGGGCAT GGAGCAGGTG TTTGAGCAGT GCCAGCAGTT
 901 TGAGGAGAAG CGGCTGGTCT TCCTGAAGGA AGTCCTGCTG GATATCAAAC
 951 GGCATCTCAA CCTAGCGGAG AACAGCAGCT ACATGCATGT CTACCGAGAA
1001 CTGGAGCAGG CCATCCGGGG GGCCGATGCC CAGGAGGACC TCAGGTGGTT
1051 CCGCAGCACC AGTGGCCCCG GGATGCCCAT GAACTGGCCG CAGTTCGAGG
1101 AGTGGAACCC AGACCTCCCG CACACCACTG CCAAGAAGGA GAAACAGCCT
1151 AAGAAGGCAG AGGGGGCCAC CCTGAGCAAT GCCACTGGGG CTGTAGAATC
1201 CACATCCCAG CTGGGGACC GTGGCAGTGT TAGCAGCTAT GACCGAGGCC
1251 AAACATATGC CACCGAGTGG TCAGACGATG AGAGCGGAAA CCCCTTCGGG
1301 GGCAATGAGG CCAATGGTGG CGCCAACCCC TTCGAGGATG ATGCCAAGGG
1351 AGTTCGTGTA CGGGCACTCT ATGACTACGA CGGTCAGGAG CAGGATGAGC
1401 TCAGCTTCAA GGCCGGAGAT GAGCTCACCA AGCTCGGAGA GGAAGACGAA
1451 CAGGGTTGGT GCCGCGGGCG GCTGGACAGC GGACAGCTGG GCCTCTATCC
1501 TGCCAACTAC GTTGACGCTA TATAGCTACC TTGCCCACCC GACTCCTCTC
1551 AGTCCTTGTC CACCGCCTTC CACCCTTCCC CTCCCCCTTG CCATAGAGTT
1601 CCAGACATAT TTTCCCATCA AGCTTTTATT TTTTTAAAAG TCAAAACAGA
1651 ACAAAAAAAA AAAAAAAAAA GAAGAAATAC GAAGAGACAG CGTTTGCAGC
1701 CTACCTGGAG GCCGGGGGGG AGGGGGCTTA GGGTGATGGC CTCCCCCACA
1751 GCGTGGGCAA GGATCTTGGG ACTAACCCAA TGTCACATCT GGTCTATAGA
1801 GTCCACCAAA GAGTCTCCTG AGTCTTGAGG GAGATCTTCT GGATCCTTCT
1851 ACCCTGTCTC GCTCTCCTAT CCCACCACAG CTGCCAGCAG CTGCCCATGT
1901 CACCTGAGCC TGGCTTCCTA AACTCTCCTG TCCCCTCTCC TGTCCCCCTT
1951 CAACGCCCCC TTCTCTTAAA GGGCCCCCAA TCTTTAGTCT TCCACTCTGC
2001 CCTGGGGGTG CTTTTCTCTT CCCAGCCCTG TCCAGTGAGG CTGGGGGAGA
2051 AGGCTGCGGA GGGGAGGGGA GTGTCTCTTC ACTCCCCCAG ACATGAAGGC
2101 AGGTGAGTGG GAGGGAGTCA TGGCCTCCCT GGCATACAGG AGAGGAAGAA
2151 GGAGAACAGA CCATCTGACC AGGCTGTGCA ACACTCCCAA TGCCAAGCCC
```

FIG. 46A

```
2201 ATTTGAGGGA TGAAAACCCT AGCTGGGCCT GTGGGCAGAG GGCTCCTCCT
2251 CAGAGCCAAT GAGCATTTGC AGAGACCCTA CCTGTCTCTT TAGTCCTTGG
2301 CAATGGGCAA AGCCTCTTCC TTGGAAAGTC CAGGGCAAAG CCAGCAACAG
2351 TAGCAACCTC CTCTCACTCT GGGGAGGAGG CATTGGCCAC CCATCCCCCT
2401 CCCTTCATGG TCATTCAGAA ACGCCACAGC CCCTCCCATC CCCAATCACT
2451 GTGTCAGCAT CAGCCTTTGT GAAGACGGTC TACAAGGCTC TCACCTGGCC
2501 AACCTAGGAG ATTCAGGGGC TCAGGAACCT AGGAGATTCA GGGGCTTGGG
2551 GAACCTCCAC CTTGGCACTG TAAGGGGAAG CCAGCAGCTC AGGCTGGTGT
2601 GAGGAAGGAA CTCTGGATGG TCACTGTAGC TTTCTTCCTT GACCTTTTAG
2651 TCCCCAACAT CCCCTCTGAA TGCTGGCAGC ACCCCCACCC CCACACACAC
2701 ACTCCCATTT CTCTAAGCCC GAGAGTCTTG AGTCTTCATT AAAGGATTCT
2751 GGGTGTGGGA GGGGACACAG GGCCTTGTGG TTGGGAAGCA GGTGGCAGGC
2801 TCTCCCTTGG GAGGATGGGG TGGGAAACGA AACAGGTCAA CCAAGACCTC
2851 TTACAGTGGA AAGTGGTCAG AGGCTGTTTC TTTGGACCTT TGGGAACACA
2901 GATTTGAGAA AGTCTCATAT TCACAGCTGG TGTCCGCTAG GCCTCTGGCC
2951 TACGGACACC CTCTGCCTTG TGAATCAGGT GACCTTTTGG GCCTCCAGGG
3001 AAAGAACAGG ACCACCATCC ATGTTCTCCG CGTCCCTTTA GCTCTCTGCT
3051 GCTTCTCCTG ACACTCAGGT CATGGACCCA AGCTTTGGGG TCCTGACCAC
3101 CGCCCCCCCC CACCCCCCTT CTCTTGACTA GGCTGCAGCA GGGCCTTCTG
3151 TTGGGTCAGT CCTCCTCAGG GCCAGGAGCA GGAACTTAGC ACTCAAGAGA
3201 CAGGGCTGTA AGCACCCACT TCCCTGTCAC TGTTTGCCCT TGGGGCTTCA
3251 GCTGCAGCCC AGGTTGGGCC CTGGAGCCCT CAGAACCGGA AGCAGGATTC
3301 AAACCTCCCC TTCTCCACAG CCCCCCCTGC CTCCCCAGAT GGTAGACATC
3351 CCCCAGCTCT TACCTTCACC CTCATCTCAG AAAGGCAAGA AGCCGCCATG
3401 TCCGCACCTT GGGGCCTGGG CTTCCCCCTC TCTGTGCCAG CGGTTCCCAG
3451 CACCTGGGGA GGGGCTGTGG CCTGACCAGA CCCCAGGCCC ACCCCACATA
3501 GTATACTAGC TGCCCACTCT GGGGCAGGAA CTGGAAAATC CATCCCTTTT
3551 GAACAACCAC CTTCAATGAC CCCCCCATC TGGGACCAGA CTTGGTCCTC
3601 AAGTTATTCA GCACCCCAG TGCAGGAGGG TCCTCCCCCC ACCCCCCGAA
3651 GTCCCTGGAG CCCGGAGCAG AGCCCACCT GTGATTCCTG GTGTTAGGGC
3701 ACCTCAAACC TTGGGCTGGA CCACACCCCT TCCCGCCATT TCCAGACCCC
3751 TACCTGTACT CCCCAGTGCT CCCCAGGGGC CTCTTGATGC TGCACGGGAC
3801 CCTGCAGGGC TCGGTCAGTG ATGTGTTTTG TCCCCAGTTA ACCGCCATCC
3851 AGCGACCTGG TTCCAGGAGG AGCTCAGGTC ACCCCCACCA CCGCCGCCAC
3901 TGCGTCTGCC GCCCTAGGCT TTCAGACATC ATTAGTTCCG ACACTTGTGA
3951 AACTCCGAGA CGTGCCGTGG TCTCAGCAAT GCACCTGTTT TATACATGAT
4001 TGTGTAATTT AAAGGTATAT AAATACAAAT ATATATATTA TATCTATATC
4051 TATCAGTTGT GACCGTATGG CTGTCGATAA AACCAGAATT C
```
(SEQ ID NO:33)

FIG. 46B

```
   1  GAATTCGTCG ACCCACGGTC CGGGAAGCCT TTCACAAGCA GATGATGGGC
  51  GGCTTCAAGG AGACCAAGGA AGCTGAGGAC GGCTTTCGGA AGGCACAGAA
 101  GCCCTGGGCC AAGAAGCTGA AAGAGGTAGA AGCAGCAAAG AAAGCCCACC
 151  ATGCAGCGTG CAAAGAGGAG AAGCTGGCTA TCTCACGAGA AGCCAACAGC
 201  AAGGCAGACC CATCCCTCAA CCCTGAACAG CTCAAGAAAT TGCAAGACAA
 251  AATAGAAAAG TGCAAGCAAG ATGTTCTTAA GACCAAAGAG AAGTATGAGA
 301  AGTCCCTGAA GGAACTCGAC CAGGGCACAC CCCAGTACAT GGAGAACATG
 351  GAGCAGGTGT TTGAGCAGTG CCAGCAGTTC GAGGAGAAAC GCCTTCGCTT
 401  CTTCCGGGAG GTTCTGCTGG AGGTTCAGAA GCACCTAGAC CTGTCCAATG
 451  TGGCTGGTTA CAAAGCCATT TACCATGACC TGGAGCAGAG CATCAGAGCA
 501  GCTGATGCAG TGGAGGACCT GAGGTGGTTC GAGCCAATCA CGGGCCGGG
 551  CATGGCCATG AACTGGCCGC AGTTTGAGGA GTGGTCCGCA GACCTGAATC
 601  GAACCCTCAG CCGGAGAGAG AAGAAGAAGT CCACTGACGG CGTCACCCTG
 651  ACGGGCATCA ACCAGACAGG CGACCAGTCT CTGCCGAGTA AGCCCAGCAG
 701  CACCCTTAAT GTCCCGAGCA ACCCCGCCCA GTCTGCGCAG TCACAGTCCA
 751  GCTACAACCC CTTCGAGGAT GAGGACGACA CGGGCAGCAC CGTCAGTGAG
 801  AAGGACGACA CTAAGGCCAA AAATGTGAGC AGCTACGAGA AGACCCAGAG
 851  CTATCCCACC GACTGGTCAG ACGATGAGTC TAACAACCCC TTCTCCTCCA
 901  CGGATGCCAA TGGGGACTCG AATCCATTCG ACGACGACGC CACCTCGGGG
 951  ACGGAAGTGC GAGTCCGGGC CCTGTATGAC TATGAGGGGC AGGAGCATGA
1001  TGAGCTGAGC TTCAAGGCTG GGGATGAGCT GACCAAGATG GAGGACGAGG
1051  ATGAGCAGGG CTGGTGCAAG GGACGCTTGG ACAACGGGCA AGTTGGCCTA
1101  TACCCGGCAA ATTATGTGGA GGCGATCCAG TGA        (SEQ ID NO:35)
```

FIG. 48

```
   1  RIRRPTVREA FHKQMMGGFK ETKEAEDGFR KAQKPWAKKL KEVEAAKKAH
  51  HAACKEEKLA ISREANSKAD PSLNPEQLKK LQDKIEKCKQ DVLKTKEKYE
 101  KSLKELDQGT PQYMENMEQV FEQCQQFEEK RLRFFREVLL EVQKHLDLSN
 151  VAGYKAIYHD LEQSIRAADA VEDLRWFRAN HGPGMAMNWP QFEEWSADLN
 201  RTLSRREKKK STDGVTLTGI NQTGDQSLPS KPSSTLNVPS NPAQSAQSQS
 251  SYNPFEDEDD TGSTVSEKDD TKAKNVSSYE KTQSYPTDWS DDESNNPFSS
 301  TDANGDSNPF DDDATSGTEV RVRALYDYEG QEHDELSFKA GDELTKMEDE
 351  DEQGWCKGRL DNGQVGLYPA NYVEAIQ           (SEQ ID NO:36)
```

FIG. 49

```
   1            AAAGGGAGG AGAGTGTCAA AAAGAAGGAT
  30 GGCGAGGAAA AAGGCAAACA GGAAGCACAA GACAAGCTGG
  70 GTCGGCTTTT CCATCAACAC CAAGAACCAG CTAAGCCAGC
 110 TGTCCAGGCA CCCTGGTCCA CTGCAGAAAA AGGGTCCACT
 150 TACCATTTCT GCACAGGAAA ATGTAAAAGT GGTGTATTAC
 190 CGGGCACTGT ACCCCTTTGA ATCCAGAAGC CATGATGAAA
 230 TCACTATCCA GCCAGGAGAC ATAGTCATGG TGGATGAAAG
 270 CCAAACTGGA GAACCCGGCT GGCTTGGAGG AGAATTAAAA
 310 GGAAAGACAG GGTGGTTCCC TGCAAACTAT GCAGAGAAAA
 350 TCCCAGAAAA TGAGGTTCCC GCTCCAGTGA AACCAGTGAC
 390 TGATTCAACA TCTGCCCCTG CCCCCAAACT GGCCTTGCGT
 430 GAGACCCCCG CCCCTTTGGC AGTAACCTCT TCAGAGCCCT
 470 CCACGACCCC TAATAACTGG GCCGACTTCA GCTCCACGTG
 510 GCCCACCAGC ACGAATGAGA AACCAGAAAC GGATAACTGG
 550 GATGCATGGG CAGCCCAGCC CTCTCTCACC GTTCCAAGTG
 590 CCGGCCAGTT AAGGCAGAGG TCCGCCTTTA CTCCAGCCAC
 630 GGCCACTGGC TCCTCCCCGT CTCCTGTGCT AGGCCAGGGT
 670 GAAAAGGTGG AGGGGCTACA AGCTCAAGCC CTATATCCTT
 710 GGAGAGCCAA AAAAGACAAC CACTTAAATT TTAACAAAAA
 750 TGATGTCATC ACCGTCCTGG AACAGCAAGA CATGTGGTGG
 790 TTTGGAGAAG TTCAAGGTCA GAAGGGTTGG TTCCCCAAGT
 830 CTTACGTGAA ACTCATTTCA GGGCCCATAA GGAAGTCTAC
 870 AAGCATGGAT TCTGGTTCTT CAGAGAGTCC TGCTAGTCTA
 910 AAGCGAGTAG CCTCTCCAGC AGCCAAGCCG GTCGTTTCGG
 950 GAGAAGAAAT TGCCCAGGTT ATTGCCTCAT ACACCGCCAC
 990 CGGCCCCGAG CAGCTCACTC TCGCCCCTGG TCAGCTGATT
1030 TTGATCCGAA AAAAGAACCC AGGTGGATGG TGGGAAGGAG
1070 AGCTGCAAGC ACGTGGGAAA AAGCGCCAGA TAGGCTGGTT
1110 CCCAGCTAAT TATGTAAAGC TTCTAAGCCC TGGGACGAGC
1150 AAAATCACTC CAACAGAGCC ACCTAAGTCA ACAGCATTAG
1190 CGGCAGTGTG CCAGGTGATT GGGATGTACG ACTACACCGC
1230 GCAGAATGAC GATGAGCTGG CCTTCAACAA GGGCCAGATC
1270 ATCAACGTCC TCAACAAGGA GGACCCTGAC TGGTGGAAAG
1310 GAGAAGTCAA TGGACAAGTG GGGCTCTTCC CATCCAATTA
1370 TGTGAAGCTG ACCACAGACA TGGACCCAAG CCAGCAATGA
                                      (SEQ ID NO:37)
```

FIG. 50

```
  1  KGRRVSKRRM ARKKANRKHK TSWVGFSINT KNQLSQLSRH
 41  PGPLQKKGPL TISAQENVKV VYYRALYPFE SRSHDEITIQ
 81  PGDIVMVDES QTGEPGWLGG ELKGKTGWFP ANYAEKIPEN
121  EVPAPVKPVT DSTSAPAPKL ALRETPAPLA VTSSEPSTTP
161  NNWADFSSTW PTSTNEKPET DNWDAWAAQP SLTVPSAGQL
201  RQRSAFTPAT ATGSSPSPVL GQGEKVEGLQ AQALYPWRAK
241  KDNHLNFNKN DVITVLEQQD MWWFGEVQGQ KGWFPKSYVK
281  LISGPIRKST SMDSGSSESP ASLKRVASPA AKPVVSGEEI
321  AQVIASYTAT GPEQLTLAPG QLILIRKKNP GGWWEGELQA
361  RGKKRQIGWF PANYVKLLSP GTSKITPTEP PKSTALAAVC
401  QVIGMYDYTA QNDDELAFNK GQIINVLNKE DPDWWKGEVN
441  GQVGLFPSNY VKLTTDMDPS QQ    (SEQ ID NO:38)
```

FIG. 51

```
  1  GAATTCGCGG CCGCGTCGAC CAAGATCATT CCTGGGAGTG
 41  AAGTAAAACG GGAAGAACCA GAAGCTTTGT ATGCAGCTGT
 81  AAATAAGAAA CCTACCTCGG CAGCCTATTC AGTTGGAGAA
121  GAATATATTG CACTTTATCC ATATTCAAGT GTGGAACCTG
161  GAGATTTGAC TTTCACAGAA GGTGAAGAAA TATTGGTGAC
201  CCAGAAAGAT GGAGAGTGGT GGACAGGAAG TATTGGAGAT
241  AGAAGTGGAA TTTTTCCATC AAACTATGTC AAACCAAAGG
281  ATCAAGAGAG TTTTGGGAGT GCTAGCAAGT CTGGAGCATC
321  AAATAAAAAA CCTGAGATTG CTCAGGTAAC TTCAGCATAT
361  GTTGCTTCTG GTTCTGAACA ACTTAGCCTT GCACCAGGAC
401  AGTTAATATT AATTCTAAAG AAAAATACAA GTGGGTGGTG
441  GCAAGGAGAG TTACAGGCCA GAGGAAAAAA GCGACAGAAA
481  GGATGGTTTC CTGCCAGTCA TGTTAAACTT TTGGGTCCAA
521  GCAGTGAAAG AGCCACACCT GCCTTTCATC CTGTATGTCA
561  GGTGATTGCT ATGTATGACT ATGCAGCAAA TAATGAAGAT
601  GAGCTCAGTT TCTCCAAGGG ACAACTCATT AATGTTATGA
641  ACAAAGATGA TCCTGATTGG TGGCAAGGAG AGATCAACGG
681  GGTGACTGGT CTCTTTCCTT CAAACTACGT TAAGATGACG
721  ACAGACTCAG ATCCAAGTCA ACAGTGA(SEQ ID NO:39)
```

FIG. 52

```
  1  EFAAASTKII PGSEVKREEP EALYAAVNKK PTSAAYSVGE
 41  EYIALYPYSS VEPGDLTFTE GEEILVTQKD GEWWTGSIGD
 81  RSGIFPSNYV KPKDQESFGS ASKSGASNKK PEIAQVTSAY
121  VASGSEQLSL APGQLILILK KNTSGWWQGE LQARGKKRQK
161  GWFPASHVKL LGPSSERATP AFHPVCQVIA MYDYAANNED
201  ELSFSKGQLI NVMNKDDPDW WQGEINGVTG LFPSNYVKMT
241  TDSDPSQQ   (SEQ ID NO:40)
```

FIG. 53

```
HSLHLHRHQGRKERARYDLEAAQDNELTFKAGEIMTVLDDSDPNWWKGETHQGIGLFPSN 60
FVTADLTAEPEMIKTEKKTVQFSDDVQVETIEPEPEPAFIDEDKMDQLLQMLQSTDPSDD 120
QPDLPELLHLEAMCHQMGPLIDEKLEDIDRKHSELSELNVKVMEALSLYTKLMNEDPMYS 180
MYAKLQNQPYYMQSSGVSGSQVYAGPPPSGAYLVAGNAQMSHLQSYSLPPEQLSSLSQAV 240
VPPSANPALPSQQTQAAYPNRSPGDLMKPGDSECRGSAEDSQMRISPPYFPTGQQA    296
(SEQ ID NO:190)
```

FIG. 55

```
IRGRVDQGEWPLPGRGTPGPSGLCVPEDQCRVRDLKGWLDSFWAKAEKEE   50
ENRRLEEKRWAEEAQRQLEQERRERELREAARREQRYQEQGGEASPQSRT  100
WEQQQEVVSRNRNEQESAVHPREIFKQKERAMSTTSISSPQPGKLRSPFL  150
QKQLTQPETHFGREPAAAISRPRADLPAEEPAPSTPPCLVQAEEEAVYEE  200
PPEQETFYEQPPLVQQQGAGSEHIDHHIQGQGLSGQGLCARALYDYQAAD  250
DTEISFDPENLITGIEVIDEGWWRGYGPDGHFGMFPANYVELIDEAEGTS  300
CPSPLRHGFLIAGRGGLGVDIQHSSRNRTPSEDEASGLPPAWQTQPVTPN  350
AAMAW 355 (SEQ ID NO:192)
```

FIG. 57

```
GRVDIERKRLELMQKKKLEDEAARKAKQGKENLWKENLRKEEEEKQKRLQEEKTQEKIQE 60
EERKAEEKQRETASVLVNYRALYPFEARNHDEMSFNSGDIIQVDEKTVGEPGWLYGSFQG 120
NFGWFPCNYVEKMPSSENEKAVSPKKALLPPTVSLSATSTSSEPLSSNQPASVTDYQNVS 180
FSNLTVNTSWQKKSAFTRTVSPGSVSPIHGQGQVVENLKAQALCSWTAKKDNHLNFSKHD 240
IITVLEQQENWWFGEVHGGRGWFPKSYVKIIPGSEVKREEPEALYAAVNKKPTSAAYSVG 300
EEYIALYPYSSVEPGDLTFTEGEEILVTQKDGEWWTGSIGDRSGIFPSNYVKPKDQESFG 360
SASKSGASNKKPEIAQVTSAYVASGSEQLSLAPGQLILILKKNTSGWWQGELQARGKKRQ 420
KGWFPASHVKLLGPSSERATPAFHPVCQVIAMYDYAANNEDELSFSKGQLINVMNKDDPD 480
WWQGEINGVTGLFPSNYVKMTTDSDPSQQ 509 (SEQ ID NO:194)
```

FIG. 59

```
CACTCTCTACACTTGCACCGGCATCAAGGACGAAAAGAAC 40
GCGCTAGATATGACTTGGAAGCTGCTCAAGACAATGAACT 80
TACTTTCAAAGCTGGAGAAATTATGACAGTTCTTGATGAC 120
AGTGATCCTAACTGGTGGAAAGGTGAAACCCATCAAGGCA 160
TAGGGTTATTTCCTTCTAATTTTGTGACTGCAGATCTCAC 200
TGCTGAACCAGAAATGATTAAAACAGAGAAGAAGACGGTA 240
CAATTTAGTGATGATGTTCAGGTAGAGACAATAGAACCAG 280
AGCCGGAACCAGCCTTTATTGATGAAGATAAAATGGACCA 320
GTTGCTACAGATGCTGCAAAGTACAGACCCCAGTGATGAT 360
CAGCCAGACCTACCAGAGCTGCTTCATCTTGAAGCAATGT 400
GTCACCAGATGGGACCTCTCATTGATGAAAAGCTGGAAGA 440
TATTGATAGAAAACATTCAGAACTCTCAGAACTTAATGTG 480
AAAGTGATGGAGGCCCTTTCCTTATATACCAAGTTAATGA 520
ACGAAGATCCGATGTATTCCATGTATGCAAAGTTACAGAA 560
TCAGCCATATTATATGCAGTCATCTGGTGTTTCTGGTTCT 600
CAGGTGTATGCAGGGCCTCCTCCAAGTGGTGCCTACCTGG 640
TTGCAGGGAACGCGCAGATGAGCCACCTCCAGAGCTACAG 680
TCTTCCCCCGGAGCAGCTGTCTTCTCTCAGCCAGGCAGTG 720
GTCCCACCATCCGCAAACCCAGCCCTTCCTAGTCAGCAGA 760
CTCAGGCCGCTTACCCAAACCGCTCCCCAGGGGACCTCAT 800
GAAGCCCGGTGATTCTGAATGCCGTGGATCTGCCGAGGAT 840
TCCCAGATGCGTATTTCTCCTCCGTACTTCCCCACAGGAC 880
AGCAGGCTTGAATAGCTGATTGCCTATGCAGGACAACAGG 920
CTTGAATAGCTGACTGCCTATGCATTCTCTTTGCTTGCCA 960
GTTTTTTGGACATCAAACTTGACAGATCCAAGATTATTAC 1000
TTTGATCTTCCCCACACCCCTCCCACCCCCGAGTCTACTA 1040
TGGTCCCATCATAGTATTCTGAAAATCAGTGAATGGCCAC 1080
TCTACCAGTTATTTCTACCAGTTTTTAGGTTCTAAACCTC 1120
AGGCATTCTGGACTCTTCTGTTCATTATCATATTTTGAAG 1160
GCATTATCTTCAAAATCTATCTAGACTCTGACCCTTTCTC 1200
CCATCTCCACCATTACTGCCGTGGCTCTTCTGCTGGTCGG 1240
CTCTCTCCTGGTGGATCCGTAATAACCTGCAGTCAGCTAT 1280
CCTGGTCCAGAAGGGAACCCCGTTAAACCCTGTTGGAATC 1320
TTATCACGCTTCTGCTCCAGAACGAACCCAGTCTGTCTGT 1360
CTCACTCAGAGTGTAAGCTACAGTCCTTATTGTGGCCATC 1400
AGGTGCTGTGTGTTCTCCAGCCCCCTCCCCACCACCGCAG 1440
TCCTGCCGGTGATCTTAGCTGCTCTCCCCTCGGAACCCCC 1480
TGCGGCCCCCTCTGCCGCAACAXTCGTGGCCTGCTGTTCC 1520
TTGAACATGCTTGGTGTTTTCTCTCCTCAAAGGCTTCTTT 1560
CTGTTTACCTGAAATGTACTTGCCTAGGGAAATCTTATCC 1600
TGGCTCACTCCGCTTACTTTTTTCCACATCTTTGCTTAAA 1640
GTTATTGCCCTTATTGGAGAAGGCACCCCTACCATAAACT 1680
AGAAATCCCTTGCCCCCAAGCTGCTCCTTT 1710
                        (SEQ ID NO:189)
```

FIG. 54

```
GAATTCGCGGCCGCGTCGACCAAGGAGAGTGGCCGCTTCC  40
AGGACGTGGGACCCCAGGCCCCAGTGGGCTCTGTGTACCA  80
GAAGACCAATGCCGTGTCAGAGATTTAAAGGGTTGGTTAG  120
ACAGCTTCTGGGCCAAAGCAGAGAAGGAGGAGGAGAACCG  160
TCGGCTGGAGGAAAAGCGGTGGGCCGAGGAGGCACAGCGG  200
CAGCTGGAGCAGGAGCGCCGGGAGCGTGAGCTGCGTGAGG  240
CTGCACGCCGGGAGCAGCGCTATCAGGAGCAGGGTGGCGA  280
GGCCAGCCCCAGAGCAGGACGTGGGAGCAGCAGCAAGAA  320
GTGGTTTCAAGGAACCGAAATGAGCAGGAGTCTGCCGTGC  360
ACCCGAGGGAGATTTTCAAGCAGAAGGAGAGGGCCATGTC  400
CACCACCTCCATCTCCAGTCCTCAGCCTGGCAAGCTGAGG  440
AGCCCCTTCCTGCAGAAGCAGCTCACCCAACCAGAGACCC  480
ACTTTGGCAGAGAGCCAGCTGCTGCCATCTCAAGGCCCAG  520
GGCAGATCTCCCTGCTGAGGAGCCGGCGCCCAGCACTCCT  560
CCATGTCTGGTGCAGGCAGAAGAGGAGGCTGTGTATGAGG  600
AACCTCCAGAGCAGGAGACCTTCTACGAGCAGCCCCCACT  640
GGTGCAGCAGCAAGGTGCTGGCTCTGAGCACATTGACCAC  680
CACATTCAGGGCCAGGGGCTCAGTGGGCAAGGGCTCTGTG  720
CCCGTGCCCTGTACGACTACCAGGCAGCCGACGACACAGA  760
GATCTCCTTTGACCCCGAGAACCTCATCACGGGCATCGAG  800
GTGATCGACGAAGGCTGGTGGCGTGGCTATGGGCCGGATG  840
GCCATTTTGGCATGTTCCCTGCCAATTACGTGGAGCTCAT  880
TGATGAGGCTGAGGGCACATCTTGCCCTTCCCCTCTCAGA  920
CATGGCTTCCTTATTGCTGGAAGAGGAGGCCTGGGAGTTG  960
ACATTCAGCACTCTTCCAGGAATAGGACCCCCAGTGAGGA  1000
TGAGGCCTCAGGGCTCCCTCCGGCTTGGCAGACTCAGCCT  1040
GTCACCCCAAATGCAGCAATGGCCTGGTGATTCCCACACA  1080
TCCTTCCTGCATCCCCCGACCCTCCCAGACAGCTTGGCTC  1120
TTGCCCCTGACAGGATACTGAGCCAAGCCCTGCCTGTGGC  1160
CAAGCCCTGAGTGGCCACTGCCAAGCTGCGGGGAAGGGTC  1200
CTGAGCAGGGGCATCTGGGAGGCTCTGGCTGCCTTCTGCA  1240
TTTATTTGCCTTTTTTCTTTTTCTCTTGCTTCTAAGGGGT  1280
GGTGGCCACCACTGTTTAGAATGACCCTTGGGAACAGTGA  1320
ACGTAGAGAATTGTTTTTAGCAGAGTTTGTGACCAAAGTC  1360
AGAGTGGATCATGGTGGTTTGGCAGCAGGGAATTTGTCTT  1400
GTTGGAGCCTGCTCTGTGCTCCCCACTCCATTTCTCTGTC  1440
CCTCTGCCTGGGCTATGGGAAGTGGGGATGCAGATGGCCA  1480
AGCTCCCACCCTGGGTATTCAAAAACGGCAGACACAACAT  1520
GTTCCTCCACGCGGCTCACTCGATGCCTGCAGGCCCCAGT  1560
GTGTGCCTCAACTGATTCTGACTTCAGGAAAAGTAACACA  1600
GAGTGGCCTTGGCCTGTTGTCTTCCCCTATTTTCTGTCCC  1640
AGCTCATCCGTGGTCGAAGCGCCCGCGAATTCCAGCTGAG  1680
CGGCCGC 1687                    (SEQ ID NO:191)
```

FIG. 56

```
GCGGCCGCGTCGACATTGAAAGGAAAAGATTAGAACTAAT       40
GCAGAAAAAGAAACTAGAAGATGAGGCTGCAAGGAAAGCA       80
AAGCAAGGAAAAGAAAACTTATGGAAAGAAAATCTTAGAA      120
AGGAGGAAGAAGAAAAACAAAAGCGACTCCAGGAAGAAAA      160
AACACAAGAAAAAATTCAAGAAGAGGAACGGAAAGCTGAG      200
GAGAAACAACGTGAGACAGCTAGTGTTTTGGTGAATTATA      240
GAGCATTATACCCCTTTGAAGCAAGGAACCATGATGAGAT      280
GAGTTTTAATTCTGGAGATATAATTCAGGTTGATGAAAAA      320
ACCGTAGGAGAACCTGGTTGGCTTTATGGTAGTTTTCAAG      360
GAAATTTTGGCTGGTTTCCATGCAATTATGTAGAAAAAAT      400
GCCATCAAGTGAAAATGAAAAAGCTGTATCTCCAAAGAAG      440
GCCTTACTTCCTCCTACAGTTTCTTTATCTGCTACCTCAA      480
CTTCCTCTGAACCACTTTCTTCAAATCAACCAGCATCAGT      520
GACTGATTATCAAAATGTATCTTTTTCAAACCTAACTGTA      560
AATACATCATGGCAGAAAAAATCAGCCTTCACTCGAACTG      600
TGTCCCCTGGATCTGTATCACCTATTCATGGACAGGGACA      640
AGTGGTAGAAAACTTAAAAGCACAGGCCCTTTGTTCCTGG      680
ACTGCAAAGAAAGATAACCACTTGAACTTCTCAAAACATG      720
ACATTATTACTGTCTTGGAGCAGCAAGAAAATTGGTGGTT      760
TGGGGAGGTGCATGGAGGAAGAGGATGGTTTCCCAAATCT      800
TATGTCAAGATCATTCCTGGGAGTGAAGTAAAACGGGAAG      840
AACCAGAAGCTTTGTATGCAGCTGTAAATAAGAAACCTAC      880
CTCGGCAGCCTATTCAGTTGGAGAAGAATATATTGCACTT      920
TATCCATATTCAAGTGTGGAACCTGGAGATTTGACTTTCA      960
CAGAAGGTGAAGAAATATTGGTGACCCAGAAAGATGGAGA     1000
GTGGTGGACAGGAAGTATTGGAGATAGAAGTGGAATTTTT     1040
CCATCAAACTATGTCAAACCAAAGGATCAAGAGAGTTTTG     1080
GGAGTGCTAGCAAGTCTGGAGCATCAAATAAAAAACCTGA     1120
GATTGCTCAGGTAACTTCAGCATATGTTGCTTCTGGTTCT     1160
GAACAACTTAGCCTTGCACCAGGACAGTTAATATTAATTC     1200
TAAAGAAAAATACAAGTGGGTGGTGGCAAGGAGAGTTACA     1240
GGCCAGAGGAAAAAAGCGACAGAAAGGATGGTTTCCTGCC     1280
AGTCATGTTAAACTTTTGGGTCCAAGTAGTGAAAGAGCCA     1320
CACCTGCCTTTCATCCTGTATGTCAGGTGATTGCTATGTA     1360
TGACTATGCAGCAAATAATGAAGATGAGCTCAGTTTCTCC     1400
AAGGGACAACTCATTAATGTTATGAACAAAGATGATCCTG     1440
ATTGGTGGCAAGGAGAGATCAACGGGGTGACTGGTCTCTT     1480
TCCTTCAAACTACGTTAAGATGACGACAGACTCAGATCCA     1520
AGTCAACAGTGACCCAATGTTGTCTTCCAGTTGTGAAAGC     1560
ACCCCAGAGACCCACTATCCAAGTTTCACTCTAGCGTGGA     1600
GGCAGGGCAGGCAGCCCTGATCAAATATCTGCTACACAAT     1640
TCGTTTACTTCGTTTGAATGTTAGAGCCACTTGTGATTAT     1680
TTTTTTGTGTTTCTAACTTACAGTTTAAATTTATTTGTAA     1720
```

FIG. 58A

```
AAAGTTAAAGGATAGTGGGTCTTTGTGTGGCTTTCCCTGC 1760
TGTTCACTCTGGCATCTTTAGCATTTTTCTTCTTTTTTAA 1800
TTTGATAATTGTAGGTCATTAGCATGCATATTGAGTTTGC 1840
CGTTATGTGGTGGGAGTTCAAACACACAAAGACCCACTAT 1880
TTGCACAAACTATTCTTACTGGTTTGGAATAGGCTGCCAT 1920
GCTTTTTTAATGTTATTGCAACATGTGTATTCATTTACAG 1960
AATTCAGATAAAATTTGCTTATGTTCTGCTATTATGTTTG 2000
ATCTAATCCTAATCACAGTGAGCTCTTAATTAGCTCAATA 2040
TGTGGTTTGCCCTCAAGTGTGCACTGTTTATTACTTTGTA 2080
ATATGCCACTATGAGTACTGACATTTAGATATGTTTAAAG 2120
GCCAAGAACTGGAAACAGCCATGCCCTGTTTTCTGTGTAT 2160
TTGGGATGGGAATAACAACATTTTGGGGGGAGCTTTTTAA 2200
ATCTCAGAGAAGAGGAAAGTGGCCTGCTCTGGCAGGTATG 2240
TGCAGTGTTTCATTTGTTCCAGTCCCAAGAATGAGCACTG 2280
TCCTATGGTAGTTCGCTTAGGATCTTTATGTGCTCTGGGC 2320
TAATGAAGGTACTGCATCATGTGCTGCAGCGTGTGTATTC 2360
TTTTTCGATGACCTATAAAGGGATTATTTTTGAGGAATGA 2400
AAGGCTCCCATCATTGACTGTGAGATGGGAAAAACCTTTC 2440
CTAGCTTAGAGCATTTATATCTTAATCCATTTTAAAGTCA 2480
GAGTTCATTGTTACCTGTTTTAATCAGGTGACTACATGTC 2520
CCAGTATACAAAGGGGCACTGGTTGACATTCTTCTTAATG 2560
TATTTAGTAAATATCATAAGAAATCCTTTAAGAGTTTAAA 2600
TGTCCCCAAAACAGACATGCGGGCTCTAGTCAAGAATGAA 2640
TTAGAGTGAAGGAAAGCTGTGTAACACCTGGCATTCCTCT 2680
GTGTTCATGGAGCTTCTTTGAGGCTCTAAGATTGATTTTA 2720
CCATCAGACTTCTCTAATACCTGTTCTTCAACCATATTGG 2760
CTACTTTGACATAAGAATTTACTTCTTTTCCTGGAATGGA 2800
AAACACTTTAAAAAATAATAACAAACATTATTATAAACTA 2840
ATATATGTGAGAGGTCGACGCGGCCGCGAATTC 2873
```

(SEQ ID NO:193)

FIG. 58B

GAATTCGTCGACCCACGCGTCCGAAATATAACTGAAGTTGGGGCACCTAC 50
TGAAGAAGAGGAAGAAAGTGAAAGTGAAGATAGTGAAGACAGTGGTGGGG 100
AGGAAGAAGATGCAGAGGAGGAAGAGGAAGAGAAAGAGGAAAATGAATCT 150
CACAAATGGTCAACCGGTGAAGAATACATCGCTGTTGGAGATTTTACTGC 200
TCAGCAAGTTGGAGATCTTACATTTAAGAAAGGGGAAATTCTCCTTGTAA 250
TTGAAAAAAAACCTGATGGTTGGTGGATAGCTAAGGATGCCAAAGGAAAT 300
GAAGGTCTTGTTCCCAGAACCTACCTAGAGCCTTATAGTGAAGAAGAAGA 350
AGGCCAAGAGTCAAGTGAAGAGGGCAGTGAAGAAGATGTAGAGGCGGTGG 400
ATGAAACAGCAGATGGAGCAGAAGTTAAGCAAAGAACTGATCCCCACTGG 450
AGTGCTGTTCAGAAAGCGATTTCAGAGGCGGGCATCTTCTGTCTTGTTAA 500
TCATGTCTCGTTTTGCTACCTAATAGTTCTGATCCGTCCCTAA 543
                              (SEQ ID NO:196)

FIG. 60

GAATTCGGCGGACTTCGCGGCCGCGTCGACGAAGAAACCT 40
GAAGGACACACTAGGCCTCGGCAAGACGCGCAGGAAGACC 80
AGCGCGCGGGATGCGTCCCCCACGCCCAGCACGGACGCCG 120
AGTACCCCGCCAATGGCAGCGGCGCCGACCGCATCTACGA 160
CCTCAACATCCCGGCCTTCGTCAAGTTCGCCTATGTGGCC 200
GAGCGGGAGGATGAGTTGTCCCTGGTGAAGGGGTCGCGCG 240
TCACCGTCATGGAGAAGTGCAGCGACGGTTGGTGGCGGGG 280
CAGCTACAACGGGCAGATCGGCTGGTTCCCCTCCAACTAC 320
GTCTTGGAGGAGGTGGACGAGGCGGTTGCGGAGTCCCCAA 360
GCTTCCTGAGCCTGCGCAAGGGCGCCTCGCTGAGCAATGG 400
CCAGGGCTCCCGCGTGCTGCATGTGGTCCAGACGCTGTAC 440
CCCTTCAGCTCAGTCACCGAGGAGGAGCTCAACTTCGAGA 480
AGGGGGAGACCATGGAGGTGATTGAGAAGCCGGAGAACGA 520
CCCCGAGTGGTGGAAATGCAAAAATGCCCGGGGCCAGGTG 560
GGCCTCGTCCCCAAAAACTACGTGGTGGTCCTCAGTGACG 600
GGCCTGCCCTGCACCCTGCGCACGCCCCACAGATAAGCTA 640
CACCGGGCCCTCGTCCAGCGGGCGCTTCGCGGGCAGAGAG 680
TGGTACTACGGGAACGTGACGCGGCACCAGGCCGAGTGCG 720
CCCTCAACGAGCGGGGCGTGGAGGGCGACTTCCTCATTAG 760
GGACAGCGAGTCCTCGCCCAGCGACTTCTCCGTGTCCCTT 800
AAAGCGTCAGGGAAGAACAAACACTTCAAGGTGCAGCTCG 840
TGGACAATGTCTACTGCATTGGGCAGCGGCGCTTCCACAC 880
CATGGACGAGCTGGTGGAACACTACAAAAAGGCGCCCATC 920
TTCACCAGCGAGCACGGGGAGAAGCTCTACCTCGTCAGGG 960
CCCTGCAGTGA 971         (SEQ ID NO:197)

FIG. 62

```
GAATTCGTCGACCCACGCGTCCGAAATATAACTGAAGTTGGGGCACCTACTGAAGAAGAGGAAGAAAGTG    70
  E  F  V  D  P  R  V  R  N  I  T  E  V  G  A  P  T  E  E  E  E  S        23

AAAGTGAAGATAGTGAAGACAGTGGTGGGGAGGAAGAAGATGCAGAGGAGGAAGAGGAAGAGAAAGAGGA   140
  E  S  E  D  S  E  D  S  G  G  E  E  D  A  E  E  E  E  E  K  E  E        47

AAATGAATCTCACAAATGGTCAACCGGTGAAGAATACATCGCTGTTGGAGATTTTACTGCTCAGCAAGTT   210
                                                   SH3
  N  E  S  H  K  W  S  T  G  E  E  Y  I  A  V [G  D  F  T  A  Q  Q  V     70

GGAGATCTTACATTTAAGAAAGGGGAAATTCTCCTTGTAATTGAAAAAAAACCTGATGGTTGGTGGATAC   280
  G  D  L  T  F  K  K  G  E  I  L  L  V  I  E  K  K  P  D  G  W  W  I     93

CTAAGGATGCCAAAGGAAATGAAGGTCTTGTTCCCAGAACCTACCTAGAGCCTTATAGTGAAGAAGAAGA   350
  A  K  D  A  K  G  N  E  G  L  V  P  R  T  Y] L  E  P  Y  S  E  E  E  E 117

AGGCCAAGAGTCAAGTGAAGAGGGCAGTGAAGAAGATGTAGAGGCGGTGGATGAAACAGCAGATGGAGCA   420
  G  Q  E  S  S  E  E  G  S  E  E  D  V  E  A  V  D  E  T  A  D  G  A    140

GAAGTTAAGCAAAGAACTGATCCCCACTGGAGTGCTGTTCAGAAAGCGATTTCAGAGGCGGGCATCTTTT   490
  E  V  K  Q  R  T  D  P  H  W  S  A  V  Q  K  A  I  S  E  A  G  I  F    163
```

FIG.61A

GTCTTGTTAATCATGTCTCGTTTTGCTACCTAATAGTTCTGATCCGTCCCTAA

C   L   V   N   H   V   S   F   C   Y   L   I   V   L   I   R   P        180

(SEQ ID NO:196)

FIG.61B

```
GAATTCGGCGGACTTCGCGGCCGCGTCGACGAAGAAACCTGAAGGACACACTAGGCCTCGGCAAGACGCG
                                                                        70
   I  R  R  T  S  R  P  R  R  R  R  N  L  K  D  T  L  G  L  G  K  T  R
                                                                        23

CAGGAAGACCAGCGCGCGGGATGCGTCCCCCACGCCCAGCACGGACGCCCAGTACCCCGCCAATGGCAGC
                                                                        140
   R  K  T  S  A  R  D  A  S  P  T  P  S  T  D  A  E  Y  P  A  N  G  S
                                                                        46

GGCGCCGACCGCATCTACGACCTCAACATCCCGGCCTTCGTCAAGTTCGCCTATGTGGCCGAGCGGGAGG
                                                                        210
                                                    SH3①
   G  A  D  R  I  Y  D  L  N  I  P  A  F  V  K [F  A  Y  V  A  E  R  E
                                                                        69

ATGAGTTGTCCCTGGTGAAGGGGTCGCGCGTCACCGTCATGGAGAAGTGCAGCGACGGTTGGTGGCGGGG
                                                                        280
   D  E  L  S  L  V  K  G  S  R  V  T  V  M  E  K  C  S  D  G  W  W  R
                                                                        93

CAGCTACAACGGGCAGATCGGCTGGTTCCCCTCCAACTACGTCTTGGAGGAGGTGGACGAGGCGGTTGCG
                                                                        350
   S  Y  N  G  Q  I  G  W  F  P  S  N  Y] V  L  E  E  V  D  E  A  V  A
                                                                        116

GAGTCCCCAAGCTTCCTGAGCCTGCGCAAGGGCGCCCTCGCTRGAGCAATGGCCAGGGCTCCCGCGTGCTGC
                                                                        420
   E  S  P  S  F  L  S  L  R  K  G  A  S  L  S  N  G  Q  G  S  R  V  L
                                                                        139

ATGTGGTCCAGACGCTGTACCCCTTCAGCTCAGTCACCGAGGAGGAGCTCAACTTCGAGAAGGGGAGCAC
                                                                        490
            SH3②
   H  V  V  Q  T  L [Y  P  F  S  S  V  T  E  E  E  L  N  F  E  K  G  E  T
                                                                        163
```

FIG.63A

```
CATGGAGGTCATTGAGAAGCCGGAGAACGACCCCGAGTGGTGGAAATGCAAAAATGCCCGGGGCCAGGTG
                                                                      560
  M  E  V  I  E  K  P  E  N  D  P  E  W  W  K  C  K  N  A  R  G  Q  V  186

GGCCTCGTCCCCAAAAACTACGTGGTGGTCCTCAGTGACGGGCCTGCCCTGCACCCTGCGCACGCCCCAC
                                                                      630
  G  L  V  P  K  N  Y] V  V  V  L  S  D  G  P  A  L  H  P  A  H  A  P  209

AGATAAGCTACACCGGGCCCTCGTCCAGCGGGCGCTTCGCGGGCAGAGAGTGGTACTACGGGAACGTGAC
                                                                      700
  Q  I  S  Y  T  G  P  S  S  S  G  R  F  A  G  R  E  W  Y  Y  G  N  V  T  233

GCGGCACCAGGCCGAGTGCGCCCTCAACGAGCGGGGCGTGGAGGGCGACTTCCTCATTAGGGACAGCGAG
                                                                      770
    R  H  Q  A  E  C  A  L  N  E  R  G  V  E  G  D  F  L  I  R  D  S  E  256

TCCTCGCCCAGCGACTTCTCCGTGTCCCTTAAAGCGTCAGGGAAGAACAAACACTTCAAGGTGCAGCTCG
                                                                      840
    S  S  P  S  D  F  S  V  S  L  K  A  S  G  K  N  K  H  F  K  V  Q  L  279

TGGACAATGTCTACTGCATTGGGCAGCGGCGCTTCCACACCATGGAGGAGCTGGTGGAACACTACAAAAA
                                                                      910
  V  D  N  V  Y  C  I  G  Q  R  R  F  M  T  M  D  E  L  V  E  H  Y  K  K  303

GGCGCCCATCTTCACCAGCGAGCACGGGGAGAAGCTCTACCTCGTCAGGGCCCTGCAGTGACGGCGCCCC
                                                            STOP      980
   A  P  I  F  T  S  E  H  G  E  K  L  Y  L  V  R  A  L  Q /322
```

(SEQ ID NO:198)

FIG.63B

```
GAATTCGCGGACTTCGCGGCCGCGTCGACACCAGTGCAGG    40
TTTTGGAATATGGAGAAGCTATTGCTAAGTTTAACTTTAA    80
TGGTGATACACAAGTAGAAATGTCCTTCAGAAAGGGTGAG   120
AGGATCACACTGCTCCGGCAGGTAGATGAGAACTGGTACG   160
AAGGGAGGATCCCGGGGACATCCCGACAAGGCATCTTCCC   200
CATCACCTACGTGGATGTGATCAAGCGACCACTGGTGAAA   240
AACCCTGTGGATTACATGGACCTGCCTTTCTCCTCCTCCC   280
CAAGTCGCAGTGCCACTGCAAGCCCACAGCAACCTCAAGC   320
CCAGCAGCGAAGAGTCACCCCCGACAGGAGTCAAACCTCA   360
CAAGATTTATTTAGCTATCAAGCATTATATAGCTATATAC   400
CACAGAATGATGATGAGTTGGAACTCCGCGATGGAGATAT   440
CGTTGATGTCATGGAAAAATGTGACGATGGATGGTTTGTT   480
GGTACTTCAAGAAGGACAAAGCAGTTTGGTACTTTTCCAG   520
GCAACTATGTAAAACCTTTGTATCTATAA (SEQ ID NO:199)
```

FIG. 64

```
GAATTCGCCGGACTTCGCGGCCGCGTCGACACCAGTGCAGGTTTTGGAATATGGAGAAGCTATTGCTAAGT
|--|--|--|--|--|--|--|--|--|--|--|--|--|--|--|--|--|--|--|--|--|--|--|--|--|--|--|--|   70
CTTAAGCGGCCTGAAGCGCCGGCGCAGCTGTGGTCACGTCCAAAACCTTATACCTCTTCGATAACGATTCA
        ┌ORF
         Ⓔ  F  A  D  F  A  A  A  S  T  P  V  Q  V  L  E  Y  G  E  A  I  A  K       23
|--|--|--|--|--|--|--|--|--|--|--|--|--|--|--|--|--|--|--|--|--|--|--|--|--|--|--|--|
TTAACTTTAATGGTGATACACAAGTAGAAATGTCCTTCAGAAAGGGTGAGAGGATCACACTGCTCCGGCA
|--|--|--|--|--|--|--|--|--|--|--|--|--|--|--|--|--|--|--|--|--|--|--|--|--|--|--|--|   140
AATTGAAATTACCACTATGTGTTCATCTTTACAGGAAGTCTTTCCCACTCTCCTAGTGTGACGAGGCCGT

F  N  F  N  G  D  T  Q  V  E  M  S  F  R  K  G  E  R  I  T  L  L  R  Q               47
|--|--|--|--|--|--|--|--|--|--|--|--|--|--|--|--|--|--|--|--|--|--|--|--|--|--|--|--|
GGTAGATGAGAACTGGTACGAAGGGAGGATCCCGGGGACATCCCGACAAGGCATCTTCCCCATCACCTAC
|--|--|--|--|--|--|--|--|--|--|--|--|--|--|--|--|--|--|--|--|--|--|--|--|--|--|--|--|   210
XXATCTACTCTTGACCATGCTTCCCTCCTAGGGCCCCTGTAGGGCTGTTCCGTAGAAGGGGTAGTGGATG

V  D  E  N  W  Y  E  G  R  I  P  G  T  S  R  Q  G  I  F  P  I  T  Y                70
|--|--|--|--|--|--|--|--|--|--|--|--|--|--|--|--|--|--|--|--|--|--|--|--|--|--|--|--|
GTGGATGTGATCAAGCGACCACTGGTGAAAAACCCTGTGGATTACATGGACCTGCCTTTCTCCTCCTCCC
|--|--|--|--|--|--|--|--|--|--|--|--|--|--|--|--|--|--|--|--|--|--|--|--|--|--|--|--|   280
CACCTACACTAGTTCGCTGGTGACCACTTTTTGGGACACCTAATGTACCTGGACGGAAAGAGGAGGAGGG

V  D  V  I  K  R  P  L  V  K  N  P  V  D  Y  M  D  L  P  F  S  S  S               93
|--|--|--|--|--|--|--|--|--|--|--|--|--|--|--|--|--|--|--|--|--|--|--|--|--|--|--|--|
CAAGTCGCAGTGCCACTGCAAGCCCACAGCAACCTCAAGCCCAGCAGCGAAGAGTCACCCCCGACAGGAG
|--|--|--|--|--|--|--|--|--|--|--|--|--|--|--|--|--|--|--|--|--|--|--|--|--|--|--|--|
GTTCAGCGTCACGGTGACGTTCGGGTGTCGTTGGAGTTCGGGTCGTCGCTTCTCAGTGGGGGCTGTCCTC   350

```
TCAAACCTCACAAGATTTATTTAGCTATCAAGCATTATATAGCTATATACCACAGAATGATGATGAGTTG
├┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┤ 420

AGTTTGGAGTGTTCTAAATAAATCGATAGTTCGTAATATATCGATATATGGTGTCTTACTACTACTCAAC
                                    SH3
  Q  T  S  Q  D  L  F  S  Y  Q  A  L [ Y  S  Y ] I  P  Q  N  D  D  E  L   140
├┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┤

GAACTCCGCGATGGAGATATCGTTGATGTCATGGAAAAATGTGACGATGGATGGTTTGTTGGTACTTCAA
                                                                        490

CTTGAGGCGCTACCTCTATAGCAACTACAGTACCTTTTTACACTGCTACCTACCAAACAACCATGAAGTT
                                               F
  E  L  R  D  G  D  I  V  D  V  M  E  K  C  D  D  G  W  F  V  G  T  S   163
├┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┤

GAAGGACAAAGCAGTTTGGTACTTTTCCAGGCAACTATGTAAAACCTTTGTATCTATAAGAAGACTGAAA
├┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┤ 560

CTTCCTGTTTCGTCAAACCATGAAAAGGTCCGTTGATACATTTTGGAAACATAGATATTCTTCTGACTTT
                                                          STOP
  R  R  T  K  Q  F  G  T  F  R  G  N  Y ] V  K  P  L  Y  L ⊙  181
```

(SEQ ID NO:200)

FIG.65B

```
AATTCAAGCGCGGGGTCTTTAGGATTTGCAGCTCCAGGAAGCGAGATGTCGAAGCCGCCACCCAAACCA    70
    N  S  S  A  G  S  L  G  F  A  A  P  G  S  E  M  S  K  P  P  P  K  P

GTCAAACCAGGGCAAGTTAAAGTCTTCAGAGCCCTGTATACGTTTGAACCCAGAACTCCAGATGAATTAT    140
  V  K  P  G  Q  V  K  V  F  R  A  L  Y  T  F  E  P  R  T  P  D  E  L

ACTTTGAGGAAGGTGATATTATCTACATTACTGACATGAGCGATACCAATTGGTGGAAAGGCACCTCCAA    210
  Y  F  E  E  G  D  I  I  Y  I  T  D  M  S  D  T  N  W  W  K  G  T  S  K

AGGCAGGACTGGACTAATTCCAAGCAACTATGTGGCTGAGCAGGCAGAATCCATTGACAATCCATTGCAT    280
   G  R  T  G  L  I  P  S  N  Y  V  A  E  Q  A  E  S  I  D  N  P  L  H

GAAGCAGCAAAAAGAGGCAACTTGAGCTGGTTGAGAGAGTGTTTGGACAACAGAGTGGGTGTTAATGGCT    350
  E  A  A  K  R  G  N  L  S  W  L  R  E  C  L  D  N  R  V  G  V  N  G

TAGACAAAGCTGGAAGCACTGCCTTATACTGGGCTTGCCACGGGGGCCACAAAGATATAGTGGAAATGCT    420
   L  D  K  A  G  S  T  A  L  Y  W  A  C  H  G  G  H  K  D  I  V  E  M  L

ATTTACTCAACCAAATATTGAACTGAACCAGCAGAACAAGTTGGGAGATACAGCTTTGCATGCTGCTGCC    490
   F  T  Q  P  N  I  E  L  N  Q  D  N  K  L  G  D  T  A  L  H  A  A  A
```

FIG.66A

```
TGGAAGGGTTATGCAGATATCGTCCAGTTGCTTCTGGCAAAAGGTGCTAGAACAGACTTAAGAAACATTG
|+++++++++|+++++++++|+++++++++|+++++++++|+++++++++|+++++++++|+++++++++| 560
  W  K  G  Y  A  D  I  V  Q  L  L  A  K  G  A  R  T  D  L  R  N  I

AGAAGAAGCTGGCCTTCGACATGGCTACCAATGCTGCCTGTGCATCTCTCCTGAAAAAGAAACAGGGAAC
|+++++++++|+++++++++|+++++++++|+++++++++|+++++++++|+++++++++|+++++++++| 630
  E  K  K  L  A  F  D  M  A  T  N  A  A  C  A  S  L  L  K  K  K  Q  G  T

AGATGCAGTTCGAACATTAAGCAATGCCGAGGACTATCTCGATGATGAAGACTCAGATTAA
|+++++++++|+++++++++|+++++++++|+++++++++|+++++++++|+++++++++|
  D  A  V  R  T  L  S  N  A  E  D  Y  L  D  D  E  D  S  D  STOP
```

(SEQ ID NO:221)

FIG.66B

POLYPEPTIDES HAVING A FUNCTIONAL DOMAIN OF INTEREST AND METHODS OF IDENTIFYING AND USING SAME

This application is a divisional of U.S. patent application Ser. No. 08/630,915 filed Apr. 3, 1996 now U.S. Pat. No. 6,309,820, which is a continuation-in-part of abandoned U.S. patent application Ser. No. 08/417,872 filed Apr. 7, 1995, now abandoned, the entire contents of which are incorporated herein by reference.

1. INTRODUCTION

The present invention is directed to polypeptides having a functional domain of interest or functional equivalents thereof. Methods of identifying these polypeptides are described, along with various methods of their use, including but not limited to targeted drug discovery.

2. BACKGROUND OF THE INVENTION

Combinatorial libraries represent exciting new tools in basic science research and drug design. It is possible through synthetic chemistry or molecular biology to generate libraries of complex polymers, with many subunit permutations. There are many guises to these libraries: random peptides, which can be synthesized on plastic pins (Geysen et al., 1987, J. Immunol. Meth. 102:259–274), beads (Lam et al., 1991, Nature 354:82–84) or in a soluble form (Houghten et al., 1991, Nature 354:84–86) or expressed on the surface of viral particles (Cwirla et al., 1990, Proc. Natl. Acad. Sci. USA 87:6378–6382; Kay et al., 1993, Gene 128:59–65; Scott and Smith, 1990, Science 249:386–390); nucleic acids (Ellington and Szostak, 1990, Nature 346:818–822; Gao et al., 1994, Proc. Natl. Acad. Sci. USA 91:11207–11211; Tuerk and Gold, 1990, Science 249:505–510); and small organic molecules (Gordon et al., 1994, J. Med. Chem. 37:1385–1401). These libraries are very useful in mapping protein-protein interactions and discovering drugs.

Phage display has become a powerful method for screening populations of peptides, mutagenized proteins, and cDNAs for members that have affinity to target molecules of interest. It is possible to generate $10^8$-$10^9$ different recombinants from which one or more clones can be selected with affinity to antigens, antibodies, cell surface receptors, protein chaperones, DNA, metal ions, etc. Screening libraries is versatile because the displayed elements are expressed on the surface of the virus as capsid-fusion proteins. The most important consequence of this arrangement is that there is a physical linkage between phenotype and genotype. There are several other advantages as well: 1) virus particles which have been isolated from libraries by affinity selection can be regenerated by simple bacterial infection, and 2) the primary structure of the displayed binding peptide or protein can be easily deduced by DNA sequencing of the cloned segment in the viral genome.

Combinatorial peptide libraries have been expressed in bacteriophage. Synthetic oligonucleotides, fixed in length, but with multiple unspecified codons can be cloned into genes III, VI, or VIII of bacteriophage M13 where they are expressed as a plurality of peptide:capsid fusion proteins. The libraries, often referred to as random peptide libraries, can be screened for binding to target molecules of interest. Usually, three to four rounds of screening can be accomplished in a week's time, leading to the isolation of one to hundreds of binding phage.

The primary structure of the binding peptides is then deduced by nucleotide sequencing of individual clones. Inspection of the peptide sequences sometimes reveals a common motif, or consensus sequence. Generally, this motif when synthesized as a soluble peptide has the full binding activity. Random peptide libraries have successfully yielded peptides that bind to the Fab site of antibodies (Cwirla et al., 1990, Proc. Natl. Acad. Sci. USA 87:6378–6382; Scott and Smith, 1990, Science 249:386–390), cell surface receptors (Doorbar and Winter, 1994, J. Mol. Biol. 244:361–369; Goodson et al., 1994, Proc. Natl. Acad. Sci. USA 91:7129–7133), cytosolic receptors (Blond-Elguindi et al., 1993, Cell 75:717–728), intracellular proteins (Daniels and Lane, 1994, J. Mol. Biol. 243:639–652; Dedman et al., 1993, J. Biol. Chem. 268:23025–23030; Sparks et al., 1994, J. Biol. Chem. 269:23853–23856), DNA (Krook et al., 1994, Biochem. Biophys. Res. Comm. 204:849–854), and many other targets (Winter, 1994, Drug Dev. Res. 33:71–89).

Most vital cellular processes are regulated by the transmission of signals throughout the cell in the form of complex interactions between proteins. As the study of signal transduction, or the flow of information throughout the cell, has broadened and matured, it has become apparent that these protein-protein interactions are often mediated by modular domains within signalling proteins. Src, both the first proto-oncogene product and the first tyrosine kinase discovered (Taylor and Shalloway, 1993, Current Opinion in Genetics and Development 3:26–34), is the prototypic modular domain-containing protein.

Src is a protein tyrosine kinase of 60 kilodaltons and is located at the plasma membrane of cells. It was first discovered in the 1970's to be the oncogenic element of Rous sarcoma virus, and in the 1980's, it was appreciated to be a component of the signal transduction system in animal cells. However, since the identification of viral and cellular forms of Src (i.e., v-Src and c-Src), their respective roles in oncogenesis, normal cell growth, and differentiation have not been completely understood.

In addition to its tyrosine kinase region (sometimes called a Src Homology 1 domain), Src contains two regions that have been found to have functionally and structurally homologous counterparts in a large number of proteins. These regions have been designated the Src Homology 2 (SH2) and Src Homology 3 (SH3) domains. SH2 and SH3 domains are modular in that they fold independently of the protein that contains them, their secondary structure places N- and C-termini close to one another in space, and they appear at variable locations (anywhere from N- to C-terminal) from one protein to the next (Cohen et al., 1995, Cell 80:237–248). SH2 domains have been well-studied and are known to be involved in binding to phosphorylated tyrosine residues (Pawson and Gish, 1992, Cell 71:359–362).

The Src-homology region 3 (SH3) of Src is a domain that is 60–70 amino acids in length and is present in many cellular proteins (Cohen et al., 1995, Cell 80:237–248; Pawson, 1995, Nature 373:573–580). Within Src, the SH3 domain is considered to be a negative inhibitory domain, because c-Src can be activated (i.e., transforming) through mutations in this domain (Jackson et al., 1993, Oncogene 8:1943–1956; Seidel-Dugan et al., 1992, Mol Cell Biol 12:1835–1845).

To deduce the binding specificity of the Abl SH3 domain, a group led by David Baltimore screened cDNA libraries with radiolabeled GST-Abl SH3 fusion protein and identified two binding cDNA clones (Cicchetti et al., 1992, Science 257:803–806). Both clones encoded proteins with proline rich regions that were later shown to be SH3 binding domains.

Subsequently, others have screened combinatorial peptide libraries and identified peptides that bound to the Src SH3 domain (Yu et al., 1994, Cell 76:933–945; Cheadle et al., 1994, J. Biol. Chem. 269:24034–24039). Using the SH3 domain of Src, Sparks et al., 1994, J. Biol. Chem. 269:23853–23856 screened phage-display random peptide libraries and identified a consensus peptide sequence that binds with specificity and high affinity to the Src SH3 domain.

The consensus from these various studies is that the optimal Src SH3 peptide ligand is RPLPPLP (SEQ ID NO:45). Recently, the structures of the peptide-SH3 domain complexes have been deduced by NMR and the peptides have been shown to bind in two possible orientations with respect to the SH3 domain (Feng et al., 1994, Science 266:1241–1247; Lim et al., 1994, Nature 372:375–379).

Since SH3 domains have been found to have such important roles in the function of crucial signalling and structural elements in the cell, a method of identifying proteins containing SH3 regions is of great interest. In this regard, it is important to note that such a method is unavailable because of the low sequence similarity of modular functional domains, including SH3. See, e.g., FIG. 6, which illustrates the minimal primary sequence homology among various known SH3 domains.

Sequence homology searches can potentially identify known proteins containing not yet recognized functional domains of interest, however, sequence homology generally needs to be >40% for this procedure to be successful. Functional domains generally are less than 40% homologous and therefore many would be missed in a sequence homology search. In addition, homology searches do not identify novel proteins; they only identify proteins already defined by nucleotide or amino acid sequence and present in the database.

Another approach is to use hybridization techniques using nucleotide probes to search expression libraries for novel proteins. This method would have limited applicability to finding novel proteins containing functional domains due to the low sequence homology of the functional domains.

Methods for isolating partner proteins involved in protein-protein interactions have generally focused on finding a ligand to a protein that has been found and characterized. Such approaches have included using anti-idiotypic antibodies that mimic the known protein to screen cDNA expression libraries for a binding ligand (Jerne, 1974, Ann. Immunol. (Inst. Pasteur) 125c:373–389; Sudol, 1994, Oncogene 9:2145–2152). Skolnick et al., 1991, Cell 65:83–90 isolated a binding partner for PI3-kinase by screening a cDNA expression library with the $^{32}$P-labeled tyrosine phosphorylated carboxyl terminus of the epidermal growth factor receptor (EGFR).

An easy method for isolating operationally defined ligands involved in protein-protein interactions and for optimally identifying an exhaustive set of modular domain-containing proteins implicated in binding with the ligands would be highly desirable.

If such a method were available, however, such a method would be useful for the isolation of any polypeptide having a functioning version of any functional domain of interest. Such a general method would be of tremendous utility in that whole families of related proteins each with its own version of the functional domain of interest could be identified. Knowledge of such related proteins would contribute greatly to our understanding of various physiological processes, including cell growth or death, malignancy, and immune reactions, to name a few. Such a method would also contribute to the development of increasingly more effective therapeutic, diagnostic, or prophylactic agents having fewer side effects.

According to the present invention, just such a method is provided.

Regarding SH3 domain-containing proteins, the method of the present invention will contribute greatly to our understanding of cell growth (Zhu et al., 1993, J. Biol. Chem. 268:1775–1779; Taylor and Shalloway, 1994, Nature 368:867–871), malignancy (Wages et al., 1992, J. Virol. 66:1866–1874; Bruton and Workman, 1993, Cancer Chemother. Pharmacol. 32:1–19), subcellular localization of proteins to the cytoskeleton and/or cellular membranes (Weng et al., 1993, J. Biol. Chem. 268:14956–14963; Bar-Sagi et al., 1993, Cell 74:83–91), signal transduction (Duchesne et al., 1993, Science 259:525–528), cell morphology (Wages et al., 1992, J. Virol. 66:1866–1874; McGlade et al., 1993, EMBO J. 12:3073–3081), neuronal differentiation Tanaka et al., 1993, Mol. Cell. Biol. 13:4409–4415), T cell activation (Reynolds et al., 1992, Oncogene 7:1949–1955), and cellular oxidase activity (McAdara and Babior, 1993, Blood 82:A28).

Citation of a reference hereinabove shall not be construed as an admission that such is prior art to the present invention.

3. SUMMARY OF THE INVENTION

In general, the present invention is directed to a method of using isolated, operationally defined ligands involved in binding interactions for optimally identifying an exhaustive set of compounds binding to such ligands. In one embodiment, the isolated ligands are peptides involved in specific protein-protein interactions and are used to identify a set of novel modular domain-containing proteins that bind to the ligands. Using this method, proteins sharing only modest similarities but a common function can be found.

The present invention is directed to a method of identifying a polypeptide or family of polypeptides having a functional domain of interest. The basic steps of the method comprise: (a) choosing a recognition unit or set of recognition units having a selective affinity for a target molecule with a functional domain of interest; (b) contacting the recognition unit with a plurality of polypeptides; and (c) identifying a polypeptide having a selective binding affinity for the recognition unit, which polypeptide includes the functional domain of interest or a functional equivalent thereof.

In one particular embodiment of the invention, exhaustive screening of proteins having a desired functional domain involves an iterative process by which ligands or recognition units for SH3 domains identified in the first round of screening are used to detect SH3 domain-containing proteins in successive expression library screens.

More particularly, the method of the present invention includes choosing a recognition unit having a selective affinity for a target molecule with a functional domain of interest. With this recognition unit (particularly under the multvalent recognition unit screening conditions taught by the present invention), it has further been discovered that a plurality of polypeptides from various sources can be examined such that certain polypeptides having a selective binding affinity for the recognition unit can be identified. The polypeptides so identified have been shown to include the functional domain of interest; that is, the functional domains found are working versions that are capable of displaying the same binding specificity as the functional domain of interest. Hence, the polypeptides identified by the present method also possess those attributes of the functional domain of interest which allow these related polypeptides to exhibit the same, similar, or analogous (but functionally equivalent) selective affinity characteristics as the domain of interest of the initial target molecule. By screening the plurality of peptides for recognition unit binding, the methods of the present invention circumvent the limitations of conventional DNA-based screening methods and allow for the identification of highly disparate protein sequences possessing functionally equivalent functional domains.

In specific embodiments of the present invention, the plurality of polypeptides is obtained from the proteins present in a cDNA expression library. The specificity of the polypeptides which bear the functional domain of interest or a functional equivalent thereof for various peptides or recognition units can subsequently be examined, allowing for a greater understanding of the physiological role of particular polypeptide/recognition unit interactions. Indeed, the present invention provides a method of targeted drug discovery based on the observed effects of a given drug candidate on the interaction between a recognition unit-polypeptide pair or a recognition unit and a "panel" of related polypeptides each with a copy or a functional equivalent of (e.g., capable of displaying the same binding specificity and thus binding to the same recognition unit as) the functional domain of interest.

The present invention also provides polypeptides comprising certain amino acid sequences. Moreover, the present invention also provides nucleic acids, including certain DNA constructs comprising certain coding sequences. Using the methods of the present invention, more than eighteen different SH3 domain-containing proteins have been identified, over half of which have not been previously described.

The present inventors have found, unexpectedly, that the valency (i.e., whether it is a monomer, dimer, tetramer, etc.) of the recognition unit that is used to screen an expression library or other source of polypeptides apparently has a marked effect upon the specificity of the recognition unit-functional domain interaction. The present inventors have discovered that recognition units in the form of small peptides, in multivalent form, have a specificity that is eased but not forfeited. In particular, biotinylated peptides bound to a multivalent (believed to be tetravalent) streptavidin-alkaline phosphatase complex have an unexpected generic specificity. This allows such peptides to be used to screen libraries to identify classes of polypeptides containing functional domains that are similar but not identical in sequence to the peptides' original target functional domains.

The present invention also provides methods for identifying potential new drug candidates (and potential lead compounds) and determining the specificities thereof. For example, knowing that a polypeptide with a functional domain of interest and a recognition unit, e.g., a binding peptide, exhibit a selective affinity for each other, one may attempt to identify a drug that can exert an effect on the polypeptide-recognition unit interaction, e.g., either as an agonist or as an antagonist (inhibitor) of the interaction. With this assay, then, one can screen a collection of candidate "drugs" for the one exhibiting the most desired characteristic, e.g., the most efficacious in disrupting the interaction or in competing with the recognition unit for binding to the polypeptide.

In addition, the present invention also provides certain assay kits and methods of using these assay kits for screening drug candidates for their ability to affect the binding of a polypeptide containing a functional domain to a recognition unit. In a particular aspect of the present invention, the assay kit comprises: (a) a polypeptide containing a functional domain of interest; and (b) a recognition unit having a selective binding affinity for the polypeptide. Yet another assay kit may comprise a plurality of polypeptides, each polypeptide containing a functional domain of interest, in which the functional domain of interest is a domain selected from the group consisting of an SH1, SH2, SH3, PH, PTB, LIM, armadillo, Notch/ankyrin repeat, zinc finger, leucine zipper, and helix-turn-helix, and at least one recognition unit having a selective affinity for each of the plurality of polypeptides.

Other objects of the present invention will be apparent to those of ordinary skill upon further consideration of the following detailed description.

4. DESCRIPTION OF THE FIGURES

FIG. 1 is a schematic representation of the general aspects of a method of identifying recognition units exhibiting a selective affinity for a target molecule with a functional domain of interest. In this illustration, the target molecule is a polypeptide with an SH3 domain, and the recognition units are peptides having a selective affinity for the SH3 domain that are expressed in a phage displayed library.

FIG. 2 illustrates the selectivities exhibited by particular recognition units that bind to the Src SH3 domain (in this case, two heptapeptides) for a "panel" of known polypeptides known to contain an SH3 domain. The non-SH3-containing protein, GST, serves as control. RPLPPLP is (SEQ ID NO:45); APPVPPR is (SEQ ID NO:203)

FIG. 3 is a schematic representation of the general method of identifying polypeptides with a functional domain of interest by screening a plurality of polypeptides using a suitable recognition unit. In the illustration, the plurality of polypeptides is obtained from a cDNA expression library, and the recognition units are SH3 domain-binding peptides.

FIG. 4 illustrates how an SH3 domain-binding peptide can be used to identify other SH3 domain-containing proteins. Shown is a schematic representation of the progression from initial selection of a target molecule with a functional domain of interest, choice of recognition unit, and identification of polypeptides that have a selective affinity for the recognition unit and include the functional domain of interest or a functional equivalent thereof.

FIG. 5 depicts filters from primary (FIG. 5B) and tertiary (FIG. 5A) screens of a λcDNA library probed with a biotinylated SH3-binding peptide recognition unit in the form of a complex with streptavidin-alkaline phosphatase (SA-AP). A mouse 16 day embryo cDNA library in λEXlox was incubated with a multivalent complex formed between biotinylated pSrcCII and SA-AP. The sites of peptide binding were detected by incubation with BCIP (5-bromo-4-chloro-3-indoyl-phosphate-p-toluidine salt) and NBT (nitroblue tetrazolium chloride) for approximately five minutes.

FIG. 6 shows an alignment of SH3 domains that illustrates the minimal primary sequence homology among various known SH3 domains. The amino acid sequences shown are SEQ ID NOs:68–111.

FIG. 7A is a schematic representation of a population of functional domains represented by the circles. "A" is a recognition unit specific to one circle only. B, on the other hand, recognizes three domains, while B1 and B2 recognize only two each. FIG. 7B illustrates an iterative method whereby new recognition units are chosen based on polypeptides uncovered with the first recognition unit(s). These new recognition units lead to the identification of other related polypeptides, etc., expanding the scope of the study to increasingly diverse members of the related population.

FIG. 8 illustrates the binding specificity of several SH3 domain recognition units. Biotinylated Class I (pSrcCI) or Class II (pSrcCII) Src SH3 domain recognition units, Crk SH3 domain recognition units (pCrk), PLCγ SH3 domain recognition units (pPLC), and Abl SH3 domain recognition units (pAbl) were tested for binding to the indicated GST-SH3 domain fusion proteins immobilized onto duplicate microtiter plate wells. Recognition units are listed along the left side of the figure; GST-SH3 domain fusion proteins are listed along the bottom. Recognition units were incubated either as multivalent complexes of biotinylated peptides and streptavidin-horseradish peroxidase (SA-HRP) (complexed) or as monovalent biotinylated peptides (uncomplexed), followed by incubation with SA-HRP. Average optical densities are shown.

FIG. 9 shows a schematic of SH3-domain containing proteins isolated using the present invention. The name, identity, type of screen, and number of individual clones derived for each sequence are indicated. Diagrams are to scale, with SH3 domains representing approximately 60 amino acids. The abbreviations AR, P, CR, E/P, and SH2 represent ankyrin repeats, proline-rich segments, Cortactin repeats, glutamate/proline-rich segments, and Src homology 2 domains, respectively. Flared ends represent putative translation initiation sites for individual cDNAs. The Mouse, Human 1, and Human 2 libraries correspond to mouse 16 day embryo, human bone marrow, and human prostate cancer cDNA libraries, respectively. For a description of the pSrcII and pCort recognition units, see Section 6.1.

FIGS. 10A and 10B depicts the sequence alignment of SH3 domains in proteins isolated using the present invention. The name and identity of each clone is indicated. Where appropriate, multiple SH3 domains from the same polypeptide are designated A, B, C, etc., from N- to C-terminal. Periods indicate gaps introduced to maximize alignment of similar residues. Positions corresponding to conserved residues shown to be involved in ligand binding in the SH3 domains of Src and Grb2/Sem5 (Tomasetto et al., 1995, Genomics 28:367–376) are presented in bold and underlined, respectively. Primary structures of SH3P1-8 and SH3P10-13 correspond to mouse, SH3P15-18, clone 5, 34, 40, 41, 45, 53, 55, 56, and 65 to human, and SH3P9 and SH3P14 to mouse (m) or human (h) cDNA clones. For sequence comparison, the sequence of the mouse c-Src SH3 domain (GenBank accession number P41240) is shown. The GenBank accession numbers for mouse Cortactin, SPY75/HS1, Crk, and human MLN50, Lyn, Fyn, and Src are U03184, D42120, S72408, X82456, M16038, P06241, and P41240, respectively. The amino acid sequences shown are SEQ ID NOs:112–140.

FIG. 11 depicts the specificity continuum described in Section 5.2.1. "SA-AP peptide complex" represents the multivalent (believed to be tetravalent) complex of streptavidin-alkaline phosphatase and biotinylated peptide described in that section.

FIG. 12 depicts the results of experiments in which peptide recognition units were synthesized and tested for their ability to bind to novel SH3 domains described in Sections 6.1 and 6.1.1. A minus indicates no binding; a plus indicates binding, with the number of pluses indicating the strength of binding. For further details, see Section 6.2. The amino acid sequences shown are SEQ ID NOs:141–168.

FIG. 13 depicts more data from the experiment depicted in FIG. 12. The amino acid sequences shown are SEQ ID NOs:169–188.

Figure 17:
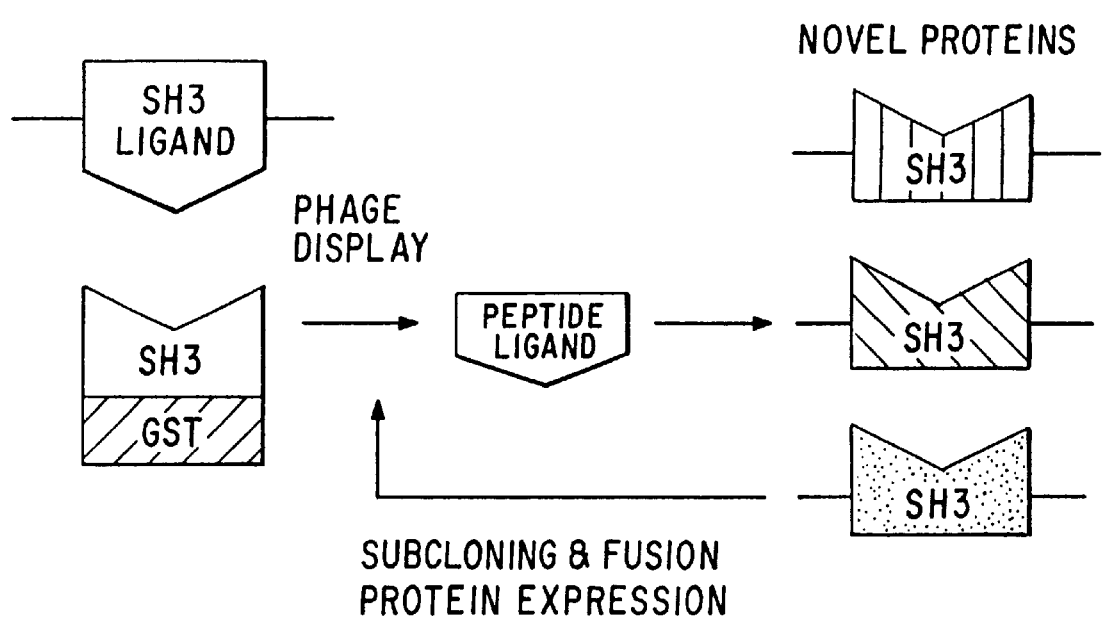

FIG. 17 illustrates a strategy for exhaustively screening an expression library for SH3 domain-containing proteins. A peptide recognition unit is generated by screening a combinatorial peptide library for binders to an SH3 domain espressed bacterially as a GST fusion protein. This peptide is then used as a multivalent streptavidin-biotinylated peptide complex to screen for a subset of the SH3 domain-containing proteins represented in a cDNA expression library. A combinatorial library is once again used to identify recognition units of SH3 domains identified in the first expression library screen; these recognition units identify overlapping sets of proteins from the expression library. With multiple iterations of this process, it should be possible to clone systematically all SH3 domains represented in a given cDNA expression library.

FIG. 18 depicts the nucleotide sequence of SH3P1, mouse p53bp2 (SEQ ID NO:5).

FIG. 19 depicts the amino acid sequence of SH3P1, mouse p53bp2 (SEQ ID NO:6).

FIG. 20 depicts the nucleotide sequence of SH3P2, a novel mouse gene (SEQ ID NO:7).

FIG. 21 depicts the amino acid sequence of SH3P2, a novel mouse gene (SEQ ID NO:8).

FIG. 22 depicts the nucleotide sequence of SH3P3, a novel mouse gene (SEQ ID NO:9).

FIG. 23 depicts the amino acid sequence of SH3P3, a novel mouse gene (SEQ ID NO:10).

FIG. 24 depicts the nucleotide sequence of SH3P4, a novel mouse gene (SEQ ID NO:11).

FIG. 25 depicts the amino acid sequence of SH3P4, a novel mouse gene (SEQ ID NO:12).

FIG. 26 depicts the nucleotide sequence of SH3P5, mouse Cortactin (SEQ ID NO:13).

FIG. 27 depicts the amino acid sequence of SH3P5, mouse Cortactin (SEQ ID NO:14).

FIG. 28 depicts the nucleotide sequence of SH3P6, mouse MLN50 (SEQ ID NO:15).

FIG. 29 depicts the amino acid sequence of SH3P6, mouse MLN50 (SEQ ID NO:16).

FIG. 30 depicts the nucleotide sequence of SH3P7, a novel mouse gene (SEQ ID NO:17).

FIG. 31 depicts the amino acid sequence of SH3P7, a novel mouse gene (SEQ ID NO:18).

FIG. 32 depicts the nucleotide sequence of SH3P8, a novel mouse gene (SEQ ID NO:19).

FIG. 33 depicts the amino acid sequence of SH3P8, a novel mouse gene (SEQ ID NO:20).

FIG. 34 depicts the nucleotide sequence of SH3P9, a novel mouse gene (SEQ ID NO:21).

FIG. 35 depicts the amino acid sequence of SH3P9, a novel mouse gene (SEQ ID NO:22).

FIG. 36 depicts the nucleotide sequence of SH3P9, a novel human gene (SEQ ID NO:23).

FIG. 37 depicts the amino acid sequence of SH3P9, a novel human gene (SEQ ID NO:24).

FIG. 38 depicts the nucleotide sequence of SH3P10, mouse HS1 (SEQ ID NO:25).

FIG. 39 depicts the amino acid sequence of SH3P10, mouse HS1 (SEQ ID NO:26).

FIG. 40 depicts the nucleotide sequence of SH3P11, mouse Crk (SEQ ID NO:27).

FIG. 41 depicts the amino acid sequence of SH3P11, mouse Crk (SEQ ID NO:28).

FIG. 42A depicts the nucleotide sequence from positions 1–2600 of SH3P12, a novel mouse gene (a portion of SEQ ID NO:29).

FIG. 42B depicts the nucleotide sequence from positions 2601–3335 of SH3P12, a novel mouse gene (a portion of SEQ ID NO:29).

FIG. 43 depicts the amino acid sequence of SH3P12, a novel mouse gene (SEQ ID NO:30).

FIG. 44 depicts the nucleotide sequence of SH3P13, a novel mouse gene (SEQ ID NO:31).

FIG. 45 depicts the amino acid sequence of SH3P13, a novel mouse gene (SEQ ID NO:32).

FIG. 46A depicts the nucleotide sequence from positions 1–2400 of SH3P14, mouse H74 (a portion of SEQ ID NO:33).

FIG. 46B depicts the nucleotide sequence from positions 2351–4091 of SH3P14, mouse H74 (a portion of SEQ ID NO:33).

FIG. 47 depicts the amino acid sequence of SH3P14, mouse H74 (SEQ ID NO:34).

FIG. 48 depicts the nucleotide sequence of SH3P14, human H74 (SEQ ID NO:35).

FIG. 49 depicts the amino acid sequence of SH3P14, human H74 (SEQ ID NO:36).

FIG. 50 depicts the nucleotide sequence of SH3P17, a novel human gene (SEQ ID NO:37).

FIG. 51 depicts the amino acid sequence of SH3P17, a novel human gene (SEQ ID NO:38).

FIG. 52A depicts the nucleotide sequence of SH3P18, a novel human gene (SEQ ID NO:39).

FIG. 53 depicts the amino acid sequence of SH3P18, a novel human gene (SEQ ID NO:40).

FIG. 54 depicts the nucleotide sequence of clone 55, a novel human gene (SEQ ID NO:189).

FIG. 55 depicts the amino acid sequence of clone 55, a novel human gene (SEQ ID NO:190).

FIG. 56 depicts the nucleotide sequence of clone 56, a novel human gene (SEQ ID NO:191).

FIG. 57 depicts the amino acid sequence of clone 56, a novel human gene (SEQ ID NO:192).

FIG. 58A depicts the nucleotide sequence from position 1–1720 of clone 65, a novel human gene (a portion of SEQ ID NO:193).

FIG. 58B depicts the nucleotide sequence from position 1721–2873 of clone 65, a novel human gene (a portion of SEQ ID NO:193).

FIG. 59 depicts the amino acid sequence of clone 65, a novel human gene (SEQ ID NO:194).

FIG. 60 depicts the nucleotide sequence of clone 34, a novel human gene (SEQ ID NO:195).

FIG. 61A depicts a portion of the amino acid sequence of clone 34, a novel human gene (a portion of SEQ ID NO:196).

FIG. 61B depicts a portion of the amino acid sequence of clone 34, a novel human gene (a portion of SEQ ID NO:196).

FIG. 62 depicts the nucleotide sequence of clone 41, a novel human gene (SEQ ID NO:197).

FIG. 63A depicts a portion of the amino acid sequence of clone 41, a novel human gene (a portion of SEQ ID NO:198).

FIG. 63B depicts a portion of the amino acid sequence of clone 41, a novel human gene (a portion of SEQ ID NO:198).

FIG. 64A depicts the nucleotide sequence of clone 53, a novel human gene (SEQ ID NO:199).

FIG. 65A depicts a portion of the amino acid sequence of clone 53, a novel human gene (a portion of SEQ ID NO:200).

FIG. 65B depicts a portion of the amino acid sequence of clone 53, a novel human gene (a portion of SEQ ID NO:200).

FIGS. 66A and 66B depicts the nucleotide sequence (SEQ ID NO:220) and amino acid sequence (SEQ ID NO:221) of clone 5, a novel human gene.

5. DETAILED DESCRIPTION OF THE INVENTION

As stated above, the present invention is related broadly to certain polypeptides having a functional domain of interest and is directed to methods of identifying and using these polypeptides. The present invention is also directed to a method of using isolated, operationally defined ligands involved in binding interactions for optimally identifying an exhaustive set of compounds binding such ligands and to compounds, target molecules, and, in one embodiment, polypeptides having a functional domain of interest and to methods of using these compounds. The detailed description that follows is provided to elucidate the invention further and to assist further those of ordinary skill who may be interested in practicing particular aspects of the invention.

First, certain definitions are in order. Accordingly, the term "polypeptide" refers to a molecule comprised of amino acid residues joined by peptide (i.e., amide) bonds and includes proteins and peptides. Hence, the polypeptides of the present invention may have single or multiple chains of covalently linked amino acids and may further contain intrachain or interchain linkages comprised of disulfide bonds. Some polypeptides may also form a subunit of a multiunit macromolecular complex. Naturally, the polypeptides can be expected to possess conformational preferences and to exhibit a three-dimensional structure. Both the conformational preferences and the three-dimensional structure will usually be defined by the polypeptide's primary (i.e., amino acid) sequence and/or the presence (or absence) of disulfide bonds or other covalent or non-covalent intrachain or interchain interactions.

The polypeptides of the present invention can be any size. As can be expected, the polypeptides can exhibit a wide variety of molecular weights, some exceeding 150 to 200 kilodaltons (kD). Typically, the polypeptides may have a molecular weight ranging from about 5,000 to about 100,000 daltons. Still others may fall in a narrower range, for example, about 10,000 to about 75,000 daltons, or about 20,000 to about 50,000 daltons.

The phrase "functional domain" refers to a region of a polypeptide which affords the capacity to perform a particular function of interest. This function may give rise to a biological, chemical, or physiological consequence that may be reversible or irreversible and which may include, but not be limited to, protein-protein interactions (e.g., binding interactions) involving the functional domain, a change in the conformation or a transformation into a different chemical state of the functional domain or of molecules acted upon by the functional domain, the transduction of an intracellular or intercellular signal, the regulation of gene or protein expression, the regulation of cell growth or death, or the activation or inhibition of an immune response. Furthermore, the functional domain of interest is defined by a particular functional domain that is present in a given target molecule. A discussion of the selection of a particular functional domain-containing target molecule is presented further below.

Many functional domains tend to be modular in that such domains may occur one or more times in a given polypeptide (or target molecule) or may be found in a family of different polypeptides. When found more than once in a given polypeptide or in different polypeptides, the modular functional domain may possess substantially the same structure, in terms of primary sequence and/or three-dimensional space, or may contain slight or great variations or modifications among the different versions of the functional domain of interest.

What is important, however, is that these related functional domains retain the functional aspects of the functional domain of interest present in the target molecule. It is stressed that, indeed, it is this functional relationship among two or more possible versions of a functional domain of interest which may be identified, defined, and exploited by the methods of the present invention. In a preferred aspect, the function of interest is the ability to bind to a molecule (e.g., a peptide) of interest.

The present invention provides a general strategy by which recognition units that bind to a functional domain-containing molecule can be used to screen expression libraries of genes (e.g., cDNA, genomic libraries) systematically for novel functional domain-containing proteins. In specific embodiments, the recognition units are prior isolated from a random peptide library, or are known peptide ligands or recognition units, or are recognition units that are identified by database searches for sequences having homology to a peptide recognition unit having the binding specificity of interest. Using the methods of the present invention, it is possible to exhaustively screen an expression library for proteins with a given functional domain.

In the prior art, novel genes (and thus their encoded protein products) are most commonly identified from cDNA libraries. Generally, an appropriate cDNA library is screened with a probe that is either an oligonucleotide or an antibody. In either case, the probe must be specific enough for the gene that is to be identified to pick that gene out from a vast background of non-relevant genes in the library. It is this need for a specific probe that is the highest hurdle that must be overcome in the prior art identification of novel genes. Another method of identifying genes from cDNA libraries is through use of the polymerase chain reaction (PCR) to amplify a segment of a desired gene from the library. PCR requires that oligonucleotides having sequence similarity to the desired gene be available.

If the probe used in prior art methods is a nucleic acid, the cDNA library may be screened without the need for expressing any protein products that might be encoded by the cDNA clones. If the probe used in prior art methods is an antibody, then it is necessary to build the cDNA library into a suitable expression vector. For a comprehensive discussion of the art of identifying genes from cDNA libraries, see Sambrook, Fritsch, and Maniatis, "Construction and Analysis of cDNA Libraries," Chapter 8 in Cloning, A Laboratory Manual, 2d ed., Cold Spring Harbor Laboratory Press, 1989. See also Sambrook, Fritsch, and Maniatis, "Screening Expression Libraries with Antibodies and Oligonucleotides," Chapter 12 in Cloning, A Laboratory Manual, 2d ed., Cold Spring Harbor Laboratory Press, 1989.

As an alternative to cDNA libraries, genomic libraries are used. When genomic libraries are used in prior art methods, the probe is virtually always a nucleic acid probe. See Sambrook, Fritsch, and Maniatis, "Analysis and Cloning of Eukaryotic Genomic DNA," Chapter 9 in Cloning, A Laboratory Manual, 2d ed., Cold Spring Harbor Laboratory Press, 1989.

In the prior art, nucleic acid probes used in screening libraries are often based upon the sequence of a known gene that is thought to be homologous to a gene that it is desired to isolate. The success of the procedure depends upon the degree of homology between the probe and the target gene being sufficiently high. Probes based upon the sequences of known functional domains in proteins had limited value because, while the sequences of the functional domains were similar enough to allow for their recognition as shared domains, the similarity was not so high that the probes could be used to screen cDNA or genomic libraries for genes containing the functional domains.

PCR may also be used to identify genes from genomic libraries. However, as in the case of using PCR to identify genes from cDNA libraries, this requires that oligonucleotides having sequence similarity to the desired gene be available.

Using the screening methods provided by the present invention, DNA encoding proteins having a desired functional domain that would not be readily identified by sequence homology can be identified by functional binding specificity to recognition units. By virtue of an ease in specificity of binding requirements conferred by the screening methods of the present invention, many novel, functionally homologous, functional domain-containing proteins can be identified. Although not intending to be bound by any mechanistic explanation, this ease in binding specificity is believed to be the result of the use of a multivalent peptide recognition unit used to screen the gene library, preferably of a valency greater than bivalent, more preferably tetravalent or greater, and most preferably the streptavidin-biotinylated peptide recognition unit complex.

In one particular embodiment of the invention, exhaustive screening of proteins having a desired functional domain involves an iterative process by which recognition units for SH3 domains identified in the first round of screening are used to detect SH3 domain-containing proteins in successive expression library screens (see FIG. 17). This strategy enables one to search "sequence space" in what might be thought of as ever-widening circles with each successive cycle. This iterative strategy can be initiated even when only one functional domain-containing protein and recognition unit are available.

This iterative process is not limited to proteins containing SH3 domains. Members within a class of other functional domains also tend to have overlapping, or at least similar recognition unit preferences, are structurally stable, and often confer similar binding properties to a wide variety of proteins. These characteristics predict that the methods of the present invention will be applicable to a wide variety of functional domain-containing proteins in addition to their applicability to SH3 domain-containing proteins.

5.1 Discovery of Novel Genes and Polypeptides Containing Functional Domains

The present invention provides methods for the identification of one or more polypeptides (in particular, a "family" of polypeptides, including the target molecule) that contains a functional domain of interest that either corresponds to or is the functional equivalent of a functional domain of interest present in a predetermined target molecule.

The present invention provides a mechanism for the rapid identification of genes (e.g., cDNAs) encoding virtually any functional domain of interest. By screening cDNA libraries or other sources of polypeptides for recognition unit binding rather than sequence similarity, the present invention circumvents the limitations of conventional DNA-based screening methods and allows for the identification of highly disparate protein sequences possessing equivalent functional activities. The ability to isolate entire repertoires of proteins containing particular modular functional domains will prove invaluable both in molecular biological investigations of the genome and in bringing new targets into drug discovery programs.

It should likewise be apparent that a wide range of polypeptides having a functional domain of interest can be identified by the process of the invention, which process comprises:
 (a) contacting a multivalent recognition unit complex with a plurality of polypeptides; and
 (b) identifying a polypeptide having a selective binding affinity for said recognition unit complex.

In a specific embodiment, the process comprises:
 (a) contacting a multivalent recognition unit complex with a plurality of polypeptides from which it is desired to identify a polypeptide having selective binding affinity for the recognition unit, in which the valency of the recognition unit in the complex is at least two, or at least four; and
 (b) identifying, and preferably recovering, a polypeptide having a selective binding affinity for the recognition unit complex.

In another specific embodiment, the process comprises a method of identifying at least one polypeptide comprising a functional domain of interest, said method comprising:
 (a) contacting one or more multivalent recognition unit complexes with a plurality of polypeptides; and
 (b) identifying at least one polypeptide having selective binding affinity for at least one of said recognition unit complexes.

In another specific embodiment, the process comprises:
 (a) contacting a multivalent recognition unit complex, which complex comprises (i) avidin or streptavidin, and (ii) biotinylated recognition units, with a plurality of polypeptides from a cDNA expression library, in which the recognition unit is a peptide having in the range of 6 to 60 amino acid residues; and
 (b) identifying a polypeptide having a selective binding affinity for said recognition unit complex.

In another specific embodiment, the process comprises a method of identifying a polypeptide having an SH3 domain of interest comprising:
 (a) contacting a multivalent recognition unit complex, which complex comprises (i) avidin or streptavidin, and (ii) biotinylated recognition units, with a plurality of polypeptides from a cDNA expression library, in which the recognition unit is a peptide having in the range of 6 to 60 amino acid residues and which selectively binds an SH3 domain; and
 (b) identifying a polypeptide having a selective binding affinity for said recognition unit complex.

In another specific embodiment, the process comprises a method of identifying a polypeptide having a functional domain of interest or a functional equivalent thereof comprising:
 (a) screening a random peptide library to identify a peptide that selectively binds a functional domain of interest; and
 (b) screening a cDNA or genomic expression library with said peptide or a binding portion thereof to identify a polypeptide that selectively binds said peptide.

In a specific embodiment of the above method, the screening step (b) is carried out by use of said peptide in the form of multiple antigen peptides (MAP) or by use of said peptide cross-linked to bovine serum albumin or keyhole limpet hemocyanin.

In another specific embodiment, the process comprises a method of identifying a polypeptide having a functional domain of interest or a functional equivalent thereof comprising:
 (a) screening a random peptide library to identify a plurality of peptides that selectively bind a functional domain of interest;
 (b) determining at least part of the amino acid sequences of said peptides;
 (c) determining a consensus sequence based upon the determined amino acid sequences of said peptides; and
 (d) screening a cDNA or genomic expression library with a peptide comprising the consensus sequence to identify a polypeptide that selectively binds said peptide.

In another specific embodiment, the process comprises a method of identifying a polypeptide having a functional domain of interest or a functional equivalent thereof comprising:
 (a) screening a random peptide library to identify a first peptide that selectively binds a functional domain of interest;
 (b) determining at least part of the amino acid sequence of said first peptide;
 (c) searching a database containing the amino acid sequences of a plurality of expressed natural proteins to identify a protein containing an amino acid sequence homologous to the amino acid sequence of said first peptide; and
 (d) screening a cDNA or genomic expression library with a second peptide comprising the sequence of said protein that is homologous to the amino acid sequence of said first peptide.

The identified polypeptide identified by the above-described methods thus should contain the functional domain of interest or a functional equivalent thereof (that is, having a functional domain that is identical, or having a functional domain that differs in sequence but is capable of binding to the same recognition unit). In a particular embodiment, the polypeptide identified is a novel polypeptide. In a preferred embodiment, the recognition unit that is used to form the multvalent recognition unit complex is isolated or identified from a random peptide library.

In a specific embodiment, the present invention provides amino acid sequences and DNA sequences encoding novel proteins containing SH3 domains. The SH3 domains vary in sequence but retain binding specificity to an SH3 domain recognition unit. Also provided are fragments and derivatives of the novel proteins containing SH3 domains as well as DNA sequences encoding the same. It will be apparent to one of ordinary skill in the art that also provided are proteins that vary slightly in sequence from the novel proteins by virtue of conservative amino acid substitutions. It will also be apparent to one of ordinary skill in the art that the novel proteins may be expressed recombinantly by standard methods. The novel proteins may also be expressed as fusion proteins with a variety of other proteins, e.g., glutathione S-transferase.

The present invention provides a purified polypeptide comprising an SH3 domain, said SH3 domain having an amino acid sequence selected from the group consisting of: SEQ ID NOs: 113–115, 118–121, 125–128, 133–139, 204–218, and 219. Also provided is a purified DNA encoding the polypeptide.

Also provided is a purified polypeptide comprising an SH3 domain, said polypeptide having an amino acid sequence selected from the group consisting of SEQ ID NOs: 8, 10, 12, 18, 20, 22, 24, 30, 32, 38, 40, 190, 192, 194, 196, 198, 200, and 221. Also provided is a purified DNA encoding the polypeptide.

Also provided is a purified DNA encoding an SH3 domain, said DNA having a sequence selected from the group consisting of SEQ ID NOs: 7, 9, 11, 17, 19, 21, 23, 29, 31, 37, 39, 189, 191, 193, 195, 197, 199, and 220. Also provided is a nucleic acid vector comprising this purified DNA. Also provided is a recombinant cell containing this nucleic acid vector.

Also provided is a purified DNA encoding a polypeptide having an amino acid sequence selected from the group consisting of: SEQ ID NOs: 8, 10, 12, 18, 20, 22, 24, 30, 32, 38, 40, 190, 192, 194, 196, 198, 200, and 221. Also provided is a nucleic acid vector comprising this purified DNA. Also provided is a recombinant cell containing this nucleic acid vector.

Also provided is a purified DNA encoding a polypeptide comprising an amino acid sequence selected from the group consisting of: SEQ ID NOs:113–115, 118–121, 125–128, 133–139, 204–218, and 219. Also provided is a nucleic acid vector comprising this purified DNA. Also provided is a recombinant cell containing this nucleic acid vector.

Also provided is a purified molecule comprising an SH3 domain of a polypeptide having an amino acid sequence selected from the group consisting of: SEQ ID NO: 8, 10, 12, 18, 20, 22, 24, 30, 32, 38, 40, 190, 192, 194, 196, 198, 200, and 221.

Also provided is a fusion protein comprising (a) an amino acid sequence comprising an SH3 domain of a polypeptide having the amino acid sequence of SEQ ID NO: 8, 10, 12, 18, 20, 22, 24, 30, 32, 38, 40, 190, 192, 194, 196, 198, 200, and 221 joined via a peptide bond to (b) an amino acid sequence of at least six, or ten, or twenty amino acids from a different polypeptide. Also provided is a purified DNA encoding the fusion protein. Also provided is a nucleic acid vector comprising the purified DNA encoding the fusion protein. Also provided is a recombinant cell containing this nucleic acid vector. Also provided is a method of producing this fusion protein comprising culturing a recombinant cell containing a nucleic acid vector encoding said fusion protein such that said fusion protein is expressed, and recovering the expressed fusion protein.

The present invention also provides a purified nucleic acid hybridizable to a nucleic acid having a sequence selected from the group consisting of: SEQ ID NOs: 7, 9, 11, 17, 19, 21, 23, 29, 31, 37, 39, 189, 191, 193, 195, 197, 199, and 220.

The present invention also provides antibodies to a polypeptide having an amino acid sequence selected from the group consisting of: SEQ ID NOs:113–115, 118–121, 125–128, 133–139, 204–218, and 219.

The present invention also provides antibodies to a polypeptide having an amino acid sequence selected from the group consisting of SEQ ID NOs: 8, 10, 12, 18, 20, 22, 24, 30, 32, 38, 40, 190, 192, 194, 196, 198, 200, and 221.

It is demonstrated by way of example herein that recognition units that comprise SH3 domain ligands derived from combinatorial peptide libraries may be used in the methods of the present invention as probes for the rapid discovery of novel proteins containing SH3 functional domains. The methods of the present invention require no prior knowledge of the characteristics of a SH3 domain's natural cellular ligand to initiate the process of discovery. One needs only enough purified SH3 domain-containing protein (by way of example, 1–5 µg) to select peptides from a random peptide library. In addition, because the methods of the present invention identify novel proteins from cDNA expression libraries based only on their binding properties, low primary sequence identity between the target SH3 domain and the SH3 domains of the novel proteins discovered need not be a limitation, provided some functional similarity between these SH3 domains is conserved. Also, the methods of the present invention are rapid, require inexpensive reagents, and employ simple and well established laboratory techniques.

Using these methods, more than eighteen different SH3 domain-containing proteins have been identified, over half of which have not been previously described. While certain of these previously unknown proteins are clearly related to known genes such as amphiphysin and drebrin, others constitute new classes of signal transduction and/or cytoskeletal proteins. These include SH3P17 and SH3P18, two members of a new family of adaptor-like proteins comprised of multiple SH3 domains; SH3P12, a novel protein with three SH3 domains and a region similar to the extracellular peptide hormone sorbin; and SH3P4, SH3P8, and SH3P13, three members of a third new family of SH3-containing proteins. These novel proteins are described more fully in Sections 6.1 and 6.1.1. The high incidence of novel proteins identified by the methods of the present invention indicates that a large number of SH3 domain-containing proteins remain to be discovered by application of the methods of the invention.

One of ordinary skill in the art would recognize that the above-described novel proteins need not be used in their entirety in the various applications of those proteins described herein. In many cases it will be sufficient to employ that portion of the novel protein that contains the functional (e.g., SH3) domain. Such exemplary portions of SH3 domain-containing proteins are shown in FIGS. 10A and 10B. Accordingly, the present invention provides derivatives (e.g., fragments and molecules comprising these fragments) of novel proteins that contain SH3 domains, e.g., as shown in FIGS. 10A and 10B. Nucleic acids encoding these fragments or other derivatives are also provided.

In another embodiment, the present invention includes a method of identifying one or more novel polypeptides having an SH3 domain, said method comprising:

(a) identifying a recognition unit having a selective affinity for the SH3 domain by screening a peptide library with the SH3 domain;

(b) producing said recognition unit;
(c) contacting said recognition unit with a source of polypeptides; and
(d) identifying one or more novel polypeptides having a selective affinity for said recognition unit, which polypeptides comprise the SH3 domain.

5.1.1 Functional Domains

Functional domains of interest in the practice of the present invention can take many forms and may perform a variety of functions. For example, such functional domains may be involved in a number of cellular, biochemical, or physiological processes, such as cellular signal transduction, transcriptional regulation, translational regulation, cell adhesion, migration or transport, cytokine secretion and other aspects of the immune response, and the like. In particular embodiments of the present invention, the functional domains of interest may consist of regions known as SH1, SH2, SH3, PH, PTB, LIM, armadillo, and Notch/ankyrin repeat. See, e.g., Pawson, 1995, Nature 373:573–580; Cohen et al., 1995, Cell 80:237–248. Functional domains may also be chosen from among regions known as zinc fingers, leucine zippers, and helix-turn-helix or helix-loop-helix. Certain functional domains may be binding domains, such as DNA-binding domains or actin-binding domains. Still other functional domains may serve as sites of catalytic activity.

In one embodiment of the invention, a suitable target molecule containing the chosen functional domain of interest is selected. In the case of an SH3 domain, for example, a number of proteins (or functional domain-containing derivatives or analogs thereof) may be selected as the target molecule, including but not limited to, the Src family of proteins: Fyn, Lck, Lyn, Src, or Yes. Still other proteins contain an SH3 domain and can be used, including, but not limited to: Abl, Crk, Nck (other oncogenes), Grb2, PLCγ, RasGAP (proteins involved in signal transduction), ABP-1, myosin-1, spectrin (proteins found in the cytoskeleton), and neutrophil NADPH oxidase (an enzyme). In the case of a catalytic site, any catalytically active protein, such as an enzyme, can be used, particularly one whose catalytic site is known. For example, the catalytic site of the protein glutathione S-transferase (GST) can be used. Other target molecules that possess catalytic activity may include, but are not limited to, protein serine/threonine kinases, protein tyrosine kinases, serine proteases, DNA or RNA polymerases, phospholipases, GTPases, ATPases, PI-kinases, DNA methylases, metabolic enzymes, or protein glycosylases.

5.1.2 Recognition Units

By the phrase "recognition unit," is meant any molecule having a selective affinity for the functional domain of the target molecule and, preferably, having a molecular weight of up to about 20,000 daltons. In a particular embodiment of the invention, the recognition unit has a molecular weight that ranges from about 100 to about 10,000 daltons.

Accordingly, preferred recognition units of the present invention possess a molecular weight of about 100 to about 5,000 daltons, preferably from about 100 to about 2,000 daltons, and most preferably from about 500 to about 1,500 daltons. As described further below, the recognition unit of the present invention can be a peptide, a carbohydrate, a nucleoside, an oligonucleotide, any small synthetic molecule, or a natural product. When the recognition unit is a peptide, the peptide preferably contains about 6 to about 60 amino acid residues.

When the recognition unit is a peptide, the peptide can have less than about 140 amino acid residues; preferably, the peptide has less than about 100 amino acid residues; preferably, the peptide has less than about 70 amino acid residues; preferably, the peptide has 20 to 50 amino acid residues; most preferably, the peptide has about 6 to 60 amino acid residues.

The peptide recognition units are preferably in the form of a multivalent peptide complex comprising avidin or streptavidin (optionally conjugated to a label such as alkaline phosphatase or horseradish peroxidase) and biotinylated peptides.

According to the present invention, a recognition unit (preferably in the form of a multvalent recognition unit complex) is used to screen a plurality of expression products of gene sequences containing nucleic acid sequences that are present in native RNA or DNA (e.g., cDNA library, genomic library).

The step of choosing a recognition unit can be accomplished in a number of ways that are known to those of ordinary skill, including but not limited to screening cDNA libraries or random peptide libraries for a peptide that binds to the functional domain of interest. See, e.g., Yu et al., 1994, Cell 76, 933–945; Sparks et al., 1994, J. Biol. Chem. 269, 23853–23856. Alternatively, a peptide or other small molecule or drug may be known to those of ordinary skill to bind to a certain target molecule and can be used. The recognition unit can even be synthesized from a lead compound, which again may be a peptide, carbohydrate, oligonucleotide, small drug molecule, or the like. The recognition unit can also be identified for use by doing searches (preferably via database) for molecules having homology for other, known recognition unit(s) having the ability to selectively bind to the functional domain of interest.

In a specific embodiment, the step of selecting a recognition unit for use can be effected by, e.g., the use of diversity libraries, such as random or combinatorial peptide or nonpeptide libraries, which can be screened for molecules that specifically bind to the functional domain of interest, e.g., an SH3 domain. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, R. B., et al., 1992, J. Mol. Biol. 227:711–718); Lenstra, 1992, J. Immunol. Meth. 152:149–157; Kay et al., 1993, Gene 128:59–65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

By way of examples of nonpeptide libraries, a benzodiazepine library (see e.g., Bunin et al., 1994, Proc. Natl. Acad. Sci. USA 91:4708–4712) can be adapted for use.

Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

The variety of non-peptide libraries that are useful in the present invention is great. For example, Ecker and Crooke, 1995, Bio/Technology 13:351–360 list benzodiazapines, hydantoins, piperazinediones, biphenyls, sugar analogs, β-mercaptoketones, arylacetic acids, acylpiperidines, benzopyrans, cubanes, xanthines, aminimides, and oxazolones as among the chemical species that form the basis of various libraries.

Non-peptide libraries can be classified broadly into two types: decorated monomers and oligomers. Decorated monomer libraries employ a relatively simple scaffold structure upon which a variety of functional groups is added. Often the scaffold will be a molecule with a known useful pharmacological activity. For example, the scaffold might be the benzodiazapine structure.

Non-peptide oligomer libraries utilize a large number of monomers that are assembled together in a ways that create new shapes that depend on the order of the monomers. Among the monomer units that have been used are carbamates, pyrrolinones, and morpholinos. Peptoids, peptide-like oligomers in which the side chain is attached to the a amino group rather than the α carbon, form the basis of another version of non-peptide oligomer libraries. The first non-peptide oligomer libraries utilized a single type of monomer and thus contained a repeating backbone. Recent libraries have utilized more than one monomer, giving the libraries added flexibility.

Screening the libraries can be accomplished by any of a variety of commonly known methods. See, e.g., the following references, which disclose screening of peptide libraries: Parmley and Smith, 1989, Adv. Exp. Med. Biol. 251:215–218; Scott and Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. Nos. 5,096,815, 5,223,409, and 5,198,346, all to Ladner et al.; Rebar and Pabo, 1993, Science 263:671–673; and PCT Publication No. WO 94/18318.

In a specific embodiment, screening to identify a recognition unit can be carried out by contacting the library members with an SH3 domain immobilized on a solid phase and harvesting those library members that bind to the SH3 domain. Examples of such screening methods, termed "panning" techniques are described by way of example in Parmley and Smith, 1988, Gene 73:305–318; Fowlkes et al., 1992, BioTechniques 13:422–427; PCT Publication No. WO 94/18318; and in references cited hereinabove.

In another embodiment, the two-hybrid system for selecting interacting proteins in yeast (Fields and Song, 1989, Nature 340:245–246; Chien et al., 1991, Proc. Natl. Acad. Sci. USA 88:9578–9582) can be used to identify recognition units that specifically bind to SH3 domains.

Where the recognition unit is a peptide, the peptide can be conveniently selected from any peptide library, including random peptide libraries, combinatorial peptide libraries, or biased peptide libraries. The term "biased" is used herein to mean that the method of generating the library is manipulated so as to restrict one or more parameters that govern the diversity of the resulting collection of molecules, in this case peptides.

Thus, a truly random peptide library would generate a collection of peptides in which the probability of finding a particular amino acid at a given position of the peptide is the same for all 20 amino acids. A bias can be introduced into the library, however, by specifying, for example, that a lysine occur every fifth amino acid or that positions 4, 8, and 9 of a decapeptide library be fixed to include only arginine. Clearly, many types of biases can be contemplated, and the present invention is not restricted to any particular bias. Furthermore, the present invention contemplates specific types of peptide libraries, such as phage-displayed peptide libraries and those that utilize a DNA construct comprising a lambda phage vector with a DNA insert.

As mentioned above, in the case of a recognition unit that is a peptide, the peptide may have about 6 to less than about 60 amino acid residues, preferably about 6 to about 25 amino acid residues, and most preferably, about 6 to about 15 amino acids. In another embodiment, a peptide recognition unit has in the range of 20–100 amino acids, or 20–50 amino acids. In the case of a bile acid receptor, for example, the recognition unit may be a bile acid, such as cholic acid or cholesterol, and may have a molecular weight of about 300 to about 600. If the functional domain relates to transcriptional control, the recognition unit may be a portion of a transcriptional factor, which may bind to a region of a gene of interest or to an RNA polymerase. The recognition unit may even be a nucleoside analog, such as cordycepin or the triphosphate thereof, capable of inhibiting RNA biosynthesis. The recognition unit may also be the carbohydrate portion of a glycoprotein, which may have a selective affinity for the asialoglycoprotein receptor, or the repeating glucan unit that exhibits a selective affinity for a cellulose binding domain or the active site of heparinase.

The selected recognition unit can be obtained by chemical synthesis or recombinant expression. It is preferably purified prior to use in screening a plurality of gene sequences.

5.1.3 Screening a Source of Polypeptides

After the recognition unit is chosen for use, the recognition unit is then contacted with a plurality of polypeptides, preferably containing a functional domain. In a particular embodiment of the invention, the plurality of polypeptides is obtained from a polypeptide expression library. The polypeptide expression library may be obtained, in turn, from cDNA, fragmented genomic DNA, and the like. In a specific embodiment, the library that is screened is a cDNA library of total poly A+ RNA of an organism, in general, or of a particular cell or tissue type or developmental stage or disease condition or stage. The expression library may utilize a number of expression vehicles known to those of ordinary skill, including but not limited to, recombinant bacteriophage, lambda phage, M13, a recombinant plasmid or cosmid, and the like.

The plurality of polypeptides or the DNA sequences encoding same may be obtained from a variety of natural or unnatural sources, such as a procaryotic or a eucaryotic cell, either a wild type, recombinant, or mutant. In particular, the plurality of polypeptides may be endogenous to microorganisms, such as bacteria, yeast, or fungi, to a virus, to an animal (including mammals, invertebrates, reptiles, birds, and insects) or to a plant cell.

In addition, the plurality of polypeptides may be obtained from more specific sources, such as the surface coat of a virion particle, a particular cell lysate, a tissue extract, or they may be restricted to those polypeptides that are expressed on the surface of a cell membrane.

Moreover, the plurality of polypeptides may be obtained from a biological fluid, particularly from humans, including but not limited to blood, plasma, serum, urine, feces, mucus, semen, vaginal fluid, amniotic fluid, or cerebrospinal fluid. The plurality of polypeptides may even be obtained from a fermentation broth or a conditioned medium, including all the polypeptide products secreted or produced by the cells previously in the broth or medium.

The step of contacting the recognition unit with the plurality of polypeptides may be effected in a number of ways. For example, one may contemplate immobilizing the recognition unit on a solid support and bringing a solution of the plurality of polypeptides in contact with the immobilized recognition unit. Such a procedure would be akin to an affinity chromatographic process, with the affinity matrix being comprised of the immobilized recognition unit. The polypeptides having a selective affinity for the recognition unit can then be purified by affinity selection. The nature of the solid support, process for attachment of the recognition unit to the solid support, solvent, and conditions of the affinity isolation or selection procedure would depend on the type of recognition unit in use but would be largely conventional and well known to those of ordinary skill in the art. Moreover, the valency of the recognition unit in the recognition unit complex used to screen the polypeptides is believed to affect the specificity of the screening step, and thus the valency can be chosen as appropriate in view of the desired specificity (see Sections 5.2 and 5.2.1).

Alternatively, one may also separate the plurality of polypeptides into substantially separate fractions comprising individual polypeptides. For instance, one can separate the plurality of polypeptides by gel electrophoresis, column chromatography, or like method known to those of ordinary skill for the separation of polypeptides. The individual polypeptides can also be produced by a transformed host cell in such a way as to be expressed on or about its outer surface. Individual isolates can then be "probed" by the recognition unit, optionally in the presence of an inducer should one be required for expression, to determine if any selective affinity interaction takes place between the recognition unit and the individual clone. Prior to contacting the recognition unit with each fraction comprising individual polypeptides, the polypeptides can optionally first be transferred to a solid support for additional convenience. Such a solid support may simply be a piece of filter membrane, such as one made of nitrocellulose or nylon.

In this manner, positive clones can be identified from a collection of transformed host cells of an expression library, which harbor a DNA construct encoding a polypeptide having a selective affinity for the recognition unit. The polypeptide produced by the positive clone includes the functional domain of interest or a functional equivalent thereof. Furthermore, the amino acid sequence of the polypeptide having a selective affinity for the recognition unit can be determined directly by conventional means of amino acid sequencing, or the coding sequence of the DNA encoding the polypeptide can frequently be determined more conveniently by use of standard DNA sequencing methods. The primary sequence can then be deduced from the corresponding DNA sequence.

If the amino acid sequence is to be determined from the polypeptide itself, one may use microsequencing techniques. The sequencing technique may include mass spectroscopy.

In certain situations, it may be desirable to wash away any unbound recognition unit from a mixture of the recognition unit and the plurality of polypeptides prior to attempting to determine or to detect the presence of a selective affinity interaction (i.e., the presence of a recognition unit that remains bound after the washing step) Such a wash step may be particularly desirable when the plurality of polypeptides is bound to a solid support.

As can be anticipated, the degree of selective affinities observed varies widely, generally falling in the range of about 1 nm to about 1 mM. In preferred embodiments of the present invention, the selective affinity is on the order of about 10 nM to about 100 $\mu$M, more preferably on the order of about 100 nM to about 10 $\mu$M, and most preferably on the order of about 100 nM to about 1 $\mu$M.

5.2. Specificity of Recognition Units

A particular recognition unit may have fairly generic selectivity for a several members (e.g., three or four or more) of a "panel" of polypeptides having the domain of interest (or different versions of the domain of interest or functional equivalents of the domain of interest) or a fairly specific selectivity for only one or two, or possibly three, of the polypeptides among a "panel" of same. Furthermore, multiple recognition units, each exhibiting a range of selectivities among a "panel" of polypeptides can be used to identify an increasingly comprehensive set of additional polypeptides that include the functional domain of interest.

Hence, in a population of related polypeptides, the functional domains of interest of each member may be schematically represented by a circle. See, by way of example, FIG. 7A. The circle of one polypeptide may overlap with that of another polypeptide. Such overlaps may be few or numerous for each polypeptide. A particular recognition unit, A, may recognize or interact with a portion of the circle of a given polypeptide which does not overlap with any other circle. Such a recognition unit would be fairly specific to that polypeptide. On the other hand, a second recognition unit, B, may recognize a region of overlap between two or more polypeptides. Such a recognition unit would consequently be less specific than the recognition unit A and may be characterized as having a more generic specificity depending on the number of polypeptides that it recognizes or interacts with.

It should also be apparent to those of ordinary skill that any number of B-type recognition units ($B_1$, $B_2$, $B_3$, etc.) can be present, each recognizing different "panels" of polypeptides. Hence, the use of multiple recognition units provides an increasingly more exhaustive population of polypeptides, each of which exhibits a variation or evolution in the functional domain of interest present in the initial target molecule. It should also be apparent to one that the present method can be applied in an iterative fashion, such that the identification of a particular polypeptide can lead to the choice of another recognition unit. See, e.g., FIG. 7B. Use of this new recognition unit will lead, in turn, to the identification of other polypeptides that contain functional domains of interest that enhance the phenotypic and/or genotypic diversity of the population of "related" polypeptides.

Hence, with a given recognition unit, one may observe interaction with only one or two different polypeptides. With other recognition units, one may find three, four, or more selective interactions. In the situation in which only a single interaction is observed, it is likely, though not mandatory, that the selective affinity interaction is between the recognition unit and a replica of the initial target molecule (or a molecule very similar structurally and "functionally" to the initial target molecule).

5.2.1. Effect of the Presentation of the Recognition Unit Complex on the Specificity of the Recognition Unit-functional Domain Interaction The present inventors have found, unexpectedly, that the valency (i.e., whether it is a monomer, dimer, tetramer, etc.) of the recognition unit that is used to screen an expression library or other source of polypeptides apparently has a marked effect upon which genes or polypeptides are identified from the expression library or source of polypeptides. In particular, the specificity of the recognition unit-functional domain interaction appears to be affected by the valency of the recognition unit in the screening process. By this specificity is meant the selectivity in the functional domains to which the recognition unit will bind in the screening step.

As discussed above, in one embodiment, recognition units are obtained by screening a source of recognition units, e.g., a phage display library, for recognition units that bind to a particular target functional domain. Alternatively, database searches for recognition units with sequence homology to known recognition units can be employed. Of course, if a recognition unit for a particular target functional domain is already known, there is no need to screen a library or other source of recognition units; one can merely synthesize that particular recognition unit. The recognition unit, however obtained, is then used to screen an expression library or other source of polypeptides, to identify polypeptides that the recognition unit binds to. A recognition unit that identifies only its target functional domain is a recognition unit that is completely specific. A recognition unit that identifies one or two other polypeptides that do not contain identically the target functional domain, from among a plurality of polypeptides (e.g., of greater than $10^4$, $10^6$, or $10^8$ complexity), in addition to identifying a molecule comprising its target functional domain, is very or highly specific. A recognition unit that identifies most other polypeptides present that do not contain its target functional domain, in addition to identifying its target functional domain, is a non-specific recognition unit. In between very specific recognition units and non-specific recognition units, the present inventors have discovered that there are recognition units that recognize a small number of molecules having functional domains other than their target functional domains. These recognition units are said to have generic specificity.

Thus, there is a "specificity continuum", from completely and very specific through generic to non-specific, that a recognition unit may evince. See FIG. 11 for a depiction of this specificity continuum. The Applicants have discovered that a major factor influencing the specificity exhibited by a recognition unit appears to be the valency of the recognition unit in the complex used to screen the expression library.

Usually, high specificity is considered to be desirable when screening a library. High specificity is exhibited, e.g., by affinity purified polyclonal antisera which, in general, are very specific. Monoclonal antibodies are also very specific. Small peptides in monovalent form, on the other hand, generally give very weak, non-specific signals when used to screen a library; thus, they are considered to be non-specific.

The present inventors have discovered that recognition units in the form of small peptides, in multivalent form, have a specificity midway between the high specificity of antibodies and the low/non-specificity of monovalent peptides. Multivalency of the recognition unit of at least two, in a recognition unit complex used to screen the gene library, is preferred, with a multivalency of at least four more preferred, to obtain a screening wherein specificity is eased but not forfeited. In particular, a multivalent (believed to be tetravalent) recognition unit complex comprising streptavidin or avidin (preferably conjugated to a label, e.g., an enzyme such as alkaline phosphatase or horseradish peroxidase, or a fluorogen, e.g. green fluorescent protein) and biotinylated peptide recognition units have an unexpected generic specificity. This allows such peptides to be used to screen libraries to identify classes of polypeptides containing functional domains that are similar but not identical to the peptides' target functional domains. These classes of polypeptides are identified despite the low level of homology at the amino acid level of the functional domains of the members of the classes.

In another specific embodiment, multivalent peptide recognition units may be in the form of multiple antigen peptides (MAP) (Tam, 1989, J. Imm. Meth. 124:53–61; Tam, 1988, Proc. Natl. Acad. Sci. USA 85:5409–5413). In this form, the peptide recognition unit is synthesized on a branching lysyl matrix using solid-phase peptide synthesis methods. Recognition units in the form of MAP may be prepared by methods known in the art (Tam, 1989, J. Imm. Meth. 124:53–61; Tam, 1988, Proc. Natl. Acad. Sci. USA 85:5409–5413), or, for example, by a stepwise solid-phase procedure on MAP resins (Applied Biosystems), utilizing methodology established by the manufacturer. MAP peptides may be synthesized comprising (recognition unit peptide)$_2$Lys$_1$, (recognition unit peptide)$_4$Lys$_3$, (recognition unit peptide)$_8$Lys$_6$ or more levels of branching.

The multivalent peptide recognition unit complexes may also be prepared by cross-linking the peptide to a carrier protein, e.g., bovine serum albumin (BSA), keyhole limpet hemocyanin (KLH), or an enzyme, by use of known cross-linking reagents. Such cross-linked peptide recognition units may be detected by, e.g., an antibody to the carrier protein or detection of the enzymatic activity of the carrier protein.

Furthermore, the present inventors have discovered what specificity is exhibited by various types of recognition units and their complexes, i.e., where these recognition units and their complexes fall in the specificity continuum. The present inventors have discovered a range of formats for presenting recognition units used to screen libraries. For example, the present inventors have determined that a peptide in the form of a bivalent fusion protein with alkaline phosphatase is very specific. The same peptide in the form of a fusion protein with the pIII protein of an M13 derived bacteriophage, expressed on the phage surface, has somewhat less, though still high, specificity. That same peptide when biotinylated in the form of a tetravalent streptavidin-alkaline phosphatase complex has generic specificity. Use of such a generically specific peptide permits the identification of a wide range of proteins from expression libraries or other sources of polypeptides, each protein containing an example of a particular functional domain.

Accordingly, the present invention provides a method of modulating the specificity of a peptide such that the peptide can be used as a recognition unit to screen a plurality of polypeptides, thus identifying polypeptides that have a functional domain. In a specific embodiment, specificity is generic so as to provide for the identification of polypeptides having a functional domain that varies in sequence from that of the target functional domain known to bind the recognition unit under conditions of high specificity. In a particular embodiment, the method comprises forming a tetravalent complex of the biotinylated peptide and streptavidin-alkaline phosphatase prior to use for screening an expression library.

5.3. Kits

The present invention is also directed to an assay kit which can be useful in the screening of drug candidates. In a particular embodiment of the present invention, an assay kit is contemplated which comprises in one or more containers (a) a polypeptide containing a functional domain of interest; and (b) a recognition unit having a selective affinity for the polypeptide. The kit optionally further comprises a detection means for determining the presence of a polypeptide-recognition unit interaction or the absence thereof.

In a specific embodiment, either the polypeptide containing the functional domain or the recognition unit is labeled. A wide range of labels can be used to advantage in the present invention, including but not limited to conjugating the recognition unit to biotin by conventional means. Alternatively, the label may comprise a fluorogen, an enzyme, an epitope, a chromogen, or a radionuclide. Preferably, the biotin is conjugated by covalent attachment to either the polypeptide or the recognition unit. The polypeptide or, preferably, the recognition unit is immobilized on a solid support. The detection means employed to detect the label will depend on the nature of the label and can be any known in the art, e.g., film to detect a radionuclide; an enzyme substrate that gives rise to a detectable signal to detect the presence of an enzyme; antibody to detect the presence of an epitope, etc.

A further embodiment of the assay kit of the present invention includes the use of a plurality of polypeptides, each polypeptide containing a functional domain of interest. The assay kit further comprises at least one recognition unit having a selective affinity for each of the plurality of polypeptides and a detection means for determining the presence of a polypeptide-recognition unit interaction or the absence thereof.

A kit is provided that comprises, in one or more containers, a first molecule comprising an SH3 domain and a second molecule that binds to the SH3 domain, i.e., a recognition unit, where the SH3 domain is a novel SH3 domain identified by the methods of the present invention.

In a specific embodiment, the present invention provides an assay kit comprising in one or more containers:
  (a) a purified polypeptide containing a functional domain of interest, in which the functional domain of is a domain selected from the group consisting of an SH1, SH2, SH3, PH, PTB, LIM, armadillo, Notch/ankyrin repeat, zinc finger, leucine zipper, and helix-turn-helix; and
  (b) a purified recognition unit having a selective binding affinity for said functional domain in said polypeptide.

In the above assay kit, the polypeptide may comprise an amino acid sequence selected from the group consisting of SEQ ID NOs: 8, 10, 12, 18, 20, 22, 24, 30, 32, 38, 40, 190, 192, 194, 196, 198, 200, 221, 113–115, 118–121, 125–128, 133–139, 204–218, and 219.

In the above assay kit, the polypeptide may comprise an amino acid sequence selected from the group consisting of SEQ ID NOs:6, 14, 16, 26, 28, 34, 36, 112, 116, 117, 122–124, 129–132, and 140.

In other embodiments of the above-described assay kit, the recognition unit may be a peptide. The recognition unit may be labeled with e.g., an enzyme, an epitope, a chromogen, or biotin.

In another specific embodiment, the present invention provides an assay kit comprising in containers:
  (a) a plurality of purified polypeptides, each polypeptide in a separate container and each polypeptide containing a functional domain of interest in which the functional domain of interest is a domain selected from the group consisting of an SH1, SH2, SH3, PH, PTB, LIM, armadillo, Notch/ankyrin repeat, zinc fingers, leucine zippers, and helix-turn-helix; and
  (b) at least one recognition unit having a selective binding affinity for said functional domain in each of said plurality of polypeptides.

The present invention also provides an assay kit comprising in one or more containers:
  (a) a plurality of purified polypeptides, each polypeptide in a separate container and each polypeptide containing an SH3 domain; and
  (b) at least one peptide having a selective affinity for the SH3 domain in each of said plurality of polypeptides.

The present invention also provides a kit comprising a plurality of purified polypeptides comprising a functional domain of interest, each polypeptide in a separate container, and each polypeptide having a functional domain of a different sequence but capable of displaying the same binding specificity.

In the above-described kits, the polypeptides may have an amino acid sequence selected from the group consisting of: SEQ ID NOs:8, 10, 12, 18, 20, 22, 24, 30, 32, 38, 40, 190, 192, 194, 196, 198, 200, 221.

In the above-described kits, the functional domain may be an SH3 domain.

The molecular components of the kits are preferably purified.

The kits of the present invention may be used in the methods for identifying new drug candidates and determining the specificities thereof that are described in Section 5.4.

5.4. Assays for the Identification of Potential Drug Candidates and Determining the Specificity Thereof The present invention also provides methods for identifying potential drug candidates (and lead compounds) and determining the specificities thereof. For example, knowing that a polypeptide with a functional domain of interest and a recognition unit, e.g., a binding peptide, exhibit a selective affinity for each other, one may attempt to identify a drug that can exert an effect on the polypeptide-recognition unit interaction, e.g., either as an agonist or as an antagonist (inhibitor) of the interaction. With this assay, one can screen a collection of candidate "drugs" for the one exhibiting the most desired characteristic, e.g., the most efficacious in disrupting the interaction or in competing with the recognition unit for binding to the polypeptide.

Alternatively, one may utilize the different selectivities that a particular recognition unit may exhibit for different polypeptides bearing the same, similar, or functionally equivalent functional domains. Thus, one may tailor the screen to identify drug candidates that exhibit more selective activities directed to specific polypeptide-recognition unit interactions, among the "panel" of possibilities. Thus, for example, a drug candidate may be screened to identify the presence or absence of an effect on particular binding interactions, potentially leading to undesirable side effects.

Indeed, an intriguing application of the present invention is described as follows. A known antiviral agent, FIAU (a halogenated nucleoside analog), is effective at given dosages against the virus that causes hepatitis B. This compound is suspected of causing toxic side effects, however, which give rise to liver failure in certain patients to whom the drug is administered. According to the present invention, an assay is provided which can be used to develop a new generation of FIAU-derived drug that maintains its effectiveness against viral replication while reducing liver toxicity. Such an assay is provided by choosing FIAU as a recognition unit having a selective affinity for a polypeptide present in the hepatitis B virus or a cell infected with the virus. This polypeptide or family of polypeptides having the functional domain of interest is obtained by allowing the chosen recognition unit, FIAU, to come into contact with an expression library comprised of the hepatitis B virus genome and/or a cDNA expression library of infected cells, according to the methods of the present invention.

Likewise, the chosen recognition unit is allowed to come into contact with a plurality of polypeptides obtained from a sample of a human liver extract or of noninfected hepatocytes. In this manner, a "panel" of polypeptides each of which exhibits a selective affinity for the chosen recognition unit is identified. As described above, this panel is used to determine the activities of drug (FIAU) homologs, analogs, or derivatives in terms of, say, selective inhibition of viral polypeptide-FIAU interaction versus liver polypeptide-FIAU interaction. Hence, those drug homologs, analogs, or derivatives that maintain a selective affinity for the viral polypeptide (or infected cell polypeptide) while failing to interact with or having a minimal binding affinity for liver polypeptides (and, hence, have reduced toxicity in the liver due to elimination of undesirable molecular interactions) can be identified and selected. Additional iterations of this process can be performed if so desired.

Therefore, the present invention contemplates an assay for screening a drug candidate comprising: (a) allowing at least one polypeptide comprising a functional domain of interest to come into contact with at least one recognition unit having a selective affinity for the polypeptide in the presence of an amount of a drug candidate, such that the polypeptide and the recognition unit are capable of interacting when brought into contact with one another in the absence of said drug candidate, and in which the functional domain of interest is a domain selected from the group consisting of an SH1, SH2, SH3, PH, PTB, LIM, armadillo, Notch/ankyrin repeat, zinc finger, leucine zipper, and helix-turn-helix; and (b) determining the effect, if any, of the presence of the amount of the drug candidate on the interaction of the polypeptide with the recognition unit.

In one embodiment, the effect of the drug candidate upon multiple, different interacting polypeptide-recognition unit pairs is determined in which at least some of said polypeptides have a functional domain that differs in sequence but is capable of displaying the same binding specificity as the functional domain in another of said polypeptides.

In another embodiment, at least one of said at least one polypeptide or recognition unit contains a consensus functional domain and consensus recognition unit, respectively.

In another embodiment, the drug candidate is an inhibitor of the polypeptide-recognition unit interaction that is identified by detecting a decrease in the binding of polypeptide to recognition unit in the presence of such inhibitor.

In another embodiment, said polypeptide is a polypeptide containing an SH3 domain produced by a method comprising:

(i) screening a peptide library with an SH3 domain to obtain one or more peptides that bind the SH3 domain;

(ii) using one of the peptides from step (i) to screen a source of polypeptides to identify one or more polypeptides containing an SH3 domain;

(iii) determining the amino acid sequence of the polypeptides identified in step (ii); and (iv) producing the one or more novel polypeptides containing an SH3 domain.

In another embodiment, said polypeptide is a polypeptide containing an SH3 domain produced by a method comprising:

(i) screening a peptide library with an SH3 domain to obtain a plurality of peptides that bind the SH3 domain;

(ii) determining a consensus sequence for the peptides obtained in step (i);

(iii) producing a peptide comprising the consensus sequence;

(iv) using the peptide comprising the consensus sequence to screen a source of polypeptides to identify one or more polypeptides containing an SH3 domain;

(v) determining the amino acid sequence of the polypeptides identified in step (iv); and (vi) producing the one or more polypeptides containing an SH3 domain.

In a preferred embodiment, the effect of the drug candidate upon multiple, different interacting polypeptide-recognition unit pairs is determined in which preferably at least some (e.g., at least 2, 3, 4, 5, 7, or 10) of said polypeptides have functional domains that vary in sequence yet are capable of displaying the same binding specificity, i.e., binding to the same recognition unit. In another specific embodiment, at least one of said polypeptides and/or recognition units contain a consensus functional domain and recognition unit, respectively (and thus are not known to be naturally expressed proteins). In one embodiment, the polypeptide is a novel polypeptide identified by the methods of the present invention. In a specific embodiment, an inhibitor of the polypeptide-recognition unit interaction is identified by detecting a decrease in the binding of polypeptide to recognition unit in the presence of such inhibitor.

A common problem in the development of new drugs is that of identifying a single, or a small number, of compounds that possess a desirable characteristic from among a background of a large number of compounds that lack that desired characteristic. This problem arises both in the testing of compounds that are natural products from plant, animal, or microbial sources and in the testing of man-made compounds. Typically, hundreds, or even thousands, of compounds are randomly screened by the use of in vitro assays such as those that monitor the compound's effect on some enzymatic activity, its ability to bind to a reference substance such as a receptor or other protein, or its ability to disrupt the binding between a receptor and its ligand.

The compounds which pass this original screening test are known as "lead" compounds. These lead compounds are then put through further testing, including, eventually, in vivo testing in animals and humans, from which the promise shown by the lead compounds in the original in vitro tests is either confirmed or refuted. See *Remington's Pharmaceutical Sciences*, 1990, A. R. Gennaro, ed., Chapter 8, pages 60–62, Mack Publishing Co., Easton, Pa.; Ecker and Crooke, 1995, Bio/Technology 13:351–360.

There is a continual need for new compounds to be tested in the in vitro assays that make up the first testing step described above. There is also a continual need for new assays by which the pharmacological activities of these compounds may be tested. It is an object of the present invention to provide such new assays to determine whether a candidate compound is capable of affecting the binding between a polypeptide containing a functional domain and a recognition unit that binds to that functional domain. In particular, it is an object of the present invention to provide polypeptides, particularly novel ones, containing functional domains and their corresponding recognition units for use in the above-described assays. The use of these polypeptides greatly expands the number of assays that may be used to screen potential drug candidates for useful pharmacological activities (as well as to identify potential drug candidates that display adverse or undesirable pharmacological activities). In one particular embodiment of the present invention, the polypeptides contain an SH3 domain.

In one embodiment of the present invention, such polypeptides are identified by a method comprising: using a recognition unit that is capable of binding to a predetermined functional domain to screen a source of polypeptides, thus identifying novel polypeptides containing the functional domain or a similar functional domain.

In a particular embodiment of the above-described method, the novel polypeptide comprises an SH3 domain and is obtained by:

(i) screening a peptide library with the SH3 domain to obtain one or more peptides that bind the SH3 domain;

(ii) using one of the peptides from step (i), preferably in the form of a multivalent complex, to screen a source of polypeptides to identify one or more novel polypeptides containing SH3 domains;

(iii) determining the amino acid sequence of the polypeptides identified in step (ii); and (iv) producing the one or more novel polypeptides containing SH3 domains.

In another embodiment of the above-described method, the novel polypeptide containing an SH3 domain is obtained by:

(i) screening a peptide library with the SH3 domain to obtain peptides that bind the SH3 domain;

(ii) determining a consensus sequence for the peptides obtained in step (i);

(iii) producing a peptide comprising the consensus sequence;

(iv) using the peptide comprising the consensus sequence to screen a source of polypeptides to identify one or more novel polypeptides containing SH3 domains;

(v) determining the amino acid sequence of the novel polypeptides identified in step (iv); and (vi) producing the one or more novel polypeptides containing SH3 domains.

One of ordinary skill in the art will recognize that it will not always be necessary to utilize the entire novel polypeptide containing the SH3 domain in the assays described herein. Often, a portion of the polypeptide that contains the SH3 domain will be sufficient, e.g., a glutathione S-transferase (GST)-SH3 domain fusion protein. See FIGS. 10A and 10B for a depiction of the portions of the exemplary novel polypeptides that contain SH3 domains.

A typical assay of the present invention consists of at least the following components: (1) a molecule (e.g., protein or polypeptide) comprising a functional-domain; (2) a recognition unit that selectively binds to the functional domain; (3) a candidate compound, suspected of having the capacity to affect the binding between the protein containing the functional domain and the recognition unit. The assay components may further comprise (4) a means of detecting the binding of the protein comprising the functional domain and the recognition unit. Such means can be e.g., a detectable label affixed to the protein comprising the functional domain, the recognition unit, or the candidate compound.

In a specific embodiment, the protein comprising the functional domain is a novel protein discovered by the methods of the present invention.

In another specific embodiment, the invention provides a method of identifying a compound that affects the binding of a molecule comprising a functional domain and a recognition unit that selectively binds to the functional domain comprising:

(a) contacting the molecule comprising the functional domain and the recognition unit under conditions conducive to binding in the presence of a candidate compound and measuring the amount of binding between the molecule and the recognition unit;

(b) comparing the amount of binding in step (a) with the amount of binding known or determined to occur between the molecule and the recognition unit in the absence of the candidate compound, where a difference in the amount of binding between step (a) and the amount of binding known or determined to occur between the molecule and the recognition unit in the absence of the candidate compound indicates that the candidate compound is a compound that affects the binding of the molecule comprising a functional domain and the recognition unit. In a specific embodiment, the molecule comprising the functional domain is a novel protein discovered by the methods of the present invention. In another specific embodiment, the functional domain is an SH3 domain.

In one embodiment, the assay comprises allowing the polypeptide containing an SH3 domain to contact a recognition unit that selectively binds to the SH3 domain in the presence and in the absence of the candidate compound under conditions such that binding of the recognition unit to the protein containing an SH3 domain will occur unless that binding is disrupted or prevented by the candidate compound. By detecting the amount of binding of the recognition unit to the protein containing an SH3 domain in the presence of the candidate compound and comparing that amount of binding to the amount of binding of the recognition unit to the protein or polypeptide containing an SH3 domain in the absence of the candidate compound, it is possible to determine whether the candidate compound affects the binding and thus is a useful lead compound for the modulation of the activity of proteins containing the SH3 domain. The effect of the candidate compound may be to either increase or decrease the binding.

One version of an assay suitable for use in the present invention comprises binding the protein containing an SH3 domain to a solid support such as the wells of a microtiter plate. The wells contain a suitable buffer and other substances to ensure that conditions in the wells permit the binding of the protein or polypeptide containing an SH3 domain to its recognition unit. The recognition unit and a candidate compound are then added to the wells. The recognition unit is preferably labeled, e.g., it might be biotinylated or labeled with a radioactive moiety, or it might be linked to an enzyme, e.g., alkaline phosphatase. After a suitable period of incubation, the wells are washed to remove any unbound recognition unit and compound. If the candidate compound does not interfere with the binding of the protein or polypeptide containing an SH3 domain to the labeled recognition unit, the labeled recognition unit will bind to the protein or polypeptide containing an SH3 domain in the well. This binding can then be detected. If the candidate compound interferes with the binding of the protein or polypeptide containing an SH3 domain and the labeled recognition unit, label will not be present in the wells, or will be present to a lesser degree than is the case when compared to control wells that contain the protein or polypeptide containing an SH3 domain and the labeled recognition unit but to which no candidate compound is added. Of course, it is possible that the presence of the candidate compound will increase the binding between the protein or polypeptide containing an SH3 domain and the labeled recognition unit. Alternatively, the recognition unit can be affixed to a solid substrate during the assay. Functional domains other than SH3 domains and their corresponding recognition units can also be used.

In a specific embodiment of the above-described method, the protein or polypeptide containing an SH3 domain is a novel protein or polypeptide containing an SH3 domain that has been identified by the methods of the present invention.

5.5. Use of Polypeptides Containing Functional Domains to Discover Polypeptides Involved in Pharmacological Activities Using the methods of the present invention, it is possible to identify and isolate large numbers of polypeptides containing functional domains, e.g., SH3 domains. Using these polypeptides, one can construct a matrix relating the polypeptides to an array of candidate drug compounds. For example, Table 1 shows such a matrix.

TABLE 1

|    | A | B | C | D | E | F | G | H | I | J |
|----|---|---|---|---|---|---|---|---|---|---|
| 1  |   |   |   |   |   |   |   |   |   |   |
| 2  |   | X |   | X |   |   |   | X |   |   |
| 3  |   |   |   |   |   |   |   |   |   |   |
| 4  |   |   |   |   |   |   |   |   |   |   |
| 5  |   |   |   |   |   | X |   |   |   |   |
| 6  |   |   |   |   |   |   |   |   |   |   |
| 7  |   |   | X |   |   |   |   | X |   |   |
| 8  |   |   |   |   |   |   |   |   |   |   |
| 9  | X |   |   |   |   |   |   |   |   |   |
| 10 |   |   |   |   |   |   |   |   |   |   |

In Table 1, the columns headed by letters at the top of the table represent different polypeptides containing SH3 domains (preferably novel polypeptides identified by the methods of the invention). The rows numbered along the left side of the table represent recognition units with various specificity to SH3 domains. For each candidate drug compound, a table such as Table 1 is generated from the results of binding assays. An X placed at the intersection of a particular numbered row and lettered column represents a positive assay for binding, i.e., the candidate drug compound affected the binding of the recognition unit of that particular row to the SH3 domain of that particular column.

Such data as that illustrated above is used to determine whether candidate drug compounds display or are at risk of displaying desirable or undesirable physiological or pharmacological activities. For example, in Table 1, the drug compound inhibits the binding of recognition unit 2 to the SH3 domains of polypeptides B, D, and H; the compound inhibits the binding of recognition unit 5 to the SH3 domain of polypeptide F; the compound inhibits the binding of recognition unit 7 to the SH3 domains of polypeptides C and H; and the compound inhibits the binding of recognition unit 9 to the SH3 domain of polypeptide A.

If interaction with polypeptide H leads to the desirable physiological or pharmacological activity, then this drug candidate might be a good lead. However, interaction with polypeptides A, B, C, D, and F would need to be evaluatated for potential side effects.

As the maps are generated and pharmacological effects observed, the maps will allow strategic assessment of the specificity necessary to obtain the desired pharmacological effect. For example, if compounds 2 and 7 are able to affect some pharmacological activity, while compounds 5 and 9 do not affect that activity, then polypeptide H is likely to be involved in that pharmacological activity. For example, if compounds 2 and 7 were both able to inhibit mast cell degranulation, while compounds 5 and 9 did not, it is likely that polypeptide H is involved in mast cell degranulation.

Accordingly, the present invention provides a method of utilizing the polypeptides comprising functional domains of the present invention in an assay to determine the partici- pation of those polypeptides in pharmacological activities. In a particular embodiment, the polypeptides comprise SH3 domains.

In another embodiment, the method comprises:

(a) contacting a drug candidate with a molecule comprising a functional domain under conditions conducive to binding, and detecting or measuring any specific binding that occurs; and (b) repeating step (a) with a plurality of different molecules, each comprising a different functional domain but capable of binding to a single predetermined recognition unit under appropriate conditions.

Preferably, at least one of said molecules is a novel polypeptide identified by the methods of the present invention. In a specific embodiment, the molecules comprise the SH3 domains of Src, Abl, Cortactin, Phospholipase Cγ, Nck, Crk, p53bp2, Amphiphysin, Grb2, RasGap, or Phosphatidylinositol 3' kinase.

The present invention also provides a method of determining the potential pharmacological activities of a molecule comprising:

(a) contacting the molecule with a compound comprising a functional domain under conditions conducive to binding;

(b) detecting or measuring any specific binding that occurs; and (c) repeating steps (a) and (b) with a plurality of different compounds, each compound comprising a functional domain of different sequence but capable of displaying the same binding specificity.

In a specific embodiment the functional domain is an SH3 domain.

In another embodiment, the compounds comprise the SH3 domains of Src, Abl, Cortactin, Phospholipase Cγ, Nck, Crk, p53bp2, Amphiphysin, Grb2, RasGap, or Phosphatidylinositol 3' kinase.

The present invention also provides a method of identifying a compound that affects the binding of a molecule comprising a functional domain to a recognition unit that selectively binds to the functional domain comprising:

(a) contacting the molecule comprising the functional domain and the recognition unit under conditions conducive to binding in the presence of a candidate compound and measuring the amount of binding between the molecule and the recognition unit and in which the functional domain of interest is a domain selected from the group consisting of an SH1, SH2, SH3, PH, PTB, LIM, armadillo, Notch/ankyrin repeat, zinc finger, leucine zipper, and helix-turn-helix;

(b) comparing the amount of binding in step (a) with the amount of binding known or determined to occur between the molecule and the recognition unit in the absence of the candidate compound, where a difference in the amount of binding between step (a) and the amount of binding known or determined to occur between the molecule and the recognition unit in the absence of the candidate compound indicates that the candidate compound is a compound that affects the binding of the molecule comprising a functional domain and the recognition unit.

In a specific embodiment, the functional domain is an SH3 domain.

5.6. Use of more than One Recognition Unit Simultaneously

It has been found that when screening a source of polypeptides with a recognition unit, it is possible to use more than one recognition unit at the same time. In particular, it has been found that as many as five different recognition units may be used simultaneously to screen a source of polypeptides.

In particular, when the recognition units are biotinylated peptides and the source of polypeptides is a cDNA expression library, the steps of preconjugation of the biotinylated peptides to streptavidin-alkaline phosphatase as well as the steps involved in screening the cDNA expression library may be carried out in essentially the same manner as is done when a single biotinylated peptide is used as a recognition unit. See Section 6.1 for details. The key difference when using more than one biotinylated peptide at a time is that the peptides are combined either before or at the step where they are placed in contact with the polypeptides from which selection occurs.

In an embodiment employing a bacteriophage expression library to express the polypeptides, when the positive clones are worked up to the level of isolated plaques, the clonal bacteriophage from the isolated plaques may be tested against each of the biotinylated peptides individually, in order to determine to which of the several peptides that were used as recognition units in the primary screen the phage are actually binding.

5.7. Use of Recognition Units from Known Amino Acid Sequences

In many cases it may not be necessary to screen a collection of substances, e.g., a peptide library, in order to obtain a recognition unit for a given functional domain. In the case of peptide recognition units, for example, it is sometimes possible to identify a recognition unit by inspection of known amino acid sequences. Stretches of these amino acid sequences that resemble known binding sequences for the functional domain can be synthesized and screened against a source of polypeptides in order to obtain a plurality of polypeptides comprising the given functional domain.

Prior to the disclosure of the present invention of methods of preparing recognition units having generic specificity, it would have been thought fruitless to pursue this approach. The expectation would have been that a recognition unit, chosen from published amino acid sequences as described above, would have been useful, at best, to identify a single protein containing a functional domain.

5.8. Isolation and Expression of Nucleic Acids Encoding Polypeptides Comprising a Functional Domain In particular aspects, the invention provides amino acid sequences of polypeptides comprising functional domains, preferably human polypeptides, and fragments and derivatives thereof which comprise an antigenic determinant (i.e., can be recognized by an antibody) or which are functionally active, as well as nucleic acid sequences encoding the foregoing. "Functionally active" material as used herein refers to that material displaying one or more functional activities, e.g., a biological activity, antigenicity (capable of binding to an antibody) immunogenicity, or comprising a functional domain that is capable of specific binding to a recognition unit. In specific embodiments, the invention provides fragments of polypeptides comprising a functional domain consisting of at least 40 amino acids, or of at least 75 amino acids. Nucleic acids encoding the foregoing are provided. Functional fragments of at least 10 or 20 amino acids are also provided.

In other specific embodiments, the invention provides nucleotide sequences and subsequences encoding polypeptides comprising a functional domain, preferably human polypeptides, consisting of at least 25 nucleotides, at least 50 nucleotides, or at least 150 nucleotides. Nucleic acids encoding fragments of the polypeptides comprising a functional domain are provided, as well as nucleic acids complementary to and capable of hybridizing to such nucleic acids. In one embodiment, such a complementary sequence may be complementary to a cDNA sequence encoding a polypeptide comprising a functional domain of at least 25 nucleotides, or of at least 100 nucleotides. In a preferred aspect, the invention utilizes cDNA sequences encoding human polypeptides comprising a functional domain or a portion thereof.

Any eukaryotic cell can potentially serve as the nucleic acid source for the molecular cloning of polypeptides comprising a functional domain. The DNA may be obtained by standard procedures known in the art (e.g., a DNA "library") by cDNA cloning, or by the cloning of genomic DNA, or fragments thereof, purified from the desired cell (see, for example Sambrook et al., 1989, Molecular Cloning, A Laboratory Manual, Cold Spring Harbor Laboratory, 2d. Ed., Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene encoding a polypeptide comprising a functional domain should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once a gene encoding a particular polypeptide comprising a functional domain has been isolated from a first species, it is a routine matter to isolate the corresponding gene from another species. identification of the specific DNA fragment from another species containing the desired gene may be accomplished in a number of ways. For example, if an amount of a portion of a gene or its specific RNA from the first species, or a fragment thereof e.g., the functional domain, is available and can be purified and labeled, the generated DNA fragments from another species may be screened by nucleic acid hybridization to the labeled probe (Benton, W. and Davis, R., 1977, Science 196, 180; Grunstein, M. And Hogness, D., 1975, Proc. Natl. Acad. Sci. U.S.A. 72, 3961). Those DNA fragments with substantial homology to the probe will hybridize. In a preferred embodiment, PCR using primers that hybridize to a known sequence of a gene of one species can be used to amplify the homolog of such gene in a different species. The amplified fragment can then be isolated and inserted into an expression or cloning vector. It is also possible to identify the appropriate fragment by restriction enzyme digestion(s) and comparison of fragment sizes with those expected according to a known restriction map if such is available. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, in vitro aggregation activity ("adhesiveness") or antigenic properties as known for the particular polypeptide comprising a functional domain from the first species. If an antibody to that particular polypeptide is available, corresponding polypeptide from another species may be identified by binding of labeled antibody to the putatively polypeptide synthesizing clones, in an ELISA (enzyme-linked immunosorbent assay)-type procedure.

Genes encoding polypeptides comprising a functional domain can also be identified by mRNA selection by nucleic acid hybridization followed by in vitro translation. In this procedure, fragments are used to isolate complementary mRNAs by hybridization. Such DNA fragments may represent available, purified DNA of genes encoding polypeptides comprising a functional domain of a first species. Immunoprecipitation analysis or functional assays (e.g., ability to bind to a recognition unit) of the in vitro translation products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against polypeptides comprising a functional domain. A radiolabelled cDNA of a gene encoding a polypeptide comprising a functional domain can be synthesized using the selected mRNA (from the adsorbed polysomes) as a template. The radiolabelled mRNA or cDNA may then be used as a probe to identify the DNA fragments that represent the gene encoding the polypeptide comprising a functional domain of another species from among other genomic DNA fragments. In a specific embodiment, human homologs of mouse genes are obtained by methods described above. In various embodiments, the human homolog is hybridizable to the mouse homolog under conditions of low, moderate, or high stringency. By way of example and not limitation, procedures using such conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which may be used are well known in the art (e.g., as employed for cross-species hybridizations).

By way of example and not limitation, procedures using conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

The identified and isolated gene encoding a polypeptide comprising a functional domain can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The nucleic acid coding for a polypeptide comprising a functional domain of the invention can be inserted into an appropriate expression vector, i.e., a vector which contains the necessary elements for the transcription and translation of the inserted protein-coding sequence. The necessary transcriptional and translational signals can also be supplied by the native gene encoding the polypeptide and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a protein or peptide fragment may be regulated by a second nucleic acid sequence so that the protein or peptide is expressed in a host transformed with the recombinant DNA molecule. For example, expression of a protein may be controlled by any promoter/enhancer element known in the art. Promoters which may be used to control gene expression include, but are not limited to, the SV40 early promoter region (Benoist and Chambon, 1981, Nature 290, 304–310), the promoter contained in the 3' long terminal repeat of Rous sarcoma virus (Yamamoto, et al., 1980, Cell 22, 787–797), the herpes thymidine kinase promoter (Wagner et al., 1981, Proc. Natl. Acad. Sci. U.S.A. 78, 1441–1445), the regulatory sequences of the metallothionein gene (Brinster et al., 1982, Nature 296, 39–42); prokaryotic expression vectors such as the β-lactamase promoter (Villa-Kamaroff, et al., 1978, Proc. Natl. Acad. Sci. U.S.A. 75, 3727–3731), or the tac promoter (DeBoer, et al., 1983, Proc. Natl. Acad. Sci. U.S.A. 80, 21–25); see also "Useful proteins from recombinant bacteria" in Scientific American, 1980, 242, 74–94; plant expression vectors comprising the nopaline synthetase promoter region (Herrera-Estrella et al., Nature 303, 209–213) or the cauliflower mosaic virus 35S RNA promoter (Gardner, et al., 1981, Nucl. Acids Res. 9, 2871), and the promoter of the photosynthetic enzyme ribulose biphosphate carboxylase (Herrera-Estrella et al., 1984, Nature 310, 115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38, 639–646; Ornitz et al., 1986, Cold Spring Harbor Symp. Quant. Biol. 50, 399–409; MacDonald, 1987, Hepatology 7, 425–515); insulin gene control region which is active in pancreatic beta cells (Hanahan, 1985, Nature 315, 115–122), immunoglobulin gene control region which is active in lymphoid cells (Grosschedl et al., 1984, Cell 38, 647–658; Adames et al., 1985, Nature 318, 533–538; Alexander et al., 1987, Mol. Cell. Biol. 7, 1436–1444), mouse mammary tumor virus control region which is active in testicular, breast, lymphoid and mast cells (Leder et al., 1986, Cell 45, 485–495), albumin gene control region which is active in liver (Pinkert et al., 1987, Genes and Devel. 1, 268–276), alpha-fetoprotein gene control region which is active in liver (Krumlauf et al., 1985, Mol. Cell. Biol. 5, 1639–1648; Hammer et al., 1987, Science 235, 53–58; alpha 1-antitrypsin gene control region which is active in the liver (Kelsey et al., 1987, Genes and Devel. 1, 161–171), beta-globin gene control region which is active in myeloid cells (Mogram et al., 1985, Nature 315, 338–340; Kollias et al., 1986, Cell 46, 89–94; myelin basic protein gene control region which is active in oligodendrocyte cells in the brain (Readhead et al., 1987, Cell 48, 703–712); myosin light chain-2 gene control region which is active in skeletal muscle (Sani, 1985, Nature 314, 283–286), and gonadotropic releasing hormone gene control region which is active in the hypothalamus (Mason et al., 1986, Science 234, 1372–1378).

Expression vectors containing inserts of genes encoding polypeptides comprising a functional domain can be identified by three general approaches: (a) nucleic acid hybridization, (b) presence or absence of "marker" gene functions, and (c) expression of inserted sequences. In the first approach, the presence of a foreign gene inserted in an expression vector can be detected by nucleic acid hybridization using probes comprising sequences that are homologous to the inserted gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the gene encoding a polypeptide comprising a functional domain is inserted within the marker gene sequence of the vector, recombinants containing the gene can be identified by the absence of the marker gene function. In the third approach, recombinant expression vectors can be identified by assaying the foreign gene product expressed by the recombinant. Such assays can be based, for example, on the physical or functional properties of the gene product in in vitro assay systems, e.g., ability to bind to recognition units.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions such as proteolytic cleavages to different extents.

In other specific embodiments, polypeptides comprising a functional domain, or fragments, analogs, or derivatives thereof may be expressed as a fusion, or chimeric protein product (comprising the polypeptide, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper reading frame, and expressing the chimeric product by methods commonly known in the art. Alternatively, such a chimeric product may be made by protein synthetic techniques, e.g., by use of a peptide synthesizer.

5.8.1. Identification and Purification of the Expressed Gene Product

Once a recombinant which expresses the gene sequence encoding a polypeptide comprising a functional domain is identified, the gene product may be analyzed. This can be achieved by assays based on the physical or functional properties of the product, including radioactive labelling of the product followed by analysis by gel electrophoresis.

Once the polypeptide comprising a functional domain is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay, including, but not limited to, binding to a recognition unit.

5.9. Derivatives and Analogs of Polypeptides Comprising a Functional Domain

The invention further provides derivatives (including but not limited to fragments) and analogs of polypeptides that are functionally active, e.g., comprising a functional domain. In a specific embodiment, the derivative or analog is functionally active, i.e., capable of exhibiting one or more functional activities associated with a full-length, wild-type polypeptide, e.g., binding to a recognition unit. As one example, such derivatives or analogs may have the antigenicity of the full-length polypeptide.

In particular, derivatives can be made by altering gene sequences encoding polypeptides comprising a functional domain by substitutions, additions or deletions that provide for functionally equivalent molecules. Due to the degeneracy of nucleotide coding sequences, other DNA sequences which encode substantially the same amino acid sequence as a gene encoding a polypeptide comprising a functional domain may be used in the practice of the present invention. These include but are not limited to nucleotide sequences comprising all or portions of such genes which are altered by the substitution of different codons that encode a functionally equivalent amino acid residue within the sequence, thus producing a silent change. Likewise, the derivatives of the invention include, but are not limited to, those containing, as a primary amino acid sequence, all or part of the amino acid sequence of a polypeptide comprising a functional domain including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Derivatives or analogs of genes encoding polypeptides comprising a functional domain include but are not limited to those polypeptides which are substantially homologous to the genes or fragments thereof, or whose encoding nucleic acid is capable of hybridizing to a nucleic acid sequence of the genes.

The derivatives and analogs of the invention can be produced by various methods known in the art. The manipulations which result in their production can occur at the gene or protein level. For example, the cloned gene sequence can be modified by any of numerous strategies known in the art (Maniatis, T., 1989, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. PCR primers can be constructed so as to introduce desired sequence changes during PCR amplification of a nucleic acid encoding the desired polypeptide. In the production of the gene encoding a derivative or analog, care should be taken to ensure that the modified gene remains within the same translational reading frame, uninterrupted by translational stop signals, in the gene region where the desired activity is encoded.

Additionally, the sequence of the genes encoding polypeptides comprising a functional domain can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem 253:6551), use of TAB® linkers (Pharmacia), etc.

Manipulations of the sequence may also be made at the protein level. Included within the scope of the invention are protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives can be chemically synthesized. For example, a peptide corresponding to a portion of a polypeptide comprising a functional domain can be synthesized by use of a peptide synthesizer. Furthermore, if desired, nonclassical amino acids or chemical amino acid analogs can be introduced as a substitution or addition into the sequence. Non-classical amino acids include but are not limited to the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids.

5.10. Antibodies to Polypeptides Comprising a Functional Domain

According to one embodiment, the invention provides antibodies and fragments thereof containing the binding domain thereof, directed against polypeptides comprising a functional domain. Accordingly, polypeptides comprising a functional domain, fragments or analogs or derivatives thereof, in particular, may be used as immunogens to generate antibodies against such polypeptides, fragments or analogs or derivatives. Such antibodies can be polyclonal, monoclonal, chimeric, single chain, Fab fragments, or from an Fab expression library. In a specific embodiment, antibodies specific to the functional domain of a polypeptide comprising a functional domain may be prepared.

Various procedures known in the art may be used for the production of polyclonal antibodies. In a particular embodiment, rabbit polyclonal antibodies to an epitope of a polypeptide comprising a functional domain, or a subsequence thereof, can be obtained. For the production of antibody, various host animals can be immunized by injection with the native polypeptide comprising a functional domain, or a synthetic version, or fragment thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhold limpet hemocyanins, dinitrophenol, and potentially useful human adjuvants such as BCG (bacille Calmette-Guerin) and corynebacterium parvum.

For preparation of monoclonal antibodies, any technique which provides for the production of antibody molecules by continuous cell lines in culture may be used. For example, the hybridoma technique originally developed by Kohler and Milstein (1975, Nature 256, 495–497), as well as the trioma technique, the human B-cell hybridoma technique (Kozbor et al., 1983, Immunology Today 4, 72), and the EBV-hybridoma technique to produce human monoclonal antibodies (Cole et al., 1985, in Monoclonal Antibodies and Cancer Therapy, Alan R. Liss, Inc., pp. 77–96).

Antibody fragments which contain the idiotype (binding domain) of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay).

6. EXAMPLES

6.1. Identification of Genes from cDNA Expression Libraries

A study was initiated to determine whether peptide recognition units could recognize functional domains that are the same as or similar to their target functional domain but that are contained in proteins other than the protein containing their target functional domain. Such "functional" screens, using recognition units of relatively small size, were not previously known and were difficult to develop because of the low degree of sequence homology among functional domain-containing proteins. Thus, for example, an oligonucleotide probe could not be designed with any degree of confidence based on the low degree of homology of primary sequences of SH3 domains.

Using SH3 domain-binding peptides from combinatorial peptide libraries as recognition units, we screened a series of mouse and human cDNA expression libraries. We found that 69 of the 74 clones isolated from the libraries encoded at least one SH3 domain. These clones represent more than 18 different SH3 domain-containing proteins, of which more than 10 have not been described previously.

The initial recognition unit chosen was a Src SH3 domain-binding peptide (termed pSrcCII) isolated from a phage-displayed random peptide library (Sparks et al., 1994, J. Biol. Chem. 269:23853–23856). pSrcCII was (biotin-SGSGGILAPPVPPRNTR—NH$_2$) (SEQ ID NO:1). pSrcCII was synthesized by standard FMOC chemistry, purified by HPLC, and its structure was confirmed by mass spectrometry and amino acid analysis. To form multivalent complexes, 50 pmol biotinylated pSrcCII peptide was incubated with 2 μg streptavidin-alkaline phosphatase (SA-AP) (for a biotin:biotin-binding site ratio of 1:1). Excess biotin-binding sites were blocked by addition of 500 pmol biotin. Alternatively, 31.2 μl of 1 mg/ml SA-AP could have been incubated with 15 μl of 0.1 mM biotinylated peptide for 30 min at 4° C. Ten μl of 0.1 mM biotin would then be added, and the solution incubated for an additional 15 min.

A λEXlox mouse 16 day embryo cDNA expression library was obtained from Novagen (Madison, Wis.). The cDNA library was screened according to published protocols (Young and Davis, 1983, Proc. Natl. Acad. Sci. USA 80:1194–1198). The library was plated at an initial density of 30,000 plaques/100 mm petri plate as follows. A library aliquot was diluted 1:1000 in SM (100 mM NaCl, 8 mM MgSO$_4$, 50 mM Tris HCl pH 7.5, 0.01% gelatin). Three μl of diluted phage were added to 1.5 ml each of SM, 10 mM CaCl$_2$/MgCl$_2$, and an overnight culture of BL21(DE3) pLysE E. coli cells. BL21 overnight cultures were grown in 2×YT medium (1.6% tryptone, 1% yeast extract, and 0.5% NaCl) supplemented with 10 mM MgSO$_4$, 0.2% maltose, and 25 μg/ml chloramphenicol. This mixture was incubated 20 min at 37° C., after which 300 μl were plated on each of 14 2×YT agar plates in 3 ml 0.8% 2×YT top agarose containing 25 μg/ml chloramphenicol. Plaques were allowed to form for 6 hours at 37° C., after which isopropyl-β-D-thiogalactopyranoside (IPTG)-soaked filters were applied. After an additional eight hours' incubation at 37° C., the filters were marked, removed from the plates, and washed three times with phosphate buffered saline (PBS; 137 mM NaCl, 2.7 mM KCl, 4.3 mM Na$_2$HPO$_4$, 1.4 mM KH$_2$PO$_4$), 0.1% Triton X-100. The filters were blocked for 1 hour in PBS, 2% bovine serum albumin (blocking solution) and subsequently incubated overnight at 4° C. with fresh blocking solution plus streptavidin-alkaline phosphatase (SA-AP) complexed peptide. Approximately 1 μg SA-AP complexed with peptide in 1 ml blocking solution was used for each filter. The filters were then subjected to four 15 minute washes with PBS, 0.1% Triton X-100. Bound SA-AP-peptide complexes were detected by incubation with 44 ml nitroblue tetrazolium chloride (NBT, 75 mg/ml in 70% dimethylformamide) and 33 ml of 5-bromo-4-chloro-3-indoyl-phosphate-p-toluidine salt (BCIP 50 mg/ml in dimethylformamide) in 10 ml of alkaline phosphatase buffer (0.1 M Tris-HCl, pH 9.4, 0.1 M NaCl, 50 mM MgCl$_2$); the signals were robust, often evident within a few minutes. Positive plaques were cored with a Pasteur pipet and placed in 1 ml SM with a drop of chloroform. Lambda phage particles are structurally resistant to chloroform, which serves as a bacteriocidal agent. These cores were allowed to diffuse into solution for at least 1 hr before subsequent platings. Phage from cores were plated in 100 μl each of SM, 10 mM CaCl$_2$/MgCl$_2$, and an overnight culture of BL21 (DE3) pLySE cells. Phage were plated with the intention of reducing the number of plaque forming units (pfu)/plate by roughly a factor of 10 with each screen (i.e., $3 \times 10^4$ in the primary screen, $3 \times 10^3$ in the secondary, and so on). This was accomplished by diluting cores 1:1000 and plating 1–10 μl/plate. Four screens were generally required to obtain isolated plaques.

Plasmids were rescued from the λEXlox phage by cre-mediated excision in BM25.8 E. coli cells. For each clone, 5 μl of a 1:100 dilution of phage were added to a solution containing 100 μl SM and 100 μl of an overnight culture of BM25.8 cells (grown in 2×YT media supplemented with 10 mM MgSO$_4$, 0.2% maltose, 34 μg/ml chloramphenicol, and 50 μg/ml kanamycin). After 30 minutes at 37° C., 100 μl of this solution were spread on an LB amp agarose plate and incubated overnight at 37° C. A single colony from each plate was used to inoculate 3 ml of 2×YT/amp and incubated overnight. Plasmid DNA was purified from the overnight culture using Promega Wizard Miniprep DNA purification kits (Promega, Madison, Wis.), extracted with an equal volume of phenol/chloroform followed by chloroform alone, and ethanol precipitated. This plasmid DNA was used to transform chemical-competent DH5α cells. Three colonies from each transformation were used to inoculate 3 ml cultures; DNA was purified as described above. Approximately, 1/20 of each individually purified DNA sample from transformed cells was digested with EcoR1 and HindIII and examined by electrophoresis on a 1% agarose gel to determine insert size and DNA quality. One DNA prep for each clone was either sequenced manually using the dideoxy method or by an automated technique that uses fluorescent dideoxynucleotide terminators. The T7 gene 10 primer located approximately 40 bp upstream of the EcoR1 restriction site was used conveniently in both cases.

Figure 1:
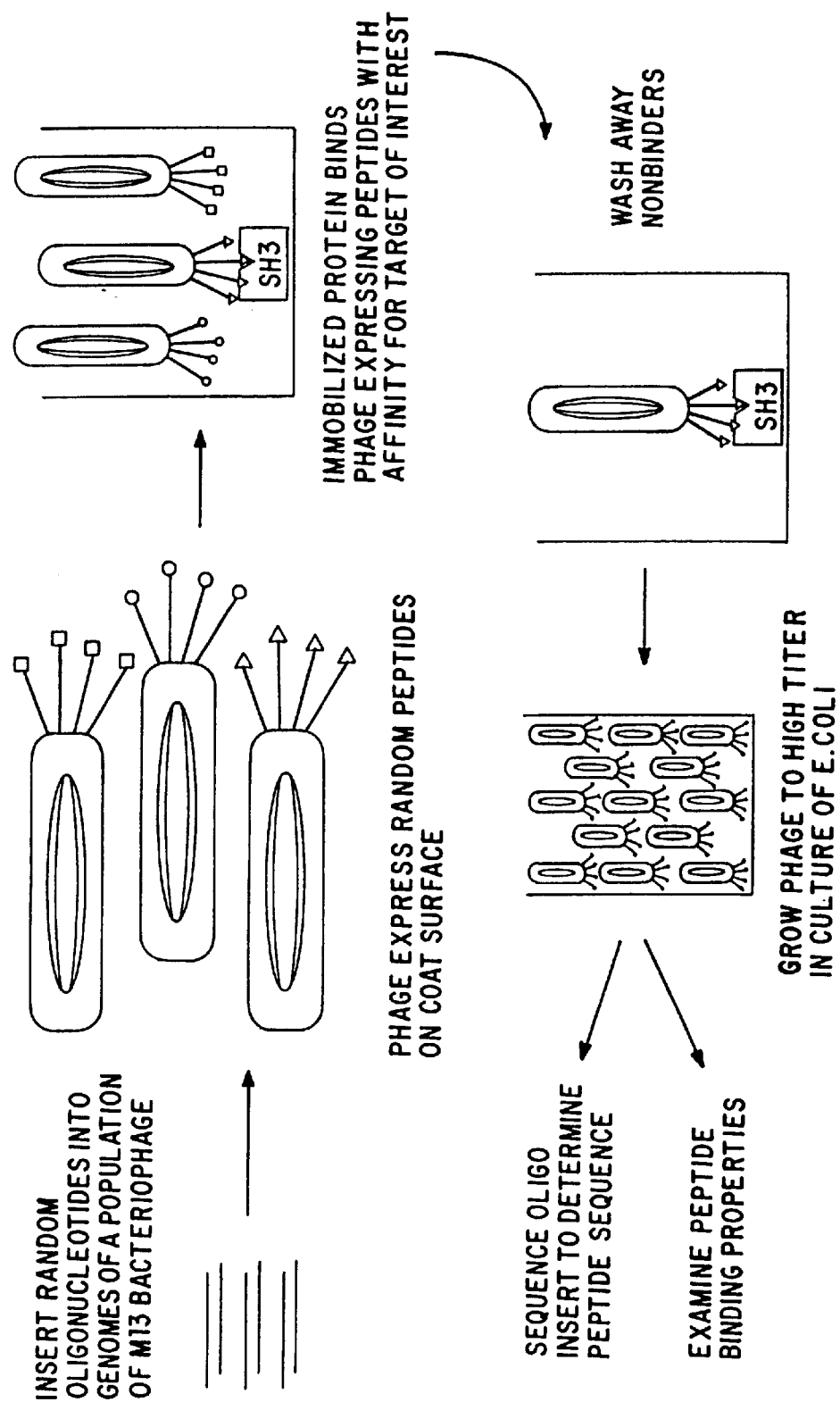
Figure 2:
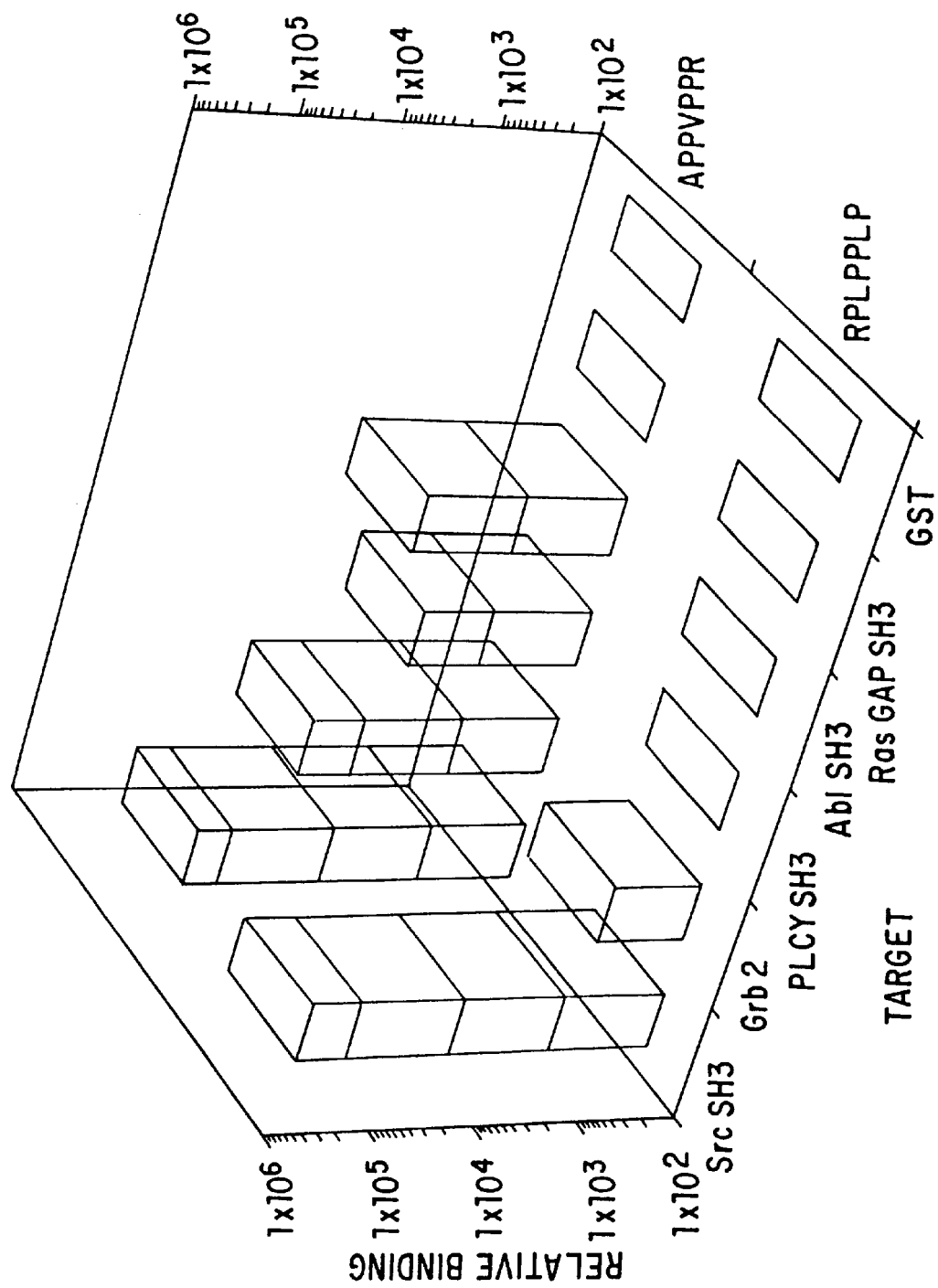
Figure 3:
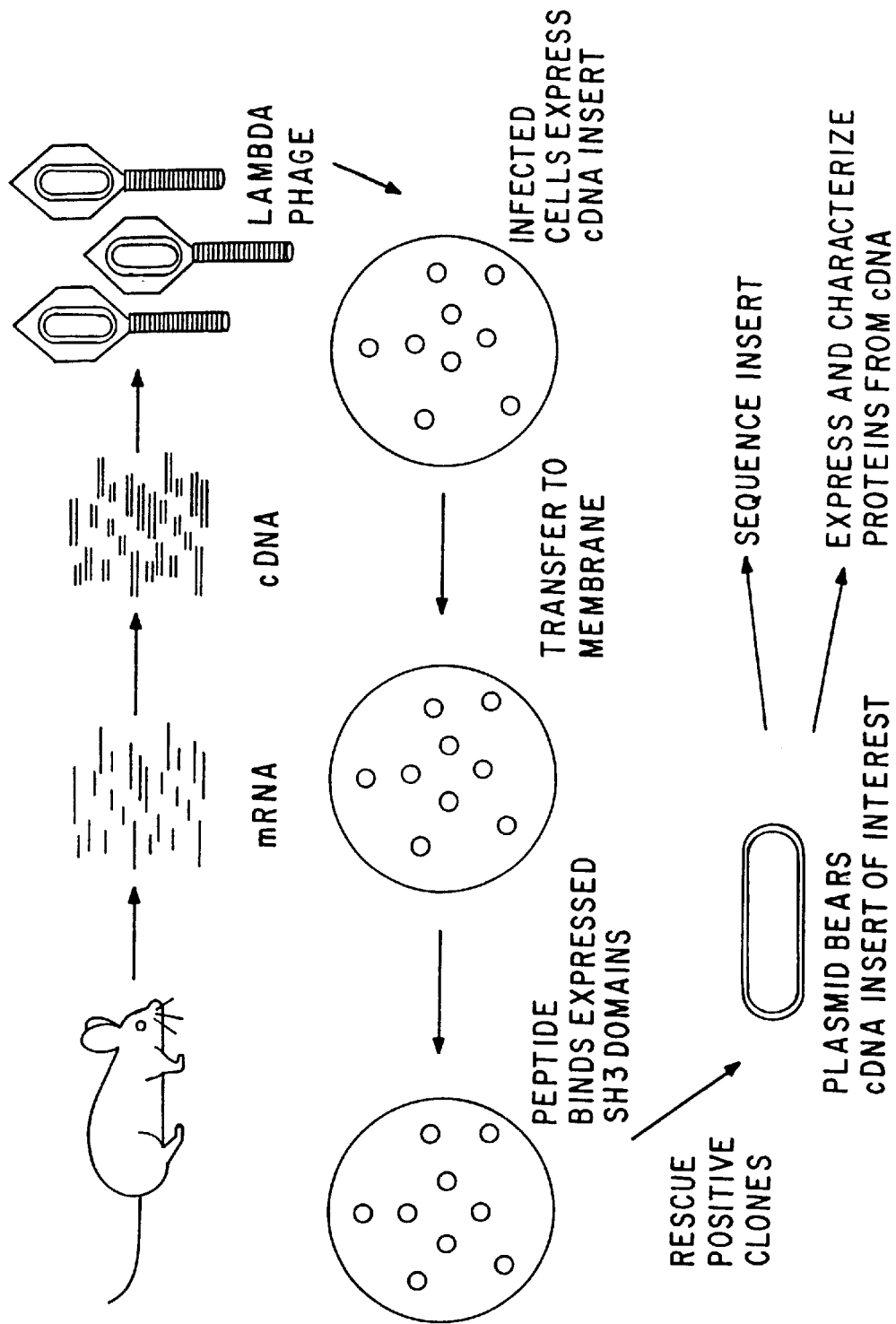
Figure 4:
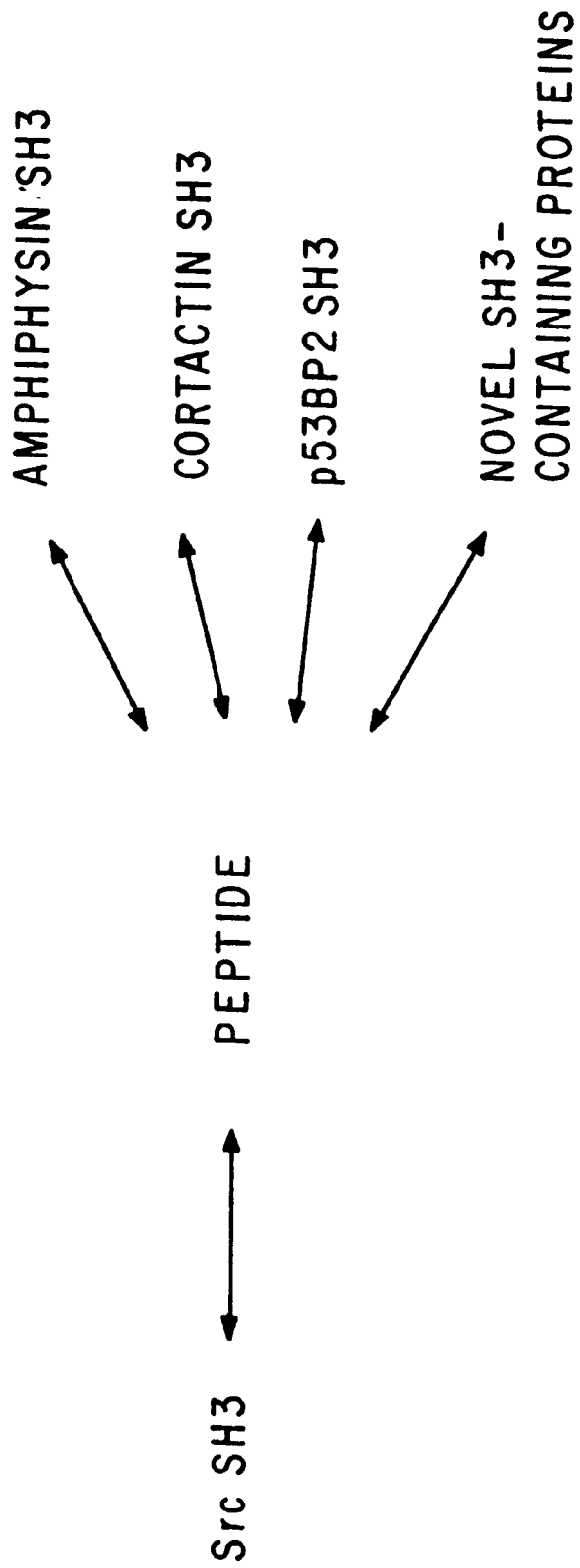
Figure 5A:
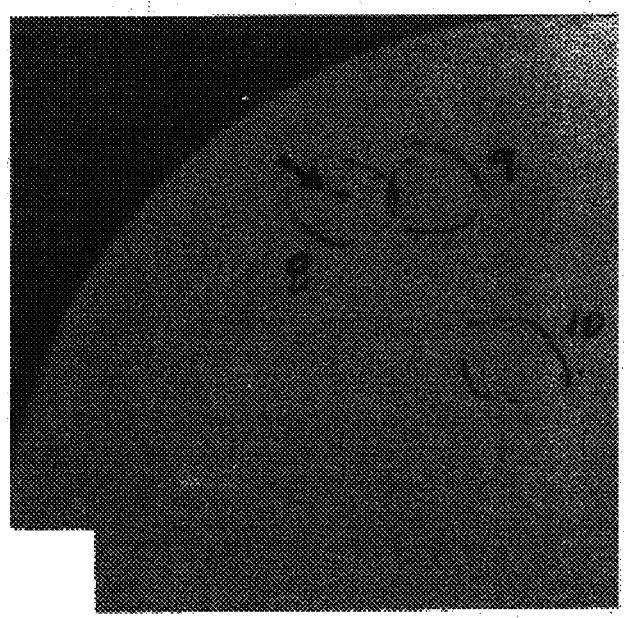
Figure 5B:
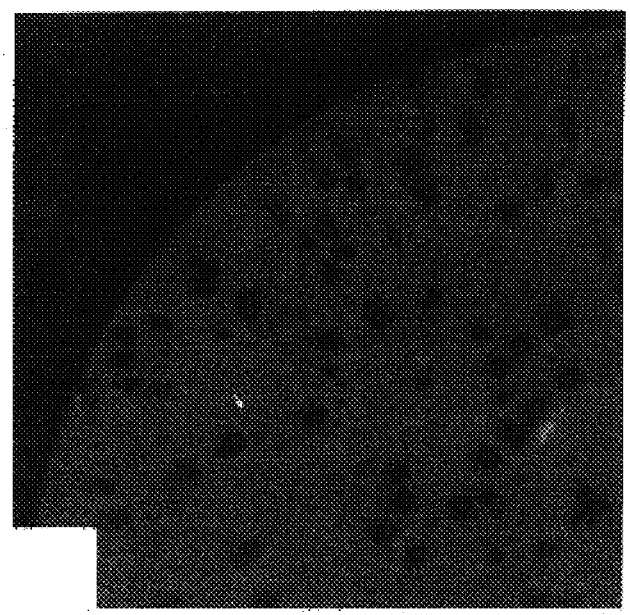
Figure 8A:
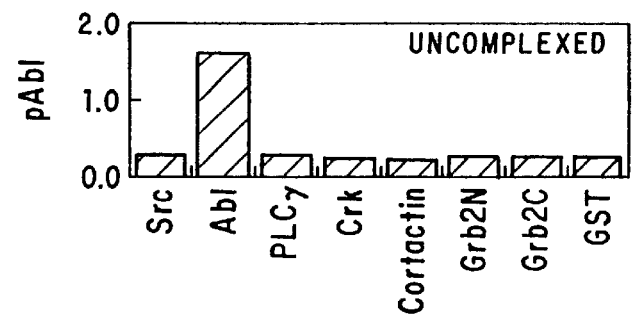
Figure 8B:
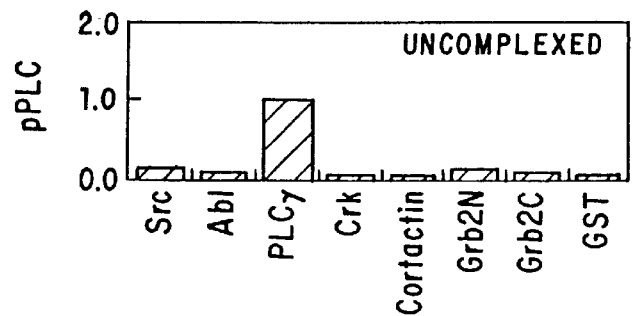
Figure 8C:
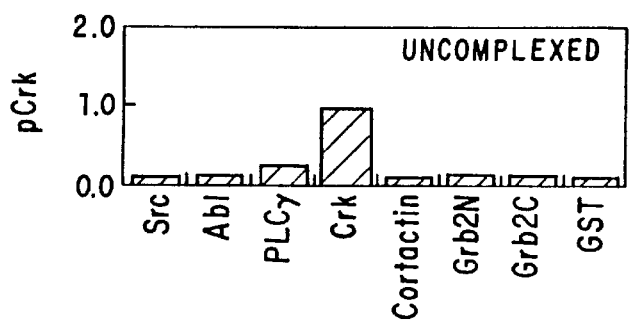
Figure 8D:
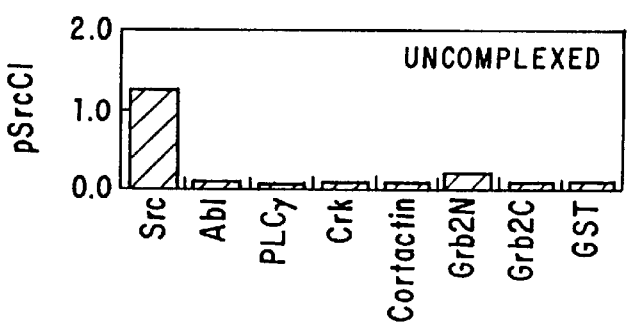
Figure 8E:
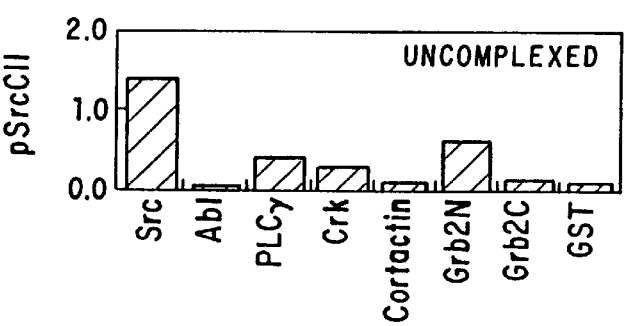
Figure 8F:
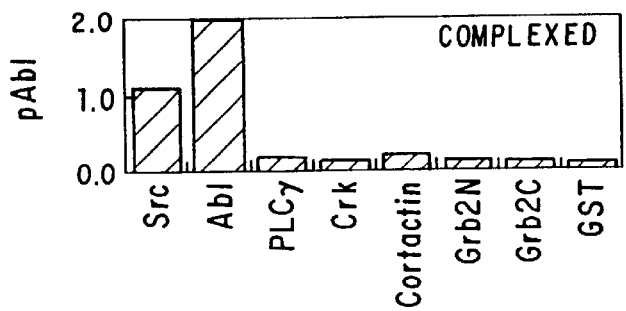
Figure 8G:
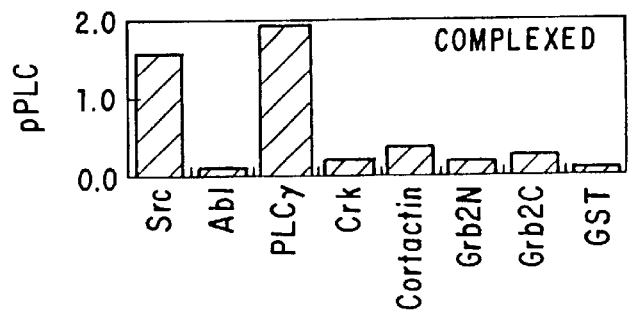
Figure 8H:
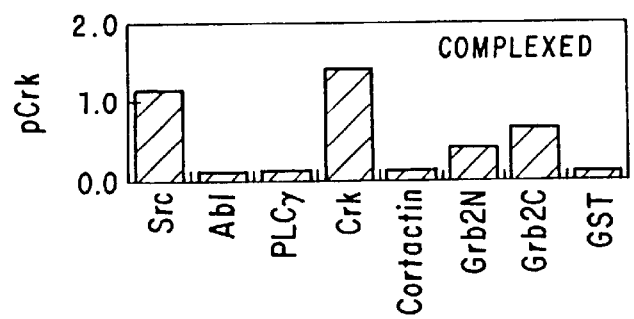
Figure 8I:
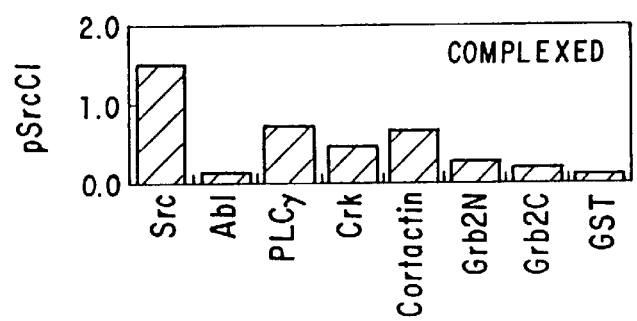
Figure 8J:
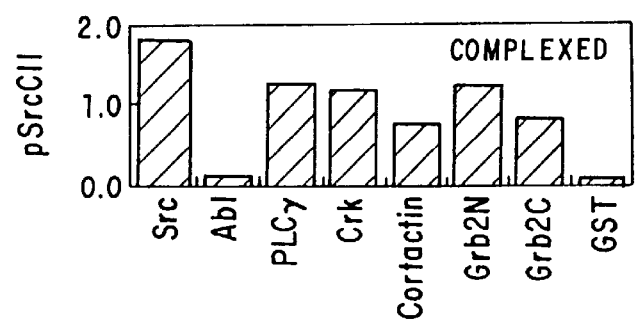

Approximately 100 of $1 \times 10^6$ plaques in the primary screen of the λEXlox 16 day mouse embryo cDNA expression library exhibited significant pSrcCII-binding activity. FIG. 5 is representative of filters from primary and tertiary screens. Of the eighteen positive clones that were isolated and sequenced, all were found to encode proteins with SH3 domains, although several clones appeared to be siblings or to originate from the same mRNA. Thus, the pSrcCII screen resulted in the identification of cDNAs encoding nine distinct SH3 domain-containing proteins (see FIG. 9). The sequences of these proteins were compared to the sequences in GenBank with the computer program BLAST. Three of these proteins corresponded to entries in GenBank. SH3P1 appears to be the murine homologue of p53bp2, a p53-binding protein, p53bp2 (Iwabuchi et al., 1994, Proc. Natl. Acad. Sci. USA 91:6098–6102); SH3P6 resembles human MLN50, a gene amplified in some breast carcinomas (Tomasetto et al., 1995, Genomics 28:367–376); and SH3P5 is Cortactin, a protein implicated in cytoskeletal organization (Wu and Parsons, 1993, J. Cell Biol. 120:1417–1426). Six of the clones did not match entries in GenBank, indicating that the present invention can be used to identify novel SH3 domain-containing proteins. Of these novel proteins, SH3P2 contains three ankyrin repeats and a proline-rich region flanking its SH3 domain; SH3P7 and SH3P9 contain sequences related to regions in the proteins drebrin (Ishikawa et al., 1994, J. Biol. Chem. 269:29928–29933) and amphiphysin (David et al., 1994, FEBS Lett. 351:73–79), respectively. Finally, the novel proteins SH3P4 and SH3P8, although not similar to any known proteins, are highly related (89% amino acid similarity) to one another.

The present invention can be used as part of an iterative process in which a recognition unit is used to identify proteins containing functional domains which are, in turn, used to derive additional recognition units for subsequent screens. For example, to define the binding specificity of these newly cloned SH3 domains, they can be overexpressed as glutathione S-transferase (GST)-fusion proteins in bacteria, which, in turn, can be used to screen a random peptide library in order to obtain recognition units which, in turn, can be used to screen cDNA libraries in order to obtain still more novel proteins containing SH3 domains.

The recognition unit binding preferences of two of the SH3 domains isolated in the pSrcCII screen described above (p53bp2 and Cortactin) have been described (Sparks et al., 1996, Proc. Natl. Acad. Sci. USA 93:1540–1544. Each of these SH3 domains recognizes recognition unit motifs related to, yet distinct from, the pSrcCII sequence. We used a synthetic peptide (pCort) containing the Cortactin SH3 recognition unit motif to screen the mouse embryo cDNA expression library. pCort was (biotin-SGSGSRLTPQSKPPLPPKPSWVSR—NH$_2$) (SEQ ID NO:2). pCort was prepared and complexed with SA-AP as above for pSrcCII. Screening of the mouse embryo library with pCort was done as above for pSrcCII.

Twenty six clones, of varying signal strength, were isolated and twenty-one were found to encode SH3 domain containing proteins. The pCort screen yielded genes corresponding to nine distinct SH3 domain-containing proteins (see FIG. 9), four of which corresponded to entries in GenBank. SH3P5 and SH3P6 are Cortactin and MLN50, discussed above; SH3P10 matched SPY75/HS1, a protein involved in IgE signaling (Fukamachi et al., 1994, J. Immunol. 152:642–652); and SH3P11 is Crk, an SH2 domain and SH3 domain-containing adaptor molecule (Knudsen et al., 1994, J. Biol. Chem. 269:32781–32787). The five novel transcripts encode SH3P7, SH3P8, and SH3P9, discussed above; SH3P13, an additional ember of the SH3P4/SH3P8 family; and SH3P12, a protein with three SH3 domains and a region sharing significant sequence similarity with the peptide hormone sorbin (Vagen-Descroiz M. et al., 1991, Eur. J. Biochem. 201:53–50).

Interestingly, the output from the pCort screen only partially overlapped with that of the pSrcCII screen: four of the nine SH3-containing proteins isolated with pCort were not identified with pSrcCII. In addition, SH3P9, the protein identified most frequently (50%) in the pSrcCII screen was isolated at a much lower frequency (7%) with the pCort probe. Thus, different recognition units can be used to identify distinct sets of SH3 domains.

In addition to possessing at least one SH3 domain, a prominent characteristic of the proteins identified in the pSrcCII and pCort screens is the position of the SH3 domain within the proteins: twelve of thirteen proteins possess SH3 domains near their C-termini. Although pSrcCII binds well to the Src SH3 domain (FIG. 8), Src (whose SH3 domain occurs near the N-terminus) was not identified in the pSrcCII screen. We suspect the bias was a consequence of the fact that the mouse embryo cDNA library was constructed using oligo-dT-primed cDNA. Alternatively, it may be that the mRNA used to prepare the library contained very little, or no, Src transcripts.

A variant of the pSrcCII peptide (T12SRC.1) was used to probe a λgt22a human prostate cancer cell line cDNA library primed with oligo-dT and a λgt11 human bone marrow library primed with random and oligo-dT primers. T12SRC.1 was (biotin-GILAPPVPPRNTR—NH$_2$) (SEQ ID NO:3). T12SRC.1 was used in the initial screens together with the peptide T12SRC.4. T12SRC.4 was (biotin-VLKRPLPIPPVTR—NH$_2$) (SEQ ID NO:4). The λgt22a human prostate cancer cell line cDNA library was made from the LNCaP prostate cancer cell line by using standard methods, i.e., the Superscript Lambda system for cDNA synthesis and cloning (Bethesda Research Laboratories, Gaithersburg, Md.). The λgt11 human bone marrow cDNA expression library was obtained from Clonetch (Palo Alto, Calif.). The human libraries were screened and positive clones isolated as described above for the mouse 16 day embryo cDNA library, except that cDNA inserts of the λgt11 and λgt22a phage were amplified by PCR rather than being rescued by cre-mediated excision. Of the $1.2 \times 10^7$ λcDNA clones screened from these libraries, 30 exhibited detectable pSrcCII-binding activity. Analysis of the positive clones revealed that they each encoded at least one SH3 domain, and that they originated from a total of six different transcripts (FIG. 9). Three of these encode proteins possessing non-C-terminal SH3 domains, indicating that the present invention can be used to identify active domains regardless of their position within a protein. Of the six proteins identified, only three matched GenBank entries. SH3P15 and SH3P16 are Fyn (Kawakami et al., 1988, Proc. Natl. Acad. Sci. USA 85:3870–3874 and Lyn (Yamanashi et al., 1987, Mol. Cell. Biol. 7:237–243), respectively, two Src-family members possessing SH3 domains with ligand preferences similar to that of the Src SH3 domain (Rickles, 1994, EMBO J. 13:5598–5604); and SH3P14 appears to be the human homologue of murine H74, a protein of unknown function. The three remaining proteins did not match entries in GenBank and include the human homolog of SH3P9, described above, and SH3P17 and SH3P18, fragments of two related (85% amino acid similarity) adaptor-like proteins comprised of at least four and three SH3 domains, respectively.

Examination of the primary sequences of the SH3 domains identified in this work reveals several interesting features (see FIG. 10). Positions important for ligand binding by the Src SH3 domain (Feng et al., 1994, Science 266:1241–1247; Lescure et al., 1992, J. Mol. Biol. 228:387–94) and essential for SH3 function in Grb2/Sem5 are conserved (Clark et al., 1992, Nature 356:340–344). In addition, the two gaps in the sequence alignment shown in FIG. 10 correspond to regions of length variation observed among previously characterized SH3 domains. Surprisingly, the SH3 domains identified in this work are not significantly more similar to one another than they are to other known SH3 domains, with the exception of the mouse and human forms of SH3P9 and SH3P14 which are 100% and 83% identical, respectively. This result indicates that SH3 domains can vary widely in primary structure and still bind proline-rich peptide recognition units selectively.

6.1.1. Nucleotide and Corresponding Amino Acid Sequences of Genes Identified from cDNA Expression Libraries The nucleotide sequences of SH3P1, SH3P2, SH3P3, SH3P4, SH3P5, SH3P6, SH3P7, SH3P8, SH3P9, SH3P10, SH3P11, SH3P12, SH3P13, and SH3P14, the mouse genes identified by screening the 16 day mouse embryo cDNA expression library with the peptides pSrcII and pCort, are shown in FIGS. 18, 20, 22, 24, 26, 28, 30, 32, 34, 38, 40, 42A and B, 44, and 46A and B, respectively. The corresponding amino acid sequences of the mouse genes SH3P1, SH3P2, SH3P3, SH3P4, SH3P5, SH3P6, SH3P7, SH3P8, SH3P9, SH3P10, SH3P11, SH3P12, SH3P13, and SH3P14 are shown in FIGS. 19, 21, 23, 25, 27, 29, 31, 33, 35, 39, 41, 43, 45, and 47, respectively.

The nucleotide sequences of SH3P9, SH3P14, SH3P17, and SH3P18, human genes identified by screening the human bone marrow and human prostate cancer cDNA expression libraries with the peptide T12SRC.1, are shown in FIGS. 36, 48, 50, and 52, respectively. The corresponding amino acid sequences of the human genes SH3P9, SH3P14, SH3P17, and SH3P18 are shown in FIGS. 37, 49, 51, and 53, respectively.

Two genes, SH3P9 and SH3P14, were isolated from both mouse and human libraries.

The sequences of SH3P15 and SH3P16 are not shown. SH3P15 is Lyn and SH3P16 is Fyn.

FIG. 54 shows the nucleotide sequence of clone 55, a novel human gene identified and isolated from a human bone marrow cDNA library (described in Section 6.1) using as recognition units a mixture of T12SRC.4 and pCort (described in Section 6.1) and the methods described in Section 6.1.

FIG. 55 shows the amino acid sequence of clone 55.

FIG. 56 shows the nucleotide sequence of clone 56, a novel human gene identified and isolated from a human bone marrow cDNA library (described in Section 6.1) using as recognition units a mixture of T12SRC.4 and pCort (described in Section 6.1) and the methods described in Section 6.1.

FIG. 57 shows the amino acid sequence of clone 56.

FIG. 58A shows the nucleotide sequence from position 1–1720 and FIG. 58B shows the nucleotide sequence from position 1720–2873 of clone 65, a novel human gene identified and isolated from a human bone marrow cDNA library (described in Section 6.1) using as recognition units a mixture of P53BP2.Con and Nck1.Con3 and the methods described in Section 6.1. P53BP2.Con and Nck1.Con3 are peptides, the amino acid sequences of which are biotin-SFAAPARPPVPPRKSRPGG—NH$_2$ (SEQ ID NO:201) and biotin-SFSFPPLPPAPGG—NH$_2$ (SEQ ID NO:202), respectively. The sequences of P53BP2.Con and Nck1.Con3 are consensus sequences of recognition units that bind to the SH3 domains of p53bp2 and Nck, respectively.

FIG. 59 shows the amino acid sequence of clone 65.

FIG. 60 shows the nucleotide sequence of clone 34, a novel human gene identified and isolated from a human prostate cancer cDNA library (described in Section 6.1) using as recognition units a mixture of T12SRC.1 and T12SRC.4 (described in Section 6.1) and the methods described in Section 6.1.

FIGS. 61A and 61B show the amino acid sequence of clone 34.

FIG. 62 shows the nucleotide sequence of clone 41, a novel human gene identified and isolated from a human bone marrow cDNA library (described in Section 6.1) using as recognition units a mixture of PXXP.NCK.S1/4 and PXXP.ABL.G1/2M and the methods described in Section 6.1. PXXP.NCK.S1/4 and PXXP.ABL.G1/2M are peptides, the amino acid sequences of which are biotin-SRSLSEVSPKPPIRSVSLSR—NH$_2$ (SEQ ID NO:222) and biotin-SRPPRWSPPPVPLPTSLDSR—NH$_2$ (SEQ ID NO:223), 30 respectively. PXXP.NCK.S1/4 and PXXP.ABL.G1/2M bind to the SH3 domains of Nck and Abl, respectively FIGS. 63A and 63B show the amino acid sequence of clone 41.

FIG. 64 shows the nucleotide sequence of clone 53, a novel human gene identified and isolated from a human prostate cancer cDNA library (described in Section 6.1) using as recognition units a mixture of PXXP.NCK.S1/4 and PXXP.ABL.G1/2M and the methods described in Section 6.1.

FIGS. 65A and 65B show the amino acid sequence of clone 53.

FIGS. 66A and 66B show the nucleotide and amino acid sequence of clone 5, a novel human gene identified and isolated from a HELA cell cDNA library using as recognition units a mixture of T12SRC.1 and T12SRC.4 (described in Section 6.1) and the methods described in Section 6.1.

6.2. Use of Peptides Resembling SH3 Domain Binding Sequences as Recognition Units We inspected a number of published amino acid sequences and identified proline-rich stretches of amino acids that resembled consensus SH3 domain binding sequences. Peptides comprising these proline-rich sequences were synthesized and tested by the methods of the present invention for their ability to specifically bind to the novel SH3 domains described in Sections 6.1 and 6.1.1. Purified SH3 domain-containing clones were spotted on a lawn of Y1090 host cells, grown for an appropriate amount of time, and plaque filter lifts were screened with biotinylated peptides complexed with streptavidin-alkaline phosphatase as described in Section 6.1.

The results are shown in FIGS. 12 and 13. As can be seen, in many cases the synthesized peptides were able to bind to the novel SH3 domains. This indicates that those synthesized peptides could have been used to identify those novel SH3 domains from sources of polypeptides.

6.3. Valency of Peptide Recognition Units Affects Specificity of Recognition Units 6.4. Preconjugation of Peptide Recognition Units with Streptavidin-Alkaline Phosphatase Increases Affinity of the Recognition Units for Targets As a preliminary test of the effect of the valency of peptide recognition units on the ability of those recognition units to be used as probes to detect SH3 domains, biotinylated peptides that had been previously shown to bind the SH3 domains of either Src or Abl were tested for their ability to bind their respective SH3 domain when either preconjugated with streptavidin-alkaline phosphatase (SA-AP) or not so preconjugated. GST-SrcSH3 and GST-AblSH3 fusion proteins (produced as described in Sparks et al., 1994, J. Biol. Chem. 269:23853–23856) were resolved by 10% SDS-PAGE and transferred to an Immobilon D nylon membranes (Millipore, New Bedford, Mass.). The membranes were incubated in blocking solution for 1 hr at 25° C. and then incubated overnight at 4° C. with either biotinylated Src SH3 domain or biotinylated Abl SH3 domain binding peptides in either multivalent (SA-AP) or monovalent format. The filters were washed three times (15 min each wash) in PBS/T and incubated with NBT and BCIP for color development. See Section 6.1 for further details of the detection process.

Figure 14:
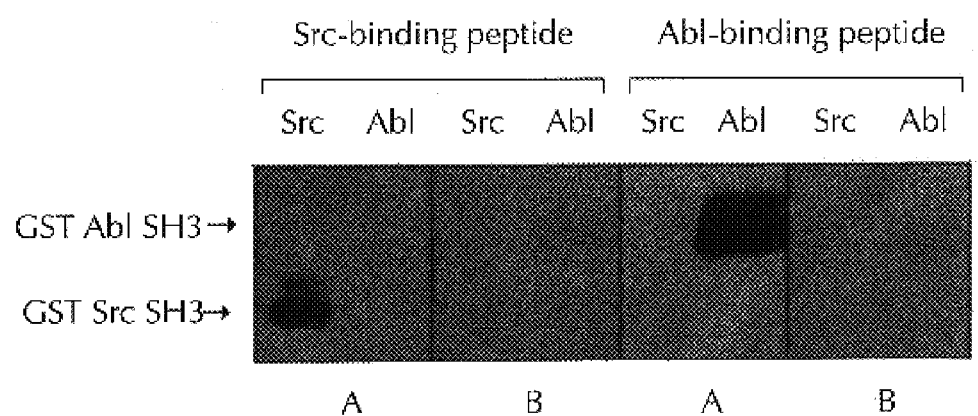
FIG. 14 illustrates the effect of preconjugation with streptavidin-alkaline phosphatase on the affinity of biotinylated peptides for SH3 domains. See Section 6.3.1 for details.

The results are shown in FIG. 14. In panels A, the biotinylated peptides were preconjugated with SA-AP and then allowed to bind to the immobilized SH3 domains. Preconjugation was as described in Section 6.1. In panels B, the peptides were first allowed to bind to the immobilized SH3 domains and then the bound peptides were detected by adding SA-AP. In both cases, color development was as in Section 6.1. The sequences of the peptides used were: Biotin-SGSGGILAPPVPPRNTR (SEQ ID NO:1) for the Src specific peptide and Biotin-SGSGSRPPRWSPPPVPLPTSLDSR (SEQ ID NO:41) for the Abl specific peptide. The results shown in FIG. 14 demonstrate that preconjugation with SA-AP dramatically increases the strength of the signal detected.

6.3.2. Preconjugation of Peptide Recognition Units with Streptavidin-Alkaline Phosphatase Results in Recognition of a Variety of SH3 Domains Two μg of each of a panel of GST-SH3 domain fusion proteins were transferred to Immobilon D nylon membranes (Millipore, New Bedford, Mass.) using a dot-blot apparatus. Biotinylated Src, Abl, or Cortactin SH3 domain-binding peptides were preconjugated to SA-AP and incubated with the filter; an alkline-phosphatase driven color reaction was used to detect peptide binding. The panel of immobilized proteins was also reacted with a polyclonal anti-GST antibody (Pharmacia, Piscataway, N.J.). Sequences of the Src, Abl, and Cortactin-binding peptides were Biotin-SGSGVLKRPLPIPPVTR (SEQ ID NO:42), Biotin-SGSGSRPPRWSPPPVPLPTSLDSR (SEQ ID NO:41), and Biotin-SGSGSRLGEFSKPPIPQKPTWMSR (SEQ ID NO:43), respectively.

Figure 15:
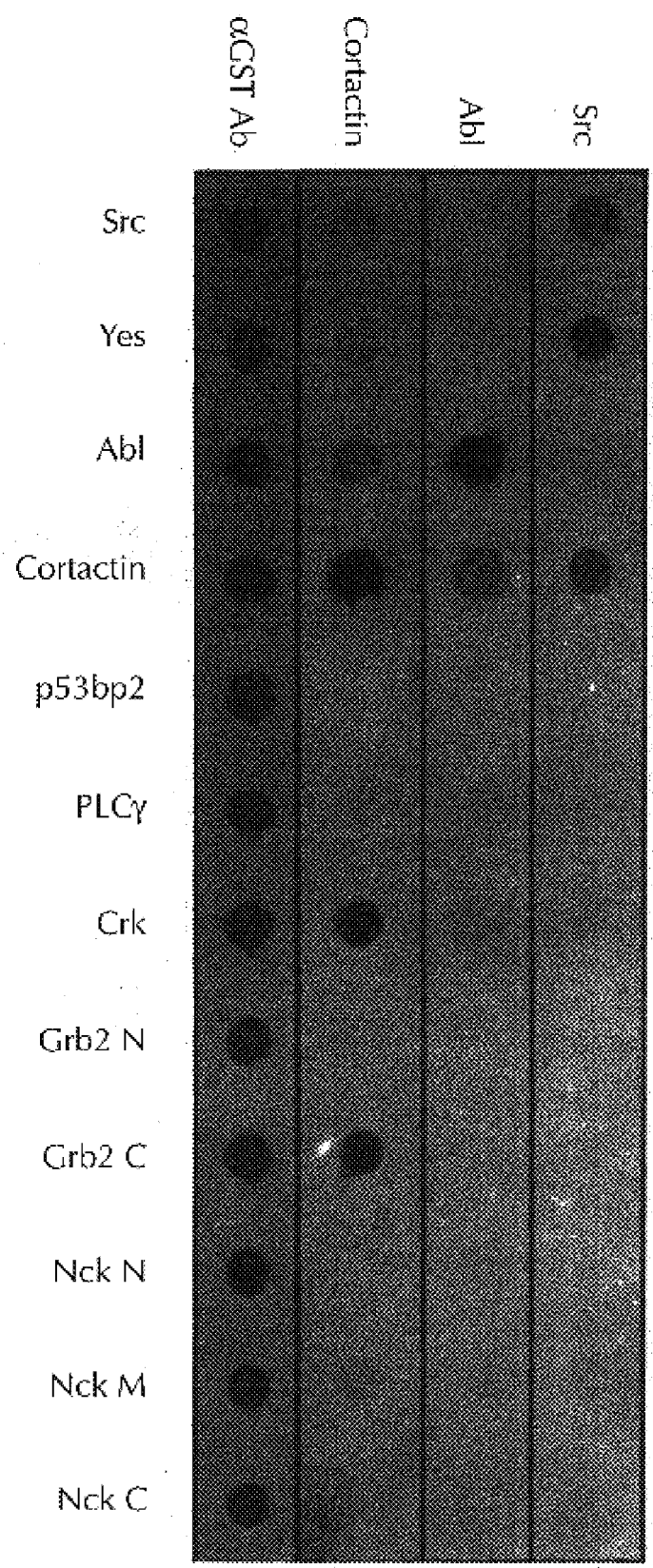
FIG. 15 illustrates the effect of preconjugation with streptavidin-alkaline phosphatase on the specificity of biotinylated peptides for GST-SH3 domain fusion proteins that have been immobilized on nylon membranes. See Section 6.3.2 for details.

As can be seen from the results shown in FIG. 15, the preconjugated biotinylated peptides recognized not only their original target SH3 domains, but related domains as well. The Src peptide recognized the SH3 domains of Yes and Cortactin as well as the SH3 domain of Src; the Abl peptide recognized the Cortactin SH3 domain as well as the Abl SH3 domain; and the Cortactin peptide recognized Src, Yes, Abl, Crk, and the C terminal Grb2 SH3 domains as well as recognizing the Cortactin SH3 domain.

The above experiment was performed utilizing SH3 domains that had been immobilized on nylon membranes. The following demonstrates that preconjugation with streptavidin also permits peptide recognition units to recognize a variety of SH3 domains when those domains are immobilized in the wells of a microtiter plate.

Five different peptide recognition units (pAbl, pPLC, pCrk, pSrcCI, pSrcCII) were tested in either multivalent or monovalent format for their ability to bind to seven different SH3 domains (Src, Abl, PLCγ, Crk, Cortactin, Grb2N, Grb2C) in an ELISA. The sequences of these peptides were as follows: pAbl, SGSGSRPPRWSPPPVPLPTSLDSR (SEQ ID NO:41); pPLC, SGSGSMPPPVPPRPPGTLGG (SEQ ID NO:66); pCrk, SGSGNYVNALPPGPPLPA-KNGG (SEQ ID NO:67); pSrcCI, SGSGVLKRPLPIP-PVTR (SEQ ID NO:42); pSrcCII, SGSGGILAPPVP-PRNTR (SEQ ID NO:1). These peptides were biotinylated as in Section 6.1.

The SH3 domains were produced as GST-SH3 fusion proteins as described in Sparks et al., 1994, J. Biol. Chem. 269:23853–23856. Their purity and concentration were confirmed by SDS-PAGE and Bradford protein assays, respectively. The GST-SH3 fusion proteins were immobilized in the wells of microtiter plates as follows: Two micrograms of each GST-SH3 fusion protein were incubated in wells of a flat bottom enzyme linked immunoabsorbent assay (ELISA) microtiter plate (Costar, Cambridge, Mass.) in 100 mM NaHCO₃ for 1 hr 25° C. One volume of SuperBlock blocking buffer (Pierce Chemical Co., Rockford, Ill.) was added to each well and incubated for an additional 30 min. Plates were washed three times with PBS/0.1% Tween-20/0.1% bovine serum albumin (BSA). Immobilized proteins were detected with SH3 domain-binding peptides in multivalent or monovalent formats using streptavidin-horseradish peroxidase (SA-HRP; Sigma Chemical Co., St. Louis, Mo.). For complexation of the biotinylated peptides and SA-HRP, peptide and SA-HRP concentrations were as described for SA-AP complexation in Section 6.1, but all incubations and washes were in PBS/0.1% Tween-20/0.1% BSA. Plates were washed five times before colorimetric reaction and before the addition of SA-HRP (monovalent format). The amount of bound SA-HRP was evaluated with the addition of 100 μl horseradish peroxidase substrate [2',2'-Azino-Bis 3-Ethylbenzthiazoline-6-Sulfonic Acid (ABTS), 0.05% hydrogen peroxide, 50 mM sodium citrate, pH 5.0]. After 5–30 minutes of reaction time, the optical densities (OD) of the microtiter plate wells were measured with a microtiter plate scanner (Molecular Devices, Sunnyvale, Calif.) set for 405 nm wavelength. The results are shown in FIG. 8. From FIG. 8 it can be seen that the tetravalent (complexed) peptides display both increased affinity and broadened specificity toward SH3 targets. Binding of complexed peptides was, however, still restricted to SH3 domains; the complexes bind to neither GST (FIG. 8) nor other unrelated proteins (data not shown). Thus, precomplexation with SA-AP decreases the specificity of the peptide recognition units but does not make the peptides non-specific. Rather, the peptides, when precomplexed, recognize a variety of SH3 domains in addition to their target domains.

6.3.3. Preconjugation of Peptide Recognition Units with Streptavidin-Alkaline Phosphatase Results in Recognition of a Variety of Expressed cDNA Clones Lambda phage clones of genes containing a variety of SH3 domains were isolated from screens of a 16 day mouse embryo cDNA expression library (Novagen, Madison, Wis.). For a description of the isolation of these cDNA clones, see Section 6.1. Phage particles corresponding to individual lambda phage cDNA recombinants were spotted onto 2xYT-1.5% agar petri plates onto which had been poured 3 ml of 2xYT-0.8% agarose with 100 μl of a BL21(DE3)pLysE *E. coli* culture grown overnight. After a 6 hr incubation at 37° C., expression of the cDNA segments was induced with IPTG-soaked nitrocellulose filters. After overnight incubation, the expressed proteins had been transferred to the filters and the filters were then incubated with either biotinylated SH3-domain binding peptides preconjugated to SA-AP or a monoclonal antibody recognizing the T7-Tag fusion peptide (αT7.10Mab; Novagen, Madison, Wis.). This antibody was used as a positive control since it recognized an epitope expressed by all the clones (part of the φ10 leader sequence common to all λEXlox recombinants). Sequences of pSrcI, pSrcII, Cortactin, and CaM (Calmodulin binding) peptides were Biotin-SGSGVLKRPLPIPPVTR (SEQ ID NO:42), Biotin-SGSGGILAPPVPPRNTR (SEQ ID NO:1), Biotin-SGSGSRLGEFSKPPIPQKPTWMSR (SEQ ID NO:43), and Biotin-STVPRWIEDSLRGGAARAQTRLASAK (SEQ ID NO:44), respectively.

Figure 16:
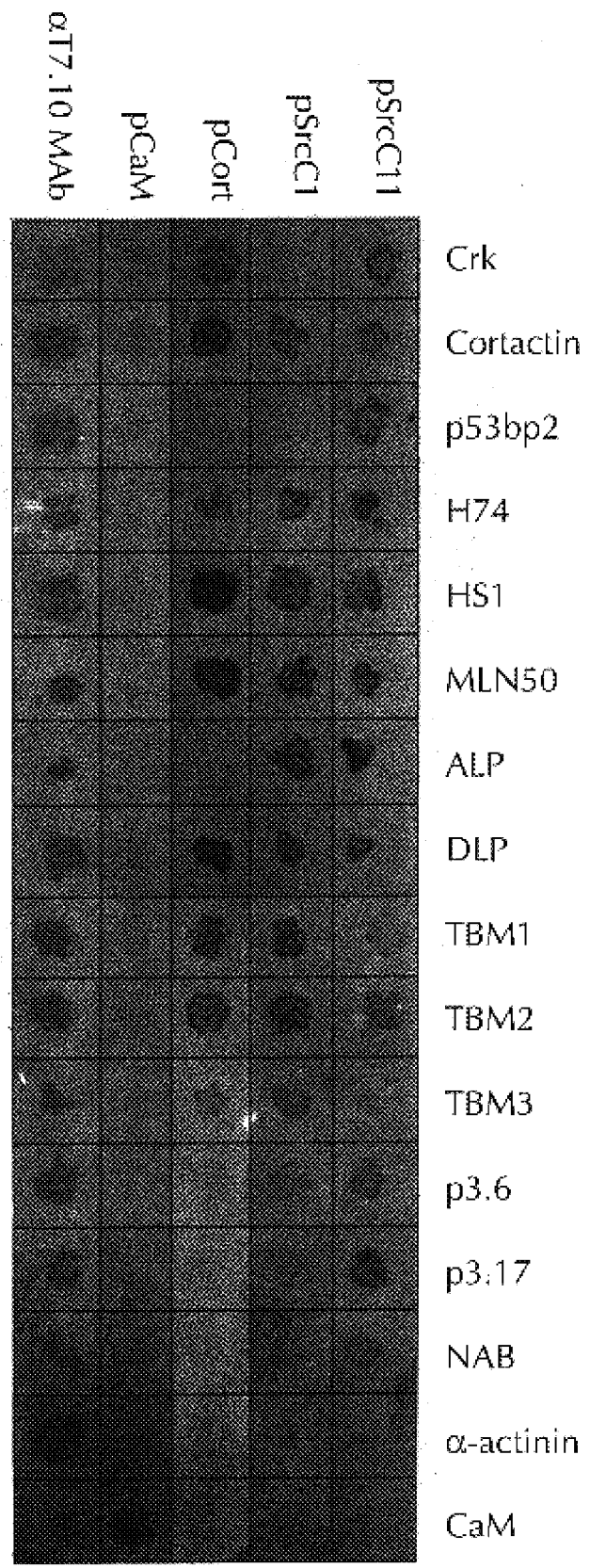
FIG. 16 illustrates the effect of preconjugation with streptavidin-alkaline phosphatase on the specificity of biotinylated peptides for proteins containing SH3 domains expressed by cDNA clones. See Section 6.3.3 for details.

The results are shown in FIG. 16. From FIG. 16 it can be seen that precomplexation with SA-AP decreases the specificity of the peptide recognition units but does not make the peptides non-specific; none of the peptides react in a significant fashion with two negative control sequences, α-actinin and calmodulin (CaM). Rather, the peptides, when precomplexed, recognize a variety of SH3 domain-containing cDNA clones in addition to clones containing their target domains.

6.4. Characterization of cDNA Clone-Encoded Proteins 6.4.1. Production of cDNA Clone-Encoded Proteins Purified DNA from all positive cDNA clones (ca. 18–20 positive clones per recognition unit) was used to transform chemical-competent BL21 cells (Hanahan et al., 1983, J. Mol. Biol. 166:557–580, the complete disclosure of which is incorporated by reference herein).

Colonies that appeared after growth overnight at 37° C. on 2xYT agar plates containing 100 μg/ml ampicillin were used to inoculate 4 ml cultures of 2xYT/amp. After 7 hours of incubation at 37° C. with shaking, IPTG was added to each culture to a final concentration of 100 μM. After an additional 2 hours of incubation, 1 ml of each culture was collected and centrifuged to pellet the cells. Cell pellets were resuspended in 400 μl 1xSDS/DTT loading buffer and boiled at 100° C. for 5 min. The resulting cell lysates were subjected to Sodium Dodecyl Sulfate-Polyacrylamide Gel Electrophoresis (SDS-PAGE) on an 8% acrylamide gel. Gels were either Coomassie stained or transferred to Immobilon D membrane (Millipore) and blotted (Towbin et al., 1979, Proc. Natl. Acad. Sci. 76:4350–4354).

Materials Used in Sections 6.1, 6.2, 6.3.1, 6.3.2, 6.3.3, and 6.4.1

| Blocking Solution | |
|---|---|
| Hepes (pH 8) | 20 mM |
| MgCl$_2$ | 5 mM |
| KCl | 1 mM |
| Dithiothreitol | 5 mM |
| Milk Powder | 5% w/v |

| -continued | |
|---|---|
| 2xYT media (1L) | |
| Bacto tryptone | 16 g |
| Yeast Extract | 10 g |
| NaCl | 5 g |
| 2xYT agar plates | |
| 2xYT + 15 g agar/L | |
| 2xYT top agarose (8%) | |
| 2xYT + 8 g agarose/L | |
| SDS/DTT loading buffer | |
| (10 mL of 5x solution) | |
| .5 M Tris base | 0.61 g |
| 8.5% SDS | 0.85 g |
| 27.5% sucrose | 2.75 g |
| 100 mM DTT | 0.154 g |
| .03% Bromophenol Blue | 3.0 mg |
| Overnight cell cultures: | |
| Inoculate media with one isolated colony of appropriate cell type and incubate 37° C. O/N with shaking BL21 (DE3) pLysE 2XYT media | |
| maltose | 0.2% |
| MgSO$_4$ | 10 mM |
| Chloramphenicol | 25 μg/mL |
| BM25.8 | |
| 2xYT media | |
| maltose | 0.2% |
| MgSO$_4$ | 10 mM |
| Chloramphenicol | 34 μg/ml |
| Kanamycin | 50 μg/ml |

6.6. Other Functional Domains and Recognition Units

In a manner similar to that described above for SH3 domains, recognition units directed to other functional domains of interest can be chosen for use in the present method. For example, as recognition units for a study of GST functional domains, the following GST-binding peptides can be used to screen a plurality of polypeptides: Class I CWSEWDGNEC (SEQ ID NO:46), CGQWADDGYC (SEQ ID NO:47), CEOWDGYGAC (SEQ ID NO:48), CWPFWDGSTC (SEQ ID NO:49), CMIWPDGEEC (SEQ ID NO:50), CESOWDGYDC (SEQ ID NO:51), CQQWKEDGWC (SEQ ID NO:52), or CLYOWDGYEC (SEQ ID NO:53); Class II—CMGDNLGDDC (SEQ ID NO:54), CMGDSLGOSC (SEQ ID NO:55), CMD-DDLGKGC (SEQ ID NO:56), CMGENLGWSC (SEQ ID NO:57), or CLGESLGWMC (SEQ ID NO:58).

Moreover, the following SH2-binding peptides can be used according to the methods of the present invention to identify SH2 domain-containing polypeptides: GDGYEE-ISP (SEQ ID NO:59) (for Src family), GDGYDEPSP (SEQ ID NO:60) (for Nck), GDGYDHPSP (SEQ ID NO:61) (for Crk), GDGYVIPSP (SEQ ID NO:62) (PLCγN), GDGYQNYSP (SEQ ID NO:63) (for PLCγC), GDGY-MAMSP (SEQ ID NO:64) (for p85PI3KN and p85PI3KC), or GDGQNYSP (SEQ ID NO:65) (for Grb2). See, Yang, Cell 72:767–778, the complete disclosure of which is incorporated by reference herein.

Further, polypeptides with a "PH" functional domain (analogous to the proteins Vav, Bcr, Msos, PLCδ, Atk, or Pleckstrin) can be identified using PH-binding peptides, such as those described by Mayer et al., Cell 73:629–630, the complete disclosure of which is incorporated by reference herein.

Other recognition units can be readily contemplated, including other synthetic, semisynthetic, or naturally derived molecules.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

```

What is claimed is:

1. A method of identifying a polypeptide comprising an SH2 domain of interest comprising:

(a) contacting a multivalent recognition unit complex with a plurality of polypeptides from a cDNA expression library, in which the recognition units are peptides having in the range 6 to 60 amino acid residues and which selectively bind an SH2 domain; and (b) identifying a polypeptide having a selective binding affinity for said recognition unit complex wherein the binding specificity of the recognition units has been decreased by incorporating said recognition units into said multivalent recognition unit complex.

2. A method of identifying a polypeptide comprising an SH2 domain of interest comprising:
  (a) contacting a multivalent recognition unit complex, which complex comprises
    (i) avidin or streptavidin, and
    (ii) biotinylated recognition units, with a plurality of polypeptides from a cDNA expression library, in which the recognition units are peptides having in the range of 6 to 60 amino acid residues and which selectively binds an SH2 domain; and
  (b) identifying a polypeptide having a selective binding affinity for said recognition unit complex;
wherein the binding specificity of the recognition units has been decreased by incorporating said recognition units into said multivalent recognition unit complex.

3. The method of claim 1, wherein the multivalent recognition unit complex comprises a complex selected from the group consisting of: (a) biotinylated recognition units and avidin or streptavidin, (b) recognition units in the form of multiple antigenic peptides, or (c) recognition units cross-linked to a carrier protein.

4. The method of any one of claim 1, 2, or 3 in which of polypeptides is obtained from a virus.

5. The method of any one of claim 1, 2, or 3 in which said expression library is a recombinant bacteriophage library.

6. The method of claim 5 in which said expression library is a recombinant M13 library.

7. The method of any one of claim 1, 2, or 3 in which said expression library is a recombinant plasmid or cosmid library.

8. The method of any one of claim 1, 2, or 3 in which said recognition unit is a peptide having 20 to 50 amino acid residues.

9. The method of claim 1 or claim 3 in which the valency of the recognition unit in the complex is at least four.

* * * * *

                       SEQUENCE LISTING (1) GENERAL INFORMATION:

(iii) NUMBER OF SEQUENCES: 227

(2) INFORMATION FOR SEQ ID NO: 1:

(i) SEQUENCE CHARACTERISTICS:
         (A) LENGTH: 17 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Other
         (D) OTHER INFORMATION: May or may not have carboxy-terminal
             amide and/or biotinylated N-terminal (xi) SEQUENCE DESCRIPTION: SEQ ID NO: 1:

Ser Gly Ser Gly Gly Ile Leu Ala Pro Pro Val Pro Pro Arg Asn Thr
1               5                  10                  15

Arg (2) INFORMATION FOR SEQ ID NO: 2:

(i) SEQUENCE CHARACTERISTICS:
         (A) LENGTH: 24 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Other
         (D) OTHER INFORMATION: May or may not have carboxy-terminal
             amide and/or biotinylated N-terminal (xi) SEQUENCE DESCRIPTION: SEQ ID NO: 2:

Ser Gly Ser Gly Ser Arg Leu Thr Pro Gln Ser Lys Pro Pro Leu Pro
1               5                  10                  15

Pro Lys Pro Ser Trp Val Ser Arg
            20

(2) INFORMATION FOR SEQ ID NO: 3:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Other
         (D) OTHER INFORMATION: May or may not have carboxy-terminal
             amide and/or biotinylated N-terminal (xi) SEQUENCE DESCRIPTION: SEQ ID NO: 3:
```

```
Gly Ile Leu Ala Pro Pro Val Pro Pro Arg Asn Thr Arg
1               5                   10
```

(2) INFORMATION FOR SEQ ID NO: 4:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (D) OTHER INFORMATION: May or may not have carboxy-terminal
            amide and/or biotinylated N-terminal (xi) SEQUENCE DESCRIPTION: SEQ ID NO: 4:

```
Val Leu Lys Arg Pro Leu Pro Ile Pro Pro Val Thr Arg
1               5                   10
```

(2) INFORMATION FOR SEQ ID NO: 5:

(i) SEQUENCE CHARACTERISTICS:
        (A) LENGTH: 605 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

```
GTGAATGCTG CAGACAGTGA CGGATGGACA CCACTGCATT GTGCTGCCTC TTGCAACAGT      60
GTCCACCTCT GCAAGCAGCT GGTGGAAAGT GGAGCCGCTA TCTTTGCCTC CACCATCAGT     120
GACATTGAGA CTGCTGCAGA CAAGTGTGAA GAGATGGAAG AGGGATACAT CCAGTGTTCC     180
CAGTTTCTGT ATGGGGTACA AGAGAAGCTG GGAGTGATGA ACAAAGGCAC CGTGTATGCT     240
TTGTGGGACT ACGAGGCCCA GAACAGCGAT GAGCTGTCCT TCCATGAAGG GGATGCCATC     300
ACCATCCTGA GGCGCAAAGA TGAAAACGAG ACCGAGTGGT GGTGGGCTCG TCTTGGGGAC     360
CGGGAGGGCT ACGTGCCCAA AAACTTGCTG GGGTTGTATC CACGGATCAA ACCCCGGCAG     420
CGAACACTTG CCTGAACCCC CTGGAGTACC ACAGTCTCGT TTGCTCCCAG GAGCTACTGG     480
AGGAGATCCC ACTGCCCTGG GAAAACTGAA GCTAGGATGG TCTCCTGGTG CTCACTTTAG     540
CAGACAGTGT CCACAATGTG AATCCCACTT CCCAGGTGAG GCCCTCTCCA GGCTGCAGGA     600
GCTGG                                                                 605
```

(2) INFORMATION FOR SEQ ID NO: 6:

(i) SEQUENCE CHARACTERISTICS:
        (A) LENGTH: 144 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 6:

```
Val Asn Ala Ala Asp Ser Asp Gly Trp Thr Pro Leu His Cys Ala Ala
1               5                   10                  15

Ser Cys Asn Ser Val His Leu Cys Lys Gln Leu Val Glu Ser Gly Ala
                20                  25                  30

Ala Ile Phe Ala Ser Thr Ile Ser Asp Ile Glu Thr Ala Ala Asp Lys
```

```
                35                  40                  45
Cys Glu Glu Met Glu Glu Gly Tyr Ile Gln Cys Ser Gln Phe Leu Tyr
             50                  55                  60

Gly Val Gln Glu Lys Leu Gly Val Met Asn Lys Gly Thr Val Tyr Ala
 65                  70                  75                  80

Leu Trp Asp Tyr Glu Ala Gln Asn Ser Asp Glu Leu Ser Phe His Glu
                 85                  90                  95

Gly Asp Ala Ile Thr Ile Leu Arg Arg Lys Asp Glu Asn Glu Thr Glu
                100                 105                 110

Trp Trp Trp Ala Arg Leu Gly Asp Arg Glu Gly Tyr Val Pro Lys Asn
            115                 120                 125

Leu Leu Gly Leu Tyr Pro Arg Ile Lys Pro Arg Gln Arg Thr Leu Ala
        130                 135                 140
```

(2) INFORMATION FOR SEQ ID NO: 7:

(i) SEQUENCE CHARACTERISTICS:
        (A) LENGTH: 1277 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

```
GAATTCAAGC TCGGGTTGCG CGCGGTCCGG AGCGGCCGCG GCCAGCGCAG GCTTGGCGCC      60
CAGTTGTCGT GTGCGTGTGG GGCTCCCGCG GCTGAGCCTG GTCGCTCCGT GTAGCGCCAT     120
GTCCAAGCCA CCTCCCAAAC CGGTCAAACC AGGGCAAGTT AAAGTCTTCA GAGCTCTATA     180
TACATTTGAA CCCAGAACTC CAGATGAATT ATACTTTGAA GAAGGAGACA TTATCTACAT     240
CACTGACATG AGTGATACCA GCTGGTGGAA AGGGACATGC AAGGGCAGAA CAGGACTGAT     300
CCCGAGCAAC TATGTGGCTG AGCAGGCAGA ATCCATTGAC AATCCATTGC ATGAAGCTGC     360
AAAAAGAGGC AACCTGAGCT GGTTGAGGGA GTGCTTGGAC AACCGGGTGG GTGTGAACGG     420
CCTGGACAAA GCTGGAAGCA CAGCCCTGTA CTGGGCCTGC ACGGTGGCC ATAAAGACAT      480
AGTGGAGGTT CTGTTTACTC AGCCGAATGT GGAGCTGAAC CAGCAGAATA AGCTGGGAGA     540
CACAGCTCTG CACGCGGNTG CCTGGAAGGG TTATGCAGAC ATTGTCCAGT TGCTACTGGC     600
AAAAGGTGCG AGGACAGACT TGAGAAACAA TGAGAAGAAG CTGGCCTTGG ACATGGCCAC     660
CAACGCTGCC TGTGCATCGC TCCTGAAGAA GAAGCAGCAG GGAACAGATG GGCTCGAAC      720
GTTAAGCAAC GCCGAGGACT ACCTCGATGA CGAAGACTCA GACTGATTCC CCCCGGGGCC     780
GCTTTGATTG TTGCCTAAAC TTCTTTTGCT TTTGCCATTC CGGAGCCTGG GTTGTTTGCC     840
AGAAGAGTAT TGATAACTGT TGCTTTTAAA GTCTGTATGA GCGCGACACT GCTGCACTGT     900
GATCTGTGAG GAGTCGTTGT GAGGGTGGCT CATTCTCACC CACGCCTTGN CAATAAGTGA     960
AGAGATACTT TGTTGTATAA AATACATATA TGCTCACCAG GGTAAAATAA ACGAAAAAAA    1020
NTTATTTCTA TTTATCAAGC TAAAAAAAAA AAGCTTGGGC CCTNTTCTAT AGTGTCACCT    1080
AAATACTAGC TTGANCCGGN TGCTAACAAA GCCCGAAAGG AAGCTGAGTT GCTGCTGCCA    1140
CCGNTGAGCA ATAACTAGCA TANCCCCTTG GGGCCTCTAA ACGGGTCTTG AGGGGTTTTT    1200
NGNTGAAAGG AGGANCTATT TCCGGATAAC CTGGNGTAAT AGGGAAGAGG CCCGNACCGA    1260
TCGCCCTTCC CAACAGA                                                  1277
```

(2) INFORMATION FOR SEQ ID NO: 8:

(i) SEQUENCE CHARACTERISTICS:
        (A) LENGTH: 251 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

Ser Gly Cys Ala Arg Ser Gly Ala Ala Ala Ser Ala Gly Leu Ala
 1               5                  10                  15

Pro Ser Cys Arg Val Arg Val Gly Leu Pro Arg Leu Ser Leu Val Ala
                20                  25                  30

Pro Cys Ser Ala Met Ser Lys Pro Pro Lys Pro Val Lys Pro Gly
         35                  40                  45

Gln Val Lys Val Phe Arg Ala Leu Tyr Thr Phe Glu Pro Arg Thr Pro
 50                      55                  60

Asp Glu Leu Tyr Phe Glu Gly Asp Ile Ile Tyr Ile Thr Asp Met
 65                  70                  75                  80

Ser Asp Thr Ser Trp Trp Lys Gly Thr Cys Lys Gly Arg Thr Gly Leu
                85                  90                  95

Ile Pro Ser Asn Tyr Val Ala Glu Gln Ala Glu Ser Ile Asp Asn Pro
            100                 105                 110

Leu His Glu Ala Ala Lys Arg Gly Asn Leu Ser Trp Leu Arg Glu Cys
        115                 120                 125

Leu Asp Asn Arg Val Gly Val Asn Gly Leu Asp Lys Ala Gly Ser Thr
130                 135                 140

Ala Leu Tyr Trp Ala Cys His Gly Gly His Lys Asp Ile Val Glu Val
145                 150                 155                 160

Leu Phe Thr Gln Pro Asn Val Glu Leu Asn Gln Gln Asn Lys Leu Gly
                165                 170                 175

Asp Thr Ala Leu His Ala Ala Trp Lys Gly Tyr Ala Asp Ile Val
            180                 185                 190

Gln Leu Leu Leu Ala Lys Gly Ala Arg Thr Asp Leu Arg Asn Asn Glu
        195                 200                 205

Lys Lys Leu Ala Leu Asp Met Ala Thr Asn Ala Ala Cys Ala Ser Leu
210                 215                 220

Leu Lys Lys Lys Gln Gln Gly Thr Asp Gly Ala Arg Thr Leu Ser Asn
225                 230                 235                 240

Ala Glu Asp Tyr Leu Asp Asp Gly Asp Ser Asp
                245                 250

(2) INFORMATION FOR SEQ ID NO: 9:

(i) SEQUENCE CHARACTERISTICS:
        (A) LENGTH: 835 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

ACTCACGNCG GTGGAGTGGT ACCGGATCGA ATTCAAGCCG CATCACTGGC ACTGGACGCC      60

AGGGCATCTT CCCTGCCAGC TACGTGCAGA TAAACCGAGA GCCCCGGCTC AGGCTTTGTG     120

ATGGATGGTCC CCAGCTCCCT GCATCACCTA ACCCGACAAC CACTGCTCAC CTAAGCAGCC    180

ACTCCCACCC CTCCTCAATA CCTGTGGACC CCACTGACTG GGGAGGTCGA ACCTCCCCTC    240

```
GACGCTCCGC CTTTCCCTTC CCCATCACCC TCCAGGAGCC CAGATCCCAA ACCCAGAGTC     300

TCAATACCCC TGGACCAACC CTGTCCCATC CTCGAGCCAC CAGCCGTCCC ATAAACCTGG     360

GACCCTCCTC CCCAAACACA GAGATACACT GGACTCCGTA CCGGGCCATG TACCAGTACA     420

GGCCCCAGAA TGAGGACGAG CTGGAACTTG AGAGGGGGA CCGTGTGGAT GTCATGCAGC      480

AATGTGACGA TGGCTGGTTT GTGGGTGTCT CCCGGCGAAC TCAGAAATTT GGGACATTCC     540

CTGGAAATTA TGTAGCCCCA GTGTGAGTGG TCTCCATGGC AGTTTGGAGC CAACGAGGAT     600

CGGGAGGGGA GCAGTAGCAC TATGGGAGGG AGAGAGGCCT TCCATAGCCT CCTCCCCAGG     660

ACCTGTGCTC CCAGCTTCTG CAGAGACCCC AGCAACTTTC CCTCCAAGCC TCCTTGAAGT     720

CCGATTCCCA CCCCGCAAGT CACAGGCATT CCTTTGACAG CCCCCTTCAC CGCCCCTCAA     780

ATACAGACAT CTGCTTTCAT GTGGGNAAAA AAAAAAATT AAAAGGTGGC CCTAT           835
```

(2) INFORMATION FOR SEQ ID NO: 10:

(i) SEQUENCE CHARACTERISTICS:
        (A) LENGTH: 175 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

```
Arg Ile Thr Gly Thr Gly Arg Gln Gly Ile Phe Pro Ala Ser Tyr Val
  1               5                  10                  15

Gln Ile Asn Arg Glu Pro Arg Leu Arg Leu Cys Asp Asp Gly Pro Gln
             20                  25                  30

Leu Pro Ala Ser Pro Asn Pro Thr Thr Thr Ala His Leu Ser Ser His
         35                  40                  45

Ser His Pro Ser Ser Ile Pro Val Asp Pro Thr Asp Trp Gly Gly Arg
     50                  55                  60

Thr Ser Pro Arg Arg Ser Ala Phe Pro Phe Pro Ile Thr Leu Gln Glu
 65                  70                  75                  80

Pro Arg Ser Gln Thr Gln Ser Leu Asn Thr Pro Gly Pro Thr Leu Ser
                 85                  90                  95

His Pro Arg Ala Thr Ser Arg Pro Ile Asn Leu Gly Pro Ser Ser Pro
            100                 105                 110

Asn Thr Glu Ile His Trp Thr Pro Tyr Arg Ala Met Tyr Gln Tyr Arg
        115                 120                 125

Pro Gln Asn Glu Asp Glu Leu Glu Leu Arg Glu Gly Asp Arg Val Asp
    130                 135                 140

Val Met Gln Gln Cys Asp Asp Gly Trp Phe Val Gly Val Ser Arg Arg
145                 150                 155                 160

Thr Gln Lys Phe Gly Thr Phe Pro Gly Asn Tyr Val Ala Pro Val
                165                 170                 175
```

(2) INFORMATION FOR SEQ ID NO: 11:

(i) SEQUENCE CHARACTERISTICS:
        (A) LENGTH: 2143 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

```
TTNNNNYYMM SKYSKKGKKK KGKWMSGRTC GATTCAAGCC GACCAGCGGC GGCCCGGCGA     60

CCCCAGCCGC CTCTCCGCAT CTGCATCTGC ATCTGCCGGC CGCGCAGCCT CCCGCATCCC    120

ATCATGTCGG TGGCAGGGCT GAAGAAGCAG TTCCACAAAG CCACTCAGAA AGTGAGTGAG    180

AAGGTGGGAG GAGCGGAAGG CACCAAGCTC GATGATGACT TCAAAGAGAT GGAGAGGAAA    240

GTGGATGTCA CCAGCAGGGC TGTGATGGAG ATAATGACAA AAACGATTGA ATACCTCCAA    300

CCCAATCCAG CTTCCAGGGC TAAGCTCAGT ATGATCAACA CCATGTCGAA AATCCGCGGC    360

CAAGAGAAGG GGCCAGGCTA CCCTCAGGCG AAGCACTGC TGGCAGAGGC CATGCTCAAG     420

TTCGGCAGGG AGCTGGGTGA TGATTGCAAC TTTGGTCCTG CTCTCGGTGA GGTGGGAGAA    480

GCCATGAGGG AGCTCTCGGA GGTCAAGGAC TCATTGGACA TGGAAGTGAA GCAGAATTTC    540

ATCGACCCCC TTCAGAATCT TCATGACAAG GATCTGAGGG AGATTCAGCA TCATCTGAAA    600

AAGCTGGAAG CCGACGCTT AGACTTTGGT TATAAGAAGA AGCGACAAGG CAAGATTCCA     660

GATGAAGAAC TCCGCCAAGC TCTGGAGAAA TTCGATGAGT CTAAAGAAAT CGCCGAGTCG    720

AGCATGTTCA ACCTCTTGGA GATGGATATA GAACAGGTGA GCCAGCTCTC CGCACTTGTT    780

CAGGCTCAGC TGGAGTACCA CAAGCAGGCA GTGCAGATCC TGCAGCAGGT CACTGTCAGA    840

CTGGAAGAAA GAATAAGACA AGCTTCATCT CAGCCAAGAA GGGAATATCA GCCCAAACCA    900

CGGATGAGCC TAGAGTTTGC CACTGGAGAC AGTACTCAGC CAACGGGGG TCTCTCCCAC     960

ACAGGCACAC CCAAACCTCC AGGTGTCCAA ATGGATCAGC CCTGCTGCCG AGCTCTGTAT   1020

GACTTGGAAC CTGAAAATGA AGGGGAATTG GCTTTTAAAG AGGGCGATAT CATCACACTC   1080

ACTAATCAGA TTGACGAGAA CTGGTATGAG GGGATGCTTC ATGGCCAGTC TGGCTTTTTC   1140

CCCATCAACT ATGTAGAAAT TCTGGTTGCT CTGCCCCATT AGGATCCTGT GCTGGCTGGC   1200

TCACCTCCTT CTGACCCAGA TAGTTAAGTT TAACCACTGC TTTGGTAATG CTGCTTCCAA   1260

TACATCACGA ATGCAGGCCG CAGTGGATGA GTCACCAAGC CCACACGTGC CCTGGGTTGA   1320

CCCGTGTGCT CCTCCAGGAG ACGCGGTGAT AGATGGTATC TTCCAAGGCC AGTGGGCCTG   1380

GTACATGCTT TAAAACACCA TCTGAGACTA GCCAGGAGTC CCAGAACTGG CTTCACAGTT   1440

CTCAGGAGGC TGTGGTTCCT GGTAACATGC CTGTGAACCA CATGGCAGAA AAACTCTCCT   1500

CACTGAAGAT ATTGTCTCTC ACCCAGGGGC CATCTCAAGG TCTCCAGTTC TCCATTTACA   1560

GAGGAGAAAG TCCTTTTTGT TGCACTTTCC CTTCCTAAAT ATGTGAGTCA CAGAATTGTT   1620

GGCAAAAACA TCCCCTCACC AGCAAGATGT CTGCTGGTTT AAGCAACTTG GTCTCTTGAT   1680

GCCATTAGCA AAAGTATTAA TTGTCCAAAG CACCTTTGTT CACTAATATC TATCTATCTA   1740

TCTATCTATC TATCTATCTA TCTATCTATC TATCTATCAT CTATCTACCT ACCTATCTAC   1800

CTATCATCTA TCTATCTATC ATCTATTATC TATCTATCTA TCTATCTATC NNTCNATCTA   1860

TCTATCTATC CATCTATCTA TCCATCATCT ATCTACCTAC CTATCTACTA TCCATCTATC   1920

TATCTATCCA TCATCTATCT ACCTACCTAT CTACTATCCA TCCATTTATC TATCTATCTA   1980

TCTATCTATC TATCTATCTA TCTCCCTCAT ACTTCTGAGA CATGGCCAGT TTTCTTCCCT   2040

CCCTGCTGTT AAGCACTTGG NAGATGAGGG GGGGGGTCCC ATTTNATTTC TGAGTGAGAT   2100

GGTGAGCAGG GTGTATGTTG GCTGTNNTNN GGGGGTGGCC CTA                     2143
```

(2) INFORMATION FOR SEQ ID NO: 12:

(i) SEQUENCE CHARACTERISTICS:
        (A) LENGTH: 352 amino acids
        (B) TYPE: amino acid (C) STRANDEDNESS: <Unknown>
          (D) TOPOLOGY: unknown (ii) MOLECULE TYPE: peptide (xi) SEQUENCE DESCRIPTION: SEQ ID NO: 12:

Met Ser Val Ala Gly Leu Lys Lys Gln Phe His Lys Ala Thr Gln Lys
1               5                   10                  15

Val Ser Glu Lys Val Gly Gly Ala Glu Gly Thr Lys Leu Asp Asp Asp
            20                  25                  30

Phe Lys Glu Met Glu Arg Lys Val Asp Val Thr Ser Arg Ala Val Met
        35                  40                  45

Glu Ile Met Thr Lys Thr Ile Glu Tyr Leu Gln Pro Asn Pro Ala Ser
50                  55                  60

Arg Ala Lys Leu Ser Met Ile Asn Thr Met Ser Lys Ile Arg Gly Gln
65                  70                  75                  80

Glu Lys Gly Pro Gly Tyr Pro Gln Ala Glu Ala Leu Leu Ala Glu Ala
                85                  90                  95

Met Leu Lys Phe Gly Arg Glu Leu Gly Asp Asp Cys Asn Phe Gly Pro
            100                 105                 110

Ala Leu Gly Glu Val Gly Glu Ala Met Arg Glu Leu Ser Glu Val Lys
        115                 120                 125

Asp Ser Leu Asp Met Glu Val Lys Gln Asn Phe Ile Asp Pro Leu Gln
130                 135                 140

Asn Leu His Asp Lys Asp Leu Arg Glu Ile Gln His His Leu Lys Lys
145                 150                 155                 160

Leu Glu Gly Arg Arg Leu Asp Phe Gly Tyr Lys Lys Arg Gln Gly
                165                 170                 175

Lys Ile Pro Asp Glu Glu Leu Arg Gln Ala Leu Glu Lys Phe Asp Glu
            180                 185                 190

Ser Lys Glu Ile Ala Glu Ser Ser Met Phe Asn Leu Leu Glu Met Asp
        195                 200                 205

Ile Glu Gln Val Ser Gln Leu Ser Ala Leu Val Gln Ala Gln Leu Glu
210                 215                 220

Tyr His Lys Gln Ala Val Gln Ile Leu Gln Gln Val Thr Val Arg Leu
225                 230                 235                 240

Glu Glu Arg Ile Arg Gln Ala Ser Ser Gln Pro Arg Arg Glu Tyr Gln
                245                 250                 255

Pro Lys Pro Arg Met Ser Leu Glu Phe Ala Thr Gly Asp Ser Thr Gln
            260                 265                 270

Pro Asn Gly Gly Leu Ser His Thr Gly Thr Pro Lys Pro Pro Gly Val
        275                 280                 285

Gln Met Asp Gln Pro Cys Cys Arg Ala Leu Tyr Asp Leu Glu Pro Glu
290                 295                 300

Asn Glu Gly Glu Leu Ala Phe Lys Glu Gly Asp Ile Ile Thr Leu Thr
305                 310                 315                 320

Asn Gln Ile Asp Glu Asn Trp Tyr Glu Gly Met Leu His Gly Gln Ser
                325                 330                 335

Gly Phe Phe Pro Ile Asn Tyr Val Glu Ile Leu Val Ala Leu Pro His
            340                 345                 350

(2) INFORMATION FOR SEQ ID NO: 13:

(i) SEQUENCE CHARACTERISTICS:
         (A) LENGTH: 1867 bases
         (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO: 13:

```
CGGGCGCGGC GGGAGCCTGG TGGACCCTGC TTTGGCGGTA ATCATTGATC ATCGCAGATG      60

CCCTCATATC CACTTTGGAT TCCTTGGATT CGGACAGACT CTGAACTGCT TTTCCCAGCA     120

AAAGAGAAAG ATGTGGAAAG CCTCTGCAGG CCATGCTGTG TCCATCACGC AGGATGATGG     180

AGGAGCTGAT GACTGGGAGA CTGATCCTGA TTTTGTGAAT GATGTGAGTG AAAAGGAGCA     240

GAGATGGGGT GCTAAAACCG TGCAGGGATC GGGGCACCAG GAACACATCA ACATTCACAA     300

GCTTCGAGAG AATGTCTTCC AAGAACACCA GACGCTCAAG GAGAAGGAGC TGGAAACGGG     360

ACCCAAGGCT TCCCACGGCT ATGGCGGGAA GTTCGGTGTG GAGCAGGATA GGATGGACAG     420

ATCAGCCGTG GGCCATGAGT ACCAGTCGAA GCTTTCCAAG CACTGCTCAC AAGTGGACTC     480

GGTCCGGGGC TTCGGAGGCA AGTTCGGTGT CCAGATGGAC AGGGTGGATC AGTCTGCTGT     540

AGGCTTTGAA TACCAGGGGA AGACTGAGAA GCATGCCTCC CAGAAAGACT ACTCTAGTGG     600

CTTCGGTGGC AAATACGGTG TGCAAGCTGA CCGTGTAGAC AAGAGTGCCG TGGGCTTTGA     660

CTACCAGGGC AAGACGGAGA AGCATGAGTC TCAGAAAGAT TACTCCAAAG GTTTTGGTGG     720

CAAATATGGG ATTGACAAGG ACAAGGTGGA TAAAAGTCCT GTGGGCTTTG AGTATCAAGG     780

CAAGACAGAG AAGCACGAAT CCCAGAAAGA CTATGTAAAA GGCTTTGGAG AAAGTTTGG      840

TGTGCAGACA GACAGACAGG ACAAGTGTGC CCTTGGCTGG GACCATCAGG AGAAGCTGCA     900

GCTGCATGAA TCCAAAAAAG ACTATAAGAC TGGTTTCGGA GGCAAATTTG GTGTTCAGTC     960

CGAGAGGCAG GACTCCTCCG CTGTGGGGTT TGATTACAAG GAGAGATTGG CCAAGCACGA    1020

GCCCCAGCAA GACTATGCCA AAGGATTCGG CGGGAAGTAT GGGGTGCAGA AGGATCGGAT    1080

GGACAAGAAT GCATCCACCT TTGAAGAAGT GGTCCAGGTG CCATCTGCCT ATCAGAAGAC    1140

TGTCCCCATT GAGGCCGTAA CCAGCAAAAC CAGTAATATC CGTGCTAACT TTGAAAACCT    1200

GGCAAAGGAG AGAGAGCAGG AGGACAGGCG GAAGGCAGAA GCCGAGAGAG CTCAGCGGAT    1260

GGCCAAAGAA AGACAGGAGC AGGAGGAGGC GCGCAGGAAG CTGGAAGAGC AAGCCAGAGC    1320

CAAGAAGCAG ACGCCCCCTG CATCCCCTAG TCCTCAACCA ATTGAAGACA GACCACCCTC    1380

CAGCCCCATC TATGAGGATG CAGCTCCGTT CAAGGCCGAG CCGAGCTACC GAGGTAGCGA    1440

ACCTGAGCCT GAGTACAGCA TCGAGGCCGC AGGCATTCCT GAGGCTGGCA GCCAGCAAGG    1500

CCTGACCTAT ACATCAGAGC CCGTGTACGA GACTACAGAG GCTCCTGGCC ACTATCAAGC    1560

AGAGGATGAC ACCTACGATG GGTATGAGAG TGACCTGGGC ATCACAGCCA TCGCCCTGTA    1620

TGACTACCAG GCTGCTGGCG ATGATGAGAT CTCCTTTGAC CCTGATGACA TCATCACCAA    1680

CATAGAAATG ATTGACGATG GCTGGTGGCG TGGGGTGTGC AAGGGCAGAT ACGGGCTCTT    1740

CCCAGCCAAG TATGTGGAGC TGCGGCAGTA GGGCTGCCAC CCAGAGCCTA CCGGCACCAG    1800

CACAGGGTTC ACACTACAGA GCATCTGCGT GTGTTTGAGT TGGTTTCTGC TTCCGTTTCT    1860

GTTTTTG                                                             1867
```

(2) INFORMATION FOR SEQ ID NO: 14:

(i) SEQUENCE CHARACTERISTICS:
        (A) LENGTH: 546 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 14:

```
Met Trp Lys Ala Ser Ala Gly His Ala Val Ser Ile Thr Gln Asp Asp
 1               5                  10                  15

Gly Gly Ala Asp Asp Trp Glu Thr Asp Pro Asp Phe Val Asn Asp Val
                20                  25                  30

Ser Glu Lys Glu Gln Arg Trp Gly Ala Lys Thr Val Gln Gly Ser Gly
            35                  40                  45

His Gln Glu His Ile Asn Ile His Lys Leu Arg Glu Asn Val Phe Gln
    50                  55                  60

Glu His Gln Thr Leu Lys Glu Lys Glu Leu Glu Thr Gly Pro Lys Ala
65                  70                  75                  80

Ser His Gly Tyr Gly Gly Lys Phe Gly Val Glu Gln Asp Arg Met Asp
                85                  90                  95

Arg Ser Ala Val Gly His Glu Tyr Gln Ser Lys Leu Ser Lys His Cys
                100                 105                 110

Ser Gln Val Asp Ser Val Arg Gly Phe Gly Gly Lys Phe Gly Val Gln
            115                 120                 125

Met Asp Arg Val Asp Gln Ser Ala Val Gly Phe Glu Tyr Gln Gly Lys
130                 135                 140

Thr Glu Lys His Ala Ser Gln Lys Asp Tyr Ser Ser Gly Phe Gly Gly
145                 150                 155                 160

Lys Tyr Gly Val Gln Ala Asp Arg Val Asp Lys Ser Ala Val Gly Phe
                165                 170                 175

Asp Tyr Gln Gly Lys Thr Glu Lys His Glu Ser Gln Lys Asp Tyr Ser
            180                 185                 190

Lys Gly Phe Gly Gly Lys Tyr Gly Ile Asp Lys Asp Lys Val Asp Lys
        195                 200                 205

Ser Ala Val Gly Phe Glu Tyr Gln Gly Lys Thr Glu Lys His Glu Ser
210                 215                 220

Gln Lys Asp Tyr Val Lys Gly Phe Gly Gly Lys Phe Gly Val Gln Thr
225                 230                 235                 240

Asp Arg Gln Asp Lys Cys Ala Leu Gly Trp Asp His Gln Glu Lys Leu
                245                 250                 255

Gln Leu His Glu Ser Gln Lys Asp Tyr Lys Thr Gly Phe Gly Gly Lys
            260                 265                 270

Phe Gly Val Gln Ser Glu Arg Gln Asp Ser Ser Ala Val Gly Phe Asp
        275                 280                 285

Tyr Lys Glu Arg Leu Ala Lys His Glu Pro Gln Gln Asp Tyr Ala Lys
    290                 295                 300

Gly Phe Gly Gly Lys Tyr Gly Val Gln Lys Asp Arg Met Asp Lys Asn
305                 310                 315                 320

Ala Ser Thr Phe Glu Glu Val Val Gln Val Pro Ser Ala Tyr Gln Lys
                325                 330                 335

Thr Val Pro Ile Glu Ala Val Thr Ser Lys Thr Ser Asn Ile Arg Ala
            340                 345                 350

Asn Phe Glu Asn Leu Ala Lys Glu Arg Glu Gln Glu Asp Arg Arg Lys
    355                 360                 365

Ala Glu Ala Glu Arg Ala Gln Arg Met Ala Lys Glu Arg Gln Glu Gln
370                 375                 380

Glu Glu Ala Arg Arg Lys Leu Glu Glu Gln Ala Arg Ala Lys Lys Gln
385                 390                 395                 400
```

```
Thr Pro Pro Ala Ser Pro Ser Pro Gln Pro Ile Glu Asp Arg Pro Pro
                405                 410                 415

Ser Ser Pro Ile Tyr Glu Asp Ala Ala Pro Phe Lys Ala Glu Pro Ser
            420                 425                 430

Tyr Arg Gly Ser Glu Pro Glu Pro Glu Tyr Ser Ile Glu Ala Ala Gly
        435                 440                 445

Ile Pro Glu Ala Gly Ser Gln Gln Gly Leu Thr Tyr Thr Ser Glu Pro
    450                 455                 460

Val Tyr Glu Thr Thr Glu Ala Pro Gly His Tyr Gln Ala Glu Asp Asp
465                 470                 475                 480

Thr Tyr Asp Gly Tyr Glu Ser Asp Leu Gly Ile Thr Ala Ile Ala Leu
                485                 490                 495

Tyr Asp Tyr Gln Ala Ala Gly Asp Asp Glu Ile Ser Phe Asp Pro Asp
            500                 505                 510

Asp Ile Ile Thr Asn Ile Glu Met Ile Asp Asp Gly Trp Trp Arg Gly
        515                 520                 525

Val Cys Lys Gly Arg Tyr Gly Leu Phe Pro Ala Asn Tyr Val Glu Leu
    530                 535                 540

Arg Gln
545

(2) INFORMATION FOR SEQ ID NO: 15:

(i) SEQUENCE CHARACTERISTICS:
        (A) LENGTH: 1199 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

AAGCAGTCCT TCACCATGGT GGCCGACACT CCGGAAAACC TCCGCCTCAA GCAACAGAGC      60

GAGCTGCAGA GTCAGGTGCG CTACAAGGAG GAGTTTGAGA GAATAAGGG CAAAGGTTTC      120

AGCGTGGTGG CAGACACGCC TGAGCTGCAG AGAATCAAGA AGACCCAGGA CCAGATCAGC     180

AATATCAAAT ACCATGAGGA GTTTGAGAAG AGCCGCATGG GGCCCAGTGG AGGAGAAGGG     240

GTGGAACCAG AGCGCCGAGA AGCCCAGGAC AGCAGCAGCT ACCGGAGGCC CACAGAGCAG     300

CAGCAGCCGC AGCCTCACCA TATCCCGACC AGTGCCCCCG TGTACCAGCA GCCCCAGCAG     360

CAGCAGATGA CCTCGTCCTA TGGTGGGTAC AAGGAGCCAG CAGCCCCTGT CTCCATACAG     420

CGCAGTGCCC CAGGTGGCGG TGGGAAACGG TACCGTGCAG TGTATGACTA CAGCGCTGCC     480

GACGAGGACG AGGTCTCCTT CCAGGATGGG ACACCATCG TCAATGTGCA CCAGATCGAT      540

GACGGCTGGA TGTACGGGAC CGTAGAGCGC ACCGGTGACA CGGGGATGCT GCCAGCCAAC     600

TACGTGGAGG CCATCTGAAC CCTGTGCCGC CCCGCCCTGT CTTCAATGCA TTCCATGGCA     660

TCACATCTGT CCTGGGGCCT GACCCGTCCA CCCTTCAGTG TCTCTGTCTT TTAAGATCTT     720

CAACTGCTTC TTTATCCCCG CCCCTCCAGC TTATTTTACC ATCCCAAGCC TTGTTCTGCC     780

CCTGTCATGG GCTCCTTCCT CTGGCAGGTT TTCCCTTGGA CCAATCAACT GATTGATTTT     840

TCTCTCTGGA TGGAACAGGC TGGGCACTCT GGGGAGGGCA GGATTGTTCT TAGCTAGGTA     900

GACTCCCAGG GCTGGGCTGA ACTAGGAGAC CCACTAAGGA GATCAGTTTA GACTGGGTGC     960

AGTGGCAAAC ACCCTTAATT CCCAGCGAAG GGAGTCAGAG GCAGGCAGAT CTGTGACTTG    1020

GAAGCCAGCC TGGTCTACAT CGAGAGTTTC AGGACAGCCA GAGCTATGTA GTGAGGCCCT    1080
```

```
GTCTCGGAGG AAGAGTGGGG GTTGGTTAGC TCTCAGCTTC ACTTCCTGCC TTAGGCTCCT      1140

CAGAACCCCT GGCCCAGCTC CCCCAACTCC CTTCCTCCTA GAGGTGGGGT GAGCTGTGC      1199
```

(2) INFORMATION FOR SEQ ID NO: 16:

(i) SEQUENCE CHARACTERISTICS:
        (A) LENGTH: 205 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 16:

```
Lys Gln Ser Phe Thr Met Val Ala Asp Thr Pro Glu Asn Leu Arg Leu
1               5                   10                  15

Lys Gln Gln Ser Glu Leu Gln Ser Gln Val Arg Tyr Lys Glu Glu Phe
            20                  25                  30

Glu Lys Asn Lys Gly Lys Gly Phe Ser Val Val Ala Asp Thr Pro Glu
        35                  40                  45

Leu Gln Arg Ile Lys Lys Thr Gln Asp Gln Ile Ser Asn Ile Lys Tyr
    50                  55                  60

His Glu Glu Phe Gly Lys Ser Arg Met Gly Pro Ser Gly Gly Glu Gly
65                  70                  75                  80

Val Glu Pro Glu Arg Arg Glu Ala Gln Asp Ser Ser Ser Tyr Arg Arg
                85                  90                  95

Pro Thr Glu Gln Gln Gln Pro Gln Pro His His Ile Pro Thr Ser Ala
            100                 105                 110

Pro Val Tyr Gln Gln Pro Gln Gln Gln Gln Met Thr Ser Ser Tyr Gly
        115                 120                 125

Gly Tyr Lys Glu Pro Ala Ala Pro Val Ser Ile Gln Arg Ser Ala Pro
    130                 135                 140

Gly Gly Gly Gly Lys Arg Tyr Arg Ala Val Tyr Asp Tyr Ser Ala Ala
145                 150                 155                 160

Asp Glu Asp Glu Val Ser Phe Gln Asp Gly Asp Thr Ile Val Asn Val
                165                 170                 175

Gln Gln Ile Asp Asp Gly Trp Met Tyr Gly Thr Val Glu Arg Thr Gly
            180                 185                 190

Asp Thr Gly Met Leu Pro Ala Asn Tyr Val Glu Ala Ile
        195                 200                 205
```

(2) INFORMATION FOR SEQ ID NO: 17:

(i) SEQUENCE CHARACTERISTICS:
        (A) LENGTH: 1302 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

```
ATGGCGGTGA ACCTGAGCCG GAACGGGCCG GCGCTGCAGG AGGCCTACGT GCGCGTAGTC       60

ACCGAGAAAT CCCCGACCGA CTGGGCTCTT TTTACCTATG AAGGCAACAG CAATGACATC      120

CGTGTGGCTG GCACAGGAGA GGGAGGCCTG GAGGAGCTGG TGGAAGAGCT CAACAGCGGG      180

AAGGTGATGT ACGCCTTCTG CAGGGTGAAG GACCCCAACT CCGGCCTGCC CAAGTTTGTC      240

CTCATCAACT GGACAGGAGA GGGTGTGAAT GATGTGCGGA AGGAGCATG TGCCAACCAC      300
```

```
GTCAGCACCA TGGCCAACTT CCTGAAGGGT GCCCACGTGA CCATCAATGC CCGGGCCGAG      360

GAGGATGTGG AGCCTGAGTG CATCATGGAG AAGGTTGCCA AGGCCTCTGG GGCCAACTAC      420

AGCTTCCATA AGGAAAGCAC CTCCTTCCAG GATGTAGGGC CGCAGGCCCC AGTGGGCTCT      480

GTGTACCAGA AGACCAATGC CATATCTGAG ATCAAGAGAG TCGGCAAGGA TAACTTCTGG      540

GCCAAAGCTG AGAAGGAAGA AGAGAACCGC CGCCTGGAGG AGAAGCGGCG TGCCGAAGAG      600

GAGCGGCAGC GGTTGGAGGA GGAGCGACGA GAGCGGGAGC TGCAGGAGGC TGCCCGACGT      660

GAGCAGCGCT ACCAGGAACA GCACAGATCA GCTGGAGCCC CGAGCAGGAC AGGTGAGCCA      720

GAGCAGGAAG CCGTTTCAAG GACCAGACAG GAGTGGGAGT CTGCTGGGCA GCAGGCCCCA      780

CACCCACGAG AGATTTTCAA GCAGAAGGAA AGGGCAATGT CCACCACCTC TGTCACCAGC      840

TCGCAGCCGG GCAAGCTGAG GAGCCCCTTC CTGCAGAAGC AACTCACTCA ACCAGAAACC      900

TCCTACGGCC GAGAGCCCAC AGCTCCTGTC TCCCGGCCTG CAGCAGGTGT CTGTGAGGAG      960

CCAGCGCCTA GCACTCTGTC TTCTGCCCAG ACAGAAGAAG AACCTACATA TGAAGTACCC     1020

CCAGAGCAGG ACACCCTCTA TGAGGAACCA CCACTGGTAC AGCAGCAAGG GGCTGGCTCC     1080

GAACACATTG ACAACTACAT GCAGAGCCAG GGCTTCAGTG ACAAGGGCT GTGCGCCCGG      1140

GCCTTGTATG ACTACCAGGC AGCTGATGAC ACCGAGATCC CCTTTGACCC TGAGAACCTA     1200

ATCACAGGCA TCGAGGTGAT TGACGAAGGC TGGTGGCGAG GCTATGGGCC TGACGGCCAC     1260

TTTGGCATGT TCCCTGCCAA CTACGTGGAG CTCATAGAGT GA                        1302

(2) INFORMATION FOR SEQ ID NO: 18:

(i) SEQUENCE CHARACTERISTICS:
        (A) LENGTH: 433 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 18:

Met Ala Val Asn Leu Ser Arg Asn Gly Pro Ala Leu Gln Glu Ala Tyr
1               5                  10                  15

Val Arg Val Val Thr Glu Lys Ser Pro Thr Asp Trp Ala Leu Phe Thr
            20                  25                  30

Tyr Glu Gly Asn Ser Asn Asp Ile Arg Val Ala Gly Thr Gly Glu Gly
        35                  40                  45

Gly Leu Glu Glu Leu Val Glu Glu Leu Asn Ser Gly Lys Val Met Tyr
    50                  55                  60

Ala Phe Cys Arg Val Lys Asp Pro Asn Ser Gly Leu Pro Lys Phe Val
65                  70                  75                  80

Leu Ile Asn Trp Thr Gly Glu Gly Val Asn Asp Val Arg Lys Gly Ala
                85                  90                  95

Cys Ala Asn His Val Ser Thr Met Ala Asn Phe Leu Lys Gly Ala His
            100                 105                 110

Val Thr Ile Asn Ala Arg Ala Glu Glu Asp Val Glu Pro Glu Cys Ile
        115                 120                 125

Met Glu Lys Val Ala Lys Ala Ser Gly Ala Asn Tyr Ser Phe His Lys
    130                 135                 140

Glu Ser Thr Ser Phe Gln Asp Val Gly Pro Gln Ala Pro Val Gly Ser
145                 150                 155                 160

Val Tyr Gln Lys Thr Asn Ala Ile Ser Glu Ile Lys Arg Val Gly Lys
```

```
                165                 170                 175
Asp Asn Phe Trp Ala Lys Ala Glu Lys Glu Glu Asn Arg Arg Leu
                180                 185                 190

Glu Glu Lys Arg Arg Ala Glu Glu Arg Gln Arg Leu Glu Glu Glu
            195                 200                 205

Arg Arg Glu Arg Glu Leu Gln Glu Ala Ala Arg Arg Glu Gln Arg Tyr
        210                 215                 220

Gln Glu Gln His Arg Ser Ala Gly Ala Pro Ser Arg Thr Gly Glu Pro
225                 230                 235                 240

Glu Gln Glu Ala Val Ser Arg Thr Arg Gln Glu Trp Glu Ser Ala Gly
                245                 250                 255

Gln Gln Ala Pro His Pro Arg Glu Ile Phe Lys Gln Lys Glu Arg Ala
            260                 265                 270

Met Ser Thr Thr Ser Val Thr Ser Ser Gln Pro Gly Lys Leu Arg Ser
            275                 280                 285

Pro Phe Leu Gln Lys Gln Leu Thr Gln Pro Glu Thr Ser Tyr Gly Arg
        290                 295                 300

Glu Pro Thr Ala Pro Val Ser Arg Pro Ala Ala Gly Val Cys Glu Glu
305                 310                 315                 320

Pro Ala Pro Ser Thr Leu Ser Ser Ala Gln Thr Glu Glu Pro Thr
                325                 330                 335

Tyr Glu Val Pro Pro Glu Gln Asp Thr Leu Tyr Glu Pro Pro Leu
            340                 345                 350

Val Gln Gln Gln Gly Ala Gly Ser Glu His Ile Asp Asn Tyr Met Gln
        355                 360                 365

Ser Gln Gly Phe Ser Gly Gln Gly Leu Cys Ala Arg Ala Leu Tyr Asp
        370                 375                 380

Tyr Gln Ala Ala Asp Asp Thr Glu Ile Ser Phe Asp Pro Glu Asn Leu
385                 390                 395                 400

Ile Thr Gly Ile Glu Val Ile Asp Glu Gly Trp Trp Arg Gly Tyr Gly
                405                 410                 415

Pro Asp Gly His Phe Gly Met Phe Pro Ala Asn Tyr Val Glu Leu Ile
            420                 425                 430

Glu (2) INFORMATION FOR SEQ ID NO: 19:

(i) SEQUENCE CHARACTERISTICS:
        (A) LENGTH: 2074 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

TTNNCACTCA CCGTCCGTGG TNNNNSTMMC SGWYNKRNTK YRRKMSSKRW YKWKKCRRKS    60

GCGGCGCCGA CCTGCGCGCG GAGGAAAGAA GTCGGTTCGG CGGCGCCGGC GGAAACCGGA   120

GTTCGAGCGG GAGGCCTGAC GGCGGCAGGC GGCATGTCGG TGGCGGGGCT GAAGAAGCAG   180

TTCTACAAGG CGAGCCAGCT GGTCAGCGAG AAGGTTGGTG GGGCCGAAGG GACCAAACTG   240

GATGATGACT TTAAAGATAT GGAAAAGAAG GTGGATGTCA CCAGCAAGGC CGTGGCAGAG   300

GTGCTGGTCA GAACCATAGA ATATCTGCAG CCTAACCCAG CCTCGAGAGC CAAGCTGACT   360

ATGCTGAACA CCGTATCCAA GATCCGGGGC CAAGTGAAGA ACCCTGGCTA CCCACAGTCA   420
```

-continued

```
GAGGGTCTGT TGGGAGAGTG CATGGTTCGC CATGGCAAGG AACTAGGTGG AGAGTCCAAC    480

TTCGGTGATG CCCTGCTAGA TGCAGGTGAG TCCATGAAGC GCCTGGCTGA GGTGAAGGAC    540

TCACTGGACA TCGAGGTCAA GCAGAACTTC ATTGACCCAC TACAGAACCT GTGTGACAAG    600

GATCTGAAGG AGATCCAGCA CCACCTGAAG AAATTGGAGG CCGCCGCCT TGACTTTGAC     660

TACAAGAAGA AGCGCCAGGG CAAGATCCCC GATGAGGAGC TGCGCCAGGC CCTAGAGAAG    720

TTCGAGGAGT CCAAGGAGGT GGCGGAGACC AGTATGCACA ACCTCCTGGA GACTGATATA    780

GAGCAGGTGA GCCAGCTCTC GGCCCTGGTG GATGCCCAGC TGGACTACCA CCGGCAGGCA    840

GTGCAGATCC TGGAGGAGCT GGCTGACAAG CTGAAGCGCA GGGTTCGGGA AGCCTCCTCA    900

CGCCCCAAGC GGGAGTTCAA GCCCCGGCCC CGGGAGCCCT TTGAGCTTGG AGAGCTGGAG    960

CAGCCCAATG GGGGATTCCC CTGTGCCCCA GCACCTAAGA TCACAGCCTC CTCATCATTT    1020

AGATCGTCAG ACAAGCCCAT CAGGATGCCC AGCAAGAGCA TGCCACCCCT GGACCAGCCA    1080

AGCTGCAAGG CGCTTTATGA TTTTGAGCCA GAGAATGATG GCGAGCTGGG CTTCCGTGAG    1140

GGGGACCTCA TCACGCTTAC CAACCAGATC GACGAGAACT GGTATGAGGG GATGCTGCAC    1200

GGCCAATCAG GCTTCTTCCC ACTCAGCTAC GTGCAGGTGC TGGTGCCTCT GCCTCAGTGA    1260

CTGGGCCTTT ACACCGCTGC CAGTCACAGT GCAGCAGCAG TCTAATGCCA AGGTGCTCTA    1320

GAAACACTAA TGTTCCTCCA GGGGGGACTC CTCCCCACTC CCTCAGCCCT GGGGCCCCCC    1380

TATCCTAAGA CTCGGAAAGG CCCACCCTGA GGTTCTATTG CCTTCCTGGT GGTATCAGCT    1440

TCCAGCTGTT TCAACCCTTC CCAGCCCGTT GCTGGCGATG GSCCNNYGCC CCCTCTCTAG    1500

GCTCTCTAGA GGCAGGCAGG TCCTTGGAAT CCCCAGCCTG CAAGCAGAGG CTGGCCAGCT    1560

CCCCAGCTCA GCACACAGAG ACACCTGGCA CCTGCTGCTC ATGAAGAAGT GCACAAGGCA    1620

CAAATGTGTA CACTTCCCAT GGGACCACAG ACCCAGCTCA GCTCTGTTGA AGACCAAGCA    1680

CAAAGGCCTT GAAGAGTGGA CATTCCCAGG TCCCTGGCAC CTTCCCTTGA GCCAGCTCCA    1740

TTGCTACTTA TTCATGTGAC TGAAGCTGAC CACAGGCAGC TGGCAGGTCC TTTTTTCAAC    1800

CAGCAGGCTA GGCTGGCCAT AGACCCAGCT CTGCCTCACC CTGCCATGTT CCAGTAATGG    1860

AGGCCTCCAG CCTGGGCTCT ATTACATTCT TCTCTACAGC TGCCCCATAA CCCGTGGCTT    1920

ATCCCTGGCA CGTGGGGCCA CACCCCACGC CCCCTGGATA GGCAACACTG TCCTGCTCCA    1980

GCCTGTGCTG ANATGAACTG TACTCCTAAT TTTTTTTTAA AAAAAAGTA TTAAATNTCT     2040

CTTTCTATAT AAAANAAAGN TGGCCCTANN NGGA                                2074
```

(2) INFORMATION FOR SEQ ID NO: 20:

(i) SEQUENCE CHARACTERISTICS:
        (A) LENGTH: 368 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 20:

```
Met Ser Val Ala Gly Leu Lys Lys Gln Phe Tyr Lys Ala Ser Gln Leu
1               5                   10                  15

Val Ser Glu Lys Val Gly Cys Ala Glu Gly Thr Lys Leu Asp Asp Asp
            20                  25                  30

Phe Lys Asp Met Glu Lys Lys Val Asp Val Thr Ser Lys Ala Val Ala
        35                  40                  45

Glu Val Leu Val Arg Thr Ile Glu Tyr Leu Gln Pro Asn Pro Ala Ser
```

```
            50                  55                  60
Arg Ala Lys Leu Thr Met Leu Asn Thr Val Ser Lys Ile Arg Gly Gln
 65                  70                  75                  80

Val Lys Asn Pro Gly Tyr Pro Gln Ser Glu Gly Leu Leu Gly Glu Cys
                 85                  90                  95

Met Val Arg His Gly Lys Glu Leu Gly Gly Glu Ser Asn Phe Gly Asp
                100                 105                 110

Ala Leu Leu Asp Ala Gly Glu Ser Met Lys Arg Leu Ala Glu Val Lys
             115                 120                 125

Asp Ser Leu Asp Ile Glu Val Lys Gln Asn Phe Ile Asp Pro Leu Gln
130                 135                 140

Asn Leu Cys Asp Lys Asp Leu Lys Glu Ile Gln His His Leu Lys Lys
145                 150                 155                 160

Leu Glu Gly Arg Arg Leu Asp Phe Asp Tyr Lys Lys Arg Gln Gly
                165                 170                 175

Lys Ile Pro Asp Glu Glu Leu Arg Gln Ala Leu Glu Lys Phe Glu Glu
                180                 185                 190

Ser Lys Glu Val Ala Glu Thr Ser Met His Asn Leu Leu Glu Thr Asp
            195                 200                 205

Ile Glu Gln Val Ser Gln Leu Ser Ala Leu Val Asp Ala Gln Leu Asp
210                 215                 220

Tyr His Arg Gln Ala Val Gln Ile Leu Glu Glu Leu Ala Asp Lys Leu
225                 230                 235                 240

Lys Arg Arg Val Arg Glu Ala Ser Ser Arg Pro Lys Arg Glu Phe Lys
                245                 250                 255

Pro Arg Pro Arg Glu Pro Phe Glu Leu Gly Leu Glu Gln Pro Asn
            260                 265                 270

Gly Gly Phe Pro Cys Ala Pro Ala Pro Lys Ile Thr Ala Ser Ser Ser
            275                 280                 285

Phe Arg Ser Ser Asp Lys Pro Ile Arg Met Pro Ser Lys Ser Met Pro
290                 295                 300

Pro Leu Asp Gln Pro Ser Cys Lys Ala Leu Tyr Asp Phe Glu Pro Glu
305                 310                 315                 320

Asn Asp Gly Glu Leu Gly Phe Arg Glu Gly Asp Leu Ile Thr Leu Thr
                325                 330                 335

Asn Gln Ile Asp Glu Asn Trp Tyr Glu Gly Met Leu His Gly Gln Ser
            340                 345                 350

Gly Phe Phe Pro Leu Ser Tyr Val Gln Val Leu Val Pro Leu Pro Gln
            355                 360                 365

(2) INFORMATION FOR SEQ ID NO: 21:

(i) SEQUENCE CHARACTERISTICS:
        (A) LENGTH: 1531 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

CCTCACTCGC TCTCCCCGCG CACGCTCCGT CTCCGTCAGT CCCCTGAGCT GTTCTAGTGC      60

GCGGCGTGGA GCCAGGGCTC AGGCTGGTGG AGCGGCCGGG GCTGGAGGCT GGGAGTGCGG     120

CGCGCACGGC CTCCCCGCGC CATTATCCGC GCTCGCTTCG GGCGAGGCCG GCGCCAGGAT     180

GGCAGAGATG GGAGCAAGG GGGTGACGGC GGGGAAGATC GCCAGCAACG TACAGAAGAA     240
```

```
GCTGACCCGA GCGCAGGAGA AGGTCCTGCA GAAACTGGGG AAGGCGGACG AGACGAAGGA      300

CGAGCAGTTT GAGCAGTGTG TCCAGAACTT CAATAAGCAG CTGACAGAGG GTACCCGGCT      360

GCAGAACGAT CTTCGCACCT ATCTGCCTTC TGTTAAAGCG ATGCACGAAG CCTCCAAGAA      420

GCTGAGTGAG TGTCTTCAGG AGGTGTACGA GCCCGAGTGG CCTGGCAGGG ATGAAGCAAA      480

CAAGATTGCA GAGAACAATG ACCTACTCTG GATGGACTAC CACCAGAAGC TGGTGGACCA      540

GGCTCTGCTG ACCATGGACA CCTACCTAGG CCAGTTCCCT GATATCAAGT CGCGCATTGC      600

CAAGCGGGGG CGGAAGCTGG TGGACTATGA CAGTGCCCGG CACCACTATG AGTCTCTTCA      660

AACCGCCAAA AAGAAGGATG AAGCCAAAAT TGCCAAGGCA GAAGAGGAGC TCATCAAAGC      720

CCAGAAGGTG TTCGAGGAGA TGAACGTGGA TCTGCAGGAG GAGCTGCCAT CCCTGTGGAA      780

CAGCCGTGTA GGTTTCTATG TCAACACGTT CCAGAGCATC GCGGGTCTGG AGGAAAACTT      840

CCATAAAGAG ATGAGTAAGC TCAATCAGAA CCTCAATGAT GTCCTGGTCA GCCTAGAGAA      900

GCAGCACGGG AGCAACACCT TCACAGTCAA GGCCCAACCC AGTGACAATG CCCCTGAGAA      960

AGGGAACAAG AGCCCGTCAC CTCCTCCAGA TGGCTCCCCT GCTGCTACCC CTGAGATCAG     1020

AGTGAACCAT GAGCCAGAGC CGGCCAGTGG GGCCTCACCC GGGGCTACCA TCCCCAAGTC     1080

CCCATCTCAG CCAGCAGAGG CCTCCGAGGT GGTGGGTGGA GCCCAGGAGC CAGGGGAGAC     1140

AGCAGCCAGT GAAGCAACCT CCAGCTCTCT TCCGGCTGTG GTGGTGGAGA CCTTCTCCGC     1200

AACTGTGAAT GGGGCGGTGG AGGGCAGCGC TGGGACTGGA CGCTTGGACC TGCCCCCGGG     1260

ATTCATGTTC AAGGTTCAAG CCCAGCATGA TTACACGGCC ACTGACACTG ATGAGCTGCA     1320

ACTCAAAGCT GGCGATGTGG TGTTGGTGAT TCCTTTCCAG AACCCAGAGG AGCAGGATGA     1380

AGGCTGGCTC ATGGGTGTGA AGGAGAGCGA CTGGAATCAG CACAAGGAAC TGGAGAAATG     1440

CCGCGGCGTC TTCCCGGAGA ATTTTACAGA GCGGGTACAG TGACGGAGGA GCCTTCCGGA     1500

GTGTGAAGAA CCTTTCCCCC AAAGATGTGT G                                    1531

(2) INFORMATION FOR SEQ ID NO: 22:

(i) SEQUENCE CHARACTERISTICS:
            (A) LENGTH: 434 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 22:

Met Ala Glu Met Gly Ser Lys Gly Val Thr Ala Gly Lys Ile Ala Ser
1               5                  10                  15

Asn Val Gln Lys Lys Leu Thr Arg Ala Gln Glu Lys Val Leu Gln Lys
                20                  25                  30

Leu Gly Lys Ala Asp Glu Thr Lys Asp Glu Gln Phe Glu Gln Cys Val
            35                  40                  45

Gln Asn Phe Asn Lys Gln Leu Thr Glu Gly Thr Arg Leu Gln Lys Asp
        50                  55                  60

Leu Arg Thr Tyr Leu Ala Ser Val Lys Ala Met His Glu Ala Ser Lys
65                  70                  75                  80

Lys Leu Ser Glu Cys Leu Gln Glu Val Tyr Glu Pro Glu Trp Pro Gly
                85                  90                  95

Arg Asp Glu Ala Asn Lys Ile Ala Glu Asn Asn Asp Leu Leu Trp Met
            100                 105                 110
```

```
Asp Tyr His Gln Lys Leu Val Asp Gln Ala Leu Leu Thr Met Asp Thr
        115                 120                 125
Tyr Leu Gly Gln Phe Pro Asp Ile Lys Ser Arg Ile Ala Lys Arg Gly
        130                 135                 140
Arg Lys Leu Val Asp Tyr Asp Ser Ala Arg His His Tyr Glu Ser Leu
145                 150                 155                 160
Gln Thr Ala Lys Lys Asp Glu Ala Lys Ile Ala Lys Ala Glu Glu
                165                 170                 175
Glu Leu Ile Lys Ala Gln Lys Val Phe Glu Met Asn Val Asp Leu
                180                 185                 190
Gln Glu Glu Leu Pro Ser Leu Trp Asn Ser Arg Val Gly Phe Tyr Val
                195                 200                 205
Asn Thr Phe Gln Ser Ile Ala Gly Leu Glu Glu Asn Phe His Lys Glu
        210                 215                 220
Met Ser Lys Leu Asn Gln Asn Leu Asn Asp Val Leu Val Ser Leu Glu
225                 230                 235                 240
Lys Gln His Gly Ser Asn Thr Phe Thr Val Lys Ala Gln Pro Ser Asp
                245                 250                 255
Asn Ala Pro Glu Lys Gly Asn Lys Ser Pro Ser Pro Pro Asp Gly
                260                 265                 270
Ser Pro Ala Ala Thr Pro Glu Ile Arg Val Asn His Glu Pro Glu Pro
        275                 280                 285
Ala Ser Gly Ala Ser Pro Gly Ala Thr Ile Pro Lys Ser Pro Ser Gln
        290                 295                 300
Pro Ala Glu Ala Ser Glu Val Val Gly Gly Ala Gln Glu Pro Gly Glu
305                 310                 315                 320
Thr Ala Ala Ser Glu Ala Thr Ser Ser Leu Pro Ala Val Val Val
                325                 330                 335
Glu Thr Phe Ser Ala Thr Val Asn Gly Ala Val Glu Gly Ser Ala Gly
        340                 345                 350
Thr Gly Arg Leu Asp Leu Pro Pro Gly Phe Met Phe Lys Val Gln Ala
        355                 360                 365
Gln His Asp Tyr Thr Ala Thr Asp Thr Asp Glu Leu Gln Leu Lys Ala
        370                 375                 380
Gly Asp Val Val Leu Val Ile Pro Phe Gln Asn Pro Glu Glu Gln Asp
385                 390                 395                 400
Glu Gly Trp Leu Met Gly Val Lys Glu Ser Asp Trp Asn Gln His Lys
                405                 410                 415
Glu Leu Glu Lys Cys Arg Gly Val Phe Pro Glu Asn Phe Thr Glu Arg
                420                 425                 430
Val Gln (2) INFORMATION FOR SEQ ID NO: 23:

(i) SEQUENCE CHARACTERISTICS:
        (A) LENGTH: 1734 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

GAATTCGTCG ACCCACGCGT CCGGTTTGAG CAGTGCGTCC AGAATTTCAA CAAGCAGCTG      60

ACGGAGGGCA CCCGGCTGCA GAAGGATCTC CGGACCTACC TGGCCTCCGT CAAAGCCATG     120
```

-continued

```
CACGAGGCTT CCAAGAAGCT GAATGAGTGT CTGCAGGAGG TGTATGAGCC CGATTGGCCC      180

GGCAGGGATG AGGCAAACAA GATCGCAGAG AACAACGACC TGCTGTGGAT GGATTACCAC      240

CAGAAGCTGG TGGACCAGGC GCTGCTGACC ATGGACACGT ACCTGGGCCA GTTCCCCGAC      300

ATCAAGTCAC GCATTGCCAA GCGGGGCGC AAGCTGGTGG ACTACGACAG TGCCCGGCAC       360

CACTACGAGT CCCTTCAAAC TGCCAAAAAG AAGGATGAAG CCAAAATTGC CAAGGCCGAG      420

GAGGAGCTCA TCAAAGCCCA GAAGGTGTTT GAGGAGATGA ATGTGGATCT GCAGGAGGAG      480

CTGCCGTCCC TGTGGAACAG CCGCGTAGGT TTCTACGTCA ACACGTTCCA GAGCATCGCG      540

GGCCTGGAGG AAAACTTCCA CAAGGAGATG AGCAAGCTCA CCAGAACCT CAATGATGTG       600

CTGGTCGGCC TGGAGAAGCA ACACGGGAGC AACACCTCCA CGGTCAAGGC CCAGCCCAGT      660

GACAACGCGC TGCAAAAGG GAACAAGAGC CCTTCGCCTC CAGATGGCTC CCCTGCCGCC       720

ACCCCCGAGA TCAGAGTCAA CCACGAGCCA GAGCCGGCCG GCGGGGCCAC GCCCGGGCC       780

ACCCTCCCCA AGTCCCCATC TCAGCCAGCA GAGGCCTCGG AGGTGGCGGG TGGGACCCAA      840

CCTGCGGCTG GAGCCCAGGA GCCAGGGGAG ACGGCGGCAA GTGAAGCAGC CTCCAGCTCT      900

CTTCCTGCTG TCGTGGTGGA GACCTTCCCA GCAACTGTGA ATGGCACCGT GGAGGGCGGC      960

AGTGGGGCCG GGCGCTTGGA CCTGCCCCCA GGTTTCATGT TCAAGGTACA GGCCCAGCAC     1020

GACTACACGG CCACTGACAC AGACGAGCTG CAGCTCAAGG CTGGTGATGT GGTGCTGGTG     1080

ATCCCCTTCC AGAACCCTGA AGAGCAGGAT GAAGGCTGGC TCATGGGCGT GAAGGAGAGC     1140

GACTGGAACC AGCACAAGGA GCTGGAGAAG TGCCGTGGCG TCTTCCCCGA GAACTTCACT     1200

GAGAGGGTCC CATGCGGCG GGGCCCAGGC AGCCTCCGGG CGTGTGAAGA ACACCTCCTC     1260

CCGAAAAATG TGTGGTTCTT TTTTTTGTTT TGTTTTCGTT TTTCATCTTT TGAAGAGCAA     1320

AGGGAAATCA AGAGGAGACC CCCAGGCAGA GGGGCGTTCT CCCAAAGATT AGGTCGTTTT     1380

CCAAAGAGCC GCGTCCCGGC AAGTCCGGCG GAATTCACCA GTGTCCTGAA GCTGCTGTGT     1440

CCTCTAGTTG AGTTCTGGCG CCCCTGCCTG TGCCCGCATG TGTGCCTGGC CGCAGGGCGG     1500

GGCTGGGGGC TGCCGAGCCA CCATGCTTGC CTGAAGCTTC GGCCGCGCCA CCCGGGCAAG     1560

GGTCCTCTTT TCCTGGCAGC TGCTGTGGGT GGGGCCCAGA CACCAGCCTA ACCTGGCTCT     1620

GCCCCGCAGA CGGTCTGTGT GCTGTTTGAA AATAAATCTT AGTGTTCAAA ACAAAATGAA     1680

ACAAAAAAAA TGATAAAAAA AAAAAAAAAA AAAAAAAAAA AAAAGGGCGG CCGC           1734
```

(2) INFORMATION FOR SEQ ID NO: 24:

(i) SEQUENCE CHARACTERISTICS:
        (A) LENGTH: 404 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 24:

```
Glu Phe Val Asp Pro Arg Val Arg Phe Glu Gln Cys Val Gln Asn Phe
  1               5                  10                  15

Asn Lys Gln Leu Thr Glu Gly Thr Arg Leu Gln Lys Asp Leu Arg Thr
             20                  25                  30

Tyr Leu Ala Ser Val Lys Ala Met His Glu Ala Ser Lys Lys Leu Asn
         35                  40                  45

Glu Cys Leu Gln Glu Val Tyr Glu Pro Asp Trp Pro Gly Arg Asp Glu
     50                  55                  60
```

```
Ala Asn Lys Ile Ala Glu Asn Asn Asp Leu Leu Trp Met Asp Tyr His
 65                  70                  75                  80

Gln Lys Leu Val Asp Gln Ala Leu Leu Thr Met Asp Thr Tyr Leu Gly
                 85                  90                  95

Gln Phe Pro Asp Ile Lys Ser Arg Ile Ala Lys Arg Gly Arg Lys Leu
            100                 105                 110

Val Asp Tyr Asp Ser Ala Arg His His Tyr Glu Ser Leu Gln Thr Ala
            115                 120                 125

Lys Lys Lys Asp Glu Ala Lys Ile Ala Lys Ala Glu Glu Leu Ile
130                 135                 140

Lys Ala Gln Lys Val Phe Glu Glu Met Asn Val Asp Leu Gln Glu Glu
145                 150                 155                 160

Leu Pro Ser Leu Trp Asn Ser Arg Val Gly Phe Tyr Val Asn Thr Phe
                165                 170                 175

Gln Ser Ile Ala Gly Leu Glu Glu Asn Phe His Lys Glu Met Ser Lys
            180                 185                 190

Leu Asn Gln Asn Leu Asn Asp Val Leu Val Gly Leu Glu Lys Gln His
            195                 200                 205

Gly Ser Asn Thr Ser Thr Val Lys Ala Gln Pro Ser Asp Asn Ala Pro
210                 215                 220

Ala Lys Gly Asn Lys Ser Pro Ser Pro Asp Gly Ser Pro Ala Ala
225                 230                 235                 240

Thr Pro Glu Ile Arg Val Asn His Glu Pro Glu Pro Ala Gly Gly Ala
                245                 250                 255

Thr Pro Gly Ala Thr Leu Pro Lys Ser Pro Ser Gln Pro Ala Glu Ala
            260                 265                 270

Ser Glu Val Ala Gly Gly Thr Gln Pro Ala Ala Gly Ala Gln Glu Pro
            275                 280                 285

Gly Glu Thr Ala Ala Ser Glu Ala Ala Ser Ser Leu Pro Ala Val
290                 295                 300

Val Val Glu Thr Phe Pro Ala Thr Val Asn Gly Thr Val Glu Gly Gly
305                 310                 315                 320

Ser Gly Ala Gly Arg Leu Asp Leu Pro Pro Gly Phe Met Phe Lys Val
                325                 330                 335

Gln Ala Gln His Asp Tyr Thr Ala Thr Asp Thr Asp Glu Leu Gln Leu
            340                 345                 350

Lys Ala Gly Asp Val Val Leu Val Ile Pro Phe Gln Asn Pro Glu Glu
            355                 360                 365

Gln Asp Glu Gly Trp Leu Met Gly Val Lys Glu Ser Asp Trp Asn Gln
370                 375                 380

His Lys Glu Leu Glu Lys Cys Arg Gly Val Phe Pro Glu Asn Phe Thr
385                 390                 395                 400

Glu Arg Val Pro
```

(2) INFORMATION FOR SEQ ID NO: 25:

(i) SEQUENCE CHARACTERISTICS:
        (A) LENGTH: 2003 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

CAGCCGCTGG AGGGGGCGCC TGGTGTAGAT GTGAAAAGCC GTAACCAGGA ACCAGTAAAG     60

| | |
|---|---|
| ATGTGGAAGT CTGTAGTGGG GCATGATGTA TCGGTTTCCG TGGAGACCCA GGGTGATGAC | 120 |
| TGGGATACAG ACCCTGACTT TGTGAATGAC ATCTCCGAGA AGGAGCAACG GTGGGGAGCC | 180 |
| AAGACCATTG AGGGCTCTGG ACGCACAGAG CACATCAACA TCCACCAGCT GAGGAACAAA | 240 |
| GTGTCAGAGG AGCACGACAT CCTCAAGAAG AAGGAGCTGG AATCGGGGCC TAAGGCATCC | 300 |
| CATGGCTATG GCGGTCAGTT TGGAGTGGAG AGAGACCGGA TGGACAAGAG TGCCGTGGGC | 360 |
| CACGAGTATG TTGCTGATGT GGAGAAACAC TCATCTCAGA CTGATGCSGC CAGAGGCTTT | 420 |
| GGGGGCAAAT ATGGAGTTGA GAGGGACCGG GCAGACAAGT CAGCGGTGGG CTTTGACTAC | 480 |
| AAAGGAGAAG TGGAAAAGCA TGCATCTCAG AAAGATTACT CTCATGGCTT TGGTGGCCGC | 540 |
| TACGGGGTAG AGAAGGATAA ACGGGACAAA GCAGCCCTGG GATACGACTA CAAAGGAGAG | 600 |
| ACGGAGAAGC ACGAGTCTCA GAGAGATTAT GCCAAGGGCT TTGGTGGCCA ATATGGAATC | 660 |
| CAGAAAGACC GAGTGGATAA GAGTGCTGTT GGCTTCAATG AAATGGAGGC CCCAACCACG | 720 |
| GCGTATAAGA ACACAACACC CATAGAAGCT GCTTCCAGTG GTGCCCGTGG GCTGAAGGCA | 780 |
| AAATTTGAGT CCCTGGCTGA GGAGAAGAGG AAGCGAGAGG AAGAAGAGAA GGCACAGCAG | 840 |
| ATGGCCAGGC AGCAACAGGA GCGAAAGGCT GTGGTAAAGA TGAGCCGAGA AGTCCAGCAG | 900 |
| CCATCCATGC CTGTGGAAGA GCCAGCGGCA CCAGCCCAGT TGCCCAAGAA GATCTCCTCA | 960 |
| GAGGTCTGGC CTCCAGCAGA GAGTCACCTA CCGCCAGAGT CTCAGCCAGT GAGAAGCAGA | 1020 |
| AGGGAATACC CTGTGCCCTC TCTGCCCACG AGGCAGTCTC CATTGCAGAA TCACTTGGAG | 1080 |
| GACAACGAGG AGCCCCCAGC TCTGCCCCCT AGGACCCCAG AAGGCCTCCA GGTGGTGGAA | 1140 |
| GAGCCAGTGT ACGAAGCAGC ACCCGAGCTG GAGCCGGAGC CAGAGCCTGA CTATGAGCCA | 1200 |
| GAGCCAGAGA CAGAGCCTGA CTATGAGGAT GTTGGGGAGT TAGATCGGCA GGATGAGGAT | 1260 |
| GCAGAGGGAG ACTATGAGGA TGTGCTGGAG CCCGANGACA CCCCTTCTCT GTCCTACCAA | 1320 |
| GCTGGACCCT CAGCTGGGGC TGGTGGTGCG GGGATCTCTG CTATAGCCCT GTATGATTAC | 1380 |
| CAAGGAGAGG GAAGCGATGA GCTTTCCTTT GATCCAGATG ACATCATCAC TGACATTGAG | 1440 |
| ATGGTGGATG AAGGCTGGTG GCGGGGCCAA TGCCGTGGCC ACTTTGGACT TTTCCCTGCA | 1500 |
| AACTATGTCA AGCTCCTCTA ATGACCAGCC CATTGTCTTC CGACTTCCCG AATTCGAAGC | 1560 |
| TGCTCTGCCT CCCTCTTCCC ACTCCATGGT ACTGCTGCAA GGACCTGGCT GAACATCATG | 1620 |
| AGATGCCTGA AGTTCTGGCA GTCTGTCTCC CGCCTCTTTA AGAGCTTTAG GTAGAATCGC | 1680 |
| TCCAGGTGGG GGTGGGGGTG GGGGTGGGAT CCCTCTGTCC CTCTGTCACC ACTCTTCCCT | 1740 |
| GAGGTAGCTC ATGAAATCAT CTTGCAGACC TGCCTCCTTC AGCCGCACCC CAGCTCTGCC | 1800 |
| AACCTTGCTC TAGAGTGCTG GGATTCCCTT GCCCCGACCC TGGGTGCCAG CCTAGAGGGG | 1860 |
| AGGCTCTCAC AGGGCTGCCT GATTCGCCCT GTTGTGCTTT TGCTCATTTT TCTTCCCTTA | 1920 |
| GCAGACAAAT TGGAACTGCC CTTCTGTTTA GTCCTAAAAC TGAAAATAAA ATGAGACTGT | 1980 |
| GGCTAAAAAA AAAAAAAAA AAA | 2003 |

(2) INFORMATION FOR SEQ ID NO: 26:

(i) SEQUENCE CHARACTERISTICS:
        (A) LENGTH: 486 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 26:

-continued

```
Met Trp Lys Ser Val Val Gly His Asp Val Ser Val Ser Val Glu Thr
 1               5                  10                  15

Gln Gly Asp Asp Trp Asp Thr Asp Pro Asp Phe Val Asn Asp Ile Ser
                20                  25                  30

Glu Lys Glu Gln Arg Trp Gly Ala Lys Thr Ile Glu Gly Ser Gly Arg
                35                  40                  45

Thr Glu His Ile Asn Ile His Gln Leu Arg Asn Lys Val Ser Glu Glu
                50                  55                  60

His Asp Ile Leu Lys Lys Lys Glu Leu Glu Ser Gly Pro Lys Ala Ser
 65                  70                  75                  80

His Gly Tyr Gly Gly Gln Phe Gly Val Glu Arg Asp Arg Met Asp Lys
                    85                  90                  95

Ser Ala Val Gly His Glu Tyr Val Ala Asp Val Glu Lys His Ser Ser
                   100                 105                 110

Gln Thr Asp Ala Ala Arg Gly Phe Gly Gly Lys Tyr Gly Val Glu Arg
                115                 120                 125

Asp Arg Ala Asp Lys Ser Ala Val Gly Phe Asp Tyr Lys Gly Glu Val
            130                 135                 140

Glu Lys His Ala Ser Gln Lys Asp Tyr Ser His Gly Phe Gly Gly Arg
145                 150                 155                 160

Tyr Gly Val Glu Lys Asp Lys Arg Asp Lys Ala Ala Leu Gly Tyr Asp
                165                 170                 175

Tyr Lys Gly Glu Thr Glu Lys His Glu Ser Gln Arg Asp Tyr Ala Lys
                180                 185                 190

Gly Phe Gly Gly Gln Tyr Gly Ile Gln Lys Asp Arg Val Asp Lys Ser
                195                 200                 205

Ala Val Gly Phe Asn Glu Met Glu Ala Pro Thr Thr Ala Tyr Lys Lys
210                 215                 220

Thr Thr Pro Ile Glu Ala Ala Ser Ser Gly Ala Arg Gly Leu Lys Ala
225                 230                 235                 240

Lys Phe Glu Ser Leu Ala Glu Gly Lys Arg Lys Arg Glu Glu Glu Glu
                245                 250                 255

Lys Ala Gln Gln Met Ala Arg Gln Gln Gln Glu Arg Lys Ala Val Val
                260                 265                 270

Lys Met Ser Arg Glu Val Gln Gln Pro Ser Met Pro Val Glu Glu Pro
                275                 280                 285

Ala Ala Pro Ala Gln Leu Pro Lys Lys Ile Ser Ser Glu Val Trp Pro
                290                 295                 300

Pro Ala Glu Ser His Leu Pro Pro Glu Ser Gln Pro Val Arg Ser Arg
305                 310                 315                 320

Arg Glu Tyr Pro Val Pro Ser Leu Pro Thr Arg Gln Ser Pro Leu Gln
                325                 330                 335

Asn His Leu Glu Asp Asn Glu Glu Pro Pro Ala Leu Pro Pro Arg Thr
                340                 345                 350

Pro Glu Gly Leu Gln Val Val Glu Pro Val Tyr Glu Ala Ala Pro
                355                 360                 365

Glu Leu Glu Pro Glu Pro Glu Pro Asp Tyr Glu Pro Glu Pro Glu Thr
                370                 375                 380

Glu Pro Asp Tyr Glu Asp Val Gly Glu Leu Asp Arg Gln Asp Glu Asp
385                 390                 395                 400

Ala Glu Gly Asp Tyr Glu Asp Val Leu Glu Pro Glu Asp Thr Pro Ser
                405                 410                 415
```

```
Leu Ser Tyr Gln Ala Gly Pro Ser Ala Gly Ala Gly Ala Gly Ile
            420                 425                 430

Ser Ala Ile Ala Leu Tyr Asp Tyr Gln Gly Glu Gly Ser Asp Glu Leu
            435                 440                 445

Ser Phe Asp Pro Asp Asp Ile Ile Thr Asp Ile Glu Met Val Asp Glu
            450                 455                 460

Gly Trp Trp Arg Gly Gln Cys Arg Gly His Phe Gly Leu Phe Pro Ala
465                 470                 475                 480

Asn Tyr Val Lys Leu Leu
                485

(2) INFORMATION FOR SEQ ID NO: 27:

(i) SEQUENCE CHARACTERISTICS:
        (A) LENGTH: 1296 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 27:
```

| | | | | |
|---|---|---|---|---|
| GGATCCCCGG | AGCCGGTCCG | CTGGGCGGGG | CGCAGGGCTG | GAGGGGCGCG | CGTGCCGGCG | 60 |
| GCGGCCCAGC | GTGAAAGCGC | GGAGGCGGCC | ATGGCGGGCA | ACTTCGACTC | GGAGGAGCGG | 120 |
| AGTAGCTGGT | ACTGGGGCCG | CCTGAGCCGG | CAGGAGGCGG | TGGCGCTATT | GCAGGGCCAG | 180 |
| CGGCACGGGG | TGTTCCTGGT | GCGGGACTCG | AGCACCAGCC | CCGGGGACTA | TGTGCTTAGC | 240 |
| GTCTCCGAAA | ACTCGCGCGT | CTCCCACTAC | ATCATCAACA | GCAGCGGCCC | GCGCCCTCCA | 300 |
| GTGCCTCCGT | CGCCCGCTCA | GCCTCCGCCG | GGAGTGAGTC | CCTCCAGCCT | CCGAATAGGA | 360 |
| GATCAAGAAT | TTGATTCATT | GCCTGCTTTA | CTGGAATTCT | ACAAAATACA | CTATTTGGAC | 420 |
| ACTACAACAT | TGATAGAACC | AGTGGCCAGA | TCAAGGCAGG | GTAGTGGAGT | GATTCTCAGG | 480 |
| CAGGAGGAGG | CAGAGTATGT | GCGGGCCCTG | TTTGACTTTA | ATGGGAATGA | TGAAGAAGAT | 540 |
| CTTCCCTTTA | AGAAAGGAGA | CATCCTGAGA | ATCCGGGATA | AGCCTGAAGA | GCAGTGGTGG | 600 |
| AATGCAGAGG | ACAGCGAAGG | AAAGAGGGGG | ATGATTCCTG | TCCCTTACGT | GGAGAAGTAT | 660 |
| AGACCTGCCT | CCGCCTCAGT | ATCGGCTCTG | ATTGGAGGTA | ACCAGGAGGG | TTCCCACCCA | 720 |
| CAGCCACTGG | GTGGGCCGGA | GCCTGGGCCC | TATGCCCAAC | CCAGCGTCAA | CACTCCGCTC | 780 |
| CCTAACCTCC | AGAATGGGCC | CATTTATGCC | AGGGTTATCC | AGAAGCGAGT | CCCTAATGCC | 840 |
| TACGACAAGA | CAGCCTTGGC | TTTGGAGGTC | GGTGAGCTGG | TAAAGGTTAC | GAAGATTAAT | 900 |
| GTGAGTGGTC | AGTGGGAAGG | GGAGTGTAAT | GGCAAACGAG | GTCACTTCCC | ATTCACACAT | 960 |
| GTCCGTCTGC | TGGATCAACA | GAATCCCGAT | GAGGACTTCA | GCTGAGTATA | GCTCGACAGT | 1020 |
| TTGCTGACAG | ATGGAACAAT | CTGTTTTCCC | CCAATTGCCA | TCTATACAAT | TTTCTTACAG | 1080 |
| GTGTCAAAGC | AGTCTAGTTT | ATATAAGCAT | TCTGTTACCT | GGGATCTTTT | TTAAGACTGA | 1140 |
| ACTACTCCAT | TCTCACTTGT | ATTTACCATA | TTCAGGGTAC | GAAACCGGAG | GCTTATGTG | 1200 |
| GTTAACTTCT | GAGTTGGCAG | TTTTAGGTGG | TAGTGGCCGT | GCCTGTATGA | GAAGACGTAA | 1260 |
| ATACATTGCC | TCCTTTCTTT | TGGGCAAAAC | AGATCA | | | 1296 |

```
(2) INFORMATION FOR SEQ ID NO: 28:

(i) SEQUENCE CHARACTERISTICS:
        (A) LENGTH: 304 amino acids
        (B) TYPE: amino acid
        (C) STRANDEDNESS: <Unknown>
```

(D) TOPOLOGY: unknown (ii) MOLECULE TYPE: peptide (xi) SEQUENCE DESCRIPTION: SEQ ID NO: 28:

```
Met Ala Gly Asn Phe Asp Ser Glu Glu Arg Ser Ser Trp Tyr Trp Gly
1               5                   10                  15
Arg Leu Ser Arg Gln Glu Ala Val Ala Leu Leu Gln Gly Gln Arg His
                20                  25                  30
Gly Val Phe Leu Val Arg Asp Ser Ser Thr Ser Pro Gly Asp Tyr Val
            35                  40                  45
Leu Ser Val Ser Glu Asn Ser Arg Val Ser His Tyr Ile Ile Asn Ser
    50                  55                  60
Ser Gly Pro Arg Pro Pro Val Pro Pro Ser Pro Ala Gln Pro Pro Pro
65                  70                  75                  80
Gly Val Ser Pro Ser Arg Leu Arg Ile Gly Asp Gln Glu Phe Asp Ser
                85                  90                  95
Leu Pro Ala Leu Leu Glu Phe Tyr Lys Ile His Tyr Leu Asp Thr Thr
            100                 105                 110
Thr Leu Ile Glu Pro Val Ala Arg Ser Arg Gln Gly Ser Gly Val Ile
    115                 120                 125
Leu Arg Gln Glu Glu Ala Glu Tyr Val Arg Ala Leu Phe Asp Phe Asn
130                 135                 140
Gly Asn Asp Glu Glu Asp Leu Pro Phe Lys Lys Gly Asp Ile Leu Arg
145                 150                 155                 160
Ile Arg Asp Lys Pro Glu Glu Gln Trp Trp Asn Ala Glu Asp Ser Glu
                165                 170                 175
Gly Lys Arg Gly Met Ile Pro Val Pro Tyr Val Glu Lys Tyr Arg Pro
            180                 185                 190
Ala Ser Ala Ser Val Ser Ala Leu Ile Gly Gly Asn Gln Glu Gly Ser
    195                 200                 205
His Pro Gln Pro Leu Gly Gly Pro Glu Pro Gly Pro Tyr Ala Gln Pro
210                 215                 220
Ser Val Asn Thr Pro Leu Pro Asn Leu Gln Asn Gly Pro Ile Tyr Ala
225                 230                 235                 240
Arg Val Ile Gln Lys Arg Val Pro Asn Ala Tyr Asp Lys Thr Ala Leu
                245                 250                 255
Ala Leu Glu Val Gly Glu Leu Val Lys Val Thr Lys Ile Asn Val Ser
            260                 265                 270
Gly Gln Trp Glu Gly Glu Cys Asn Gly Lys Arg Gly His Phe Pro Phe
    275                 280                 285
Thr His Val Arg Leu Leu Asp Gln Gln Asn Pro Asp Glu Asp Phe Ser
290                 295                 300
```

(2) INFORMATION FOR SEQ ID NO: 29:

(i) SEQUENCE CHARACTERISTICS:
        (A) LENGTH: 3345 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 29:

```
CCTCACCGNN CCTGGTGTAG GTACCGGATC GAATTCAAGC GAAAAACAGA GCGGGGCTGA    60
CTGTAGCGTG GAGCGCGAGC CGGGCTGGAC GCGCGCAAGC CCTTGCCGGG GACCCGCGAG   120
```

-continued

```
GCAAGCAGTC TCCCTGTGGA GCGTCGTCCT CCATCCCTGT AAGCACCGTT ACAGAGAATG    180

AAACAAGGGC AGAAGTTACA GAGCCCGTGA GGCATCTTCA AATAGAAGAC TGGAGACTAG    240

AAAAAGAATA TTGCCAGGAG TTGGCATCCA TTGGAAGACC TTGAGATCCT CTCAGCTCAG    300

AACTCCAGGA CCGATGCATC TTCCCACCAC CTTGAAGCAC TGAGCCCTCC AGAGCTGCAT    360

CTGGGAAGAC TCGCCTGCCT CCAGCATGAG TTCTGAATGT GATGTTGGAA GCTCTAAAGC    420

TGTGGTGAAT GGCTTGGCAT CTGGCAACCA TGGACCAGAC AAAGACATGG ACCCTACCAA    480

AATCTGCACT GGGAAAGGAA CAGTGACTCT TCGGGCCTCG TCTTCCTACA GGGGAACCCC    540

AAGCAGCAGC CCTGTGAGCC CCAGGAATC TCCGAAGCAT GAAAGCAAGT CAGATGAATG     600

GAAACTTTCT TCCAGTGCAG ATACCAATGG CAACGCCCAG CCCTCCCAC TTGCTGCCAA     660

GGGCTATAGA AGTGTGCATC CCAGCCTTTC TGCTGACAAG CCCCAGGGCA GTCCTTTACT    720

AAACGAAGTT TCTTCTTCCC ACATTGAAAC CGATTCCCAA GACTTCCCTC CAACAAGCAG    780

ACCTTCGTCT GCCTACCCCT CCACCACCAT CGTCAACCCT ACCATTGTGC TCCTGCAGCA    840

CAATCGAGAG CAGCAAAAGC GACTCAGTAG TCTTTCAGAT CCTGCCTCAG AGAAGAGC     900

GGGTGAGCAG GACCCAGTAC CAACCCCAGC AGAACTCACT TCGCCCGGCA GGGCTTCTGA    960

GAGAAGGGCA AAGGATGCTA GCAGACGGGT GGTGAGGAGC GCACAGGACC TGAGCGATGT   1020

GTCTACAGAT GAAGTGGGCA TTCCACTCCG GAATACCGAG CGATCGAAAG ACTGGTACAA   1080

AACTATGTTT AAACAGATCC ACAAACTGAA CAGAGATGAT GATTCTGATG TCCATTCCCC   1140

TCGATACTCC TTCTCTGATG ACACAAAGTC TCCCCTTTCT GTGCCTCGCT CAAAAAGTGA   1200

GATGAACTAC ATCGAAGGGG AGAAAGTGGT TAAGAGGTCC GCCACACTCC CCCTCCCAGC   1260

CCGCTCTTCC TCACTCAAGT CCAGCCCGGA AGAAACGAC TGGGAGCCCC TAGATAAGAA    1320

AGTGGATACG AGAAAATACC GAGCAGAGCC CAAAAGCATT TACGAATATC AGCCGGGCAA   1380

GTCTTCGGTC CTGACCAATG AGAAGATGAG TCGGGATATA AGCCCAGAAG AGATAGATTT   1440

AAAGAATGAA CCTTGGTATA AATTCTTTTC GGAATTGGAG TTTGGGAGAC CGAGCTCAGC   1500

AGTCAGCCCG ACTCCAGACA TTACGTCAGA GCCTCCTGGA TATATCTATT CTTCCAACTT   1560

CCATGCAGTG AAGAGAGAAT CGGACGGGAC CCCCGGGGGT CTCGCTAGCT GGAGAATGA    1620

GAGGCAGATC TATAAGAGTG TCTTGGAAGG TGGCGACATC CCTCTTCAGG GCCTCAGTGG   1680

GCTCAAGCGA CCTTCCAGCT CAGCTTCCAC TAAAGATTCA GAGTCACCAA GACATTTTAT   1740

ACCAGCTGAT TACTTGGAGT CCACAGAAGA ATTTATTCGG AGACGGCACG ATGATAAAGA   1800

GAAACTTTTA GCGGACCAGA GACGACTAA GCGCGAGCAA GAAGAGGCCG ATATTGCAGC    1860

TCGCCGCCAC ACAGGTGTCA TCCCGACTCA TCATCAGTTT ATCACTAATG AGCGCTTTGG   1920

GGACCTCCTC AATATAGATG ATACGGCCAA AAGGAAATCT GGGTTAGAGA TGAGACCTGC   1980

TCGAGCCAAA TTTGACTTTA AAGCCCAGAC CCTGAAGGAG CTGCCTCTGC AGAAGGGAGA   2040

CGTTGTTTAC ATCTACAGAC AGATTGACCA GAACTGGTAT GAAGGTGAAC ACCATGGCCG   2100

GGTGGGAATC TTCCCACGCA CCTATATCGA GCTTCTTCCT CCAGCTGAGA AGGCTCAGCC   2160

CAGAAAGTTG GCACCCGTAC AAGTTTTGGA ATATGGAGAA GCCATTGCAA AGTTTAACTT   2220

TAATGGAGAT ACACAAGTAG AAATGTCTTT CCGAAAGGGG GAGAGGATCA CGCTGCTCCG   2280

ACAGGTGGAT GAGAACTGGT ATGAAGGGAG GATTCCTGGG ACATCTCGCC AAGGCATTTT   2340

CCCTATCACC TATGTAGATG TGCTTAAGAG GCCATTGGTG AAAACCCCTG TGGATTACAT   2400

CGACCTGCCT TATTCTTCTT CCCCAAGTCG CAGTGCCACT GTGAGCCCAC AGGCTTCTCA   2460
```

```
TCATTCATTG AGCGCAGGAC CTGATCTCAC AGAATCTGAA AAGAACTATG TGCAACCTCA    2520

AGCCCAGCAG CGAAGAGTCA CCCCAGACAG GAGTCAGCCC TCACTGGATT TGTGTAGCTA    2580

CCAAGCGTTA TATAGTTATG TGCCACAGAA CGATGATGAG TTGGAACTCC GAGATGGAGA    2640

TATTGTTGAT GTCATGGAAA AATGTGACGA TGGATGGTTT GTTGGCACTT CGAGAAGGAC    2700

GAGGCAGTTT GGTACTTTTC CAGGCAACTA TGTAAAACCT TTATATCTAT AAGAAGACTA    2760

AAAAGCACAG AGATTATTTT TTATCGGAGG ATGAAGCATC ATTCATGAAC TGGTCTCTTT    2820

ATTTAAGTAC TGAGTCAGTA AGAAAACTAA TGCAGTTGGT AAAGAAAGAA TTCAAAGAAG    2880

GAACAGAGAA GTGTGTTTGA AACCCATTGT GTATCAGGGA TTAACTATCT GCTGAAGACA    2940

TCTGTATTTA CATGACTGCT TCTGGGAGCT GCTCTAGCCC CCGCTGCTTG GGAATCTGA     3000

TCTGGAGCAT GTCCATGAGC AACATTAGCC AAAAAAAAAA GCTTGGGCCC TATTCTATAG    3060

TGTCACCTAA ATACTAGCTT GATCCGGCTG CTAACAAAGC CCGAAAGGAA GCTGAGTTGC    3120

TGCTGCCACC GCTGAGCAAT AACTAGCATA ACCCCTTGGG GCCTCTAAAC GGGTCTTGAG    3180

GGGTTTTTTG GCTGAAAGGA GGAACTATAT CCGGATAACC TGGCGTAATA GCGAAGAGGC    3240

CCGCACCGAT CGCCCTTCCC AACAGTTGGG CAGCCTGAAT GGCGAATGGA CGCGCCCTGT    3300

AGCGGCGCAT TAAGCGCGGC GGGTGTGGTG GTTACGCGCA GGGTG                    3345
```

(2) INFORMATION FOR SEQ ID NO: 30:

(i) SEQUENCE CHARACTERISTICS:
        (A) LENGTH: 788 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 30:

```
Met Ser Ser Glu Cys Asp Val Gly Ser Ser Lys Ala Val Val Asn Gly
1               5                   10                  15

Leu Ala Ser Gly Asn His Gly Pro Asp Lys Asp Met Asp Pro Thr Lys
            20                  25                  30

Ile Cys Thr Gly Lys Gly Thr Val Thr Leu Arg Ala Ser Ser Ser Tyr
        35                  40                  45

Arg Gly Thr Pro Ser Ser Pro Val Ser Pro Gln Glu Ser Pro Lys
    50                  55                  60

His Glu Ser Lys Ser Asp Glu Trp Lys Leu Ser Ser Ala Asp Thr
65                  70                  75                  80

Asn Gly Asn Ala Gln Pro Ser Pro Leu Ala Ala Lys Gly Tyr Arg Ser
            85                  90                  95

Val His Pro Ser Leu Ser Ala Asp Lys Pro Gln Gly Ser Pro Leu Leu
            100                 105                 110

Asn Glu Val Ser Ser Ser His Ile Glu Thr Asp Ser Gln Asp Phe Pro
            115                 120                 125

Pro Thr Ser Arg Pro Ser Ser Ala Tyr Pro Ser Thr Thr Ile Val Asn
            130                 135                 140

Pro Thr Ile Val Leu Leu Gln His Asn Arg Glu Gln Gln Lys Arg Leu
145                 150                 155                 160

Ser Ser Leu Ser Asp Pro Ala Ser Glu Arg Arg Ala Gly Glu Gln Asp
            165                 170                 175

Pro Val Pro Thr Pro Ala Glu Leu Thr Ser Pro Gly Arg Ala Ser Glu
            180                 185                 190
```

-continued

```
Arg Arg Ala Lys Asp Ala Ser Arg Arg Val Val Arg Ser Ala Gln Asp
            195                 200                 205
Leu Ser Asp Val Ser Thr Asp Glu Val Gly Ile Pro Leu Arg Asn Thr
    210                 215                 220
Glu Arg Ser Lys Asp Trp Tyr Lys Thr Met Phe Lys Gln Ile His Lys
225                 230                 235                 240
Leu Asn Arg Asp Asp Asp Ser Asp Val His Ser Pro Arg Tyr Ser Phe
                245                 250                 255
Ser Asp Asp Thr Lys Ser Pro Leu Ser Val Pro Arg Ser Lys Ser Glu
            260                 265                 270
Met Asn Tyr Ile Glu Gly Lys Val Val Lys Arg Ser Ala Thr Leu
        275                 280                 285
Pro Leu Pro Ala Arg Ser Ser Ser Leu Lys Ser Ser Pro Glu Arg Asn
    290                 295                 300
Asp Trp Glu Pro Leu Asp Lys Lys Val Asp Thr Arg Lys Tyr Arg Ala
305                 310                 315                 320
Glu Pro Lys Ser Ile Tyr Glu Tyr Gln Pro Gly Lys Ser Ser Val Leu
                325                 330                 335
Thr Asn Glu Lys Met Ser Arg Asp Ile Ser Pro Glu Ile Asp Leu
            340                 345                 350
Lys Asn Glu Pro Trp Tyr Lys Phe Phe Ser Glu Leu Glu Phe Gly Arg
        355                 360                 365
Pro Ser Ser Ala Val Ser Pro Thr Pro Asp Ile Thr Ser Glu Pro Pro
    370                 375                 380
Gly Tyr Ile Tyr Ser Ser Asn Phe His Ala Val Lys Arg Glu Ser Asp
385                 390                 395                 400
Gly Thr Pro Gly Gly Leu Ala Ser Leu Glu Asn Glu Arg Gln Ile Tyr
                405                 410                 415
Lys Ser Val Leu Glu Gly Gly Asp Ile Pro Leu Gln Gly Leu Ser Gly
            420                 425                 430
Leu Lys Arg Pro Ser Ser Ser Ala Ser Thr Lys Asp Ser Glu Ser Pro
        435                 440                 445
Arg His Phe Ile Pro Ala Asp Tyr Leu Glu Ser Thr Glu Glu Phe Ile
    450                 455                 460
Arg Arg Arg His Asp Asp Lys Glu Lys Leu Leu Ala Asp Gln Arg Arg
465                 470                 475                 480
Leu Lys Arg Glu Gln Glu Glu Ala Asp Ile Ala Ala Arg Arg His Thr
                485                 490                 495
Gly Val Ile Pro Thr His His Gln Phe Ile Thr Asn Glu Arg Phe Gly
            500                 505                 510
Asp Leu Leu Asn Ile Asp Asp Thr Ala Lys Arg Lys Ser Gly Leu Glu
        515                 520                 525
Met Arg Pro Ala Arg Ala Lys Phe Asp Phe Lys Ala Gln Thr Leu Lys
    530                 535                 540
Glu Leu Pro Leu Gln Lys Gly Asp Val Val Tyr Ile Tyr Arg Gln Ile
545                 550                 555                 560
Asp Gln Asn Trp Tyr Glu Gly Glu His His Gly Arg Val Gly Ile Phe
                565                 570                 575
Pro Arg Thr Tyr Ile Glu Leu Leu Pro Pro Ala Glu Lys Ala Gln Pro
            580                 585                 590
Arg Lys Leu Ala Pro Val Gln Val Leu Glu Tyr Gly Glu Ala Ile Ala
        595                 600                 605
Lys Phe Asn Phe Asn Gly Asp Thr Gln Val Glu Met Ser Phe Arg Lys
```

|     |     |     |     |     |     |     |     |     |     |     |     |
| --- | --- | --- | --- | --- | --- | --- | --- | --- | --- | --- | --- |
|     |     | 610 |     |     | 615 |     |     | 620 |     |     |     |
| Gly | Glu | Arg | Ile | Thr | Leu | Leu | Arg | Gln | Val | Asp | Glu |
| 625 |     |     |     | 630 |     |     |     | 635 |     |     | 640 |
| Asn | Trp | Tyr | Glu |     |     |     |     |     |     |     |     |
| Gly | Arg | Ile | Pro | Gly | Thr | Ser | Arg | Gln | Gly | Ile | Phe |
|     |     |     | 645 |     |     |     |     | 650 |     |     |     |
| Pro | Ile | Thr | Tyr |     |     |     |     |     |     |     |     |
|     |     |     | 655 |     |     |     |     |     |     |     |     |
| Val | Asp | Val | Leu | Lys | Arg | Pro | Leu | Val | Lys | Thr | Pro |
|     |     |     | 660 |     |     |     |     | 665 |     |     |     |
| Val | Asp | Tyr | Ile |     |     |     |     |     |     |     |     |
|     |     |     | 670 |     |     |     |     |     |     |     |     |
| Asp | Leu | Pro | Tyr | Ser | Ser | Pro | Ser | Arg | Ser | Ala | Thr |
|     |     |     | 675 |     |     |     |     | 680 |     |     |     |
| Val | Ser | Pro |     |     |     |     |     |     |     |     |     |
|     |     | 685 |     |     |     |     |     |     |     |     |     |
| Gln | Ala | Ser | His | His | Ser | Leu | Ser | Ala | Gly | Pro | Asp |
|     |     | 690 |     |     |     | 695 |     |     |     |     | 700 |
| Leu | Thr | Glu | Ser |     |     |     |     |     |     |     |     |
| Glu | Lys | Asn | Tyr | Val | Gln | Pro | Gln | Ala | Gln | Gln | Arg |
| 705 |     |     |     | 710 |     |     |     | 715 |     |     |     |
| Arg | Val | Thr | Pro |     |     |     |     |     |     |     |     |
|     |     |     | 720 |     |     |     |     |     |     |     |     |
| Asp | Arg | Ser | Gln | Pro | Ser | Leu | Asp | Leu | Cys | Ser | Tyr |
|     |     |     |     | 725 |     |     |     | 730 |     |     |     |
| Gln | Ala | Leu | Tyr |     |     |     |     |     |     |     |     |
|     |     |     | 735 |     |     |     |     |     |     |     |     |
| Ser | Tyr | Val | Pro | Gln | Asn | Asp | Asp | Glu | Leu | Glu | Leu |
|     |     |     |     | 740 |     |     |     | 745 |     |     |     |
| Arg | Asp | Gly | Asp |     |     |     |     |     |     |     |     |
|     |     | 750 |     |     |     |     |     |     |     |     |     |
| Ile | Val | Asp | Val | Met | Glu | Lys | Cys | Asp | Asp | Gly | Trp |
|     |     |     | 755 |     |     |     |     | 760 |     |     |     |
| Phe | Val | Gly | Thr |     |     |     |     |     |     |     |     |
|     |     |     | 765 |     |     |     |     |     |     |     |     |
| Ser | Arg | Arg | Thr | Arg | Gln | Phe | Gly | Thr | Phe | Pro | Gly |
|     |     |     | 770 |     |     |     | 775 |     |     |     |     |
| Asn | Tyr | Val | Lys |     |     |     |     |     |     |     |     |
|     |     |     | 780 |     |     |     |     |     |     |     |     |
| Pro | Leu | Tyr | Leu |     |     |     |     |     |     |     |     |
| 785 |     |     |     |     |     |     |     |     |     |     |     |

(2) INFORMATION FOR SEQ ID NO: 31:

(i) SEQUENCE CHARACTERISTICS:
        (A) LENGTH: 1636 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 31:

```
TTNNCACTCA CCGTCCTGGT GATGGTACCG GATCGAATTC AAGCGTGGCC GTGGCCGTGG      60
GGCGCGCGGG GACCGCCCGG GGTGCCCGCT CCGCTCAGCG TCCGGGCCGC GTGGTCCGGC     120
GGAGCCCCGA GACCACCCCC GGGCGGGGCG CCGCCGCGAT GTCGGTGGCT GGGCTCAAGA     180
AGCAGTTCCA CAAAGCCAGC CAGCTGTTTA GTGAAAAAAT AAGTGGTGCC GAAGGAACGA     240
AGCTAGATGA AGAATTTCTG AACATGGAAA AGAAAATAGA TATCACCAGT AAAGCTGTTG     300
CAGAAATCCT TTCAAAAGCC ACAGAGTATC TCCAACCCAA TCCAGCATAC AGAGCTAAGC     360
TAGGAATGCT GAACACTGTG TCGAAGCTCC GAGGGCAGGT GAAGGCCACC GGCTACCCAC     420
AGACGGAAGG CTTGCTGGGG GACTGCATGC TGAAGTATGG CAAGGAGCTC GGAGAAGACT     480
CTGCTTTTGG CAACTCGTTG GTAGATGTTG GTGAGGCCCT GAAACTCATG GCTGAGGTGA     540
AAGACTCTCT GGATATTAAT GTGAAGCAAA CTTTTATTGA CCCACTGCAG CTACTGCAAG     600
ACAAAGATTT AAAGGAGATC GGGCACCACC TGAGAAAGCT GGAAGGCCGT CGCCTGGATT     660
ATGATTATAA AAAGCGGCGG GTAGGTAAGA TCCCCGAGGA AGAAATCAGA CAAGCAGTAG     720
AGAAGTTTGA AGAGTCAAAG GAGTTGGCCG AAAGGAGCAT GTTTAATTTT TTAGAAAATG     780
ATGTAGAGCA AGTGAGCCAG CTGGCTGTGT TTGTAGAGGC GGCATTAGAC TATCACAGGC     840
AGTCCACAGA GATCCTCCAG GAGCTGCAGA GCAAGCTGGA GTTGCGAATA TCTCTTGCAT     900
CCAAAGTCCC CAAGCGAGAA TTCATGCCAA AGCCTGTGAA CATGAGTTCC ACCGATGCCA     960
```

```
ATGGGGTCGG ACCCAGCTCT TCATCAAAGA CACCAGGTAC TGACACTCCC GCGGACCAGC    1020

CCTGCTGTCG TGGTCTCTAT GACTTTGAGC CAGAAAATGA AGGAGAATTA GGATTTAAAG    1080

AAGGGGACAT CATTACATTA ACCAATCAGA TAGATGAAAA CTGGTATGAA GGGATGCTTC    1140

GTGGGGAATC CGGCTTCTTC CCCATTAATT ACGTGGAAGT CATTGTGCCT TTACCTCCGT    1200

AAATGTGTCT TTTGGACCTA ACTTCAGAAC TGAAATGAAT TGGCACCAGT GCTCTCTCAG    1260

TGTGGTGTTC TGTGACANCC TCGCTCTCTG GCCCACTTAA TCACTTTTGT ATGTGTGTTT    1320

TCTTTATAAT GTATTTTGTA TCAATTTAAT TTGTATAACT GATTTCTTTG TCCTAACTCA    1380

TAAAAATAGT TTTCTTCTTG TTCTAAAAAG TCATTGGTTA AATGTATTTG CTTCCTGTTG    1440

CTAAAACGAG TAAATTGCGC CCATTCGAAT GGCCTGGGTA GTCCTTGACT GCAGTGGGAA    1500

CGCACCCTTT GCAGCCATGA AAGCTAAAGG TTTGTTTCCT GACATTATTG ATGGCCTCTG    1560

GTCTTTTCCT GTTTTAAGCT TACCTGTGAA CAGCCCAATA AACNTGACAC ACTGTANAAT    1620

AANAAGGGTG GCCCNA                                                    1636
```

(2) INFORMATION FOR SEQ ID NO: 32:

(i) SEQUENCE CHARACTERISTICS:
        (A) LENGTH: 347 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 32:

```
Met Ser Val Ala Gly Leu Lys Lys Gln Phe His Lys Ala Ser Gln Leu
1               5                   10                  15

Phe Ser Glu Lys Ile Ser Gly Ala Glu Gly Thr Lys Leu Asp Glu Glu
            20                  25                  30

Phe Leu Asn Met Glu Lys Lys Ile Asp Ile Thr Ser Lys Ala Val Ala
                35                  40                  45

Glu Ile Leu Ser Lys Ala Thr Glu Tyr Leu Gln Pro Asn Pro Ala Tyr
    50                  55                  60

Arg Ala Lys Leu Gly Met Leu Asn Thr Val Ser Lys Leu Arg Gly Gln
65                  70                  75                  80

Val Lys Ala Thr Gly Tyr Pro Gln Thr Glu Gly Leu Leu Gly Asp Cys
                85                  90                  95

Met Leu Lys Tyr Gly Lys Glu Leu Gly Glu Asp Ser Ala Phe Gly Asn
                100                 105                 110

Ser Leu Val Asp Val Gly Glu Ala Leu Lys Leu Met Ala Glu Val Lys
            115                 120                 125

Asp Ser Leu Asp Ile Asn Val Lys Gln Thr Phe Ile Asp Pro Leu Gln
130                 135                 140

Leu Leu Gln Asp Lys Asp Leu Lys Glu Ile Gly His His Leu Arg Lys
145                 150                 155                 160

Leu Glu Gly Arg Arg Leu Asp Tyr Asp Tyr Lys Lys Arg Arg Val Gly
                165                 170                 175

Lys Ile Pro Glu Glu Glu Ile Arg Gln Ala Val Glu Lys Phe Glu Glu
                180                 185                 190

Ser Lys Glu Leu Ala Glu Arg Ser Met Phe Asn Phe Leu Glu Asn Asp
            195                 200                 205

Val Glu Gln Val Ser Gln Leu Ala Val Phe Val Glu Ala Ala Leu Asp
    210                 215                 220
```

```
Tyr His Arg Gln Ser Thr Glu Ile Leu Gln Glu Leu Gln Ser Lys Leu
225                 230                 235                 240

Glu Leu Arg Ile Ser Leu Ala Ser Lys Val Pro Lys Arg Glu Phe Met
            245                 250                 255

Pro Lys Pro Val Asn Met Ser Ser Thr Asp Ala Asn Gly Val Gly Pro
            260                 265                 270

Ser Ser Ser Ser Lys Thr Pro Gly Thr Asp Thr Pro Ala Asp Gln Pro
        275                 280                 285

Cys Cys Arg Gly Leu Tyr Asp Phe Glu Pro Glu Asn Glu Gly Glu Leu
290                 295                 300

Gly Phe Lys Glu Gly Asp Ile Ile Thr Leu Thr Asn Gln Ile Asp Glu
305                 310                 315                 320

Asn Trp Tyr Glu Gly Met Leu Arg Gly Glu Ser Gly Phe Phe Pro Ile
                325                 330                 335

Asn Tyr Val Glu Val Ile Val Pro Leu Pro Pro
                340                 345

(2) INFORMATION FOR SEQ ID NO: 33:

(i) SEQUENCE CHARACTERISTICS:
        (A) LENGTH: 4091 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 33:

CGGGCTTGAG GCTGGGCCGC CGCCGCCGCC CGCTTTGCCA CCCGCCCCGC TGATGGTGTC      60

CGGTGCTCCG GCGCCCAGGG ACACAGACCG GGAGCAGGAC CACTTCTCTC ACCTCCGGAT     120

CTCTCCTGCT TCCGCAGCCT GTGAGCAGCA GGCCTGCTAA CTGCAGATCC ACAACCGCAC     180

AGCTCGCTAC AGGTGCACCA TGTCTGGCTC CTACGATGAG GCCTCAGAGG AGATCACAGA     240

TAGCTTCTGG GAGGTGGGGA ACTACAAGCG ACGGTGAAG CGCATCGACG ATGGGCACCG      300

CCTGTGCAAC GACCTCATGA GCTGCGTGCA GGAGCGCGCC AAGATCGAGA AGGCATACGC     360

GCAGCAGCTC ACCGACTGGG CCAAGCGCTG GCGCCAGCTC ATCGAGAAAG GTCCTCAGTA     420

TGGCAGCCTG GAGCGGGCGT GGGGCGCCAT GATGACAGAA GCAGATAAGG TCAGCGAGCT     480

GCACCAGGAG GTGAAGAACA GCCTGCTGAA TGAGGACCTG GAGAAAGTCA AGAACTGGCA     540

GAAGGATGCC TATCACAAGC AGATCATGGG TGGCTTCAAG GAGACGAAAG AGGCCGAGGA     600

TGGCTTCCGA AAGGCCCAGA AGCCCTGGGC TAAAAAGATG AAGGAGCTAG AGGCGGCCAG     660

GAAGGCCTAT CACTTGGCTT GTAAGGAGGA AAGGCTGGCC ATGACCCGGG AGATGAACAG     720

TAAGACAGAG CAGTCGGTCA CCCCTGAACA GCAGAAGAAA CTTGTGGACA AGTGGACAA      780

ATGCAGACAG GATGTGCAAA AGACTCAGGA GAAGTATGAG AAGGTCCTGG AAGATGTGGG     840

CAAGACCACA CCACAGTACA TGGAGGGCAT GGAGCAGGTG TTTGAGCAGT GCCAGCAGTT     900

TGAGGAGAAG CGGCTGGTCT TCCTGAAGGA AGTCCTGCTG GATATCAAAC GGCATCTCAA     960

CCTAGCGGAG AACAGCAGCT ACATGCATGT CTACCGAGAA CTGGAGCAGG CCATCCGGGG    1020

GGCCGATGCC CAGGAGGACC TCAGGTGGTT CCGCAGCACC AGTGGCCCCG GGATGCCCAT    1080

GAACTGGCCG CAGTTCGAGG AGTGGAACCC AGACCTCCCG CACACCACTG CCAAGAAGGA    1140

GAAACAGCCT AAGAAGGCAG AGGGGCCAC CCTGAGCAAT GCCACTGGGG CTGTAGAATC     1200

CACATCCCAG GCTGGGGACC GTGGCAGTGT TAGCAGCTAT GACCGAGGCC AAACATATGC    1260
```

```
CACCGAGTGG TCAGACGATG AGAGCGGAAA CCCCTTCGGG GGCAATGAGG CCAATGGTGG    1320

CGCCAACCCC TTCGAGGATG ATGCCAAGGG AGTTCGTGTA CGGGCACTCT ATGACTACGA    1380

CGGTCAGGAG CAGGATGAGC TCAGCTTCAA GGCCGGAGAT GAGCTCACCA AGCTCGGAGA    1440

GGAAGACGAA CAGGGTTGGT GCCGCGGGCG GCTGGACAGC GGACAGCTGG GCCTCTATCC    1500

TGCCAACTAC GTTGAGGCTA TATAGCTACC TTGCCCACCC GACTCCTCTC AGTCCTTGTC    1560

CACCGCCTTC CACCCTTCCC CTCCCCCTTG CCATAGAGTT CCAGACATAT TTTCCGATCA    1620

AGCTTTTATT TTTTTAAAAG TCAAAACAGA ACAAAAAAAA AAAAAAAAA GAAGAAATAC     1680

GAAGAGACAG CGTTTGCAGC CTACCTGGAG GCCGGGGGG AGGGGGCTTA GGGTGATGGC     1740

CTCCCCCACA GCGTGGGCAA GGATCTTGGG ACTAACCCAA TGTCACATCT GGTCTATAGA    1800

GTCCACCAAA GAGTCTCCTG AGTCTTGAGG GAGATCTTCT GGATCCTTCT ACCCTGTCTC    1860

GCTCTCCTAT CCCACCACAG CTGCCAGCAG CTGCCCATGT CACCTGAGCC TGGCTTCCTA    1920

AACTCTCCTG TCCCCTCTCC TGTCCCCCTT CAACGCCCCC TTCTCTTAAA GGGCCCCCAA    1980

TCTTTAGTCT TCCACTCTGC CCTGGGGGTG CTTTTCTCTT CCCAGCCCTG TCCAGTGAGG    2040

CTGGGGGAGA AGGCTGCGGA GGGGAGGGGA GTGTCTCTTC ACTCCCCCAG ACATGAAGGC    2100

AGGTGAGTGG GAGGGAGTCA TGGCCTCCCT GGCATACAGG AGAGGAAGAA GGAGAACAGA    2160

CCATCTGACC AGGCTGTGCA ACACTCCCAA TGCCAAGCCC ATTTGAGGGA TGAAAACCCT    2220

AGCTGGGCCT GTGGGCAGAG GGCTCCTCCT CAGAGCCAAT GAGCATTTGC AGAGACCCTA    2280

CCTGTCTCTT TAGTCCTTGG CAATGGGCAA AGCCTCTTCC TTGGAAAGTC CAGGGCAAAG    2340

CCAGCAACAG TAGCAACCTC CTCTCACTCT GGGGAGGAGG CATTGGCCAC CCATCCCCCT    2400

CCCTTCATGG TCATTCAGAA ACGCCACAGC CCCTCCCATC CCCAATCACT GTGTCAGCAT    2460

CAGCCTTTGT GAAGACGGTC TACAAGGCTC TCACCTGGCC AACCTAGGAG ATTCAGGGGC    2520

TCAGGAACCT AGGAGATTCA GGGGCTTGGG GAACCTCCAC CTTGGCACTG TAAGGGGAAG    2580

CCAGCAGCTC AGGCTGGTGT GAGGAAGGAA CTCTGGATGG TCACTGTAGC TTTCTTCCTT    2640

GACCTTTTAG TCCCCAACAT CCCCTCTGAA TGCTGGCAGC ACCCCACCC CCACACACAC     2700

ACTCCCATTT CTCTAAGCCC GAGAGTCTTG AGTCTTCATT AAAGGATTCT GGGTGTGGGA    2760

GGGGACACAG GGCCTTGTGG TTGGGAAGCA GGTGGCAGGC TCTCCCTTGG GAGGATGGGG    2820

TGGGAAACGA AACAGGTCAA CCAAGACCTC TTACAGTGGA AAGTGGTCAG AGGCTGTTTC    2880

TTTGGACCTT TGGGAACACA GATTTGAGAA AGTCTCATAT TCACAGCTGG TGTCCGCTAG    2940

GCCTCTGGCC TACGGACACC CTCTGCCTTG TGAATCAGGT GACCTTTTGG GCCTCCAGGG    3000

AAAGAACAGG ACCACCATCC ATGTTCTCCG CGTCCCTTTA GCTCTCTGCT GCTTCTCCTC    3060

ACACTCAGGT CATGGACCCA AGCTTTGGGG TCCTGACCAC CGCCCCCCCC CACCCCCTT    3120

CTCTTGACTA GGCTGCAGCA GGGCCTTCTG TTGGGTCAGT CCTCCTCAGG GCCAGGAGCA    3180

GGAACTTAGC ACTCAAGAGA CAGGGCTGTA AGCACCCACT TCCCTGTCAC TGTTTGCCCT    3240

TGGGGCTTCA GCTGCAGCCC AGGTTGGGCC CTGGAGCCCT CAGAACCGGA AGCAGGATTC    3300

AAACCTCCCC TTCTCCACAG CCCCCCCTGC CTCCCCAGAT GGTAGACATC CCCCAGCTCT    3360

TACCTTCACC CTCATCTCAG AAAGGCAAGA AGCCGCCATG TCCGCACCTT GGGGCCTGGG    3420

CTTCCCCCTC TCTGTGCCAG CGGTTCCCAG CACCTGGGGA GGGGCTGTGG CCTGACCAGA    3480

CCCCAGGCCC ACCCCACATA GTATACTAGC TGCCCACTCT GGGGCAGGAA CTGGAAAATC    3540

CATCCCTTTT GAACAACCAC CTTCAATGAC CCCCCCCATC TGGGACCAGA CTTGGTCCTC    3600
```

```
AAGTTATTCA GCACCCCCAG TGCAGGAGGG TCCTCCCCCC ACCCCCCGAA GTCCCTGGAG    3660

CCCGGAGCAG AGCCCCACCT GTGATTCCTG GTGTTAGGGC ACCTCAAACC TTGGGCTGGA    3720

CCACACCCCT TCCCGCCATT TCCAGACCCC TACCTGTACT CCCCAGTGCT CCCCAGGGGC    3780

CTCTTGATGC TGCACGGGAC CCTGCAGGGC TCGGTCAGTG ATGTGTTTTG TCCCCAGTTA    3840

ACCGCCATCC AGCGACCTGG TTCCAGGAGG AGCTCAGGTC ACCCCACCA CCGCCGCCAC     3900

TGCGTCTGCC GCCCTAGGCT TTCAGACATC ATTAGTTCCG ACACTTGTGA AACTCCGAGA    3960

CGTGCCGTGG TCTCAGCAAT GCACCTGTTT TATACATGAT TGTGTAATTT AAAGGTATAT    4020

AAATACAAAT ATATATATTA TATCTATATC TATCAGTTGT GACCGTATGG CTGTCGATAA    4080

AACCAGAATT C                                                        4091
```

(2) INFORMATION FOR SEQ ID NO: 34:

(i) SEQUENCE CHARACTERISTICS:
        (A) LENGTH: 441 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 34:

```
Met Ser Gly Ser Tyr Asp Glu Ala Ser Glu Glu Ile Thr Asp Ser Phe
1               5                   10                  15

Trp Glu Val Gly Asn Tyr Lys Arg Thr Val Lys Arg Ile Asp Asp Gly
                20                  25                  30

His Arg Leu Cys Asn Asp Leu Met Ser Cys Val Gln Glu Arg Ala Lys
            35                  40                  45

Ile Glu Lys Ala Tyr Ala Gln Gln Leu Thr Asp Trp Ala Lys Arg Trp
        50                  55                  60

Arg Gln Leu Ile Glu Lys Gly Pro Gln Tyr Gly Ser Leu Glu Arg Ala
65                  70                  75                  80

Trp Gly Ala Met Met Thr Glu Ala Asp Lys Val Ser Glu Leu His Gln
                85                  90                  95

Glu Val Lys Asn Ser Leu Leu Asn Glu Asp Leu Glu Lys Val Lys Asn
            100                 105                 110

Trp Gln Lys Asp Ala Tyr His Lys Gln Ile Met Gly Gly Phe Lys Glu
        115                 120                 125

Thr Lys Glu Ala Glu Asp Gly Phe Arg Lys Ala Gln Lys Pro Trp Ala
    130                 135                 140

Lys Lys Met Lys Glu Leu Glu Ala Ala Lys Ala Tyr His Leu Ala
145                 150                 155                 160

Cys Lys Glu Glu Arg Leu Ala Met Thr Arg Glu Met Asn Ser Lys Thr
                165                 170                 175

Glu Gln Ser Val Thr Pro Glu Gln Gln Lys Leu Val Asp Lys Val
            180                 185                 190

Asp Lys Cys Arg Gln Asp Val Gln Lys Thr Gln Glu Lys Tyr Glu Lys
        195                 200                 205

Val Leu Glu Asp Val Gly Lys Thr Thr Pro Gln Tyr Met Glu Gly Met
    210                 215                 220

Glu Gln Val Phe Glu Gln Cys Gln Gln Phe Glu Glu Lys Arg Leu Val
225                 230                 235                 240

Phe Leu Lys Glu Val Leu Leu Asp Ile Lys Arg His Leu Asn Leu Ala
                245                 250                 255
```

```
Glu Asn Ser Ser Tyr Met His Val Tyr Arg Glu Leu Glu Gln Ala Ile
            260                 265                 270

Arg Gly Ala Asp Ala Gln Glu Asp Leu Arg Trp Phe Arg Ser Thr Ser
            275                 280                 285

Gly Pro Gly Met Pro Met Asn Trp Pro Gln Phe Glu Glu Trp Asn Pro
            290                 295                 300

Asp Leu Pro His Thr Thr Ala Lys Lys Glu Lys Gln Pro Lys Lys Ala
305                 310                 315                 320

Glu Gly Ala Thr Leu Ser Asn Ala Thr Gly Ala Val Glu Ser Thr Ser
                325                 330                 335

Gln Ala Gly Asp Arg Gly Ser Val Ser Ser Tyr Asp Arg Gly Gln Thr
            340                 345                 350

Tyr Ala Thr Glu Trp Ser Asp Glu Ser Gly Asn Pro Phe Gly Gly
            355                 360                 365

Asn Glu Ala Asn Gly Gly Ala Asn Pro Phe Glu Asp Asp Ala Lys Gly
            370                 375                 380

Val Arg Val Arg Ala Leu Tyr Asp Tyr Asp Gly Gln Glu Gln Asp Glu
385                 390                 395                 400

Leu Ser Phe Lys Ala Gly Asp Glu Leu Thr Lys Leu Gly Glu Glu Asp
                405                 410                 415

Glu Gln Gly Trp Cys Arg Gly Arg Leu Asp Ser Gly Gln Leu Gly Leu
            420                 425                 430

Tyr Pro Ala Asn Tyr Val Glu Ala Ile
            435                 440
```

(2) INFORMATION FOR SEQ ID NO: 35:

(i) SEQUENCE CHARACTERISTICS:
        (A) LENGTH: 1133 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 35:

```
GAATTCGTCG ACCCACGGTC CGGGAAGCCT TTCACAAGCA GATGATGGGC GGCTTCAAGG      60

AGACCAAGGA AGCTGAGGAC GGCTTTCGGA AGGCACAGAA GCCCTGGGCC AAGAAGCTGA     120

AAGAGGTAGA AGCAGCAAAG AAAGCCCACC ATGCAGCGTG CAAAGAGGAG AAGCTGGCTA     180

TCTCACGAGA AGCCAACAGC AAGGCAGACC CATCCCTCAA CCCTGAACAG CTCAAGAAAT     240

TGCAAGACAA AATAGAAAAG TGCAAGCAAG ATGTTCTTAA GACCAAAGAG AAGTATGAGA     300

AGTCCCTGAA GGAACTCGAC CAGGGCACAC CCCAGTACAT GGAGAACATG GAGCAGGTGT     360

TTGAGCAGTG CCAGCAGTTC GAGGAGAAAC GCCTTCGCTT CTTCCGGGAG GTTCTGCTGG     420

AGGTTCAGAA GCACCTAGAC CTGTCCAATG TGGCTGGTTA CAAAGCCATT TACCATGACC     480

TGGAGCAGAG CATCAGAGCA GCTGATGCAG TGGAGGACCT GAGGTGGTTC CGAGCCAATC     540

ACGGGCCGGG CATGGCCATG AACTGGCCGC AGTTTGAGGA GTGGTCCGCA GACCTGAATC     600

GAACCCTCAG CCGGAGAGAG AAGAAGAAGT CCACTGACGG CGTCACCCTG ACGGGCATCA     660

ACCAGACAGG CGACCAGTCT CTGCCGAGTA AGCCCAGCAG CACCCTTAAT GTCCCGAGCA     720

ACCCCGCCCA GTCTGCGCAG TCACAGTCCA GCTACAACCC CTTCGAGGAT GAGGACGACA     780

CGGGCAGCAC CGTCAGTGAG AAGGACGACA CTAAGGCCAA AAATGTGAGC AGCTACGAGA     840

AGACCCAGAG CTATCCCACC GACTGGTCAG ACGATGAGTC TAACAACCCC TTCTCCTCCA     900
```

```
CGGATGCCAA TGGGGACTCG AATCCATTCG ACGACGACGC CACCTCGGGG ACGGAAGTGC    960

GAGTCCGGGC CCTGTATGAC TATGAGGGGC AGGAGCATGA TGAGCTGAGC TTCAAGGCTG   1020

GGGATGAGCT GACCAAGATG GAGGACGAGG ATGAGCAGGG CTGGTGCAAG GGACGCTTGG   1080

ACAACGGGCA AGTTGGCCTA TACCCGGCAA ATTATGTGGA GGCGATCCAG TGA          1133
```

(2) INFORMATION FOR SEQ ID NO: 36:

(i) SEQUENCE CHARACTERISTICS:
        (A) LENGTH: 377 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 36:

```
Arg Ile Arg Arg Pro Thr Val Arg Glu Ala Phe His Lys Gln Met Met
 1               5                  10                  15

Gly Gly Phe Lys Glu Thr Lys Glu Ala Glu Asp Gly Phe Arg Lys Ala
                20                  25                  30

Gln Lys Pro Trp Ala Lys Lys Leu Lys Glu Val Glu Ala Ala Lys Lys
            35                  40                  45

Ala His His Ala Ala Cys Lys Glu Glu Lys Leu Ala Ile Ser Arg Glu
        50                  55                  60

Ala Asn Ser Lys Ala Asp Pro Ser Leu Asn Pro Glu Gln Leu Lys Lys
65                  70                  75                  80

Leu Gln Asp Lys Ile Glu Lys Cys Lys Gln Asp Val Leu Lys Thr Lys
                85                  90                  95

Glu Lys Tyr Glu Lys Ser Leu Lys Glu Leu Asp Gln Gly Thr Pro Gln
               100                 105                 110

Tyr Met Glu Asn Met Glu Gln Val Phe Glu Gln Cys Gln Gln Phe Glu
            115                 120                 125

Glu Lys Arg Leu Arg Phe Phe Arg Glu Val Leu Leu Glu Val Gln Lys
        130                 135                 140

His Leu Asp Leu Ser Asn Val Ala Gly Tyr Lys Ala Ile Tyr His Asp
145                 150                 155                 160

Leu Glu Gln Ser Ile Arg Ala Ala Asp Ala Val Glu Asp Leu Arg Trp
                165                 170                 175

Phe Arg Ala Asn His Gly Pro Gly Met Ala Met Asn Trp Pro Gln Phe
            180                 185                 190

Glu Glu Trp Ser Ala Asp Leu Asn Arg Thr Leu Ser Arg Arg Glu Lys
        195                 200                 205

Lys Lys Ser Thr Asp Gly Val Thr Leu Thr Gly Ile Asn Gln Thr Gly
210                 215                 220

Asp Gln Ser Leu Pro Ser Lys Pro Ser Ser Thr Leu Asn Val Pro Ser
                225                 230                 235                 240

Asn Pro Ala Gln Ser Ala Gln Ser Gln Ser Ser Tyr Asn Pro Phe Glu
            245                 250                 255

Asp Glu Asp Asp Thr Gly Ser Thr Val Ser Glu Lys Asp Asp Thr Lys
        260                 265                 270

Ala Lys Asn Val Ser Ser Tyr Glu Lys Thr Gln Ser Tyr Pro Thr Asp
    275                 280                 285

Trp Ser Asp Asp Glu Ser Asn Asn Pro Phe Ser Ser Thr Asp Ala Asn
290                 295                 300

Gly Asp Ser Asn Pro Phe Asp Asp Asp Ala Thr Ser Gly Thr Glu Val
```

```
                305                 310                 315                 320
Arg Val Arg Ala Leu Tyr Asp Tyr Glu Gly Gln Glu His Asp Glu Leu
                    325                 330                 335

Ser Phe Lys Ala Gly Asp Glu Leu Thr Lys Met Glu Asp Glu Asp Glu
                    340                 345                 350

Gln Gly Trp Cys Lys Gly Arg Leu Asp Asn Gly Gln Val Gly Leu Tyr
                    355                 360                 365

Pro Ala Asn Tyr Val Glu Ala Ile Gln
                    370                 375

(2) INFORMATION FOR SEQ ID NO: 37:

(i) SEQUENCE CHARACTERISTICS:
        (A) LENGTH: 1400 amino acids
        (B) TYPE: amino acid
        (C) STRANDEDNESS: single
        (D) TOPOLOGY: linear (ii) MOLECULE TYPE: DNA (xi) SEQUENCE DESCRIPTION: SEQ ID NO: 37:

Ala Ala Ala Ala Gly Gly Gly Ala Gly Gly Ala Gly Ala Gly Thr Gly
1                   5                   10                  15

Thr Cys Ala Ala Ala Ala Gly Ala Ala Gly Gly Ala Thr Gly Gly
                    20                  25                  30

Cys Gly Ala Gly Gly Ala Ala Ala Ala Gly Gly Cys Ala Ala Ala
                    35                  40                  45

Cys Ala Gly Gly Ala Ala Gly Cys Ala Cys Ala Ala Gly Ala Cys Ala
    50                  55                  60

Ala Gly Cys Thr Gly Gly Thr Cys Gly Gly Cys Thr Thr Thr Thr
65                  70                  75                  80

Cys Cys Ala Thr Cys Ala Ala Cys Ala Cys Ala Ala Gly Ala Ala
                    85                  90                  95

Cys Cys Ala Gly Cys Thr Ala Ala Gly Cys Cys Ala Gly Cys Thr Gly
                    100                 105                 110

Thr Cys Cys Ala Gly Gly Cys Ala Cys Cys Thr Gly Gly Thr Cys
    115                 120                 125

Cys Ala Cys Thr Gly Cys Ala Gly Ala Ala Ala Ala Gly Gly Gly
    130                 135                 140

Thr Cys Cys Ala Cys Thr Thr Ala Cys Cys Ala Thr Thr Cys Thr
145                 150                 155                 160

Gly Cys Ala Cys Ala Gly Gly Ala Ala Ala Thr Gly Thr Ala Ala
        165                 170                 175

Ala Ala Gly Thr Gly Gly Thr Gly Thr Ala Thr Ala Cys Cys Gly
        180                 185                 190

Gly Gly Cys Ala Cys Thr Gly Thr Ala Cys Cys Cys Thr Thr Thr
        195                 200                 205

Gly Ala Ala Thr Cys Cys Ala Gly Ala Ala Gly Cys Cys Ala Thr Gly
        210                 215                 220

Ala Thr Gly Ala Ala Ala Thr Cys Ala Cys Ala Thr Cys Cys Ala
225                 230                 235                 240

Gly Cys Cys Ala Gly Gly Ala Gly Ala Cys Ala Thr Ala Gly Thr Cys
                    245                 250                 255

Ala Thr Gly Gly Thr Gly Gly Ala Thr Gly Ala Ala Gly Cys Cys
        260                 265                 270

Ala Ala Ala Cys Thr Gly Gly Ala Gly Ala Ala Cys Cys Cys Gly Gly
```

```
            275                 280                 285
Cys Thr Gly Gly Cys Thr Thr Gly Ala Gly Ala Gly Ala Ala
    290                 295                 300
Thr Thr Ala Ala Ala Ala Gly Gly Ala Ala Gly Ala Cys Ala Gly
305                 310                 315                 320
Gly Gly Thr Gly Gly Thr Thr Cys Cys Cys Thr Gly Cys Ala Ala
                325                 330                 335
Cys Thr Ala Thr Gly Cys Ala Gly Ala Gly Ala Ala Ala Thr Cys
            340                 345                 350
Cys Cys Ala Gly Ala Ala Ala Thr Gly Ala Gly Gly Thr Thr Cys
        355                 360                 365
Cys Cys Gly Cys Thr Cys Cys Ala Gly Thr Gly Ala Ala Cys Cys
    370                 375                 380
Ala Gly Thr Gly Ala Cys Thr Gly Ala Thr Cys Ala Ala Cys Ala
385                 390                 395                 400
Thr Cys Thr Gly Cys Cys Cys Thr Gly Cys Cys Cys Cys Ala
                405                 410                 415
Ala Ala Cys Thr Gly Gly Cys Cys Thr Thr Gly Cys Gly Thr Gly Ala
            420                 425                 430
Gly Ala Cys Cys Cys Cys Gly Cys Cys Cys Thr Thr Gly
        435                 440                 445
Gly Cys Ala Gly Thr Ala Ala Cys Cys Thr Cys Thr Thr Cys Ala Gly
    450                 455                 460
Ala Gly Cys Cys Cys Thr Cys Cys Ala Cys Gly Ala Cys Cys Cys
465                 470                 475                 480
Thr Ala Ala Thr Ala Ala Cys Thr Gly Gly Cys Cys Gly Ala Cys
                485                 490                 495
Thr Thr Cys Ala Gly Cys Thr Cys Cys Ala Cys Gly Thr Gly Gly Cys
            500                 505                 510
Cys Cys Ala Cys Cys Ala Gly Cys Ala Cys Gly Ala Ala Thr Gly Ala
        515                 520                 525
Gly Ala Ala Ala Cys Cys Gly Ala Ala Ala Cys Gly Gly Ala Thr
    530                 535                 540
Ala Ala Cys Thr Gly Gly Gly Ala Thr Gly Cys Ala Thr Gly Gly
545                 550                 555                 560
Cys Ala Gly Cys Cys Ala Gly Cys Cys Cys Thr Cys Thr Cys Thr
                565                 570                 575
Cys Ala Cys Cys Gly Thr Thr Cys Cys Ala Ala Gly Thr Gly Cys Cys
            580                 585                 590
Gly Gly Cys Cys Ala Gly Thr Thr Ala Ala Gly Gly Cys Ala Gly Ala
        595                 600                 605
Gly Gly Thr Cys Cys Gly Cys Cys Thr Thr Ala Cys Thr Cys Cys
    610                 615                 620
Ala Gly Cys Cys Ala Cys Gly Gly Cys Cys Ala Cys Thr Gly Gly Cys
625                 630                 635                 640
Thr Cys Cys Thr Cys Cys Cys Gly Thr Cys Thr Cys Thr Gly
                645                 650                 655
Thr Gly Cys Thr Ala Gly Gly Cys Cys Ala Gly Gly Thr Gly Ala
            660                 665                 670
Ala Ala Ala Gly Gly Thr Gly Gly Ala Gly Gly Gly Cys Thr Ala
        675                 680                 685
Cys Ala Ala Gly Cys Thr Cys Ala Ala Gly Cys Cys Thr Ala Thr
    690                 695                 700
```

-continued

```
Ala Thr Cys Cys Thr Thr Gly Gly Ala Gly Ala Gly Cys Cys Ala Ala
705                 710                 715                 720
Ala Ala Ala Ala Gly Ala Cys Ala Ala Cys Cys Ala Cys Thr Thr Ala
            725                 730                 735
Ala Ala Thr Thr Thr Thr Ala Ala Cys Ala Ala Ala Ala Ala Thr Gly
        740                 745                 750
Ala Thr Gly Thr Cys Ala Thr Cys Ala Cys Cys Gly Thr Cys Cys Thr
            755                 760                 765
Gly Gly Ala Ala Cys Ala Gly Cys Ala Ala Gly Ala Cys Ala Thr Gly
    770                 775                 780
Thr Gly Gly Thr Gly Gly Thr Thr Gly Gly Ala Gly Ala Ala Ala Gly
785                 790                 795                 800
Thr Thr Cys Ala Ala Gly Gly Thr Cys Ala Gly Ala Ala Gly Gly Gly
            805                 810                 815
Thr Thr Gly Gly Thr Thr Cys Cys Cys Ala Ala Gly Thr Cys Thr
        820                 825                 830
Thr Ala Cys Gly Thr Gly Ala Ala Ala Cys Thr Cys Ala Thr Thr Thr
            835                 840                 845
Cys Ala Gly Gly Gly Cys Cys Cys Ala Thr Ala Ala Gly Gly Ala Ala
    850                 855                 860
Gly Thr Cys Thr Ala Cys Ala Ala Gly Cys Ala Thr Gly Gly Ala Thr
865                 870                 875                 880
Thr Cys Thr Gly Gly Thr Thr Cys Thr Thr Cys Ala Gly Ala Gly Ala
            885                 890                 895
Gly Thr Cys Cys Thr Gly Cys Thr Ala Gly Thr Cys Thr Ala Ala Ala
            900                 905                 910
Gly Cys Gly Ala Gly Thr Ala Gly Cys Cys Thr Cys Thr Cys Cys Ala
    915                 920                 925
Gly Cys Ala Gly Cys Ala Ala Gly Cys Cys Gly Ala Gly Cys Cys
    930                 935                 940
Ala Ala Gly Cys Cys Gly Gly Thr Cys Gly Thr Thr Thr Cys Gly Gly
945                 950                 955                 960
Gly Ala Gly Ala Ala Gly Ala Ala Thr Thr Gly Cys Cys Ala
            965                 970                 975
Gly Gly Thr Thr Ala Thr Thr Gly Cys Cys Thr Cys Ala Thr Ala Cys
            980                 985                 990
Ala Cys Cys Gly Cys Cys Ala Cys Cys Gly Gly Cys Cys Cys Gly
    995                 1000                1005
Ala Gly Cys Ala Gly Cys Thr Cys Ala Cys Thr Cys Thr Cys Gly Cys
    1010                1015                1020
Cys Cys Cys Thr Gly Gly Thr Cys Ala Gly Cys Thr Gly Ala Thr Thr
1025                1030                1035                1040
Thr Thr Gly Ala Thr Cys Cys Gly Ala Ala Ala Ala Ala Gly Ala
            1045                1050                1055
Ala Cys Cys Cys Ala Gly Gly Thr Gly Gly Ala Thr Gly Gly Thr Gly
    1060                1065                1070
Gly Gly Ala Ala Gly Gly Ala Gly Ala Gly Cys Thr Gly Cys Ala Ala
        1075                1080                1085
Gly Cys Ala Cys Gly Thr Gly Gly Ala Ala Ala Ala Gly Cys
    1090                1095                1100
Gly Cys Cys Ala Gly Ala Thr Ala Gly Gly Cys Thr Gly Gly Thr Thr
1105                1110                1115                1120
```

```
Cys Cys Cys Ala Gly Cys Thr Ala Ala Thr Thr Ala Thr Gly Thr Ala
            1125                1130                1135

Ala Ala Gly Cys Thr Thr Cys Thr Ala Ala Gly Cys Cys Cys Thr Gly
            1140                1145                1150

Gly Gly Ala Cys Gly Ala Gly Cys Ala Ala Ala Thr Cys Ala Cys
            1155                1160                1165

Thr Cys Cys Ala Ala Cys Ala Gly Ala Gly Cys Ala Cys Cys Thr
    1170                1175                1180

Ala Ala Gly Thr Cys Ala Ala Cys Ala Gly Cys Ala Thr Thr Ala Gly
1185                1190                1195                1200

Cys Gly Gly Cys Ala Gly Thr Gly Thr Gly Cys Cys Ala Gly Gly Thr
                1205                1210                1215

Gly Ala Thr Thr Gly Gly Ala Thr Gly Thr Ala Cys Gly Ala Cys
                1220                1225                1230

Thr Ala Cys Ala Cys Cys Gly Cys Gly Cys Ala Gly Ala Ala Thr Gly
            1235                1240                1245

Ala Cys Gly Ala Thr Gly Ala Gly Cys Thr Gly Gly Cys Cys Thr Thr
    1250                1255                1260

Cys Ala Ala Cys Ala Ala Gly Gly Gly Cys Cys Ala Gly Ala Thr Cys
1265                1270                1275                1280

Ala Thr Cys Ala Ala Cys Gly Thr Cys Cys Thr Cys Ala Ala Cys Ala
            1285                1290                1295

Ala Gly Gly Ala Gly Gly Ala Cys Cys Cys Thr Gly Ala Cys Thr Gly
            1300                1305                1310

Gly Thr Gly Gly Ala Ala Ala Gly Gly Ala Gly Ala Ala Gly Thr Cys
            1315                1320                1325

Ala Ala Thr Gly Gly Ala Cys Ala Ala Gly Thr Gly Gly Gly Cys
    1330                1335                1340

Thr Cys Thr Thr Cys Cys Cys Ala Thr Cys Cys Ala Ala Thr Thr Ala
1345                1350                1355                1360

Thr Gly Thr Gly Ala Ala Gly Cys Thr Gly Ala Cys Cys Ala Cys Ala
            1365                1370                1375

Gly Ala Cys Ala Thr Gly Gly Ala Cys Cys Cys Ala Ala Gly Cys Cys
            1380                1385                1390

Ala Gly Cys Ala Ala Thr Gly Ala
            1395                1400

(2) INFORMATION FOR SEQ ID NO: 38:

(i) SEQUENCE CHARACTERISTICS:
        (A) LENGTH: 462 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 38:

Lys Gly Arg Arg Val Ser Lys Arg Arg Met Ala Arg Lys Lys Ala Asn
1               5                   10                  15

Arg Lys His Lys Thr Ser Trp Val Gly Phe Ser Ile Asn Thr Lys Asn
                20                  25                  30

Gln Leu Ser Gln Leu Ser Arg His Pro Gly Pro Leu Gln Lys Lys Gly
            35                  40                  45

Pro Leu Thr Ile Ser Ala Gln Glu Asn Val Lys Val Tyr Tyr Arg
    50                  55                  60
```

-continued

```
Ala Leu Tyr Pro Phe Glu Ser Arg Ser His Asp Glu Ile Thr Ile Gln
 65                  70                  75                  80

Pro Gly Asp Ile Val Met Val Asp Glu Ser Gln Thr Gly Glu Pro Gly
                 85                  90                  95

Trp Leu Gly Gly Glu Leu Lys Gly Lys Thr Gly Trp Phe Pro Ala Asn
            100                 105                 110

Tyr Ala Glu Lys Ile Pro Glu Asn Glu Val Pro Ala Pro Val Lys Pro
        115                 120                 125

Val Thr Asp Ser Thr Ser Ala Pro Ala Pro Lys Leu Ala Leu Arg Glu
    130                 135                 140

Thr Pro Ala Pro Leu Ala Val Thr Ser Ser Glu Pro Ser Thr Thr Pro
145                 150                 155                 160

Asn Asn Trp Ala Asp Phe Ser Ser Thr Trp Pro Thr Ser Thr Asn Glu
                165                 170                 175

Lys Pro Glu Thr Asp Asn Trp Asp Ala Trp Ala Ala Gln Pro Ser Leu
            180                 185                 190

Thr Val Pro Ser Ala Gly Gln Leu Arg Gln Arg Ser Ala Phe Thr Pro
        195                 200                 205

Ala Thr Ala Thr Gly Ser Ser Pro Ser Pro Val Leu Gly Gln Gly Glu
    210                 215                 220

Lys Val Glu Gly Leu Gln Ala Gln Ala Leu Tyr Pro Trp Arg Ala Lys
225                 230                 235                 240

Lys Asp Asn His Leu Asn Phe Asn Lys Asn Asp Val Ile Thr Val Leu
                245                 250                 255

Glu Gln Gln Asp Met Trp Trp Phe Gly Glu Val Gln Gly Gln Lys Gly
            260                 265                 270

Trp Phe Pro Lys Ser Tyr Val Lys Leu Ile Ser Gly Pro Ile Arg Lys
        275                 280                 285

Ser Thr Ser Met Asp Ser Gly Ser Ser Glu Ser Pro Ala Ser Leu Lys
    290                 295                 300

Arg Val Ala Ser Pro Ala Ala Lys Pro Val Val Ser Gly Glu Glu Ile
305                 310                 315                 320

Ala Gln Val Ile Ala Ser Tyr Thr Ala Thr Gly Pro Glu Gln Leu Thr
                325                 330                 335

Leu Ala Pro Gly Gln Leu Ile Leu Ile Arg Lys Lys Asn Pro Gly Gly
            340                 345                 350

Trp Trp Glu Gly Glu Leu Gln Ala Arg Gly Lys Lys Arg Gln Ile Gly
        355                 360                 365

Trp Phe Pro Ala Asn Tyr Val Lys Leu Leu Ser Pro Gly Thr Ser Lys
    370                 375                 380

Ile Thr Pro Thr Glu Pro Pro Lys Ser Thr Ala Leu Ala Ala Val Cys
385                 390                 395                 400

Gln Val Ile Gly Met Tyr Asp Tyr Thr Ala Gln Asn Asp Asp Glu Leu
                405                 410                 415

Ala Phe Asn Lys Gly Gln Ile Ile Asn Val Leu Asn Lys Glu Asp Pro
            420                 425                 430

Asp Trp Trp Lys Gly Glu Val Asn Gly Gln Val Gly Leu Phe Pro Ser
        435                 440                 445

Asn Tyr Val Lys Leu Thr Thr Asp Met Asp Pro Ser Gln Gln
    450                 455                 460
```

(2) INFORMATION FOR SEQ ID NO: 39:

(i) SEQUENCE CHARACTERISTICS:

(A) LENGTH: 747 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 39:

GAATTCGCGG CCGCGTCGAC CAAGATCATT CCTGGGAGTG AAGTAAAACG GGAAGAACCA      60

GAAGCTTTGT ATGCAGCTGT AAATAAGAAA CCTACCTCGG CAGCCTATTC AGTTGGAGAA     120

GAATATATTG CACTTTATCC ATATTCAAGT GTGGAACCTG GAGATTTGAC TTTCACAGAA     180

GGTGAAGAAA TATTGGTGAC CCAGAAAGAT GGAGAGTGGT GGACAGGAAG TATTGGAGAT     240

AGAAGTGGAA TTTTTCCATC AAACTATGTC AAACCAAAGG ATCAAGAGAG TTTTGGGAGT     300

GCTAGCAAGT CTGGAGCATC AAATAAAAAA CCTGAGATTG CTCAGGTAAC TTCAGCATAT     360

GTTGCTTCTG GTTCTGAACA ACTTAGCCTT GCACCAGGAC AGTTAATATT AATTCTAAAG     420

AAAAATACAA GTGGGTGGTG GCAAGGAGAG TTACAGGCCA GAGGAAAAAA GCGACAGAAA     480

GGATGGTTTC CTGCCAGTCA TGTTAAACTT TTGGGTCCAA GCAGTGAAAG AGCCACACCT     540

GCCTTTCATC CTGTATGTCA GGTGATTGCT ATGTATGACT ATGCAGCAAA TAATGAAGAT     600

GAGCTCAGTT TCTCCAAGGG ACAACTCATT AATGTTATGA ACAAAGATGA TCCTGATTGG     660

TGGCAAGGAG AGATCAACGG GGTGACTGGT CTCTTTCCTT CAAACTACGT TAAGATGACG     720

ACAGACTCAG ATCCAAGTCA ACAGTGA                                        747

(2) INFORMATION FOR SEQ ID NO: 40:

(i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 40:

Glu Phe Ala Ala Ala Ser Thr Lys Ile Ile Pro Gly Ser Glu Val Lys
1               5                   10                  15

Arg Glu Glu Pro Glu Ala Leu Tyr Ala Ala Val Asn Lys Lys Pro Thr
            20                  25                  30

Ser Ala Ala Tyr Ser Val Gly Glu Glu Tyr Ile Ala Leu Tyr Pro Tyr
        35                  40                  45

Ser Ser Val Glu Pro Gly Asp Leu Thr Phe Thr Glu Gly Glu Glu Ile
    50                  55                  60

Leu Val Thr Gln Lys Asp Gly Glu Trp Trp Thr Gly Ser Ile Gly Asp
65                  70                  75                  80

Arg Ser Gly Ile Phe Pro Ser Asn Tyr Val Lys Pro Lys Asp Gln Glu
                85                  90                  95

Ser Phe Gly Ser Ala Ser Lys Ser Gly Ala Ser Asn Lys Lys Pro Glu
            100                 105                 110

Ile Ala Gln Val Thr Ser Ala Tyr Val Ala Ser Gly Ser Glu Gln Leu
        115                 120                 125

Ser Leu Ala Pro Gly Gln Leu Ile Leu Ile Leu Lys Lys Asn Thr Ser
    130                 135                 140

Gly Trp Trp Gln Gly Glu Leu Gln Ala Arg Gly Lys Lys Arg Gln Lys
145                 150                 155                 160

Gly Trp Phe Pro Ala Ser His Val Lys Leu Leu Gly Pro Ser Ser Glu

```
                    165                 170                 175
Arg Ala Thr Pro Ala Phe His Pro Val Cys Gln Val Ile Ala Met Tyr
            180                 185                 190
Asp Tyr Ala Ala Asn Asn Glu Asp Glu Leu Ser Phe Ser Lys Gly Gln
        195                 200                 205
Leu Ile Asn Val Met Asn Lys Asp Asp Pro Asp Trp Trp Gln Gly Glu
    210                 215                 220
Ile Asn Gly Val Thr Gly Leu Phe Pro Ser Asn Tyr Val Lys Met Thr
225                 230                 235                 240
Thr Asp Ser Asp Pro Ser Gln Gln
                245

(2) INFORMATION FOR SEQ ID NO: 41:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (D) OTHER INFORMATION: Biotinylated N-terminal (xi) SEQUENCE DESCRIPTION: SEQ ID NO: 41:

Ser Gly Ser Gly Ser Arg Pro Pro Arg Trp Ser Pro Pro Val Pro
1               5                   10                  15
Leu Pro Thr Ser Leu Asp Ser Arg
            20

(2) INFORMATION FOR SEQ ID NO: 42:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (D) OTHER INFORMATION: Biotinylated N-terminal (xi) SEQUENCE DESCRIPTION: SEQ ID NO: 42:

Ser Gly Ser Gly Val Leu Lys Arg Pro Leu Pro Ile Pro Pro Val Thr
1               5                   10                  15
Arg (2) INFORMATION FOR SEQ ID NO: 43:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (D) OTHER INFORMATION: Biotinylated N-terminal (xi) SEQUENCE DESCRIPTION: SEQ ID NO: 43:
```

```
Ser Glu Ser Gly Ser Arg Leu Gly Glu Phe Ser Lys Pro Pro Ile Pro
 1               5                  10                  15

Gln Lys Pro Thr Trp Met Ser Arg
            20
```

(2) INFORMATION FOR SEQ ID NO: 44:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (D) OTHER INFORMATION: Biotinylated N-terminal (xi) SEQUENCE DESCRIPTION: SEQ ID NO: 44:

```
Ser Thr Val Pro Arg Trp Ile Glu Asp Ser Leu Arg Gly Gly Ala Ala
 1               5                  10                  15

Arg Ala Gln Thr Arg Leu Ala Ser Ala Lys
            20                  25
```

(2) INFORMATION FOR SEQ ID NO: 45:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 45:

```
Arg Pro Leu Pro Pro Leu Pro
 1               5
```

(2) INFORMATION FOR SEQ ID NO: 46:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 46:

```
Cys Trp Ser Glu Trp Asp Gly Asn Glu Cys
 1               5                  10
```

(2) INFORMATION FOR SEQ ID NO: 47:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 47:

```
Cys Gly Gln Trp Ala Asp Asp Gly Tyr Cys
 1               5                  10
```

(2) INFORMATION FOR SEQ ID NO: 48:

```
        (i) SEQUENCE CHARACTERISTICS:
            (A) LENGTH: 10 amino acids
            (B) TYPE: amino acid
            (C) STRANDEDNESS: <Unknown>
            (D) TOPOLOGY: unknown (ii) MOLECULE TYPE: peptide (ix) FEATURE:
            (A) NAME/KEY: Other
            (B) LOCATION: 3
            (D) OTHER INFORMATION: Undefined (xi) SEQUENCE DESCRIPTION: SEQ ID NO: 48:

Cys Glu Xaa Trp Asp Gly Tyr Gly Ala Cys
1               5                   10

(2) INFORMATION FOR SEQ ID NO: 49:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 49:

Cys Trp Pro Phe Trp Asp Gly Ser Thr Cys
1               5                   10

(2) INFORMATION FOR SEQ ID NO: 50:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 50:

Cys Met Ile Trp Pro Asp Gly Glu Glu Cys
1               5                   10

(2) INFORMATION FOR SEQ ID NO: 51:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: unknown (ii) MOLECULE TYPE: peptide (ix) FEATURE:
            (A) NAME/KEY: Other
            (B) LOCATION: 4
            (D) OTHER INFORMATION: Undefined (xi) SEQUENCE DESCRIPTION: SEQ ID NO: 51:

Cys Glu Ser Xaa Trp Asp Gly Tyr Asp Cys
1               5                   10

(2) INFORMATION FOR SEQ ID NO: 52:

(i) SEQUENCE CHARACTERISTICS:
            (A) LENGTH: 10 amino acids
            (B) TYPE: amino acid
            (C) STRANDEDNESS: <Unknown>
```

(D) TOPOLOGY: unknown (ii) MOLECULE TYPE: peptide (xi) SEQUENCE DESCRIPTION: SEQ ID NO: 52:

Cys Gln Gln Trp Lys Glu Asp Gly Trp Cys
1               5                   10

(2) INFORMATION FOR SEQ ID NO: 53:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (ix) FEATURE:
        (A) NAME/KEY: Other
        (B) LOCATION: 4
        (D) OTHER INFORMATION: Undefined (xi) SEQUENCE DESCRIPTION: SEQ ID NO: 53:

Cys Leu Tyr Xaa Trp Asp Gly Tyr Glu Cys
1               5                   10

(2) INFORMATION FOR SEQ ID NO: 54:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 54:

Cys Met Gly Asp Asn Leu Gly Asp Asp Cys
1               5                   10

(2) INFORMATION FOR SEQ ID NO: 55:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (ix) FEATURE:
        (A) NAME/KEY: Other
        (B) LOCATION: 8
        (D) OTHER INFORMATION: Undefined (xi) SEQUENCE DESCRIPTION: SEQ ID NO: 55:

Cys Met Gly Asp Ser Leu Gly Xaa Ser Cys
1               5                   10

(2) INFORMATION FOR SEQ ID NO: 56:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 56:

Cys Met Asp Asp Asp Leu Gly Lys Gly Cys
1               5                   10

(2) INFORMATION FOR SEQ ID NO: 57:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 57:

Cys Met Gly Glu Asn Leu Gly Trp Ser Cys
1               5                   10

(2) INFORMATION FOR SEQ ID NO: 58:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 58:

Cys Leu Gly Glu Ser Leu Gly Trp Met Cys
1               5                   10

(2) INFORMATION FOR SEQ ID NO: 59:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 59:

Gly Asp Gly Tyr Glu Glu Ile Ser Pro
1               5

(2) INFORMATION FOR SEQ ID NO: 60:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 60:

Gly Asp Gly Tyr Asp Glu Pro Ser Pro
1               5

(2) INFORMATION FOR SEQ ID NO: 61:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 61:

Gly Asp Gly Tyr Asp His Pro Ser Pro
1               5

(2) INFORMATION FOR SEQ ID NO: 62:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 62:

Gly Asp Gly Tyr Val Ile Pro Ser Pro
1               5

(2) INFORMATION FOR SEQ ID NO: 63:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 63:

Gly Asp Gly Tyr Gln Asn Tyr Ser Pro
1               5

(2) INFORMATION FOR SEQ ID NO: 64:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 64:

Gly Asp Gly Tyr Met Ala Met Ser Pro
1               5

(2) INFORMATION FOR SEQ ID NO: 65:

(i) SEQUENCE CHARACTERISTICS:
            (A) LENGTH: 8 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 65:

Gly Asp Gly Gln Asn Tyr Ser Pro
1               5

(2) INFORMATION FOR SEQ ID NO: 66:

(i) SEQUENCE CHARACTERISTICS:
            (A) LENGTH: 20 amino acids
            (B) TYPE: amino acid
            (C) STRANDEDNESS: <Unknown>
            (D) TOPOLOGY: unknown (ii) MOLECULE TYPE: peptide (ix) FEATURE:
    (A) NAME/KEY: Other
    (D) OTHER INFORMATION: Biotinylated N-terminal (xi) SEQUENCE DESCRIPTION: SEQ ID NO: 66:

Ser Gly Ser Gly Ser Met Pro Pro Val Pro Pro Arg Pro Pro Gly
1               5                   10                  15

Thr Leu Gly Gly
            20

(2) INFORMATION FOR SEQ ID NO: 67:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: unknown (ii) MOLECULE TYPE: peptide (ix) FEATURE:
        (A) NAME/KEY: Other
        (D) OTHER INFORMATION: Biotinylated N-terminal (xi) SEQUENCE DESCRIPTION: SEQ ID NO: 67:

Ser Gly Ser Gly Asn Tyr Val Asn Ala Leu Pro Pro Gly Pro Leu
1               5                   10                  15

Pro Ala Lys Asn Gly Gly
            20

(2) INFORMATION FOR SEQ ID NO: 68:

(i) SEQUENCE CHARACTERISTICS:
        (A) LENGTH: 40 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 68:

Thr Val Ile Gln Asp Tyr Glu Pro Arg Leu Thr Asp Glu Ile Arg Ile
1               5                   10                  15

Ser Leu Gly Glu Lys Val Lys Ile Leu Ala Thr His Thr Asp Cys Leu
            20                  25                  30

Val Glu Lys Cys Asn Thr Arg Lys
            35                  40

(2) INFORMATION FOR SEQ ID NO: 69:

(i) SEQUENCE CHARACTERISTICS:
        (A) LENGTH: 46 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 69:

Arg Ala Leu Phe Asp Tyr Asp Lys Thr Lys Asp Cys Gly Phe Leu Ser
1               5                   10                  15

Gln Ala Leu Ser Phe Arg Phe Gly Asp Val Leu His Val Ile Asp Ala
            20                  25                  30

Gly Asp Glu Glu Gln Ala Arg Arg Val His Ser Asp Ser Glu
            35                  40                  45

(2) INFORMATION FOR SEQ ID NO: 70:

(i) SEQUENCE CHARACTERISTICS:
        (A) LENGTH: 46 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 70:

Arg Ala Gln Phe Asp Tyr Asp Pro Lys Lys Asp Asn Leu Ile Pro Cys
1               5                   10                  15

Lys Glu Ala Gly Leu Lys Phe Ala Thr Gly Asp Ile Ile Gln Ile Ile
            20                  25                  30

Asn Lys Asp Asp Ser Asn Gln Gly Arg Val Glu Gly Ser Ser
        35                  40                  45

(2) INFORMATION FOR SEQ ID NO: 71:

(i) SEQUENCE CHARACTERISTICS:
        (A) LENGTH: 45 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 71:

Arg Thr His Pro His Tyr Glu Lys Glu Ser Pro Tyr Gly Leu Ser Phe
1               5                   10                  15

Asn Lys Gly Glu Val Phe Arg Ala Val Asp Thr Leu Tyr Asn Gly Lys
            20                  25                  30

Leu Gly Ser Ala Ile Arg Ile Gly Lys Asn His Lys Glu
        35                  40                  45

(2) INFORMATION FOR SEQ ID NO: 72:

(i) SEQUENCE CHARACTERISTICS:
        (A) LENGTH: 41 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 72:

Val Ala Ile Lys Ala Tyr Thr Ala Val Glu Gly Asp Glu Val Ser Leu
1               5                   10                  15

Leu Glu Gly Glu Ala Val Glu Val Ile His Lys Leu Leu Asp Gly Val
            20                  25                  30

Ile Arg Lys Asp Asp Val Thr Gly Tyr
        35                  40

(2) INFORMATION FOR SEQ ID NO: 73:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 73:

```
Arg Ala Ile Leu Pro Tyr Thr Lys Val Pro Asp Thr Asp Glu Ile Ser
1               5                   10                  15

Phe Leu Lys Gly Asp Met Phe Ile Val His Asn Glu Leu Glu Asp Met
                20                  25                  30

Trp Val Thr Asn Leu Arg Thr
            35
```

(2) INFORMATION FOR SEQ ID NO: 74:

(i) SEQUENCE CHARACTERISTICS:
        (A) LENGTH: 42 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 74:

```
Arg Ala Val Tyr Ala Tyr Glu Pro Gln Thr Pro Glu Leu Ala Ile
1               5                   10                  15

Gln Glu Asp Asp Leu Leu Tyr Leu Leu Gln Lys Ser Asp Ile Asp Asp
                20                  25                  30

Thr Val Lys Lys Arg Val Ile Gly Ser Asp
            35                  40
```

(2) INFORMATION FOR SEQ ID NO: 75:

(i) SEQUENCE CHARACTERISTICS:
        (A) LENGTH: 40 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 75:

```
Lys Ala Lys Tyr Ser Tyr Gln Ala Gln Thr Ser Lys Glu Leu Ser Phe
1               5                   10                  15

Met Glu Gly Glu Phe Phe Tyr Val Ser Gly Asp Glu Lys Asp Lys Ala
                20                  25                  30

Ser Asn Pro Ser Thr Gly Lys Glu
            35                  40
```

(2) INFORMATION FOR SEQ ID NO: 76:

(i) SEQUENCE CHARACTERISTICS:
        (A) LENGTH: 41 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 76:

```
Ala His Arg Val Leu Phe Gly Phe Val Pro Glu Thr Lys Glu Glu Leu
1               5                   10                  15

Gln Val Met Pro Gly Asn Ile Val Phe Val Leu Lys Lys Gly Asn Asp
                20                  25                  30

Ala Thr Val Met Phe Asn Gly Gln Lys
            35                  40
```

(2) INFORMATION FOR SEQ ID NO: 77:

```
    (i) SEQUENCE CHARACTERISTICS:
        (A) LENGTH: 43 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 77:

Arg Gly Ile Val Gln Tyr Asp Phe Met Ala Glu Ser Gln Asp Glu Leu
1               5                  10                  15

Thr Ile Lys Ser Gly Asp Lys Val Tyr Ile Leu Asp Asp Lys Lys Ser
            20                  25                  30

Lys Asp Met Cys Gln Leu Val Asp Ser Gly Lys
        35                  40

(2) INFORMATION FOR SEQ ID NO: 78:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 78:

Gln Ala Leu Phe Asp Pro Asp Pro Gln Glu Asp Gly Glu Leu Gly Phe
1               5                  10                  15

Arg Arg Gly Asp Phe Ile His Val Met Asp Asn Ser Asp Pro Asn Lys
            20                  25                  30

Gly Ala Cys His Gly Gln
        35

(2) INFORMATION FOR SEQ ID NO: 79:

(i) SEQUENCE CHARACTERISTICS:
        (A) LENGTH: 41 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 79:

Gln Ala Leu Tyr Pro Phe Ser Ser Ser Asn Asp Glu Glu Leu Asn Phe
1               5                  10                  15

Glu Lys Gly Asp Val Met Asp Val Ile Glu Lys Pro Glu Asn Asp Pro
            20                  25                  30

Glu Lys Cys Arg Lys Ile Asn Gly Met
        35                  40

(2) INFORMATION FOR SEQ ID NO: 80:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 80:

Val Ala Met Tyr Asp Phe Gln Ala Thr Glu Ala His Asp Leu Arg Leu
1               5                  10                  15
```

-continued

```
Glu Arg Gly Gln Glu Tyr Ile Ile Leu Glu Lys Asn Asp Leu His Arg
            20                  25                  30
Ala Arg Asp Lys Tyr Gly Trp
            35

(2) INFORMATION FOR SEQ ID NO: 81:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 81:

Val Ala Leu Tyr Asp Tyr Asn Pro Met Asn Ala Asn Asp Leu Gln Leu
1               5                   10                  15
Arg Lys Gly Asp Glu Tyr Phe Ile Leu Glu Ser Asn Leu Pro Arg
            20                  25                  30
Ala Arg Asp Lys Asn Gly Gln
            35

(2) INFORMATION FOR SEQ ID NO: 82:

(i) SEQUENCE CHARACTERISTICS:
        (A) LENGTH: 40 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 82:

Val Ala Leu Tyr Asp Phe Val Ala Ser Gly Asp Asn Thr Leu Ser Ile
1               5                   10                  15
Thr Lys Gly Glu Lys Leu Arg Val Leu Gly Tyr Asn His Asn Gly Glu
            20                  25                  30
Glu Ala Gln Thr Lys Asn Gly Gln
            35                  40

(2) INFORMATION FOR SEQ ID NO: 83:

(i) SEQUENCE CHARACTERISTICS:
        (A) LENGTH: 40 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 83:

Val Ala Leu Tyr Asp Tyr Glu Ser Arg Thr Glu Thr Asp Leu Ser Phe
1               5                   10                  15
Lys Lys Gly Glu Arg Leu Gln Ile Val Asn Asn Thr Glu Gly Asp Leu
            20                  25                  30
Ala His Ser Leu Ser Thr Gly Gln
            35                  40

(2) INFORMATION FOR SEQ ID NO: 84:

(i) SEQUENCE CHARACTERISTICS:
        (A) LENGTH: 40 amino acids
        (B) TYPE: amino acid
        (C) STRANDEDNESS: <Unknown>
```

(D) TOPOLOGY: unknown (ii) MOLECULE TYPE: peptide (xi) SEQUENCE DESCRIPTION: SEQ ID NO: 84:

Ile Ala Leu Tyr Asp Tyr Glu Ala Arg Thr Glu Asp Leu Thr Phe
1               5                  10                  15

Thr Lys Gly Glu Lys Phe His Ile Leu Asn Asn Thr Glu Gly Asp Glu
            20                  25                  30

Ala Arg Ser Leu Ser Ser Gly Lys
        35                  40

(2) INFORMATION FOR SEQ ID NO: 85:

(i) SEQUENCE CHARACTERISTICS:
          (A) LENGTH: 40 amino acids
          (B) TYPE: amino acid
          (C) STRANDEDNESS: <Unknown>
          (D) TOPOLOGY: unknown (ii) MOLECULE TYPE: peptide (xi) SEQUENCE DESCRIPTION: SEQ ID NO: 85:

Val Ala Leu Tyr Asp Tyr Glu Ala Arg Thr Glu Asp Leu Ser Phe
1               5                  10                  15

His Lys Gly Glu Lys Phe Gln Ile Leu Asn Ser Ser Glu Gly Asp Glu
            20                  25                  30

Ala Arg Ser Leu Thr Thr Gly Glu
        35                  40

(2) INFORMATION FOR SEQ ID NO: 86:

(i) SEQUENCE CHARACTERISTICS:
          (A) LENGTH: 40 amino acids
          (B) TYPE: amino acid
          (C) STRANDEDNESS: <Unknown>
          (D) TOPOLOGY: unknown (ii) MOLECULE TYPE: peptide (xi) SEQUENCE DESCRIPTION: SEQ ID NO: 86:

Val Ala Leu Tyr Asp Tyr Glu Ala Arg Thr Thr Glu Asp Leu Ser Phe
1               5                  10                  15

Lys Lys Gly Glu Arg Phe Gln Ile Ile Asn Asn Thr Glu Gly Asp Glu
            20                  25                  30

Ala Arg Ser Ile Ala Thr Gly Lys
        35                  40

(2) INFORMATION FOR SEQ ID NO: 87:

(i) SEQUENCE CHARACTERISTICS:
          (A) LENGTH: 40 amino acids
          (B) TYPE: amino acid
          (C) STRANDEDNESS: <Unknown>
          (D) TOPOLOGY: unknown (ii) MOLECULE TYPE: peptide (xi) SEQUENCE DESCRIPTION: SEQ ID NO: 87:

Val Ala Leu Tyr Asp Tyr Glu Ala Arg Thr Gly Asp Asp Leu Thr Phe
1               5                  10                  15

Thr Lys Gly Glu Lys Phe His Ile Leu Asn Asn Thr Glu Tyr Asp Glu
            20                  25                  30

Ala Arg Ser Leu Ser Ser Gly His 35                  40

(2) INFORMATION FOR SEQ ID NO: 88:

(i) SEQUENCE CHARACTERISTICS:
        (A) LENGTH: 40 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 88:

Val Ala Leu Tyr Asp Tyr Glu Ala Arg Ile Ser Glu Asp Leu Ser Phe
1               5                   10                  15

Lys Lys Gly Glu Arg Leu Gln Ile Ile Asn Thr Ala Asp Gly Asp Tyr
              20                  25                  30

Ala Arg Ser Leu Ile Thr Asn Ser
              35                  40

(2) INFORMATION FOR SEQ ID NO: 89:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 89:

Val Ala Leu Tyr Asp Tyr Glu Ala Ile His His Glu Asp Leu Ser Phe
1               5                   10                  15

Gln Lys Gly Asp Gln Met Val Val Leu Glu Glu Ser Gly Glu Lys Ala
              20                  25                  30

Arg Ser Leu Ala Thr Arg Lys
              35

(2) INFORMATION FOR SEQ ID NO: 90:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 90:

Val Ala Leu Tyr Pro Tyr Asp Gly Ile His Pro Asp Asp Leu Ser Phe
1               5                   10                  15

Lys Lys Gly Glu Lys Met Lys Val Leu Glu Glu His Gly Glu Lys Ala
              20                  25                  30

Lys Ser Leu Leu Thr Lys Lys
              35

(2) INFORMATION FOR SEQ ID NO: 91:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 91:

Val Ala Leu Pro Asp Tyr Ala Ala Val Asn Asp Arg Asp Leu Gln Val
1               5                   10                  15

Leu Lys Gly Glu Lys Leu Gln Val Leu Arg Ser Thr Gly Asp Leu Ala
            20                  25                  30

Arg Ser Leu Val Thr Gly Arg
        35

(2) INFORMATION FOR SEQ ID NO: 92:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 92:

Ile Ala Leu His Ser Tyr Glu Pro Ser His Asp Gly Asp Leu Gly Phe
1               5                   10                  15

Glu Lys Gly Glu Gln Leu Arg Ile Leu Glu Gln Ser Gly Glu Lys Ala
            20                  25                  30

Gln Ser Leu Thr Thr Gly Gln
        35

(2) INFORMATION FOR SEQ ID NO: 93:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 93:

Val Ala Lys Phe Asp Tyr Val Ala Gln Gln Glu Gln Glu Leu Asp Ile
1               5                   10                  15

Lys Lys Asn Glu Arg Leu Trp Leu Leu Asp Asp Ser Lys Ser Trp Val
            20                  25                  30

Arg Asn Ser Met Asn Lys
        35

(2) INFORMATION FOR SEQ ID NO: 94:

(i) SEQUENCE CHARACTERISTICS:
        (A) LENGTH: 42 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 94:

Arg Ala Ile Tyr Asp Tyr Glu Gln Val Gln Asn Ala Asp Glu Glu Leu
1               5                   10                  15

Thr Phe His Glu Asn Asp Val Phe Asp Val Phe Asp Asp Lys Asp Ala
            20                  25                  30

Asp Leu Val Lys Ser Thr Val Ser Asn Glu
        35              40

(2) INFORMATION FOR SEQ ID NO: 95:

```
    (i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 95:

Val Ala Leu Tyr Asp Tyr Gln Gly Glu Gly Ser Asp Glu Leu Ser Phe
1               5                   10                  15

Asp Pro Asp Asp Val Ile Thr Asp Ile Glu Met Val Asp Glu Gly Arg
            20                  25                  30

Gly Arg Cys His Gly His
            35

(2) INFORMATION FOR SEQ ID NO: 96:

(i) SEQUENCE CHARACTERISTICS:
        (A) LENGTH: 40 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 96:

Thr Ala Glu Tyr Asp Tyr Asp Ala Ala Glu Asp Asn Glu Leu Thr Phe
1               5                   10                  15

Val Glu Asn Asp Lys Ile Ile Asn Ile Glu Phe Val Asp Asp Asp Leu
            20                  25                  30

Gly Glu Leu Glu Lys Asp Gly Ser
            35                  40

(2) INFORMATION FOR SEQ ID NO: 97:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 97:

Tyr Val Lys Phe Asn Tyr Asn Ala Glu Arg Gly Asp Glu Leu Ser Leu
1               5                   10                  15

Ile Lys Gly Thr Lys Val Ile Val Met Glu Lys Cys Ser Asp Gly Arg
            20                  25                  30

Gly Ser Tyr Asn Gly Gln
            35

(2) INFORMATION FOR SEQ ID NO: 98:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 98:

Lys Ala Arg Tyr Asp Phe Cys Ala Arg Asp Arg Ser Glu Leu Ser Leu
1               5                   10                  15
```

Lys Glu Gly Asp Ile Ile Lys Ile Leu Asn Lys Lys Gly Gln Gln Trp
                20                  25                  30

Arg Gly Glu Ile Tyr Gly Arg
        35

(2) INFORMATION FOR SEQ ID NO: 99:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 99:

Ile Ala Lys Tyr Asp Phe Lys Ala Thr Ala Asp Asp Glu Leu Ser Phe
1               5                   10                  15

Lys Arg Gly Asp Ile Leu Lys Val Leu Asn Glu Glu Cys Asp Gln Tyr
                20                  25                  30

Lys Ala Glu Leu Asn Gly Lys
        35

(2) INFORMATION FOR SEQ ID NO: 100:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 100:

Lys Ala Leu Tyr Asp Tyr Lys Ala Lys Arg Ser Asp Glu Leu Ser Phe
1               5                   10                  15

Cys Arg Gly Ala Leu Ile His Asn Val Ser Lys Glu Pro Gly Trp Lys
                20                  25                  30

Gly Asp Tyr Gly Thr Arg Ile
        35

(2) INFORMATION FOR SEQ ID NO: 101:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 101:

Lys Ala Leu Phe Asp Tyr Lys Ala Gln Arg Glu Asp Glu Leu Thr Phe
1               5                   10                  15

Ile Lys Ser Ala Ile Ile Gln Asn Val Glu Lys Gln Glu Gly Trp Arg
                20                  25                  30

Gly Asp Tyr Gly Gly Lys Lys
        35

(2) INFORMATION FOR SEQ ID NO: 102:

(i) SEQUENCE CHARACTERISTICS:
        (A) LENGTH: 38 amino acids
        (B) TYPE: amino acid (C) STRANDEDNESS: <Unknown>
        (D) TOPOLOGY: unknown (ii) MOLECULE TYPE: peptide (xi) SEQUENCE DESCRIPTION: SEQ ID NO: 102:

Lys Ala Leu Tyr Asp Tyr Asp Ala Gln Thr Gly Asp Glu Leu Thr Phe
1               5                   10                  15

Lys Glu Gly Asp Thr Ile Ile Val His Gln Lys Asp Pro Ala Trp Glu
            20                  25                  30

Gly Glu Leu Asn Gly Lys
        35

(2) INFORMATION FOR SEQ ID NO: 103:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 103:

Arg Ala Leu Tyr Asp Phe Ala Ala Glu Asn Pro Asp Glu Leu Thr Phe
1               5                   10                  15

Asn Glu Gly Ala Val Val Thr Val Ile Asn Lys Ser Asn Pro Trp Glu
            20                  25                  30

Gly Glu Leu Asn Gly Gln
        35

(2) INFORMATION FOR SEQ ID NO: 104:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 104:

Lys Ala Leu Tyr Asp Tyr Asp Ala Ser Ser Thr Asp Glu Leu Ser Phe
1               5                   10                  15

Lys Glu Gly Asp Ile Ile Phe Ile Val Gln Lys Asp Asn Gly Thr Glu
            20                  25                  30

Gly Glu Leu Lys Ser Gly Gln
        35

(2) INFORMATION FOR SEQ ID NO: 105:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 105:

Glu Ala Leu Phe Ser Tyr Glu Ala Thr Gln Pro Glu Asp Leu Glu Phe
1               5                   10                  15

Gln Glu Gly Asp Ile Ile Leu Val Leu Ser Lys Val Asn Glu Leu Glu
            20                  25                  30

```
Gly Glu Cys Lys Gly Lys
        35

(2) INFORMATION FOR SEQ ID NO: 106:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 106:

Arg Ala Ile Ala Asp Tyr Glu Lys Thr Ser Gly Ser Glu Met Ala Leu
1               5                  10                  15

Ser Thr Gly Asp Val Val Glu Val Val Glu Lys Ser Glu Ser Gly Phe
                20                  25                  30

Cys Gln Met Lys Ala Lys
        35

(2) INFORMATION FOR SEQ ID NO: 107:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 107:

Met Ala Leu Val Asp Phe Gln Ala Arg Ser Pro Arg Glu Val Thr Met
1               5                  10                  15

Lys Lys Gly Asp Val Leu Thr Leu Leu Ser Ser Ile Asn Lys Asp Lys
                20                  25                  30

Val Glu Ala Ala Asp His
        35

(2) INFORMATION FOR SEQ ID NO: 108:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 108:

Tyr Ala Ile Val Leu Tyr Asp Phe Lys Ala Glu Lys Ala Asp Glu Leu
1               5                  10                  15

Thr Thr Tyr Val Gly Glu Asn Leu Phe Ile Cys Ala His His Asn Cys
                20                  25                  30

Glu Ile Ala Lys Pro Ile Gly Arg Leu Gly Gly
        35                  40

(2) INFORMATION FOR SEQ ID NO: 109:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: unknown (ii) MOLECULE TYPE: peptide
```

(xi) SEQUENCE DESCRIPTION: SEQ ID NO: 109:

Val Ala Ala Tyr Asp Phe Asn Tyr Pro Ile Lys Lys Asp Ser Ser Ser
1               5                   10                  15

Gln Leu Leu Ser Val Gln Gln Gly Glu Thr Ile Tyr Ile Leu Asn Lys
                20                  25                  30

Asn Ser Ser Gly Asp Gly Leu Val Ile Asp Asp
            35                  40

(2) INFORMATION FOR SEQ ID NO: 110:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 110:

Met Arg Phe Gln Thr Thr Ala Ile Ser Asp Tyr Glu Asn Ser Ser Asn
1               5                   10                  15

Pro Ser Phe Leu Lys Phe Ser Ala Gly Asp Thr Ile Ile Val Ile Glu
                20                  25                  30

Val Leu Glu Asp Cys Asp Gly
            35

(2) INFORMATION FOR SEQ ID NO: 111:

(i) SEQUENCE CHARACTERISTICS:
        (A) LENGTH: 55 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 111:

Arg Ala Leu Val Asp Tyr Lys Lys Glu Arg Glu Glu Asp Ile Asp Leu
1               5                   10                  15

His Leu Gly Asp Ile Leu Thr Val Asn Lys Gly Ser Leu Val Ala Leu
                20                  25                  30

Gly Phe Ser Asp Gly Gln Glu Ala Arg Pro Glu Glu Ile Leu Asn Gly
            35                  40                  45

Tyr Asn Glu Thr Thr Gly Glu
        50                  55

(2) INFORMATION FOR SEQ ID NO: 112:

(i) SEQUENCE CHARACTERISTICS:
        (A) LENGTH: 60 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 112:

Asn Lys Gly Thr Val Tyr Ala Leu Trp Asp Tyr Glu Ala Gln Asn Ser
1               5                   10                  15

Asp Glu Leu Ser Phe His Glu Gly Asp Ala Ile Thr Ile Leu Arg Arg
                20                  25                  30

Lys Asp Glu Asn Glu Thr Glu Trp Trp Trp Ala Arg Leu Gly Asp Arg

```
                35                  40                  45
Glu Gly Tyr Val Pro Lys Asn Leu Leu Gly Leu Tyr
 50                  55                  60

(2) INFORMATION FOR SEQ ID NO: 113:

(i) SEQUENCE CHARACTERISTICS:
        (A) LENGTH: 57 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 113:

Gln Val Lys Val Phe Arg Ala Leu Tyr Thr Phe Glu Pro Arg Thr Pro
 1               5                  10                  15

Asp Glu Leu Tyr Phe Glu Gly Asp Ile Ile Tyr Ile Thr Asp Met
                20                  25                  30

Ser Asp Thr Ser Trp Trp Lys Gly Thr Cys Lys Gly Arg Thr Gly Leu
            35                  40                  45

Ile Pro Ser Asn Tyr Val Ala Glu Gln
 50                  55

(2) INFORMATION FOR SEQ ID NO: 114:

(i) SEQUENCE CHARACTERISTICS:
        (A) LENGTH: 59 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 114:

His Trp Thr Pro Tyr Arg Ala Met Tyr Gln Tyr Arg Pro Gln Asn Glu
 1               5                  10                  15

Asp Glu Leu Glu Leu Arg Glu Gly Asp Arg Val Asp Val Met Gln Gln
                20                  25                  30

Cys Asp Asp Gly Trp Phe Val Gly Val Ser Arg Arg Thr Gln Lys Phe
            35                  40                  45

Gly Thr Phe Pro Gly Asn Tyr Val Ala Pro Val
 50                  55

(2) INFORMATION FOR SEQ ID NO: 115:

(i) SEQUENCE CHARACTERISTICS:
        (A) LENGTH: 57 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 115:

Asp Gln Pro Ser Cys Lys Ala Leu Tyr Asp Phe Glu Pro Glu Asn Asp
 1               5                  10                  15

Gly Glu Leu Gly Phe Arg Glu Gly Asp Leu Ile Thr Leu Thr Asn Gln
                20                  25                  30

Ile Asp Glu Asn Trp Tyr Glu Gly Met Leu His Gly Gln Ser Gly Phe
            35                  40                  45

Phe Pro Leu Ser Tyr Val Gln Val Leu
 50                  55
```

(2) INFORMATION FOR SEQ ID NO: 116:

(i) SEQUENCE CHARACTERISTICS:
        (A) LENGTH: 57 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 116:

```
Leu Gly Ile Thr Ala Ile Ala Leu Tyr Asp Tyr Gln Ala Ala Gly Asp
1               5                   10                  15

Asp Glu Ile Ser Phe Asp Pro Asp Asp Ile Ile Thr Asn Ile Glu Met
            20                  25                  30

Ile Asp Asp Gly Trp Trp Arg Gly Val Cys Lys Gly Arg Tyr Gly Leu
        35                  40                  45

Phe Pro Ala Asn Tyr Val Glu Leu Arg
50                  55
```

(2) INFORMATION FOR SEQ ID NO: 117:

(i) SEQUENCE CHARACTERISTICS:
        (A) LENGTH: 59 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 117:

```
Gly Gly Lys Arg Tyr Arg Ala Val Tyr Asp Tyr Ser Ala Ala Asp Glu
1               5                   10                  15

Asp Glu Val Ser Phe Gln Asp Gly Asp Thr Ile Val Asn Val Gln Gln
            20                  25                  30

Ile Asp Asp Gly Trp Met Tyr Gly Thr Val Glu Arg Thr Gly Asp Thr
        35                  40                  45

Gly Met Leu Pro Ala Asn Tyr Val Glu Ala Ile
50                  55
```

(2) INFORMATION FOR SEQ ID NO: 118:

(i) SEQUENCE CHARACTERISTICS:
        (A) LENGTH: 58 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 118:

```
Gln Gly Leu Cys Ala Arg Ala Leu Tyr Asp Tyr Gln Ala Ala Asp Asp
1               5                   10                  15

Thr Glu Ile Ser Phe Asp Pro Glu Asn Leu Ile Thr Gly Ile Glu Val
            20                  25                  30

Ile Asp Glu Gly Trp Trp Arg Gly Tyr Gly Pro Asp Gly His Phe Gly
        35                  40                  45

Met Phe Pro Ala Asn Tyr Val Glu Leu Ile
50                  55
```

(2) INFORMATION FOR SEQ ID NO: 119:

(i) SEQUENCE CHARACTERISTICS:
        (A) LENGTH: 57 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 119:

Asp Gln Pro Cys Cys Arg Ala Leu Tyr Asp Leu Glu Pro Glu Asn Glu
1               5                   10                  15

Gly Glu Leu Ala Phe Lys Glu Gly Asp Ile Ile Thr Leu Thr Asn Gln
            20                  25                  30

Ile Asp Glu Asn Trp Tyr Glu Gly Met Leu His Gly Gln Ser Gly Phe
        35                  40                  45

Phe Pro Ile Asn Tyr Val Glu Ile Leu
    50                  55

(2) INFORMATION FOR SEQ ID NO: 120:

(i) SEQUENCE CHARACTERISTICS:
        (A) LENGTH: 72 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 120:

Phe Met Phe Lys Val Gln Ala Gln His Asp Tyr Thr Ala Thr Asp Thr
1               5                   10                  15

Asp Glu Leu Gln Leu Lys Ala Gly Asp Val Val Leu Val Ile Pro Phe
            20                  25                  30

Gln Asn Pro Glu Glu Gln Asp Glu Gly Trp Leu Met Gly Val Lys Glu
        35                  40                  45

Ser Asp Trp Asn Gln His Lys Glu Leu Glu Lys Cys Arg Gly Val Phe
    50                  55                  60

Pro Glu Asn Phe Thr Glu Arg Val
            65                  70

(2) INFORMATION FOR SEQ ID NO: 121:

(i) SEQUENCE CHARACTERISTICS:
        (A) LENGTH: 72 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 121:

Phe Met Lys Lys Val Gln Ala Gln His Asp Tyr Thr Ala Thr Asp Thr
1               5                   10                  15

Asp Glu Leu Gln Leu Lys Ala Gly Asp Val Val Leu Val Ile Pro Phe
            20                  25                  30

Gln Asn Pro Glu Glu Gln Asp Glu Gly Trp Leu Met Gly Val Lys Glu
            35                  40                  45

Ser Asp Trp Asn Gln His Lys Glu Leu Glu Lys Cys Arg Gly Val Phe
    50                  55                  60

Pro Glu Asn Phe Thr Glu Arg Val
65                  70

(2) INFORMATION FOR SEQ ID NO: 122:

(i) SEQUENCE CHARACTERISTICS:
        (A) LENGTH: 57 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 122:

Ala Gly Ile Ser Ala Ile Ala Leu Tyr Asp Tyr Gln Gly Glu Gly Ser
1               5                   10                  15

Asp Glu Leu Ser Phe Asp Pro Asp Ile Ile Thr Asp Ile Glu Met
            20                  25                  30

Val Asp Glu Gly Trp Trp Arg Gly Gln Cys Arg Gly His Phe Gly Leu
        35                  40                  45

Phe Pro Ala Asn Tyr Val Lys Leu Leu
50                  55

(2) INFORMATION FOR SEQ ID NO: 123:

(i) SEQUENCE CHARACTERISTICS:
        (A) LENGTH: 58 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 123:

Glu Ala Glu Tyr Val Arg Ala Leu Phe Asp Phe Asn Gly Asn Asp Glu
1               5                   10                  15

Glu Asp Leu Pro Phe Lys Lys Gly Asp Ile Leu Arg Ile Arg Asp Lys
            20                  25                  30

Pro Glu Glu Gln Trp Trp Asn Ala Glu Asp Ser Glu Gly Lys Arg Gly
        35                  40                  45

Met Ile Pro Val Pro Tyr Val Glu Lys Tyr
50                  55

(2) INFORMATION FOR SEQ ID NO: 124:

(i) SEQUENCE CHARACTERISTICS:
        (A) LENGTH: 54 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 124:

Arg Val Ile Gln Lys Arg Val Pro Asn Ala Tyr Asp Lys Thr Ala Leu
1               5                   10                  15

Ala Leu Glu Val Gly Glu Leu Val Lys Val Thr Lys Ile Asn Val Ser
            20                  25                  30

Gly Gln Trp Glu Gly Glu Cys Asn Gly Lys Arg Gly His Phe Pro Phe
        35                  40                  45

Thr His Val Arg Leu Leu
50

(2) INFORMATION FOR SEQ ID NO: 125:

(i) SEQUENCE CHARACTERISTICS:
        (A) LENGTH: 57 amino acids (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 125:

Glu Met Arg Pro Ala Arg Ala Lys Phe Asp Phe Lys Ala Gln Thr Leu
1               5                  10                 15

Lys Glu Leu Pro Leu Gln Lys Gly Asp Val Val Tyr Ile Tyr Arg Gln
             20                  25                 30

Ile Asp Gln Asn Trp Tyr Glu Gly Glu His His Gly Arg Val Gly Ile
         35                  40                 45

Phe Pro Arg Thr Tyr Ile Glu Leu Leu
    50                  55

(2) INFORMATION FOR SEQ ID NO: 126:

(i) SEQUENCE CHARACTERISTICS:
            (A) LENGTH: 59 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 126:

Glu Tyr Gly Glu Ala Ile Ala Lys Phe Asn Phe Asn Gly Asp Thr Gln
1               5                  10                 15

Val Glu Met Ser Phe Arg Lys Gly Glu Arg Ile Thr Leu Leu Arg Gln
             20                  25                 30

Val Asp Glu Asn Trp Tyr Glu Gly Arg Ile Pro Gly Thr Ser Arg Gln
         35                  40                 45

Gly Ile Phe Pro Ile Thr Tyr Val Asp Val Leu
    50                  55

(2) INFORMATION FOR SEQ ID NO: 127:

(i) SEQUENCE CHARACTERISTICS:
            (A) LENGTH: 59 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 127:

Asp Leu Cys Ser Tyr Gln Ala Leu Tyr Ser Tyr Val Pro Gln Asn Asp
1               5                  10                 15

Asp Glu Leu Glu Leu Arg Asp Gly Asp Ile Val Asp Val Met Glu Lys
             20                  25                 30

Cys Asp Asp Gly Trp Phe Val Gly Thr Ser Arg Arg Thr Arg Gln Phe
         35                  40                 45

Gly Thr Phe Pro Gly Asn Tyr Val Lys Pro Leu
    50                  55

(2) INFORMATION FOR SEQ ID NO: 128:

(i) SEQUENCE CHARACTERISTICS:
            (A) LENGTH: 57 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 128:

| Asp | Gln | Pro | Cys | Cys | Arg | Gly | Leu | Tyr | Asp | Phe | Glu | Pro | Glu | Asn | Glu |
|---|---|---|---|---|---|---|---|---|---|---|---|---|---|---|---|
| 1 | | | | 5 | | | | | 10 | | | | | 15 | |

| Gly | Glu | Leu | Gly | Phe | Lys | Glu | Gly | Asp | Ile | Ile | Thr | Leu | Thr | Asn | Gln |
|---|---|---|---|---|---|---|---|---|---|---|---|---|---|---|---|
| | | | 20 | | | | | 25 | | | | | 30 | | |

| Ile | Asp | Glu | Asn | Trp | Tyr | Glu | Gly | Met | Leu | Arg | Gly | Glu | Ser | Gly | Phe |
|---|---|---|---|---|---|---|---|---|---|---|---|---|---|---|---|
| | | | 35 | | | | | 40 | | | | | 45 | | |

| Phe | Pro | Ile | Asn | Tyr | Val | Glu | Val | Ile |
|---|---|---|---|---|---|---|---|---|
| | 50 | | | | | 55 | | |

(2) INFORMATION FOR SEQ ID NO: 129:

(i) SEQUENCE CHARACTERISTICS:
        (A) LENGTH: 59 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 129:

| Thr | Glu | Val | Arg | Val | Arg | Ala | Leu | Tyr | Asp | Tyr | Glu | Gly | Gln | Glu | His |
|---|---|---|---|---|---|---|---|---|---|---|---|---|---|---|---|
| 1 | | | | 5 | | | | | 10 | | | | | 15 | |

| Asp | Glu | Leu | Ser | Phe | Lys | Ala | Gly | Asp | Glu | Leu | Thr | Lys | Met | Glu | Asp |
|---|---|---|---|---|---|---|---|---|---|---|---|---|---|---|---|
| | | | 20 | | | | | 25 | | | | | 30 | | |

| Glu | Asp | Glu | Gln | Gly | Trp | Cys | Lys | Gly | Arg | Leu | Asp | Asn | Gly | Gln | Val |
|---|---|---|---|---|---|---|---|---|---|---|---|---|---|---|---|
| | | | 35 | | | | | 40 | | | | | 45 | | |

| Gln | Leu | Tyr | Pro | Ala | Asn | Tyr | Val | Glu | Ala | Ile |
|---|---|---|---|---|---|---|---|---|---|---|
| | 50 | | | | | 55 | | | | |

(2) INFORMATION FOR SEQ ID NO: 130:

(i) SEQUENCE CHARACTERISTICS:
        (A) LENGTH: 59 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 130:

| Lys | Gly | Val | Arg | Val | Arg | Ala | Leu | Tyr | Asp | Tyr | Asp | Gly | Gln | Glu | Gln |
|---|---|---|---|---|---|---|---|---|---|---|---|---|---|---|---|
| 1 | | | | 5 | | | | | 10 | | | | | 15 | |

| Asp | Glu | Leu | Ser | Phe | Lys | Ala | Gly | Asp | Glu | Leu | Thr | Lys | Leu | Gly | Glu |
|---|---|---|---|---|---|---|---|---|---|---|---|---|---|---|---|
| | | | 20 | | | | | 25 | | | | | 30 | | |

| Glu | Asp | Glu | Gln | Gly | Trp | Cys | Arg | Gly | Arg | Leu | Asp | Ser | Gly | Gln | Leu |
|---|---|---|---|---|---|---|---|---|---|---|---|---|---|---|---|
| | | | 35 | | | | | 40 | | | | | 45 | | |

| Gly | Leu | Tyr | Pro | Ala | Asn | Tyr | Val | Glu | Ala | Ile |
|---|---|---|---|---|---|---|---|---|---|---|
| | 50 | | | | | 55 | | | | |

(2) INFORMATION FOR SEQ ID NO: 131:

(i) SEQUENCE CHARACTERISTICS:
        (A) LENGTH: 58 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 131:

```
Gln Gly Asp Ile Val Val Ala Leu Tyr Pro Tyr Asp Gly Ile His Pro
1               5                   10                  15

Asp Asp Leu Ser Phe Lys Lys Gly Glu Lys Met Lys Val Leu Glu Glu
                20                  25                  30

His Gly Glu Trp Trp Lys Ala Lys Ser Leu Leu Thr Lys Lys Glu Gly
                35                  40                  45

Phe Ile Pro Ser Asn Tyr Val Ala Lys Leu
        50                  55
```

(2) INFORMATION FOR SEQ ID NO: 132:

(i) SEQUENCE CHARACTERISTICS:
        (A) LENGTH: 59 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 132:

```
Gly Val Thr Leu Phe Val Ala Leu Tyr Asp Tyr Glu Ala Arg Thr Glu
1               5                   10                  15

Asp Asp Leu Ser Phe His Lys Gly Glu Lys Phe Gln Ile Leu Asn Ser
                20                  25                  30

Ser Glu Gly Asp Trp Trp Glu Ala Arg Ser Leu Thr Thr Gly Glu Thr
                35                  40                  45

Gly Tyr Ile Pro Ser Asn Tyr Val Ala Pro Val
        50                  55
```

(2) INFORMATION FOR SEQ ID NO: 133:

(i) SEQUENCE CHARACTERISTICS:
        (A) LENGTH: 59 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 133:

```
Lys Val Val Tyr Tyr Arg Ala Leu Tyr Pro Phe Glu Ser Arg Ser His
1               5                   10                  15

Asp Glu Ile Thr Ile Gln Pro Gly Asp Ile Val Met Val Asp Glu Ser
                20                  25                  30

Gln Thr Gly Glu Pro Gly Trp Leu Gly Gly Glu Leu Lys Gly Lys Thr
                35                  40                  45

Gly Trp Phe Pro Ala Asn Tyr Ala Glu Lys Ile
        50                  55
```

(2) INFORMATION FOR SEQ ID NO: 134:

(i) SEQUENCE CHARACTERISTICS:
        (A) LENGTH: 56 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 134:

```
Glu Gly Leu Gln Ala Gln Ala Leu Tyr Pro Trp Arg Ala Lys Lys Asp
1               5                   10                  15

Asn His Leu Asn Phe Asn Lys Asn Asp Val Ile Thr Val Leu Glu Gln
```

-continued

```
                20                  25                  30
Gln Asp Met Trp Trp Phe Gly Glu Val Gln Gly Gln Lys Gly Trp Phe
         35                  40                  45

Pro Lys Ser Tyr Val Lys Leu Ile
 50                  55
```

(2) INFORMATION FOR SEQ ID NO: 135:

(i) SEQUENCE CHARACTERISTICS:
        (A) LENGTH: 62 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 135:

```
Gly Glu Glu Ile Ala Gln Val Ile Ala Ser Tyr Thr Ala Thr Gly Pro
 1               5                  10                  15

Glu Gln Leu Thr Leu Ala Pro Gly Gln Leu Ile Leu Ile Arg Lys Lys
                20                  25                  30

Asn Pro Gly Gly Trp Trp Glu Gly Glu Leu Gln Ala Arg Gly Lys Lys
         35                  40                  45

Arg Gln Ile Gly Trp Phe Pro Ala Asn Tyr Val Lys Leu Leu
 50                  55                  60
```

(2) INFORMATION FOR SEQ ID NO: 136:

(i) SEQUENCE CHARACTERISTICS:
        (A) LENGTH: 57 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 136:

```
Ala Val Cys Gln Val Ile Ala Met Tyr Asp Tyr Thr Ala Gln Asn Asp
 1               5                  10                  15

Asp Glu Leu Ala Phe Asn Lys Gly Gln Ile Ile Asn Val Leu Asn Lys
                20                  25                  30

Glu Asp Pro Asp Trp Trp Lys Gly Glu Val Asn Gly Gln Val Gly Leu
         35                  40                  45

Phe Pro Ser Asn Tyr Val Lys Leu Thr
 50                  55
```

(2) INFORMATION FOR SEQ ID NO: 137:

(i) SEQUENCE CHARACTERISTICS:
        (A) LENGTH: 56 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 137:

```
Val Gly Glu Glu Tyr Ile Ala Leu Tyr Pro Tyr Ser Ser Val Glu Pro
 1               5                  10                  15

Gly Asp Leu Thr Phe Thr Glu Gly Glu Ile Leu Val Thr Gln Lys
                20                  25                  30

Asp Gly Glu Trp Trp Thr Gly Ser Ile Gly Asp Arg Ser Gly Ile Phe
         35                  40                  45
```

Pro Ser Asn Tyr Val Lys Pro Lys
    50                  55

(2) INFORMATION FOR SEQ ID NO: 138:

(i) SEQUENCE CHARACTERISTICS:
        (A) LENGTH: 62 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 138:

Lys Pro Glu Ile Ala Gln Val Thr Ser Ala Tyr Val Ala Ser Gly Ser
1               5                   10                  15

Glu Gln Leu Ser Leu Ala Pro Gly Gln Leu Ile Leu Ile Leu Lys Lys
            20                  25                  30

Asn Thr Ser Gly Trp Trp Gln Gly Glu Leu Gln Ala Arg Gly Lys Lys
        35                  40                  45

Arg Gln Lys Gly Trp Phe Pro Ala Ser Tyr Val Lys Leu Leu
    50                  55                  60

(2) INFORMATION FOR SEQ ID NO: 139:

(i) SEQUENCE CHARACTERISTICS:
        (A) LENGTH: 57 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 139:

Pro Val Cys Gln Val Ile Gly Met Tyr Asp Tyr Ala Ala Asn Asn Glu
1               5                   10                  15

Asp Glu Leu Ser Phe Ser Lys Gly Gln Leu Ile Asn Val Met Asn Lys
            20                  25                  30

Asp Asp Pro Asp Trp Trp Gln Gly Glu Ile Asn Gly Val Thr Gly Leu
        35                  40                  45

Phe Pro Ser Asn Tyr Val Leu Glu Glu
    50                  55

(2) INFORMATION FOR SEQ ID NO: 140:

(i) SEQUENCE CHARACTERISTICS:
        (A) LENGTH: 59 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 140:

Gly Val Thr Thr Phe Val Ala Leu Tyr Asp Tyr Glu Ser Arg Thr Glu
1               5                   10                  15

Thr Asp Leu Ser Phe Lys Lys Gly Glu Arg Leu Gln Ile Val Asn Asn
            20                  25                  30

Thr Glu Gly Asp Trp Trp Leu Ala His Ser Leu Thr Thr Gly Gln Thr
        35                  40                  45

Gly Tyr Ile Pro Ser Asn Tyr Val Ala Pro Ser
    50                  55

(2) INFORMATION FOR SEQ ID NO: 141:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 141:

```
Pro Gly Thr Pro Pro Pro Pro Tyr Thr Val Gly Pro Gly Tyr
1               5                   10
```

(2) INFORMATION FOR SEQ ID NO: 142:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 142:

```
His Gly Pro Thr Pro Pro Pro Pro Tyr Thr Val Gly Pro
1               5                   10
```

(2) INFORMATION FOR SEQ ID NO: 143:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 143:

```
Tyr Val Gln Pro Pro Pro Pro Tyr Pro Gly Pro Met
1               5                   10
```

(2) INFORMATION FOR SEQ ID NO: 144:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 144:

```
Pro Gly Tyr Pro Tyr Pro Pro Pro Pro Glu Phe Tyr
1               5                   10
```

(2) INFORMATION FOR SEQ ID NO: 145:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 145:

```
Pro Gly Thr Pro Ala Pro Pro Tyr Thr Val Gly Pro Gly Tyr
1               5                   10
```

(2) INFORMATION FOR SEQ ID NO: 146:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 146:

```
Pro Gly Thr Pro Pro Ala Pro Tyr Thr Val Gly Pro Gly Tyr
1               5                   10
```

(2) INFORMATION FOR SEQ ID NO: 147:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 147:

```
Asp Ser Gly Val Arg Pro Leu Pro Pro Leu Pro Asp Pro Gly Val
1               5                   10                  15
```

(2) INFORMATION FOR SEQ ID NO: 148:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 148:

```
Val Arg Pro Leu Pro Pro Leu Pro Glu Glu Leu Pro Arg Pro Arg
1               5                   10                  15
Pro Pro Pro Glu Asp
                20
```

(2) INFORMATION FOR SEQ ID NO: 149:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 149:

```
Pro Pro Pro Ala Leu Pro Pro Pro Arg Pro Val Ala Asp Lys
1               5                   10                  15
```

(2) INFORMATION FOR SEQ ID NO: 150:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 150:

Ala Pro Ala Pro Pro Gly Pro Pro Arg Pro Ala Ala Ala Ala
1               5                   10                  15

(2) INFORMATION FOR SEQ ID NO: 151:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 151:

Gly Gly Gly Phe Pro Pro Leu Pro Pro Pro Tyr Leu Pro Pro Leu
1               5                   10                  15

Gly (2) INFORMATION FOR SEQ ID NO: 152:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 152:

Ser Ile Ser Pro Arg Pro Arg Pro Gly Arg Pro Val Ser Gly
1               5                   10                  15

(2) INFORMATION FOR SEQ ID NO: 153:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 153:

Pro Pro Pro Glu His Ile Pro Pro Pro Arg Pro Lys Arg Ile Leu
1               5                   10                  15

Glu (2) INFORMATION FOR SEQ ID NO: 154:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 154:

Lys Glu Gly Glu Arg Ala Leu Pro Ser Ile Pro Lys Leu Ala Asn
1               5                   10                  15

(2) INFORMATION FOR SEQ ID NO: 155:

(i) SEQUENCE CHARACTERISTICS:
        (A) LENGTH: 16 amino acids
        (B) TYPE: amino acid (C) STRANDEDNESS: <Unknown>
        (D) TOPOLOGY: unknown (ii) MOLECULE TYPE: peptide (xi) SEQUENCE DESCRIPTION: SEQ ID NO: 155:

Ser Arg Leu Lys Pro Ala Pro Pro Pro Pro Ala Ala Ser Ala Gly
1               5                   10                  15

(2) INFORMATION FOR SEQ ID NO: 156:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 156:

Gln Ala Ser Leu Pro Pro Val Pro Pro Arg Asp Leu Leu Leu Pro
1               5                   10                  15

(2) INFORMATION FOR SEQ ID NO: 157:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 157:

Pro Val Pro Pro Thr Leu Arg Asp Leu Pro Pro Pro Pro Pro Asp
1               5                   10                  15

Arg Pro Tyr Ser
            20

(2) INFORMATION FOR SEQ ID NO: 158:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 158:

Ser Asp Gln Gly Arg Asn Leu Pro Gly Thr Pro Val Pro Ala Ser
1               5                   10                  15

(2) INFORMATION FOR SEQ ID NO: 159:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 159:

Arg His Ser Arg Arg Gln Leu Pro Pro Val Pro Pro Lys Pro Arg Pro
1               5                   10                  15

Leu Leu (2) INFORMATION FOR SEQ ID NO: 160:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 160:

Glu Lys Val Gly Phe Pro Val Thr Pro Gln Val Pro Leu Arg Pro Met
1               5                   10                  15

Thr Tyr (2) INFORMATION FOR SEQ ID NO: 161:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 161:

Pro Gln Pro His Arg Val Leu Pro Thr Ser Pro Ser Asp Ile Ala
1               5                   10                  15

(2) INFORMATION FOR SEQ ID NO: 162:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 162:

Ala Asp Phe Gln Pro Pro Tyr Phe Pro Pro Tyr Gln Pro Ile Tyr
1               5                   10                  15

Pro Gln Ser (2) INFORMATION FOR SEQ ID NO: 163:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 163:

Ser Ser Ala Ala Pro Pro Pro Pro Arg Arg Ala Thr Pro Glu Lys
1               5                   10                  15

(2) INFORMATION FOR SEQ ID NO: 164:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (ii) MOLECULE TYPE: peptide -continued (xi) SEQUENCE DESCRIPTION: SEQ ID NO: 164:

Ser Lys Lys Gly Val Met Thr Ala Pro Pro Pro Pro Pro Pro Val
1               5                   10                  15
        Tyr Glu Pro Gly Gly
                20

(2) INFORMATION FOR SEQ ID NO: 165:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 165:

Glu Ala Phe Gln Pro Gln Glu Pro Asp Phe Pro Pro Pro Pro Asp
1               5                   10                  15
Leu Glu (2) INFORMATION FOR SEQ ID NO: 166:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 166:

Asp Glu Leu Ala Pro Pro Lys Pro Pro Leu Pro Glu Gly Glu Val Pro
1               5                   10                  15
Pro Pro Arg Pro Pro Pro Pro Glu
                20

(2) INFORMATION FOR SEQ ID NO: 167:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 167:

Pro Gln Arg Arg Ala Pro Ala Val Pro Pro Ala Arg Pro Gly Ser Arg
1               5                   10                  15

(2) INFORMATION FOR SEQ ID NO: 168:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 168:

Leu Gly Gly Ala Pro Pro Val Pro Ser Arg Pro Gly Ala Ser Pro Asp
1               5                   10                  15
Gly (2) INFORMATION FOR SEQ ID NO: 169:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 169:

```
Pro Pro Pro Pro Leu Pro Pro Leu Pro Leu Pro Pro Leu Lys Lys Arg
1               5                   10                  15
Gly Asn His
```

(2) INFORMATION FOR SEQ ID NO: 170:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 170:

```
Ala Ala Glu Glu Pro Pro Ala Pro Pro Pro Pro Pro Pro Pro Glu Asp
1               5                   10                  15
Pro Gly Gly
```

(2) INFORMATION FOR SEQ ID NO: 171:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 171:

```
Asp Glu Glu Val Asn Ile Pro Pro His Thr Pro Val Arg Thr Val
1               5                   10                  15
```

(2) INFORMATION FOR SEQ ID NO: 172:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 172:

```
Ser Ala Glu Gly Asn Ser Asn Pro Pro Lys Pro Leu Lys Lys Leu Arg
1               5                   10                  15
Phe Asp
```

(2) INFORMATION FOR SEQ ID NO: 173:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown

```
        (ii) MOLECULE TYPE: peptide (xi) SEQUENCE DESCRIPTION: SEQ ID NO: 173:

Ala Trp Met Trp Gly Ser Pro Pro Glu Glu Glu Gly Trp Phe
 1               5                  10

(2) INFORMATION FOR SEQ ID NO: 174:

(i) SEQUENCE CHARACTERISTICS:
            (A) LENGTH: 16 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 174:

Ala Glu Trp Leu Glu Gly Pro Pro Trp Tyr Asp Arg Lys Glu Gly Phe
 1               5                  10                  15

(2) INFORMATION FOR SEQ ID NO: 175:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 175:

Gly Leu Glu Gly Trp Tyr Trp Glu Arg Gly Trp Val
 1               5                  10

(2) INFORMATION FOR SEQ ID NO: 176:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 176:

Trp Gly Leu Asp Gly Trp Leu Val Asp Gly Trp Ser
 1               5                  10

(2) INFORMATION FOR SEQ ID NO: 177:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 177:

Gly Ile Leu Ala Pro Pro Val Pro Pro Arg Asn Thr Arg
 1               5                  10

(2) INFORMATION FOR SEQ ID NO: 178:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: unknown
```

```
    (ii) MOLECULE TYPE: peptide (xi) SEQUENCE DESCRIPTION: SEQ ID NO: 178:

Val Leu Lys Arg Pro Leu Pro Ile Pro Pro Val Thr Arg
1               5                   10

(2) INFORMATION FOR SEQ ID NO: 179:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 179:

Val Leu Lys Arg Pro Leu Pro Pro Leu Pro Val Thr Arg
1               5                   10

(2) INFORMATION FOR SEQ ID NO: 180:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 180:

Ser Arg Ser Leu Ser Glu Val Ser Pro Lys Pro Pro Ile Arg Ser Val
1               5                   10                  15

Ser Leu Ser Arg
            20

(2) INFORMATION FOR SEQ ID NO: 181:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 181:

Ser Arg Pro Pro Arg Trp Ser Pro Pro Val Pro Leu Pro Thr Ser
1               5                   10                  15

Leu Asp Ser Arg
            20

(2) INFORMATION FOR SEQ ID NO: 182:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 182:

Ser Arg Leu Gly Glu Phe Ser Lys Pro Pro Ile Pro Gln Lys Pro Thr
1               5                   10                  15

Trp Met Ser Arg
```

20

(2) INFORMATION FOR SEQ ID NO: 183:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 183:

Ser Phe Ala Ala Pro Ala Arg Pro Pro Val Pro Pro Arg Lys Ser Arg
1               5                   10                  15
Pro Gly Gly (2) INFORMATION FOR SEQ ID NO: 184:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 184:

Ser Tyr Asp Ala Ser Ser Ala Pro Gln Arg Pro Pro Leu Pro Val Arg
1               5                   10                  15
Lys Ser Arg Pro Gly Gly
            20

(2) INFORMATION FOR SEQ ID NO: 185:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 185:

Ser Pro Pro Pro Val Pro Pro Arg Pro Pro Ala Thr Leu Gly Gly
1               5                   10                  15

(2) INFORMATION FOR SEQ ID NO: 186:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 186:

Ser Val Pro Ala Pro Pro Pro Leu Pro Pro Lys Ser Gly Gly
1               5                   10

(2) INFORMATION FOR SEQ ID NO: 187:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 187:

Ser Phe Ser Phe Pro Pro Leu Pro Pro Ala Pro Gly Gly
1               5                   10

(2) INFORMATION FOR SEQ ID NO: 188:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 188:

Ser Val Pro Leu Pro Pro Leu Arg Thr Val Ser Leu Gly Gly
1               5                   10

(2) INFORMATION FOR SEQ ID NO: 189:

(i) SEQUENCE CHARACTERISTICS:
        (A) LENGTH: 1710 bases
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO: 189:

```
CACTCTCTAC ACTTGCACCG GCATCAAGGA CGAAAAGAAC GCGCTAGATA TGACTTGGAA      60
GCTGCTCAAG ACAATGAACT TACTTTCAAA GCTGGAGAAA TTATGACAGT TCTTGATGAC     120
AGTGATCCTA ACTGGTGGAA AGGTGAAACC CATCAAGGCA TAGGGTTATT TCCTTCTAAT     180
TTTGTGACTG CAGATCTCAC TGCTGAACCA GAAATGATTA AACAGAGAAA GAAGACGGTA     240
CAATTTAGTG ATGATGTTCA GGTAGAGACA ATAGAACCAG AGCCGGAACC AGCCTTTATT     300
GATGAAGATA AAATGGACCA GTTGCTACAG ATGCTGCAAA GTACAGACCC CAGTGATGAT     360
CAGCCAGACC TACCAGAGCT GCTTCATCTT GAAGCAATGT GTCACCAGAT GGGACCTCTC     420
ATTGATGAAA AGCTGGAAGA TATTGATAGA AAACATTCAG AACTCTCAGA ACTTAATGTG     480
AAAGTGATGG AGGCCCTTTC CTTATATACC AAGTTAATGA ACGAAGATCC GATGTATTCC     540
ATGTATGCAA AGTTACAGAA TCAGCCATAT TATATGCAGT CATCTGGTGT TTCTGGTTCT     600
CAGGTGTATG CAGGGCCTCC TCCAAGTGGT GCCTACCTGG TTGCAGGGAA CGCGCAGATG     660
AGCCACCTCC AGAGCTACAG TCTTCCCCCG GAGCAGCTGT CTTCTCTCAG CCAGGCAGTG     720
GTCCCACCAT CCGCAAACCC AGCCCTTCCT AGTCAGCAGA CTCAGGCCGC TTACCCAAAC     780
CGCTCCCCAG GGGACCTCAT GAAGCCCGGT GATTCTGAAT GCCGTGGATC TGCCGAGGAT     840
TCCCAGATGC GTATTTCTCC TCCGTACTTC CCCACAGGAC AGCAGGCTTG AATAGCTGAT     900
TGCCTATGCA GGACAACAGG CTTGAATAGC TGACTGCCTA TGCATTCTCT TTGCTTGCCA     960
GTTTTTTGGA CATCAAACTT GACAGATCCA AGATTATTAC TTTGATCTTC CCCACACCCC    1020
TCCCACCCCC GAGTCTACTA TGGTCCCATC ATAGTATTCT GAAAATCAGT GAATGGCCAC    1080
TCTACCAGTT ATTTCTACCA GTTTTTAGGT TCTAAACCTC AGGCATTCTG GACTCTTCTG    1140
TTCATTATCA TATTTTGAAG GCATTATCTT CAAAATCTAT CTAGACTCTG ACCCTTTCTC    1200
CCATCTCCAC CATTACTGCC GTGGCTCTTC TGCTGGTCGG CTCTCTCCTG GTGGATCCGT    1260
```

-continued

```
AATAACCTGC AGTCAGCTAT CCTGGTCCAG AAGGGAACCC CGTTAAACCC TGTTGGAATC    1320

TTATCACGCT TCTGCTCCAG AACGAACCCA GTCTGTCTGT CTCACTCAGA GTGTAAGCTA    1380

CAGTCCTTAT TGTGGCCATC AGGTGCTGTG TGTTCTCCAG CCCCCTCCCC ACCACCGCAG    1440

TCCTGCCGGT GATCTTAGCT GCTCTCCCCT CGGAACCCCC TGCGGCCCCC TCTGCCGCAA    1500

CANTCGTGGC CTGCTGTTCC TTGAACATGC TTGGTGTTTT CTCTCCTCAA AGGCTTCTTT    1560

CTGTTTACCT GAAATGTACT TGCCTAGGGA AATCTTATCC TGGCTCACTC CGCTTACTTT    1620

TTTCCACATC TTTGCTTAAA GTTATTGCCC TTATTGGAGA AGGCACCCCT ACCATAAACT    1680

AGAAATCCCT TGCCCCCAAG CTGTTCCTTT                                     1710
```

(2) INFORMATION FOR SEQ ID NO: 190:

(i) SEQUENCE CHARACTERISTICS:
        (A) LENGTH: 296 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 190:

```
His Ser Leu His Leu His Arg His Gln Gly Arg Lys Glu Arg Ala Arg
1               5                   10                  15

Tyr Asp Leu Glu Ala Ala Gln Asp Asn Glu Leu Thr Phe Lys Ala Gly
            20                  25                  30

Glu Ile Met Thr Val Leu Asp Asp Ser Asp Pro Asn Trp Trp Lys Gly
        35                  40                  45

Glu Thr His Gln Gly Ile Gly Leu Phe Pro Ser Asn Phe Val Thr Ala
    50                  55                  60

Asp Leu Thr Ala Glu Pro Glu Met Ile Lys Thr Glu Lys Lys Thr Val
65                  70                  75                  80

Gln Phe Ser Asp Asp Val Gln Val Glu Thr Ile Glu Pro Glu Pro Glu
                85                  90                  95

Pro Ala Phe Ile Asp Glu Asp Lys Met Asp Gln Leu Leu Gln Met Leu
            100                 105                 110

Gln Ser Thr Asp Pro Ser Asp Asp Gln Pro Asp Leu Pro Glu Leu Leu
        115                 120                 125

His Leu Glu Ala Met Cys His Gln Met Gly Pro Leu Ile Asp Glu Lys
    130                 135                 140

Leu Glu Asp Ile Asp Arg Lys His Ser Glu Leu Ser Glu Leu Asn Val
145                 150                 155                 160

Lys Val Met Glu Ala Leu Ser Leu Tyr Thr Lys Leu Met Asn Glu Asp
                165                 170                 175

Pro Met Tyr Ser Met Tyr Ala Lys Leu Gln Asn Gln Pro Tyr Tyr Met
            180                 185                 190

Gln Ser Ser Gly Val Ser Gly Ser Gln Val Tyr Ala Gly Pro Pro Pro
        195                 200                 205

Ser Gly Ala Tyr Leu Val Ala Gly Asn Ala Gln Met Ser His Leu Gln
    210                 215                 220

Ser Tyr Ser Leu Pro Pro Glu Gln Leu Ser Leu Ser Gln Ala Val
225                 230                 235                 240

Val Pro Pro Ser Ala Asn Pro Ala Leu Pro Ser Gln Gln Thr Gln Ala
                245                 250                 255

Ala Tyr Pro Asn Arg Ser Pro Gly Asp Leu Met Lys Pro Gly Asp Ser
            260                 265                 270
```

```
Glu Cys Arg Gly Ser Ala Glu Asp Ser Gln Met Arg Ile Ser Pro Pro
        275                 280                 285
Tyr Phe Pro Thr Gly Gln Gln Ala
    290                 295
```

(2) INFORMATION FOR SEQ ID NO: 191:

(i) SEQUENCE CHARACTERISTICS:
        (A) LENGTH: 1687 bases
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO: 191:

```
GAATTCGCGG CCGCGTCGAC CAAGGAGAGT GGCCGCTTCC AGGACGTGGG ACCCCAGGCC    60

CCAGTGGGCT CTGTGTACCA GAAGACCAAT GCCGTGTCAG AGATTTAAAG GGTTGGTTAG   120

ACAGCTTCTG GGCCAAAGCA GAGAAGGAGG AGGAGAACCG TCGGCTGGAG GAAAAGCGGT   180

GGGCCGAGGA GGCACAGCGG CAGCTGGAGC AGGAGCGCCG GGAGCGTGAG CTGCGTGAGG   240

CTGCACGCCG GGAGCAGCGC TATCAGGAGC AGGGTGGCGA GGCCAGCCCC CAGAGCAGGA   300

CGTGGGAGCA GCAGCAAGAA GTGGTTTCAA GGAACCGAAA TGAGCAGGAG TCTGCCGTGC   360

ACCCGAGGGA GATTTTCAAG CAGAAGGAGA GGGCCATGTC CACCACCTCC ATCTCCAGTC   420

CTCAGCCTGG CAAGCTGAGG AGCCCCTTCC TGCAGAAGCA GCTCACCCAA CCAGAGACCC   480

ACTTTGGCAG AGAGCCAGCT GCTGCCATCT CAAGGCCCAG GGCAGATCTC CCTGCTGAGG   540

AGCCGGCGCC CAGCACTCCT CCATGTCTGG TGCAGGCAGA GAGGAGGCT GTGTATCAGG   600

AACCTCCAGA GCAGGAGACC TTCTACGAGC AGCCCCCACT GGTGCAGCAG CAAGGTGCTG   660

GCTCTGAGCA CATTGACCAC CACATTCAGG CCAGGGGCT CAGTGGGCAA GGGCTCTGTG   720

CCCGTGCCCT GTACGACTAC CAGGCAGCCC ACGACACAGA GATCTCCTTT GACCCCGAGA   780

ACCTCATCAC GGGCATCGAG GTGATCGACG AAGGCTGGTG GCGTGGCTAT GGGCCGGATG   840

GCCATTTTGG CATGTTCCCT GCCAATTACG TGGAGCTCAT TGATGAGGCT GAGGGCACAT   900

CTTGCCCTTC CCCTCTCAGA CATGGCTTCC TTATTGCTGG AAGAGGAGGC CTGGGAGTTG   960

ACATTCAGCA CTCTTCCAGG AATAGGACCC CCAGTGAGGA TGAGGCCTCA GGGCTCCCTC  1020

CGGCTTGGCA GACTCAGCCT GTCACCCCAA ATGCAGCAAT GGCCTGGTGA TTCCCACACA  1080

TCCTTCCTGC ATCCCCCGAC CCTCCCAGAC AGCTTGGCTC TTGCCCCTGA CAGGATACTG  1140

AGCCAAGCCC TGCCTGTGGC CAAGCCCTGA GTGGCCACTG CCAAGCTGCG GGGAAGGGTC  1200

CTGAGCAGGG GCATCTGGGA GGCTCTGGCT GCCTTCTGCA TTTATTTGCC TTTTTTCTTT  1260

TTCTCTTGCT TCTAAGGGGT GGTGGCCACC ACTGTTTAGA ATGACCCTTG GAACAGTGA   1320

ACGTAGAGAA TTGTTTTTAG CAGAGTTTGT GACCAAAGTC AGAGTGGATC ATGGTGGTTT  1380

GGCAGCAGGG AATTTGTCTT GTTGGAGCCT GCTCTGTGCT CCCCACTCCA TTTCTCTGTC  1440

CCTCTGCCTG GGCTATGGGA AGTGGGGATG CAGATGGCCA AGCTCCCACC CTGGGTATTC  1500

AAAAACGGCA GACACAACAT GTTCCTCCAC GCGGCTCACT CGATGCCTGC AGGCCCCAGT  1560

GTGTGCCTCA ACTGATTCTG ACTTCAGGAA AAGTAACACA GAGTGGCCTT GGCCTGTTGT  1620

CTTCCCCTAT TTTCTGTCCC AGCTCATCCG TGGTCGAAGC GCCCGCGAAT TCCAGCTGAG  1680

CGGCCGC                                                           1687
```

(2) INFORMATION FOR SEQ ID NO: 192:

(i) SEQUENCE CHARACTERISTICS:
        (A) LENGTH: 355 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 192:

```
Ile Arg Gly Arg Val Asp Gln Gly Glu Trp Pro Leu Pro Gly Arg Gly
 1               5                  10                  15

Thr Pro Gly Pro Ser Gly Leu Cys Val Pro Glu Asp Gln Cys Arg Val
            20                  25                  30

Arg Asp Leu Lys Gly Trp Leu Asp Ser Phe Trp Ala Lys Ala Glu Lys
        35                  40                  45

Glu Glu Glu Asn Arg Arg Leu Glu Glu Lys Arg Trp Ala Glu Ala
    50                  55                  60

Gln Arg Gln Leu Glu Gln Glu Arg Arg Glu Arg Glu Leu Arg Glu Ala
65                  70                  75                  80

Ala Arg Arg Glu Gln Arg Tyr Gln Glu Gln Gly Gly Glu Ala Ser Pro
                85                  90                  95

Gln Ser Arg Thr Trp Glu Gln Gln Glu Val Val Ser Arg Asn Arg
            100                 105                 110

Asn Glu Gln Glu Ser Ala Val His Pro Arg Glu Ile Phe Lys Gln Lys
        115                 120                 125

Glu Arg Ala Met Ser Thr Thr Ser Ile Ser Ser Pro Gln Pro Gly Lys
    130                 135                 140

Leu Arg Ser Pro Phe Leu Gln Lys Gln Leu Thr Gln Pro Glu Thr His
145                 150                 155                 160

Phe Gly Arg Glu Pro Ala Ala Ala Ile Ser Arg Pro Arg Ala Asp Leu
                165                 170                 175

Pro Ala Glu Glu Pro Ala Pro Ser Thr Pro Pro Cys Leu Val Gln Ala
            180                 185                 190

Glu Glu Glu Ala Val Tyr Glu Glu Pro Pro Glu Gln Glu Thr Phe Tyr
        195                 200                 205

Glu Gln Pro Pro Leu Val Gln Gln Gln Gly Ala Gly Ser Glu His Ile
    210                 215                 220

Asp His His Ile Gln Gly Gln Gly Leu Ser Gly Gln Gly Leu Cys Ala
225                 230                 235                 240

Arg Ala Leu Tyr Asp Tyr Gln Ala Ala Asp Asp Thr Glu Ile Ser Phe
                245                 250                 255

Asp Pro Glu Asn Leu Ile Thr Gly Ile Glu Val Ile Asp Glu Gly Trp
            260                 265                 270

Trp Arg Gly Tyr Gly Pro Asp Gly His Phe Gly Met Phe Pro Ala Asn
        275                 280                 285

Tyr Val Glu Leu Ile Asp Glu Ala Glu Gly Thr Ser Cys Pro Ser Pro
    290                 295                 300

Leu Arg His Gly Phe Leu Ile Ala Gly Arg Gly Gly Leu Gly Val Asp
305                 310                 315                 320

Ile Gln His Ser Ser Arg Asn Arg Thr Pro Ser Glu Asp Glu Ala Ser
                325                 330                 335

Gly Leu Pro Pro Ala Trp Gln Thr Gln Pro Val Thr Pro Asn Ala Ala
            340                 345                 350

Met Ala Trp
```

355

(2) INFORMATION FOR SEQ ID NO: 193:

(i) SEQUENCE CHARACTERISTICS:
  (A) LENGTH: 2873 bases
  (B) TYPE: nucleic acid
  (C) STRANDEDNESS: single
  (D) TOPOLOGY: unknown (ii) MOLECULE TYPE: DNA (xi) SEQUENCE DESCRIPTION: SEQ ID NO: 193:

```
GCGGCCGCGT CGACATTGAA AGGAAAAGAT TAGAACTAAT GCAGAAAAAG AAACTAGAAG     60
ATGAGGCTGC AAGGAAAGCA AAGCAAGGAA AAGAAAACTT ATGGAAAGAA AATCTTAGAA    120
AGGAGGAAGA AGAAAAACAA AAGCGACTCC AGGAAGAAAA AACACAAGAA AAAATTCAAG    180
AAGAGGAACG GAAAGCTGAG GAGAAACAAC GTGAGACAGC TAGTGTTTTC GTGAATTATA    240
GAGCATTATA CCCCTTTGAA GCAAGGAACC ATGATGAGAT GAGTTTTAAT TCTGGAGATA    300
TAATTCAGGT TGATGAAAAA ACCGTAGGAG AACCTGGTTG GCTTTATGGT AGTTTTCAAG    360
GAAATTTTGG CTGGTTTCCA TGCAATTATG TAGAAAAAAT GCCATCAAGT GAAAATGAAA    420
AAGCTGTATC TCCAAAGAAG GCCTTACTTC CTCCTACAGT TTCTTTATCT GCTACCTCAA    480
CTTCCTCTGA ACCACTTTCT TCAAATCAAC CAGCATCAGT GACTGATTAT CAAAATGTAT    540
CTTTTTCAAA CCTAACTCTA AATACATCAT GGCAGAAAAA ATCAGCCTTC ACTCGAACTG    600
TGTCCCCTGG ATCTGTATCA CCTATTCATG ACAGGGACA AGTGGTAGAA AACTTAAAAG    660
CACAGGCCCT TTGTTCCTGG ACTGCAAAGA AAGATAACCA CTTGAACTTC TCAAAACATG    720
ACATTATTAC TGTCTTGGAG CAGCAAGAAA ATTGGTGGTT TGGGGAGGTG CATGGAGGAA    780
GAGGATGGTT TCCCAAATCT TATGTCAAGA TCATTCCTGG GAGTGAAGTA AAACGGGAAG    840
AACCAGAAGC TTTGTATGCA GCTGTAAATA AGAAACCTAC CTCGGCAGCC TATTCAGTTG    900
GAGAAGAATA TATTGCACTT TATCCATATT CAAGTGTGGA ACCTGAGAT TTGACTTTCA    960
CAGAAGGTGA AGAAATATTG GTGACCCAGA AAGATGGAGA GTGGTGGACA GGAAGTATTG   1020
GAGATAGAAG TGGAATTTTT CCATCAAACT ATGTCAAACC AAAGGATCAA GAGAGTTTTG   1080
GGAGTGCTAG CAAGTCTGGA GCATCAAATA AAAAACCTGA GATTGCTCAG GTAACTTCAG   1140
CATATGTTGC TTCTGGTTCT GAACAACTTA GCCTTGCACC AGGACAGTTA ATATTAATTC   1200
TAAAGAAAAA TACAAGTGGG TGGTGGCAAG GAGAGTTACA GGCCAGAGGA AAAAAGCGAC   1260
AGAAAGGATG GTTTCCTGCC AGTCATGTTA AACTTTTGGG TCCAAGTAGT GAAAGAGCCA   1320
CACCTGCCTT TCATCCTGTA TGTCAGGTGA TTGCTATGTA TGACTATGCA GCAAATAATG   1380
AAGATGAGCT CAGTTTCTCC AAGGGACAAC TCATTAATGT TATGAACAAA GATGATCCTG   1440
ATTGGTGGCA AGGAGAGATC AACGGGGTGA CTGGTCTCTT TCCTTCAAAC TACGTTAAGA   1500
TGACGACAGA CTCAGATCCA AGTCAACAGT GACCCAATGT TGTCTTCCAG TTGTGAAAGC   1560
ACCCCAGAGA CCCACTATCC AAGTTTCACT CTAGCGTGGA GGCAGGGCAG GCAGCCCTGA   1620
TCAAATATCT CCTACACAAT TCGTTTACTT CGTTTGAATG TTAGAGCCAC TTGTGATTAT   1680
TTTTTTGTGT TTCTAACTTA CAGTTTAAAT TTATTTGTAA AAAGTTAAAG GATAGTGGGT   1740
CTTTGTGTGG CTTTCCCTGC TGTTCACTCT GGCATCTTTA GCATTTTTCT TCTTTTTTAA   1800
TTTGATAATT GTAGGTCATT AGCATGCATA TTGAGTTTGC CCTTATGTGG TGGGAGTTCA   1860
AACACACAAA GACCCACTAT TTGCACAAAC TATTCTTACT GGTTTGGAAT AGGCTGCCAT   1920
```

```
GCTTTTTTAA TGTTATTGCA ACATGTGTAT TCATTTACAG AATTCAGATA AAATTTGCTT    1980

ATGTTCTGCT ATTATGTTTG ATCTAATCCT AATCACAGTG AGCTCTTAAT TAGCTCAATA    2040

TGTGGTTTGC CCTCAAGTGT GCACTGTTTA TTACTTTGTA ATATGCCACT ATGAGTACTG    2100

ACATTTAGAT ATGTTTAAAG GCCAAGAACT GGAAACAGCC ATGCCCTGTT TTCTGTGTAT    2160

TTGGGATGGG AATAACAACA TTTTGGGGGG AGCTTTTTAA ATCTCAGAGA AGAGGAAAGT    2220

GGCCTGCTCT GGCAGGTATG TGCAGTGTTT CATTTGTTCC AGTCCCAAGA ATGAGCACTG    2280

TCCTATGGTA GTTCGCTTAG GATCTTTATG TGCTCTGGGC TAATGAAGGT ACTGCATCAT    2340

GTGCTGCAGC GTGTGTATTC TTTTTCGATG ACCTATAAAG GGATTATTTT TGAGGAATGA    2400

AAGGCTCCCA TCATTGACTG TGAGATGGGA AAAACCTTTC CTAGCTTAGA GCATTTATAT    2460

CTTAATCCAT TTTAAAGTCA GAGTTCATTG TTACCTGTTT TAATCAGGTG ACTACATGTC    2520

CCAGTATACA AAGGGGCACT GGTTGACATT CTTCTTAATG TATTTAGTAA ATATCATAAG    2580

AAATCCTTTA AGAGTTTAAA TGTCCCCAAA ACAGACATGC GGGCTCTAGT CAAGAATGAA    2640

TTAGAGTGAA GGAAAGCTGT GTAACACCTG GCATTCCTCT GTGTTCATGG AGCTTCTTTG    2700

AGGCTCTAAG ATTGATTTTA CCATCAGACT TCTCTAATAC CTGTTCTTCA ACCATATTGG    2760

CTACTTTGAC ATAAGAATTT ACTTCTTTTC CTGGAATGGA AAACACTTTA AAAAATAATA    2820

ACAAACATTA TTATAAACTA ATATATGTGA GAGGTCGACG CGGCCGCGAA TTC          2873
```

(2) INFORMATION FOR SEQ ID NO: 194:

(i) SEQUENCE CHARACTERISTICS:
        (A) LENGTH: 509 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 194:

```
Gly Arg Val Asp Ile Glu Arg Lys Arg Leu Glu Leu Met Gln Lys Lys
1               5                   10                  15

Lys Leu Glu Asp Glu Ala Ala Arg Lys Ala Lys Gln Gly Lys Glu Asn
            20                  25                  30

Leu Trp Lys Glu Asn Leu Arg Lys Glu Glu Glu Lys Gln Lys Arg
        35                  40                  45

Leu Gln Glu Glu Lys Thr Gln Glu Lys Ile Gln Glu Glu Arg Lys
50                  55                  60

Ala Glu Glu Lys Gln Arg Glu Thr Ala Ser Val Leu Val Asn Tyr Arg
65                  70                  75                  80

Ala Leu Tyr Pro Phe Glu Ala Arg Asn His Asp Glu Met Ser Phe Asn
                85                  90                  95

Ser Gly Asp Ile Ile Gln Val Asp Glu Lys Thr Val Gly Glu Pro Gly
                100                 105                 110

Trp Leu Tyr Gly Ser Phe Gln Gly Asn Phe Gly Trp Phe Pro Cys Asn
            115                 120                 125

Tyr Val Glu Lys Met Pro Ser Ser Glu Asn Glu Lys Ala Val Ser Pro
        130                 135                 140

Lys Lys Ala Leu Leu Pro Pro Thr Val Ser Leu Ser Ala Thr Ser Thr
145                 150                 155                 160

Ser Ser Glu Pro Leu Ser Ser Asn Gln Pro Ala Ser Val Thr Asp Tyr
                165                 170                 175

Gln Asn Val Ser Phe Ser Asn Leu Thr Val Asn Thr Ser Trp Gln Lys
```

```
                    180               185               190
Lys Ser Ala Phe Thr Arg Thr Val Ser Pro Gly Ser Val Ser Pro Ile
    195               200               205

His Gly Gln Gly Gln Val Val Glu Asn Leu Lys Ala Gln Ala Leu Cys
210               215               220

Ser Trp Thr Ala Lys Lys Asp Asn His Leu Asn Phe Ser Lys His Asp
225               230               235               240

Ile Ile Thr Val Leu Glu Gln Gln Asn Trp Trp Phe Gly Glu Val
                245               250               255

His Gly Gly Arg Gly Trp Phe Pro Lys Ser Tyr Val Lys Ile Ile Pro
                260               265               270

Gly Ser Glu Val Lys Arg Glu Glu Pro Glu Ala Leu Tyr Ala Ala Val
    275               280               285

Asn Lys Lys Pro Thr Ser Ala Ala Tyr Ser Val Gly Glu Glu Tyr Ile
290               295               300

Ala Leu Tyr Pro Tyr Ser Ser Val Glu Pro Gly Asp Leu Thr Phe Thr
305               310               315               320

Glu Gly Glu Glu Ile Leu Val Thr Gln Lys Asp Gly Glu Trp Trp Thr
                325               330               335

Gly Ser Ile Gly Asp Arg Ser Gly Ile Phe Pro Ser Asn Tyr Val Lys
                340               345               350

Pro Lys Asp Gln Glu Ser Phe Gly Ser Ala Ser Lys Ser Gly Ala Ser
                355               360               365

Asn Lys Lys Pro Glu Ile Ala Gln Val Thr Ser Ala Tyr Val Ala Ser
    370               375               380

Gly Ser Glu Gln Leu Ser Leu Ala Pro Gly Gln Leu Ile Leu Ile Leu
385               390               395               400

Lys Lys Asn Thr Ser Gly Trp Trp Gln Gly Glu Leu Gln Ala Arg Gly
                405               410               415

Lys Lys Arg Gln Lys Gly Trp Phe Pro Ala Ser His Val Lys Leu Leu
                420               425               430

Gly Pro Ser Ser Glu Arg Ala Thr Pro Ala Phe His Pro Val Cys Gln
                435               440               445

Val Ile Ala Met Tyr Asp Tyr Ala Ala Asn Asn Glu Asp Glu Leu Ser
450               455               460

Phe Ser Lys Gly Gln Leu Ile Asn Val Met Asn Lys Asp Asp Pro Asp
465               470               475               480

Trp Trp Gln Gly Glu Ile Asn Gly Val Thr Gly Leu Phe Pro Ser Asn
                485               490               495

Tyr Val Lys Met Thr Thr Asp Ser Asp Pro Ser Gln Gln
                500               505

(2) INFORMATION FOR SEQ ID NO: 195:

(i) SEQUENCE CHARACTERISTICS:
        (A) LENGTH: 543 bases
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO: 195:

GAATTCGTCG ACCCACGCGT CCGAAATATA ACTGAAGTTG GGGCACCTAC TGAAGAAGAG    60

GAAGAAAGTG AAAGTGAAGA TAGTGAAGAC AGTGGTGGGG AGGAAGAAGA TGCAGAGGAG   120
```

```
GAAGAGGAAG AGAAAGAGGA AAATGAATCT CACAAATGGT CAACCGGTGA AGAATACATC      180

GCTGTTGGAG ATTTTACTGC TCAGCAAGTT GGAGATCTTA CATTTAAGAA AGGGGAAATT      240

CTCCTTGTAA TTGAAAAAAA ACCTGATGGT TGGTGGATAG CTAAGGATGC CAAAGGAAAT      300

GAAGGTCTTG TTCCCAGAAC CTACCTAGAG CCTTATAGTG AAGAAGAAGA AGGCCAAGAG      360

TCAAGTGAAG AGGGCAGTGA AGAAGATGTA GAGGCGGTGG ATGAAACAGC AGATGGAGCA      420

GAAGTTAAGC AAAGAACTGA TCCCCACTGG AGTGCTGTTC AGAAAGCGAT TCAGAGGCG      480

GGCATCTTCT GTCTTGTTAA TCATGTCTCG TTTTGCTACC TAATAGTTCT GATCCGTCCC      540

TAA                                                                   543
```

(2) INFORMATION FOR SEQ ID NO: 196:

(i) SEQUENCE CHARACTERISTICS:
        (A) LENGTH: 180 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 196:

```
Glu Phe Val Asp Pro Arg Val Arg Asn Ile Thr Glu Val Gly Ala Pro
1               5                  10                  15

Thr Glu Glu Glu Glu Ser Glu Ser Glu Asp Ser Glu Asp Ser Gly
            20                  25                  30

Gly Glu Glu Glu Asp Ala Glu Glu Glu Glu Lys Glu Glu Asn
            35                  40                  45

Glu Ser His Lys Trp Ser Thr Gly Glu Glu Tyr Ile Ala Val Gly Asp
 50                  55                  60

Trp Thr Ala Gln Gln Val Gly Asp Leu Thr Phe Lys Lys Gly Glu Ile
 65                  70                  75                  80

Leu Leu Val Ile Glu Lys Lys Pro Asp Gly Trp Trp Ile Ala Lys Asp
                85                  90                  95

Ala Lys Gly Asn Glu Gly Leu Val Pro Arg Thr Tyr Leu Glu Pro Tyr
                100                 105                 110

Ser Glu Glu Glu Glu Gly Gln Glu Ser Ser Glu Glu Gly Ser Glu Glu
            115                 120                 125

Asp Val Glu Ala Val Asp Glu Thr Ala Asp Gly Ala Glu Val Lys Gln
            130                 135                 140

Arg Thr Asp Pro His Trp Ser Ala Val Gln Lys Ala Ile Ser Glu Ala
145                 150                 155                 160

Gly Ile Phe Cys Leu Val Asn His Val Ser Phe Cys Tyr Leu Ile Val
                165                 170                 175

Leu Ile Arg Pro
            180
```

(2) INFORMATION FOR SEQ ID NO: 197:

(i) SEQUENCE CHARACTERISTICS:
        (A) LENGTH: 971 bases
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO: 197:

```
GAATTCGGCG GACTTGCGGG CCGCGTCGAC GAAGAAACCT GAAGGACACA CTAGGCCTCG       60
```

-continued

```
GCAAGACGCG CAGGAAGACC AGCGCGCGGG ATGCGTCCCC CACGCCCAGC ACGGACGCCG    120

AGTACCCCGC CAATGGCAGC GGCGCCGACC GCATCTACGA CCTCAACATC CCGGCCTTCG    180

TCAAGTTCGC CTATGTGGCC GAGCGGGAGG ATGAGTTGTC CCTGGTGAAG GGGTCGCGCG    240

TCACCGTCAT GGAGAAGTGC AGCGACGGTT GGTGGCGGGG CAGCTACAAC GGGCAGATCG    300

GCTGGTTCCC CTCCAACTAC GTCTTGGAGG AGGTGGACGA GGCGGTTGCG GAGTCCCCAA    360

GCTTCCTGAG CCTGCGCAAG GGCGCCTCGC TGAGCAATGG CCAGGGCTCC CGCGTGCTGC    420

ATGTGGTCCA GACGCTGTAC CCCTTCAGCT CAGTCACCGA GGAGGAGCTC AAGTTCGAGA    480

AGGGGGAGAC CATGGAGGTG ATTGAGAAGC CGGAGAACGA CCCCGAGTGG TGGAAATGCA    540

AAAATGCCCG GGGCCAGGTG GGCCTCGTCC CCAAAAACTA CGTGGTGGTC CTCAGTGACG    600

GGCCTGCCCT GCACCCTGCG CACGCCCCAC AGATAAGCTA CACCGGGCCC TCGTCGAGCG    660

GCGCTTCGCG GGGCAGAGAG TGGTACTACG GGAACGTGAC GCGGCACCAG GCCGAGTGCG    720

CCCTCAACGA GCGGGGCGTG GAGGGCGACT TCCTCATTAG GGACAGCGAG TCCTCGCCCA    780

GCGACTTCTC CGTGTCCCTT AAAGCGTCAG GGAAGAACAA ACACTTCAAG GTGCAGCTCG    840

TGGACAATGT CTACTGCATT GGGCAGCGGC GCTTCCACAC CATGGACGAG CTGGTGGAAC    900

ACTACAAAAA GGCGCCCATC TTCACCAGCG AGCACGGGGA GAAGCTCTAC CTCGTCAGGG    960

CCCTGCAGTG A                                                        971
```

(2) INFORMATION FOR SEQ ID NO: 198:

(i) SEQUENCE CHARACTERISTICS:
        (A) LENGTH: 322 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 198:

```
Ile Arg Arg Thr Ser Arg Pro Arg Arg Arg Asn Leu Lys Asp Thr
1               5                   10                  15

Leu Gly Leu Gly Lys Thr Arg Arg Lys Thr Ser Ala Arg Asp Ala Ser
                20                  25                  30

Pro Thr Pro Ser Thr Asp Ala Glu Tyr Pro Ala Asn Gly Ser Gly Ala
            35                  40                  45

Asp Arg Ile Tyr Asp Leu Asn Ile Pro Ala Phe Val Lys Phe Ala Tyr
    50                  55                  60

Val Ala Glu Arg Glu Asp Glu Leu Ser Leu Val Lys Gly Ser Arg Val
65                  70                  75                  80

Thr Val Met Glu Lys Cys Ser Asp Gly Trp Trp Arg Gly Ser Tyr Asn
                85                  90                  95

Gly Gln Ile Gly Trp Phe Pro Ser Asn Tyr Val Leu Glu Glu Val Asp
            100                 105                 110

Glu Ala Val Ala Glu Ser Pro Ser Phe Leu Ser Leu Arg Lys Gly Ala
        115                 120                 125

Ser Leu Ser Asn Gly Gln Gly Ser Arg Val Leu His Val Val Gln Thr
    130                 135                 140

Leu Tyr Pro Phe Ser Ser Val Thr Glu Glu Leu Asn Phe Glu Lys
145                 150                 155                 160

Gly Glu Thr Met Glu Val Ile Glu Lys Pro Glu Asn Asp Pro Glu Trp
                165                 170                 175
```

Trp Lys Cys Lys Asn Ala Arg Gly Gln Val Gly Leu Val Pro Lys Asn
            180                 185                 190

Tyr Val Val Leu Ser Asp Gly Pro Ala Leu His Pro Ala His Ala
        195                 200                 205

Pro Gln Ile Ser Tyr Thr Gly Pro Ser Ser Gly Arg Phe Ala Gly
    210                 215                 220

Arg Glu Trp Tyr Tyr Gly Asn Val Thr Arg His Gln Ala Glu Cys Ala
225                 230                 235                 240

Leu Asn Glu Arg Gly Val Glu Gly Asp Phe Leu Ile Arg Asp Ser Glu
                245                 250                 255

Ser Ser Pro Ser Asp Phe Ser Val Ser Leu Lys Ala Ser Gly Lys Asn
            260                 265                 270

Lys His Phe Lys Val Gln Leu Val Asp Asn Val Tyr Cys Ile Gly Gln
        275                 280                 285

Arg Arg Phe His Thr Met Asp Glu Leu Val Glu His Tyr Lys Lys Ala
    290                 295                 300

Pro Ile Phe Thr Ser Glu His Gly Glu Lys Leu Tyr Leu Val Arg Ala
305                 310                 315                 320

Leu Gln (2) INFORMATION FOR SEQ ID NO: 199:

(i) SEQUENCE CHARACTERISTICS:
        (A) LENGTH: 549 bases
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO: 199:

GAATTCGCGG ACTTCGCGGC CGCGTCGACA CCAGTGCAGG TTTTGGAATA TGGAGAAGCT    60

ATTGCTAAGT TTAACTTTAA TGGTGATACA CAAGTAGAAA TGTCCTTCAG AAAGGGTGAG   120

AGGATCACAC TGCTCCGGCA GGTAGATGAG AACTGGTACG AAGGGAGGAT CCCGGGGACA   180

TCCCGACAAG GCATCTTCCC CATCACCTAC GTGGATCTGA TCAAGCGACC ACTGGTGAAA   240

AACCCTGTGG ATTACATGGA CCTGCCTTTC TCCTCCTCCC CAAGTCGCAG TGCCACTGCA   300

AGCCCACAGC AACCTCAAGC CCAGCAGCGA AGAGTCACCC CCGACAGGAG TCAAACCTCA   360

CAAGATTTAT TTAGCTATCA AGCATTATAT AGCTATATAC CACAGAATGA TGATGAGTTG   420

GAACTCCGCG ATGGAGATAT CGTTGATGTC ATGGAAAAAT GTGACGATGG ATGGTTTGTT   480

GGTACTTCAA GAAGGACAAA GCAGTTTGGT ACTTTTCCAG GCAACTATGT AAAACCTTTG   540

TATCTATAA                                                          549

(2) INFORMATION FOR SEQ ID NO: 200:

(i) SEQUENCE CHARACTERISTICS:
        (A) LENGTH: 182 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 200:

Glu Phe Ala Asp Phe Ala Ala Ala Ser Thr Pro Val Gln Val Leu Glu
1               5                   10                  15

Tyr Gly Glu Ala Ile Ala Lys Phe Asn Phe Asn Gly Asp Thr Gln Val

```
                   20                  25                  30
Glu Met Ser Phe Arg Lys Gly Glu Arg Ile Thr Leu Leu Arg Gln Val
            35                  40                  45
Asp Glu Asn Trp Tyr Glu Gly Arg Ile Pro Gly Thr Ser Arg Gln Gly
 50                  55                  60
Ile Phe Pro Ile Thr Tyr Val Asp Val Ile Lys Arg Pro Leu Val Lys
 65                  70                  75                  80
Asn Pro Val Asp Tyr Met Asp Leu Pro Phe Ser Ser Pro Ser Arg
                 85                  90                  95
Ser Ala Thr Ala Ser Pro Gln Gln Pro Gln Ala Gln Gln Arg Arg Val
            100                 105                 110
Thr Pro Gln Arg Ser Gln Thr Ser Gln Asp Leu Phe Ser Tyr Gln Ala
            115                 120                 125
Leu Tyr Ser Tyr Ile Pro Gln Asn Asp Asp Glu Leu Glu Leu Arg Asp
            130                 135                 140
Gly Asp Ile Val Asp Val Met Glu Lys Cys Asp Asp Gly Trp Phe Val
145                 150                 155                 160
Gly Thr Ser Arg Arg Thr Lys Gln Phe Gly Thr Phe Pro Gly Asn Tyr
                165                 170                 175
Val Lys Pro Leu Tyr Leu
            180
```

(2) INFORMATION FOR SEQ ID NO: 201:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (D) OTHER INFORMATION: May or may not have carboxy-terminal
            amide and/or biotinylated N-terminal (xi) SEQUENCE DESCRIPTION: SEQ ID NO: 201:

```
Ser Phe Ala Ala Pro Ala Arg Pro Pro Val Pro Pro Arg Lys Ser Arg
 1               5                  10                  15
Pro Gly Gly
```

(2) INFORMATION FOR SEQ ID NO: 202:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (D) OTHER INFORMATION: May or may not have carboxy-terminal
            amide and/or biotinylated N-terminal (xi) SEQUENCE DESCRIPTION: SEQ ID NO: 202:

```
Ser Phe Ser Phe Pro Pro Leu Pro Pro Ala Pro Gly Gly
 1               5                  10
```

(2) INFORMATION FOR SEQ ID NO: 203:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 203:

Ala Pro Pro Val Pro Pro Arg
1               5

(2) INFORMATION FOR SEQ ID NO: 204:

(i) SEQUENCE CHARACTERISTICS:
        (A) LENGTH: 55 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 204:

Gln Val Lys Val Phe Arg Ala Leu Tyr Thr Phe Glu Pro Arg Thr Pro
1               5                   10                  15

Asp Glu Leu Tyr Phe Glu Glu Gly Asp Ile Ile Tyr Ile Thr Asp Mer
                20                  25                  30

Asp Thr Asn Trp Trp Lys Gly Thr Ser Gly Arg Thr Gly Leu Ile Pro
            35                  40                  45

Ser Asn Tyr Val Ala Glu Gln
            50              55

(2) INFORMATION FOR SEQ ID NO: 205:

(i) SEQUENCE CHARACTERISTICS:
        (A) LENGTH: 58 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 205:

Thr Gly Glu Glu Tyr Ile Ala Val Gly Asp Phe Thr Ala Gln Gln Val
1               5                   10                  15

Gly Asp Leu Thr Phe Lys Lys Gly Glu Ile Leu Leu Val Ile Glu Lys
                20                  25                  30

Lys Pro Asp Gly Trp Trp Ile Ala Lys Asp Ala Lys Gly Asn Glu Gly
            35                  40                  45

Leu Val Pro Arg Thr Tyr Leu Glu Pro Tyr
            50              55

(2) INFORMATION FOR SEQ ID NO: 206:

(i) SEQUENCE CHARACTERISTICS:
        (A) LENGTH: 57 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 206:

Tyr Leu Glu Lys Val Val Ala Ile Tyr Asp Tyr Thr Lys Asp Lys Glu
1               5                   10                  15

```
Asp Glu Leu Ser Phe Gln Glu Gly Ala Ile Ile Tyr Val Ile Lys Lys
            20                  25                  30

Asn Asp Asp Gly Trp Tyr Glu Gly Val Met Asn Gly Thr Val Gly Leu
        35                  40                  45

Ser Pro Gly Asn Tyr Val Glu Ser Ile
    50                  55
```

(2) INFORMATION FOR SEQ ID NO: 207:

(i) SEQUENCE CHARACTERISTICS:
        (A) LENGTH: 57 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 207:

```
Leu Asn Ile Pro Ala Phe Val Lys Phe Ala Tyr Val Ala Glu Arg Glu
1               5                   10                  15

Asp Glu Leu Ser Leu Val Lys Gly Ser Arg Val Thr Val Met Glu Lys
            20                  25                  30

Cys Ser Asp Gly Trp Trp Arg Gly Ser Tyr Asn Gly Gln Ile Gly Trp
        35                  40                  45

Phe Pro Ser Asn Tyr Val Leu Glu Glu
    50                  55
```

(2) INFORMATION FOR SEQ ID NO: 208:

(i) SEQUENCE CHARACTERISTICS:
        (A) LENGTH: 61 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 208:

```
Val Leu His Val Val Gln Thr Leu Tyr Pro Phe Ser Ser Val Thr Glu
1               5                   10                  15

Glu Glu Leu Asn Glu Phe Glu Lys Gly Glu Thr Met Glu Val Ile Glu
            20                  25                  30

Lys Pro Glu Asn Asp Pro Glu Trp Trp Lys Cys Lys Asn Ala Arg Gly
        35                  40                  45

Gln Val Gly Leu Val Pro Lys Asn Tyr Val Val Leu
    50                  55                  60
```

(2) INFORMATION FOR SEQ ID NO: 209:

(i) SEQUENCE CHARACTERISTICS:
        (A) LENGTH: 57 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 209:

```
Glu Glu Val Val Val Val Ala Lys Phe Asp Tyr Val Ala Gln Gln Glu
1               5                   10                  15

Gln Glu Leu Asp Ile Lys Lys Asn Glu Arg Leu Trp Leu Leu Asp Asp
            20                  25                  30

Ser Lys Ser Trp Trp Arg Val Arg Asn Ser Met Asn Lys Thr Gly Phe
```

```
                 35                  40                  45

Val Pro Ser Asn Tyr Val Glu Arg Lys
 50                  55
```

(2) INFORMATION FOR SEQ ID NO: 210:

(i) SEQUENCE CHARACTERISTICS:
        (A) LENGTH: 58 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 210:

```
Leu Met Asn Pro Ala Tyr Val Lys Phe Asn Tyr Met Ala Glu Arg Glu
 1               5                  10                  15

Asp Glu Leu Ser Leu Ile Lys Gly Thr Lys Val Ile Val Met Glu Lys
                 20                  25                  30

Ile Cys Ser Asp Gly Trp Trp Thr Gly Ser Tyr Asn Gly Gln Val Gly
                 35                  40                  45

Trp Phe Pro Ser Asn Tyr Val Thr Glu Glu
 50                  55
```

(2) INFORMATION FOR SEQ ID NO: 211:

(i) SEQUENCE CHARACTERISTICS:
        (A) LENGTH: 60 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 211:

```
Val Leu His Val Val Gln Ala Leu Tyr Pro Phe Ser Ser Ser Asn Asp
 1               5                  10                  15

Glu Glu Leu Asn Phe Glu Lys Gly Asp Val Met Asp Val Ile Glu Lys
                 20                  25                  30

Pro Glu Asn Asp Pro Glu Trp Trp Lys Cys Arg Lys Ile Asn Gly Met
                 35                  40                  45

Val Gly Leu Val Pro Lys Asn Tyr Val Thr Val Met
 50                  55                  60
```

(2) INFORMATION FOR SEQ ID NO: 212:

(i) SEQUENCE CHARACTERISTICS:
        (A) LENGTH: 59 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 212:

```
Asp Leu Phe Ser Tyr Gln Ala Leu Tyr Ser Tyr Ile Pro Gln Asn Asp
 1               5                  10                  15

Asp Glu Leu Glu Leu Arg Asp Gly Asp Ile Val Asp Val Met Glu Lys
                 20                  25                  30

Cys Asp Asp Gly Trp Phe Val Gly Thr Ser Arg Arg Thr Lys Gln Phe
                 35                  40                  45

Gly Thr Phe Pro Gly Asn Tyr Val Lys Pro Leu
 50                  55
```

(2) INFORMATION FOR SEQ ID NO: 213:

(i) SEQUENCE CHARACTERISTICS:
        (A) LENGTH: 57 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 213:

Gln Gly Arg Lys Glu Arg Ala Arg Tyr Asp Leu Glu Ala Ala Gln Asp
1               5                   10                  15

Asn Glu Leu Thr Phe Lys Ala Gly Glu Ile Met Thr Val Leu Asp Asp
            20                  25                  30

Ser Asp Pro Asn Trp Trp Lys Gly Glu Arg His Gln Gly Ile Gly Leu
        35                  40                  45

Phe Pro Ser Asn Phe Val Thr Ala Asp
50                  55

(2) INFORMATION FOR SEQ ID NO: 214:

(i) SEQUENCE CHARACTERISTICS:
        (A) LENGTH: 58 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 214:

Gln Gly Leu Cys Ala Arg Ala Leu Tyr Asp Tyr Gln Ala Ala Asp Asp
1               5                   10                  15

Thr Glu Ile Ser Phe Asp Pro Glu Asn Leu Ile Thr Gly Ile Glu Val
            20                  25                  30

Ile Asp Glu Gly Trp Trp Arg Gly Tyr Gly Pro Asp Gly His Phe Gly
        35                  40                  45

Met Phe Pro Ala Asn Tyr Val Glu Leu Ile
50                  55

(2) INFORMATION FOR SEQ ID NO: 215:

(i) SEQUENCE CHARACTERISTICS:
        (A) LENGTH: 59 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 215:

Leu Val Leu Asn Tyr Thr Ala Leu Tyr Pro Phe Glu Ala Arg Asn His
1               5                   10                  15

Cys Glu Met Ser Phe Asn Ser Gly Asp Ile Ile Gln Val Asp Glu Lys
            20                  25                  30

Thr Val Gly Glu Pro Gly Trp Leu Tyr Gly Ser Phe Gln Gly Asn Phe
            35                  40                  45

Gly Trp Phe Pro Cys Asn Tyr Val Glu Lys Met
50                  55

(2) INFORMATION FOR SEQ ID NO: 216:

(i) SEQUENCE CHARACTERISTICS:
    (A) LENGTH: 58 amino acids
    (B) TYPE: amino acid
    (C) STRANDEDNESS: <Unknown>
    (D) TOPOLOGY: unknown (ii) MOLECULE TYPE: peptide (xi) SEQUENCE DESCRIPTION: SEQ ID NO: 216:

Val Glu Asn Leu Lys Ala Gln Ala Leu Cys Ser Trp Thr Ala Lys Lys
1               5                   10                  15

Asp Asn His Leu Asn Phe Ser Lys His Asp Ile Ile Thr Val Leu Glu
            20                  25                  30

Gln Gln Glu Asn Phe Trp Trp Phe Gly Glu Val His Gly Gly Arg Gly
        35                  40                  45

Trp Phe Pro Lys Ser Tyr Val Lys Ile Ile
50                  55

(2) INFORMATION FOR SEQ ID NO: 217:

(i) SEQUENCE CHARACTERISTICS:
        (A) LENGTH: 56 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 217:

Val Gly Glu Glu Tyr Ile Ala Leu Tyr Pro Tyr Ser Ser Val Glu Pro
1               5                   10                  15

Gly Asp Leu Thr Phe Thr Glu Gly Glu Glu Ile Leu Val Thr Gln Lys
            20                  25                  30

Asp Gly Glu Trp Trp Thr Gly Ser Ile Gly Asp Arg Ser Gly Ile Phe
        35                  40                  45

Pro Ser Asn Tyr Val Lys Pro Lys
50                  55

(2) INFORMATION FOR SEQ ID NO: 218:

(i) SEQUENCE CHARACTERISTICS:
        (A) LENGTH: 62 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 218:

Lys Pro Glu Ile Ala Gln Val Thr Ser Ala Tyr Val Ala Ser Gly Ser
1               5                   10                  15

Glu Gln Leu Ser Leu Ala Pro Gly Gln Leu Ile Leu Ile Leu Lys Lys
            20                  25                  30

Asn Thr Ser Gly Trp Trp Gln Gly Glu Leu Gln Ala Arg Gly Lys Lys
        35                  40                  45

Arg Gln Lys Gly Trp Phe Pro Ala Ser Trp Val Lys Leu Leu
50                  55                  60

(2) INFORMATION FOR SEQ ID NO: 219:

(i) SEQUENCE CHARACTERISTICS:
        (A) LENGTH: 57 amino acids
        (B) TYPE: amino acid
        (C) STRANDEDNESS: <Unknown>

(D) TOPOLOGY: unknown (ii) MOLECULE TYPE: peptide (xi) SEQUENCE DESCRIPTION: SEQ ID NO: 219:

Pro Val Cys Gln Val Ile Ala Met Tyr Asp Tyr Ala Ala Asn Asn Glu
1               5                  10                 15

Asp Glu Leu Ser Phe Ser Lys Gly Gln Leu Ile Asn Val Met Asn Lys
            20                  25                 30

Asp Asp Pro Asp Trp Trp Gln Gly Glu Ile Asn Gly Val Thr Gly Leu
        35                  40                 45

Phe Pro Ser Asn Tyr Val Lys Met Thr
    50                  55

(2) INFORMATION FOR SEQ ID NO: 220:

(i) SEQUENCE CHARACTERISTICS:
        (A) LENGTH: 691 bases
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO: 220:

AATTCAAGCG CGGGGTCTTT AGGATTTGCA GCTCCAGGAA GCGAGATGTC GAAAGCCGCC      60

ACCCAAACCA GTCAAACCAG GGCAAGTTAA AGTCTTCAGA GCCCTGTATA CGTTTGAACC     120

CAGAACTCCA GATGAATTAT ACTTTGAGGA AGGTGATATT ATCTACATTA CTGACATGAG     180

CGATACCAAT TGGTGGAAAG GCACCTCCAA AGGCAGGACT GGACTAATTC CAAGCAACTA     240

TGTGGCTGAG CAGGCAGAAT CCATTGACAA TCCATTGCAT GAAGCAGCAA AAAGAGGCAA     300

CTTGAGCTGG TTGAGAGAGT GTTTGGACAA CAGAGTGGGT GTTAATGGCT TAGACAAACC     360

TGGAAGCACT GCCTTATACT GGGCTTGCCA CGGGGGCCAC AAAGATATAG TGGAAATGCT     420

ATTTACTCTA CCAAATATTG AACTGAACCA GCAGAACAAG TTGGGAGATA CAGCTTTGCA     480

TGCTGCTGCC TGGAAGGGTT ATGCAGATAT CGTCCAGTTG CTTCTGGCAA AAGGTGCTAG     540

AACAGACTTA AGAAACATTG AGAAGAAGCT GGCCTTCGAC ATGGCTACCA ATGCTGCCTG     600

TGCATCTCTC CTGAAAAAGA AACAGGGAAC AGATGCAGTT CGAACATTAA GCAATGCCGA     660

GGACTATCTC GATGATGAAG ACTCAGATTA A                                   691

(2) INFORMATION FOR SEQ ID NO: 221:

(i) SEQUENCE CHARACTERISTICS:
        (A) LENGTH: 229 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 221:

Asn Ser Ser Ala Gly Ser Leu Gly Phe Ala Ala Pro Gly Ser Glu Met
1               5                  10                 15

Ser Lys Pro Pro Lys Pro Val Lys Pro Gly Gln Val Lys Val Phe
            20                  25                 30

Arg Ala Leu Tyr Thr Phe Glu Pro Arg Thr Pro Asp Glu Leu Tyr Phe
        35                  40                 45

Glu Glu Gly Asp Ile Ile Tyr Ile Thr Asp Met Ser Asp Thr Asn Trp
50                  55                  60

Trp Lys Gly Thr Ser Lys Gly Arg Thr Gly Leu Ile Pro Ser Asn Tyr
65                  70                  75                  80

Val Ala Glu Gln Ala Glu Ser Ile Asp Asn Pro Leu His Glu Ala Ala
                85                  90                  95

Lys Arg Gly Asn Leu Ser Trp Leu Arg Glu Cys Leu Asp Asn Arg Val
                100                 105                 110

Gly Val Asn Gly Leu Asp Lys Ala Gly Ser Thr Ala Leu Tyr Trp Ala
            115                 120                 125

Cys His Gly Gly His Lys Asp Ile Val Glu Met Leu Phe Thr Gln Pro
            130                 135                 140

Asn Ile Glu Leu Asn Gln Gln Asn Lys Leu Gly Asp Thr Ala Leu His
145                 150                 155                 160

Ala Ala Ala Trp Lys Gly Tyr Ala Asp Ile Val Gln Leu Leu Leu Ala
                165                 170                 175

Lys Gly Ala Arg Thr Asp Leu Arg Asn Ile Glu Lys Lys Leu Ala Phe
                180                 185                 190

Asp Met Ala Thr Asn Ala Ala Cys Ala Ser Leu Leu Lys Lys Lys Gln
                195                 200                 205

Gly Thr Asp Ala Val Arg Thr Leu Ser Asn Ala Glu Asp Tyr Leu Asp
                210                 215                 220

Asp Glu Asp Ser Asp
225

(2) INFORMATION FOR SEQ ID NO: 222:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (D) OTHER INFORMATION: May or may not have carboxy-terminal
            amide and/or biotinylated N-terminal (xi) SEQUENCE DESCRIPTION: SEQ ID NO: 222:

Ser Arg Ser Leu Ser Glu Val Ser Pro Lys Pro Pro Ile Arg Ser Val
1               5                   10                  15

Ser Leu Ser Arg
            20

(2) INFORMATION FOR SEQ ID NO: 223:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (D) OTHER INFORMATION: May or may not have carboxy-terminal
            amide and/or biotinylated N-terminal (xi) SEQUENCE DESCRIPTION: SEQ ID NO: 223:

Ser Arg Pro Pro Arg Trp Ser Pro Pro Val Pro Leu Pro Thr Ser
1               5                   10                  15

Leu Asp Ser Arg
        20

(2) INFORMATION FOR SEQ ID NO: 224:

(i) SEQUENCE CHARACTERISTICS:
        (A) LENGTH: 693 bass pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 43..681

(xi) SEQUENCE DESCRIPTION: SEQ ID NO: 224:

```
TNNNCACTCA CGTCGGTGGT GTTGGTACGG ATCGATTCAA GCACGAGACG AAGACGGAAC    60
CGGAGCCGGG CGCGCGGACG GCGGACGCGG GTCCTGAGAA AGCCGAAGAT GGCAGTGAAT   120
GTGTACTCTA CGTCAGTCAC CAGTGATAAC CTAAGTCGAC ATGACATGCT GGCTTGGATC   180
AATGAATCTC TGCAGTTGAA TCTGACAAAG ATAGAACAGT TGTGTTCAGG GGCTGCATAT   240
TGTCAGTTTA TGGACATGCT CTTCCCTGGA TCCATTGCCT TGAAGAAAGT GAAATTCCAA   300
GCTAAGCTAG AACATGAATA TATCCAGAAC TTCAAAATAC TACAAGCAGG CTTCAAGAGG   360
ATGGGCGTTG ACAAAATAAT TCCTGTGGAT AAATTAGTAA AAGGAAAATT TCAGGACAAT   420
TTTGAATTTG TTCAATGGTT CAAGAAGTTT TTTGATGCAA ATTATGATGG AAAAGAGTAT   480
GATCCTGTAG CTGCCAGACA AGGTCAAGAA ACTGCAGTGG NTCCTTCTCT TGTCGCCCCA   540
GCTTTGAGTA AACCGAAGAA ACCTCTCGGN TCCAGTACTG CAGNCCCACA GAGACCCATT   600
GNAACACAGA GGACTACTGC AGNTCCTAAG GNTGGCCCCG GAATGGTGCG AAAGAATCCT   660
GGTGTGGNNA ATGGAGGATG ATGANGCAGC TNT                                693
```

(2) INFORMATION FOR SEQ ID NO: 225:

(i) SEQUENCE CHARACTERISTICS:
        (A) LENGTH: 217 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 225:

```
Arg Ile Asp Ser Ser Thr Arg Arg Arg Asn Arg Ser Arg Ala Arg
1               5                  10                  15

Gly Arg Arg Thr Arg Val Leu Arg Lys Pro Lys Met Ala Val Asn Val
                20                  25                  30

Tyr Ser Thr Ser Val Thr Ser Asp Asn Leu Ser Arg His Asp Met Leu
            35                  40                  45

Ala Trp Ile Asn Glu Ser Leu Asn Leu Gln Leu Thr Lys Ile Glu Gln
        50                  55                  60

Leu Cys Ser Gly Ala Ala Tyr Cys Gln Phe Met Asp Met Leu Phe Pro
65                  70                  75                  80
```

```
Gly Ser Ile Ala Leu Lys Lys Val Lys Phe Gln Ala Lys Leu Glu His
                85                  90                  95

Glu Tyr Ile Gln Asn Phe Lys Ile Leu Gln Ala Gly Phe Lys Arg Met
            100                 105                 110

Gly Val Asp Lys Ile Ile Pro Val Asp Lys Leu Val Lys Gly Lys Phe
            115                 120                 125

Gln Asp Asn Phe Glu Phe Val Gln Trp Phe Lys Lys Phe Phe Asp Ala
        130                 135                 140

Asn Tyr Asp Gly Lys Glu Tyr Asp Pro Val Ala Ala Arg Gln Gly Gln
145                 150                 155                 160

Glu Thr Ala Val Xaa Pro Ser Leu Val Ala Pro Ala Leu Ser Lys Pro
                165                 170                 175

Lys Lys Pro Leu Gly Ser Ser Thr Ala Xaa Pro Gln Arg Pro Ile Xaa
            180                 185                 190

Thr Gln Arg Thr Thr Ala Xaa Pro Lys Xaa Gly Pro Gly Met Val Arg
        195                 200                 205

Lys Asn Pro Gly Val Xaa Asn Gly Gly
    210                 215
```

(2) INFORMATION FOR SEQ ID NO: 226:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 226:

```
Ser Gly Ser Gly Leu Ala Pro Pro Lys Pro Pro Leu Pro Glu Gly Glu
1               5                   10                  15
Val
```

(2) INFORMATION FOR SEQ ID NO: 227:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 227:

```
Gly Asp Gly Tyr Leu Glu Leu Ser Pro
1               5
```